(12) United States Patent
Hu et al.

(10) Patent No.: US 11,795,436 B2
(45) Date of Patent: Oct. 24, 2023

(54) DERIVATION OF HEPATIC STEM CELLS AND MATURE LIVER CELL TYPES AND USES THEREOF

(71) Applicants: AGENCY FOR SCIENCE, TECHNOLOGY AND RESEARCH, Singapore (SG); NATIONAL UNIVERSITY OF SINGAPORE, Singapore (SG)

(72) Inventors: Yuanyu Hu, Singapore (SG); Huck Hui Ng, Singapore (SG); Yock Young Dan, Singapore (SG)

(73) Assignees: Agency for Science, Technology and Research, Singapore (SG); National University of Singapore, Singapore (SG)

( * ) Notice: Subject to any disclaimer, the term of this patent is extended or adjusted under 35 U.S.C. 154(b) by 454 days.

(21) Appl. No.: 16/865,820

(22) Filed: May 4, 2020

(65) Prior Publication Data

US 2020/0354683 A1 Nov. 12, 2020

Related U.S. Application Data

(62) Division of application No. 15/735,321, filed as application No. PCT/SG2016/050270 on Jun. 10, 2016, now Pat. No. 10,683,484.

(30) Foreign Application Priority Data

Jun. 12, 2015 (SG) .......................... 10201504657Y
Jun. 12, 2015 (SG) .......................... 10201504659X

(51) Int. Cl.
| | | |
|---|---|---|
| *C12N 5/071* | (2010.01) | |
| *A61K 35/407* | (2015.01) | |
| *C12N 5/00* | (2006.01) | |
| *A61P 1/16* | (2006.01) | |

(52) U.S. Cl.
CPC .......... *C12N 5/0672* (2013.01); *A61K 35/407* (2013.01); *A61P 1/16* (2018.01); *C12N 5/0037* (2013.01); *C12N 5/067* (2013.01); *C12N 5/0679* (2013.01); *C12N 2501/01* (2013.01); *C12N 2501/11* (2013.01); *C12N 2501/395* (2013.01); *C12N 2501/415* (2013.01); *C12N 2501/42* (2013.01)

(58) Field of Classification Search
CPC .. C12N 5/0672; C12N 5/067; C12N 2501/01; C12N 2501/11; C12N 2501/395; C12N 2501/415; C12N 2501/42
See application file for complete search history.

(56) References Cited

U.S. PATENT DOCUMENTS

| | | | |
|---|---|---|---|
| 10,683,484 B2 | 6/2020 | Hu et al. | |
| 2005/0260748 A1* | 11/2005 | Chang ................. | C12N 5/0672 |
| | | | 435/366 |
| 2012/0093769 A1 | 4/2012 | Chang et al. | |
| 2017/0191030 A1* | 7/2017 | Huch Ortega ....... | C12N 5/0671 |

FOREIGN PATENT DOCUMENTS

| | | |
|---|---|---|
| CN | 1742082 A | 3/2006 |
| CN | 101356264 A | 1/2009 |
| CN | 101384705 A | 3/2009 |
| CN | 101868533 A | 10/2010 |
| CN | 103249404 A | 8/2013 |
| CN | 103989710 A | 8/2014 |
| CN | 104531611 A | 4/2015 |
| EP | 3307874 | 4/2018 |
| WO | 2002/064748 A2 | 8/2002 |
| WO | 2005033126 A1 | 4/2005 |
| WO | 2007/071339 A1 | 6/2007 |
| WO | 2014/152321 A1 | 9/2014 |
| WO | 2015/140257 A1 | 9/2015 |
| WO | 2016200340 A1 | 12/2016 |

OTHER PUBLICATIONS

U.S. Appl. No. 15/735,321, "Non-Final Office Action", dated Sep. 17, 2019, 10 pages.
U.S. Appl. No. 15/735,321, "Notice of Allowance", dated Feb. 10, 2020, 8 pages.
Zheng, et al., "Experimental Study on the Isolation, in-vitro Culture and the Relevant Test of the Rat Hair Follicle Stem Cells", Chinese Journal of Orthopedics and Traumatology, vol. 22, No. 2, Feb. 28, 2014, pp. 8-14.

(Continued)

*Primary Examiner* — Taeyoon Kim
(74) *Attorney, Agent, or Firm* — Kilpatrick Townsend & Stockton LLP

(57) ABSTRACT

This application describes liver stem cells (LSC), and differentiated hepatocytes, cholangiocytes, and 3D cellular structures derived therefrom. Methods for producing LSC and mature, differentiated hepatocytes and cholangiocytes in culture are provided. Also provided are cell culture systems and cell culture media for producing a homogenous population of liver stem cells that remain in an undifferentiated state over multiple passages in culture. The LSC and methods are useful for producing homogenous populations of hepatocytes and cholangiocytes for downstream applications. The LSC can be transplanted into subjects to treat liver diseases.

16 Claims, 39 Drawing Sheets

Specification includes a Sequence Listing.

(56) References Cited

OTHER PUBLICATIONS

Schmelzer, et al., "The Phenotypes of Pluropotent Human Hepatic Progenitors", Stem Cells, 2006, vol. 24, pp. 1852-1858.
International Search Report received in the corresponding International Application No. PCT/SG2016/050270, dated Aug. 22, 2016.
Misra, L., et al., "Liver Stem Cells and Hepatocellular Carcinoma", Hepatology, 2009, vol. 49, No. 1, pp. 318-329.
Noushin, Dianat, et al., "Generation of functional cholangiocyte-like cells from human pluripotent stem cells and HepaRG cells", Hepatology, vol. 60, No. 2, Jun. 2014, pp. 700-714.
Schmelzer, E., et al., "The Phenotypes of Pluripotent Human Hepatic Progenitors", Stem Cells, 2006, vol. 24, pp. 1852-1858.

* cited by examiner

Mouse liver epithelial cell sorting scheme:

FIG. 7B
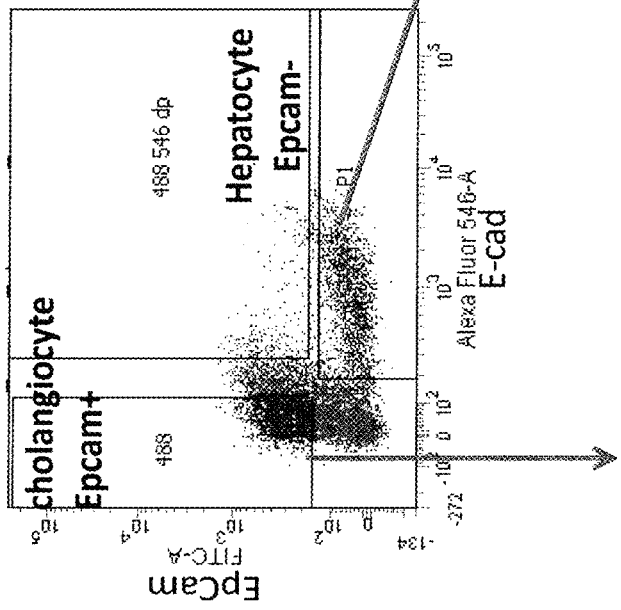
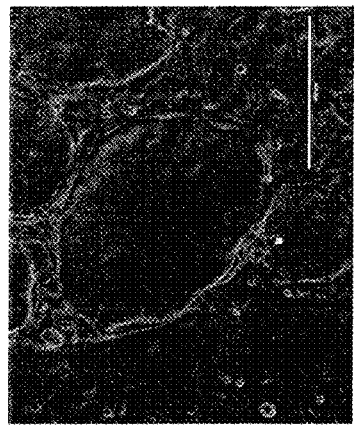
Epcam+ cholangiocyte lineage derived LSC
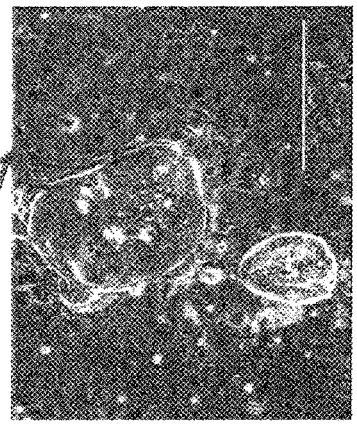
Epcam- hepatocyte lineage derived LSC

DMEM/F12 medium with 10% FBS Without N2 and B27
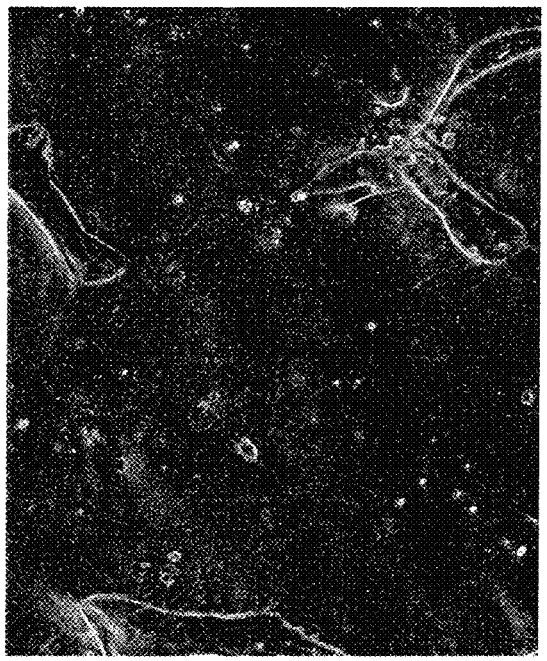
LSC culture medium with N2 B27
FIG. 13

LSC could be derived from 3T3J2, Swiss3T3, NIH3T3, L1 and other fibroblast feeders FIG. 15
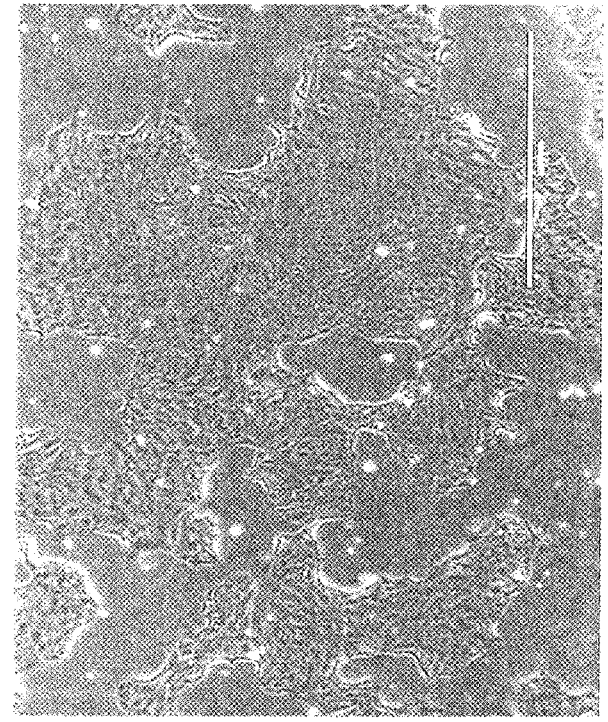
Col I+IV / Lam 511/521 coating  P5
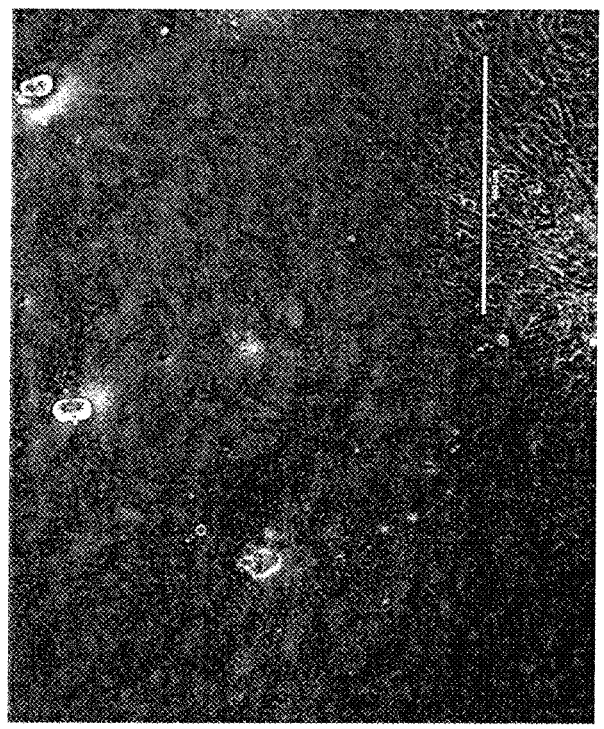
Col I+IV / Lam 511/521 coating  P1

Liver stem cell criteria:
1. Bilineage differentiation potential
2. Self renewal : long term culture 3D bile duct differentiation

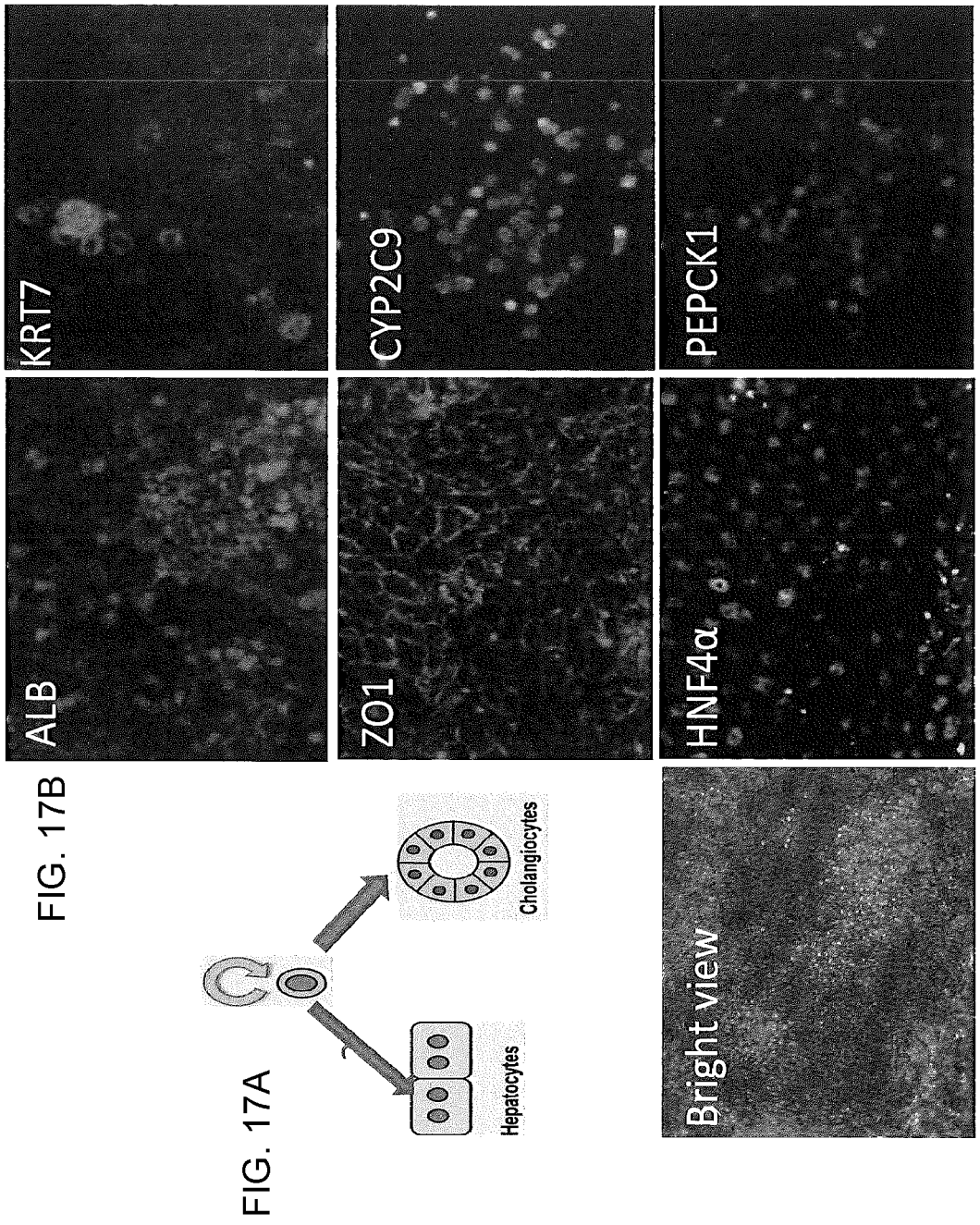

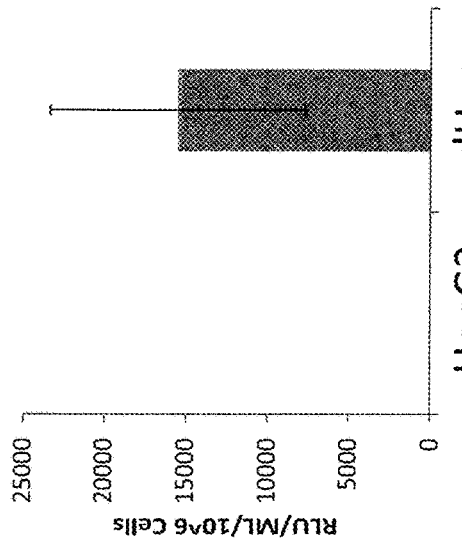
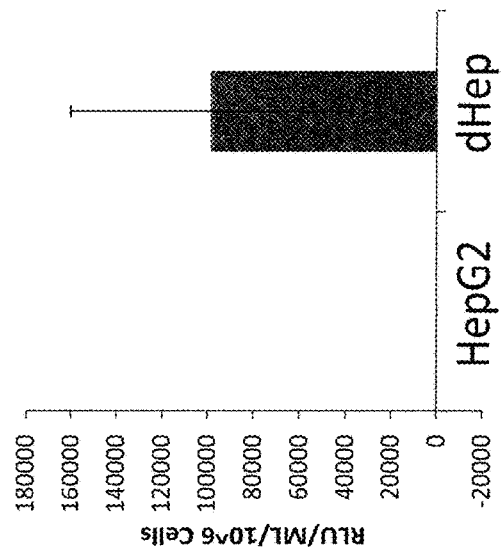
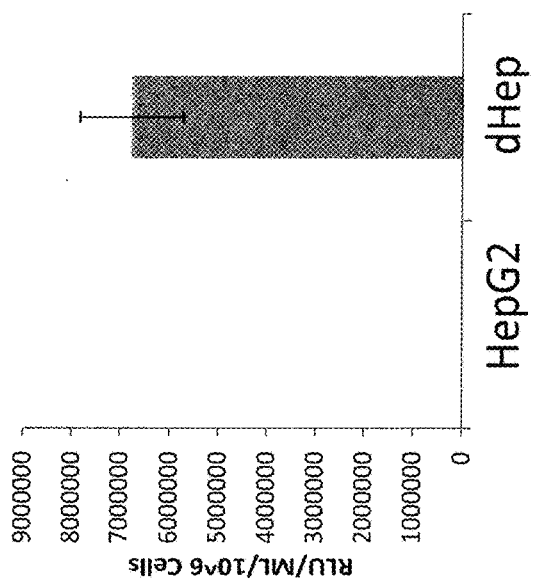
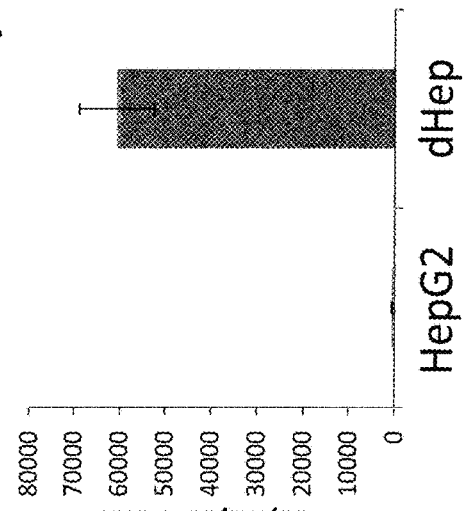
FIG. 20A

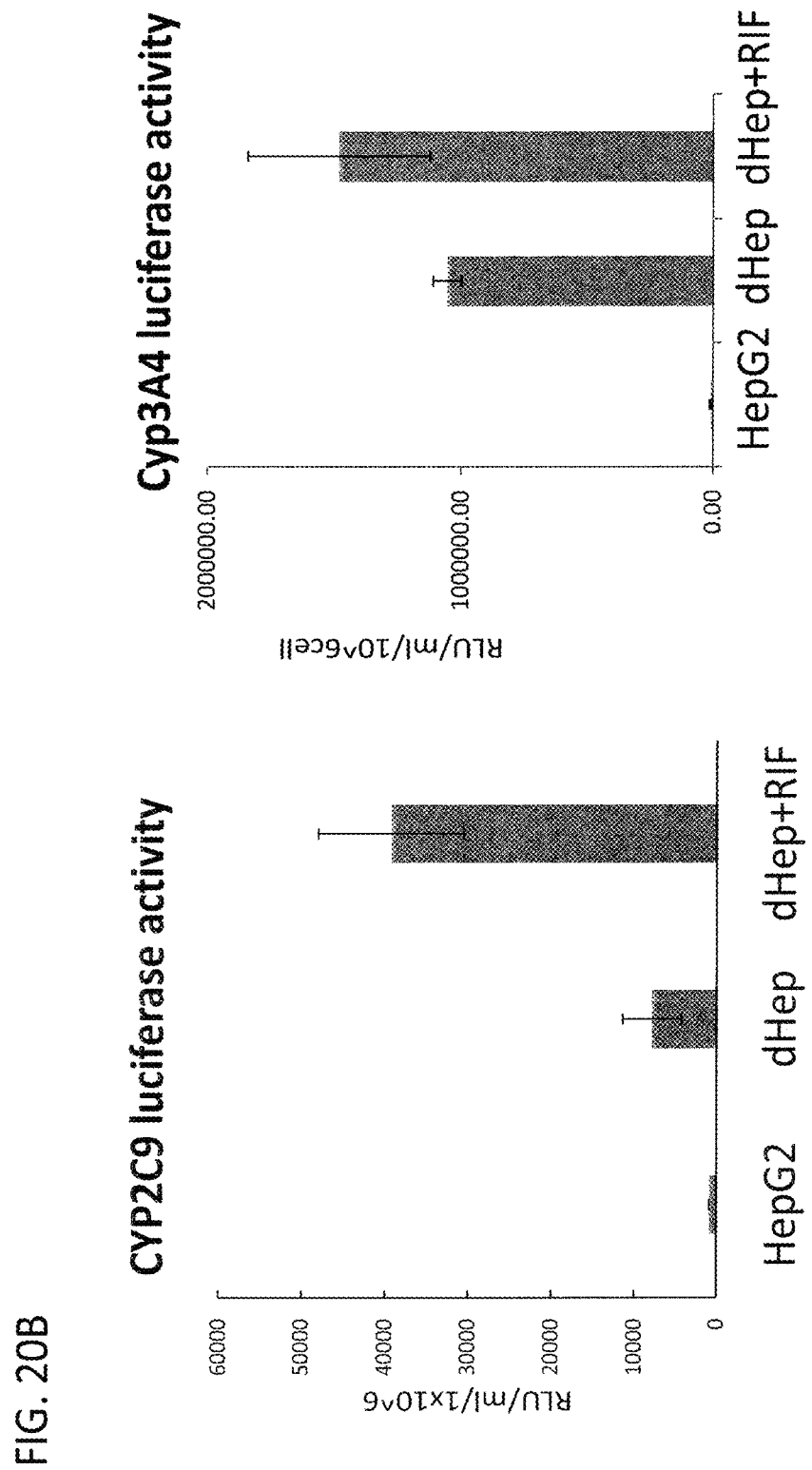

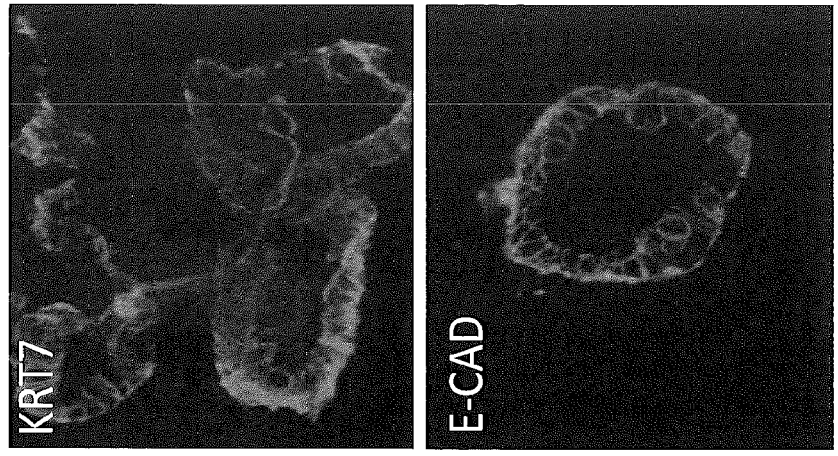
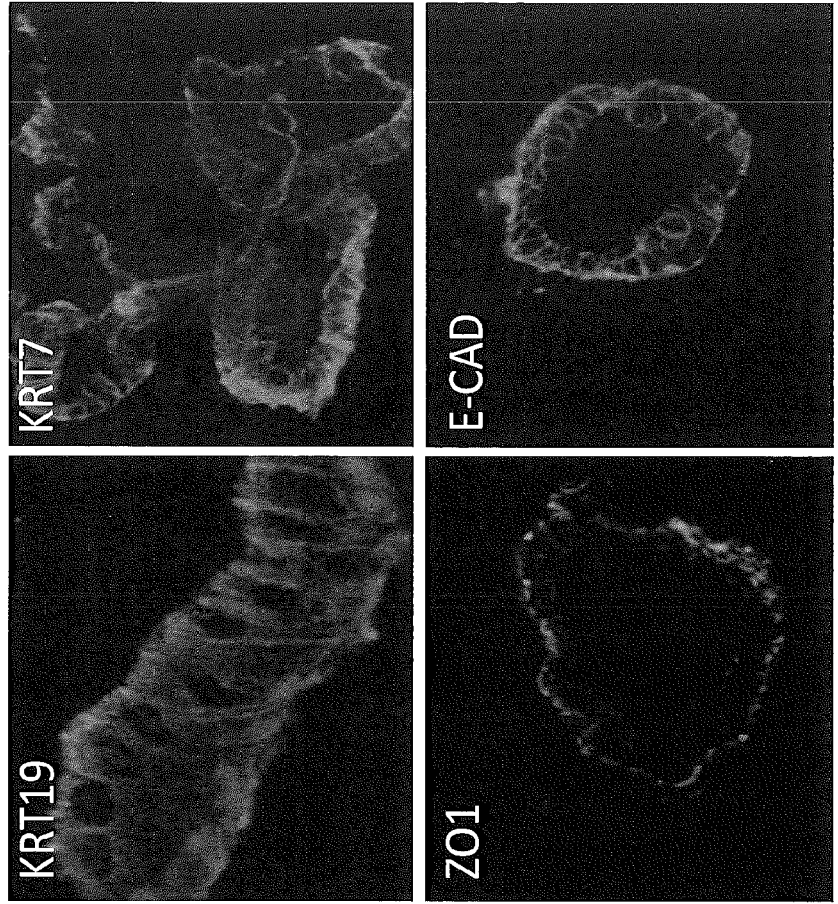
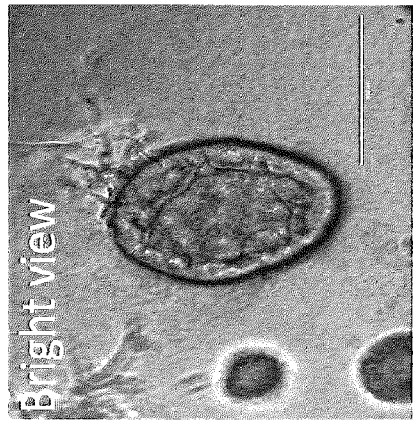
FIG. 29A
FIG. 29B

Human specific Albumin ELISA test by using mouse serum

| NSG mice | Human ALB (ng/ml) |
|---|---|
| HCC transplanted | 491.12 |
| Untransplanted control | 0.00 |

Transplanted mice blood serum contains human ALB

A. Schematic of transplantation into TA liver cirrhosis mice models for liver regeneration B. Liver Function test

| TA-mice | Alb (g/L) |
|---|---|
| Control-1 | 6.21 |
| Control-2 | 6.99 |
| Control-3 | 4.68 |
| LSC transplanted-1 | 37.11 |
| LSC transplanted-2 | 33.52 |
| LSC transplanted-3 | 26.10 |
| LSC transplanted-4 | 33.63 |
| LSC transplanted-5 | 33.35 |
| LSC transplanted-6 | 51.98 |

SEQUENCE LISTING

<160> NUMBER OF SEQ ID NOS: 42

<210> SEQ ID NO 1
<211> LENGTH: 17
<212> TYPE: PRT
<213> ORGANISM: Homo sapiens

<400> SEQUENCE: 1

Cys Asp Asp Tyr Tyr Tyr Gly Phe Gly Cys Asn Lys Phe Cys Arg Pro
1               5                   10                  15

Arg

```
<210> SEQ ID NO 2
<211> LENGTH: 509
<212> TYPE: PRT
<213> ORGANISM: Homo sapiens

<400> SEQUENCE: 2
```

| | | | | | | | | | | | | | | |
|---|---|---|---|---|---|---|---|---|---|---|---|---|---|---|
| Met | Asn | Leu | Leu | Asp | Pro | Phe | Met | Lys | Met | Thr | Asp | Glu | Gln | Glu | Lys |
| 1 | | | | 5 | | | | | 10 | | | | | 15 | |

| Gly | Leu | Ser | Gly | Ala | Pro | Ser | Pro | Thr | Met | Ser | Glu | Asp | Ser | Ala | Gly |
|---|---|---|---|---|---|---|---|---|---|---|---|---|---|---|---|
| | | | 20 | | | | 25 | | | | 30 | | | | |

| Ser | Pro | Cys | Pro | Ser | Gly | Ser | Gly | Ser | Asp | Thr | Glu | Asn | Thr | Arg | Pro |
|---|---|---|---|---|---|---|---|---|---|---|---|---|---|---|---|
| | | 35 | | | | | 40 | | | | | 45 | | | |

| Gln | Glu | Asn | Thr | Phe | Pro | Lys | Gly | Glu | Pro | Asp | Leu | Lys | Lys | Glu | Ser |
|---|---|---|---|---|---|---|---|---|---|---|---|---|---|---|---|
| | 50 | | | | | 55 | | | | | 60 | | | | |

| Glu | Glu | Asp | Lys | Phe | Pro | Val | Cys | Ile | Arg | Glu | Ala | Val | Ser | Gln | Val |
|---|---|---|---|---|---|---|---|---|---|---|---|---|---|---|---|
| 65 | | | | | 70 | | | | | 75 | | | | | 80 |

| Leu | Lys | Gly | Tyr | Asp | Trp | Thr | Leu | Val | Pro | Met | Pro | Val | Arg | Val | Asn |
|---|---|---|---|---|---|---|---|---|---|---|---|---|---|---|---|
| | | | | 85 | | | | | 90 | | | | | 95 | |

| Gly | Ser | Ser | Lys | Asn | Lys | Pro | His | Val | Lys | Arg | Pro | Met | Asn | Ala | Phe |
|---|---|---|---|---|---|---|---|---|---|---|---|---|---|---|---|
| | | | 100 | | | | | 105 | | | | | 110 | | |

| Met | Val | Trp | Ala | Gln | Ala | Ala | Arg | Arg | Lys | Leu | Ala | Asp | Gln | Tyr | Pro |
|---|---|---|---|---|---|---|---|---|---|---|---|---|---|---|---|
| | | 115 | | | | | 120 | | | | | 125 | | | |

| His | Leu | His | Asn | Ala | Glu | Leu | Ser | Lys | Thr | Leu | Gly | Lys | Leu | Trp | Arg |
|---|---|---|---|---|---|---|---|---|---|---|---|---|---|---|---|
| | 130 | | | | | 135 | | | | | 140 | | | | |

| Leu | Leu | Asn | Glu | Ser | Glu | Lys | Arg | Pro | Phe | Val | Glu | Glu | Ala | Glu | Arg |
|---|---|---|---|---|---|---|---|---|---|---|---|---|---|---|---|
| 145 | | | | | 150 | | | | | 155 | | | | | 160 |

| Leu | Arg | Val | Gln | His | Lys | Lys | Asp | His | Pro | Asp | Tyr | Lys | Tyr | Gln | Pro |
|---|---|---|---|---|---|---|---|---|---|---|---|---|---|---|---|
| | | | | 165 | | | | | 170 | | | | | 175 | |

| Arg | Arg | Arg | Lys | Ser | Val | Lys | Asn | Gly | Gln | Ala | Glu | Ala | Glu | Glu | Ala |
|---|---|---|---|---|---|---|---|---|---|---|---|---|---|---|---|
| | | | 180 | | | | | 185 | | | | | 190 | | |

| Thr | Glu | Gln | Thr | His | Ile | Ser | Pro | Asn | Ala | Ile | Phe | Lys | Ala | Leu | Gln |
|---|---|---|---|---|---|---|---|---|---|---|---|---|---|---|---|
| | | 195 | | | | | 200 | | | | | 205 | | | |

| Ala | Asp | Ser | Pro | His | Ser | Ser | Gly | Met | Ser | Glu | Val | His | Ser | Pro |
|---|---|---|---|---|---|---|---|---|---|---|---|---|---|---|
| | 210 | | | | | 215 | | | | | 220 | | | |

| Gly | Glu | His | Ser | Gly | Gln | Ser | Gln | Gly | Pro | Pro | Thr | Pro | Pro | Thr | Thr |
|---|---|---|---|---|---|---|---|---|---|---|---|---|---|---|---|
| 225 | | | | | 230 | | | | | 235 | | | | | 240 |

| Pro | Lys | Thr | Asp | Val | Gln | Pro | Gly | Lys | Ala | Asp | Leu | Lys | Arg | Glu | Gly |
|---|---|---|---|---|---|---|---|---|---|---|---|---|---|---|---|
| | | | 245 | | | | | 250 | | | | | 255 | | |

| Arg | Pro | Leu | Pro | Glu | Gly | Gly | Arg | Gln | Pro | Pro | Ile | Asp | Phe | Arg | Asp |
|---|---|---|---|---|---|---|---|---|---|---|---|---|---|---|---|
| | | 260 | | | | | 265 | | | | | 270 | | | |

| Val | Asp | Ile | Gly | Glu | Leu | Ser | Ser | Asp | Val | Ile | Ser | Asn | Ile | Glu | Thr |
|---|---|---|---|---|---|---|---|---|---|---|---|---|---|---|---|
| | 275 | | | | | 280 | | | | | 285 | | | | |

| Phe | Asp | Val | Asn | Glu | Phe | Asp | Gln | Tyr | Leu | Pro | Pro | Asn | Gly | His | Pro |
|---|---|---|---|---|---|---|---|---|---|---|---|---|---|---|---|
| 290 | | | | | 295 | | | | | 300 | | | | | |

| Gly | Val | Pro | Ala | Thr | His | Gly | Gln | Val | Thr | Tyr | Thr | Gly | Ser | Tyr | Gly |
|---|---|---|---|---|---|---|---|---|---|---|---|---|---|---|---|
| 305 | | | | | 310 | | | | | 315 | | | | | 320 |

| Ile | Ser | Ser | Thr | Ala | Ala | Thr | Pro | Ala | Ser | Ala | Gly | His | Val | Trp | Met |
|---|---|---|---|---|---|---|---|---|---|---|---|---|---|---|---|
| | | | 325 | | | | | 330 | | | | | 335 | | |

| Ser | Lys | Gln | Gln | Ala | Pro | Pro | Pro | Pro | Gln | Gln | Pro | Pro | Gln | Ala |
|---|---|---|---|---|---|---|---|---|---|---|---|---|---|---|
| | | 340 | | | | | 345 | | | | | 350 | | |

| Pro | Pro | Ala | Pro | Gln | Ala | Pro | Pro | Gln | Pro | Gln | Ala | Ala | Pro | Pro | Gln |
|---|---|---|---|---|---|---|---|---|---|---|---|---|---|---|---|
| | | 355 | | | | | 360 | | | | | 365 | | | |

```
Gln Pro Ala Ala Pro Pro Gln Gln Pro Gln Ala His Thr Leu Thr Thr
370                 375                 380

Leu Ser Ser Glu Pro Gly Gln Ser Gln Arg Thr His Ile Lys Thr Glu
385                 390                 395                 400

Gln Leu Ser Pro Ser His Tyr Ser Glu Gln Gln His Ser Pro Gln
            405                 410                 415

Gln Ile Ala Tyr Ser Pro Phe Asn Leu Pro His Tyr Ser Pro Ser Tyr
            420                 425                 430

Pro Pro Ile Thr Arg Ser Gln Tyr Asp Tyr Thr Asp His Gln Asn Ser
            435                 440                 445

Ser Ser Tyr Tyr Ser His Ala Ala Gly Gln Gly Thr Gly Leu Tyr Ser
450                 455                 460

Thr Phe Thr Tyr Met Asn Pro Ala Gln Arg Pro Met Tyr Thr Pro Ile
465                 470                 475                 480

Ala Asp Thr Ser Gly Val Pro Ser Ile Pro Gln Thr His Ser Pro Gln
                485                 490                 495

His Trp Glu Gln Pro Val Tyr Thr Gln Leu Thr Arg Pro
            500                 505

<210> SEQ ID NO 3
<211> LENGTH: 400
<212> TYPE: PRT
<213> ORGANISM: Homo sapiens

<400> SEQUENCE: 3

Met Thr Ser Tyr Ser Tyr Arg Gln Ser Ser Ala Thr Ser Ser Phe Gly
1               5                   10                  15

Gly Leu Gly Gly Gly Ser Val Arg Phe Gly Pro Gly Val Ala Phe Arg
            20                  25                  30

Ala Pro Ser Ile His Gly Gly Ser Gly Gly Arg Gly Val Ser Val Ser
        35                  40                  45

Ser Ala Arg Phe Val Ser Ser Ser Ser Gly Ala Tyr Gly Gly Gly
50                  55                  60

Tyr Gly Gly Val Leu Thr Ala Ser Asp Gly Leu Leu Ala Gly Asn Glu
65                  70                  75                  80

Lys Leu Thr Met Gln Asn Leu Asn Asp Arg Leu Ala Ser Tyr Leu Asp
                85                  90                  95

Lys Val Arg Ala Leu Glu Ala Ala Asn Gly Glu Leu Glu Val Lys Ile
            100                 105                 110

Arg Asp Trp Tyr Gln Lys Gln Gly Pro Gly Pro Ser Arg Asp Tyr Ser
        115                 120                 125

His Tyr Tyr Thr Thr Ile Gln Asp Leu Arg Asp Lys Ile Leu Gly Ala
130                 135                 140

Thr Ile Glu Asn Ser Arg Ile Val Leu Gln Ile Asp Asn Ala Arg Leu
145                 150                 155                 160

Ala Ala Asp Asp Phe Arg Thr Lys Phe Glu Thr Glu Gln Ala Leu Arg
                165                 170                 175

Met Ser Val Glu Ala Asp Ile Asn Gly Leu Arg Arg Val Leu Asp Glu
            180                 185                 190

Leu Thr Leu Ala Arg Thr Asp Leu Glu Met Gln Ile Glu Gly Leu Lys
        195                 200                 205

Glu Glu Leu Ala Tyr Leu Lys Lys Asn His Glu Glu Glu Ile Ser Thr
210                 215                 220

Leu Arg Gly Gln Val Gly Gly Gln Val Ser Val Glu Val Asp Ser Ala
225                 230                 235                 240
```

Pro Gly Thr Asp Leu Ala Lys Ile Leu Ser Asp Met Arg Ser Gln Tyr
                245                 250                 255

Glu Val Met Ala Glu Gln Asn Arg Lys Asp Ala Glu Ala Trp Phe Thr
            260                 265                 270

Ser Arg Thr Glu Glu Leu Asn Arg Glu Val Ala Gly His Thr Glu Gln
        275                 280                 285

Leu Gln Met Ser Arg Ser Glu Val Thr Asp Leu Arg Arg Thr Leu Gln
    290                 295                 300

Gly Leu Glu Ile Glu Leu Gln Ser Gln Leu Ser Met Lys Ala Ala Leu
305                 310                 315                 320

Glu Asp Thr Leu Ala Glu Thr Glu Ala Arg Phe Gly Ala Gln Leu Ala
                325                 330                 335

His Ile Gln Ala Leu Ile Ser Gly Ile Glu Ala Gln Leu Gly Asp Val
            340                 345                 350

Arg Ala Asp Ser Glu Arg Gln Asn Gln Glu Tyr Gln Arg Leu Met Asp
        355                 360                 365

Ile Lys Ser Arg Leu Glu Gln Glu Ile Ala Thr Tyr Arg Ser Leu Leu
    370                 375                 380

Glu Gly Gln Glu Asp His Tyr Asn Asn Leu Ser Ala Ser Lys Val Leu
385                 390                 395                 400

<210> SEQ ID NO 4
<211> LENGTH: 469
<212> TYPE: PRT
<213> ORGANISM: Homo sapiens

<400> SEQUENCE: 4

Met Ser Ile His Phe Ser Ser Pro Val Phe Thr Ser Arg Ser Ala Ala
1               5                   10                  15

Phe Ser Gly Arg Gly Ala Gln Val Arg Leu Ser Ser Ala Arg Pro Gly
            20                  25                  30

Gly Leu Gly Ser Ser Ser Leu Tyr Gly Leu Gly Ala Ser Arg Pro Arg
        35                  40                  45

Val Ala Val Arg Ser Ala Tyr Gly Gly Pro Val Gly Ala Gly Ile Arg
    50                  55                  60

Glu Val Thr Ile Asn Gln Ser Leu Leu Ala Pro Leu Arg Leu Asp Ala
65                  70                  75                  80

Asp Pro Ser Leu Gln Arg Val Arg Gln Glu Ser Glu Gln Ile Lys
            85                  90                  95

Thr Leu Asn Asn Lys Phe Ala Ser Phe Ile Asp Lys Val Arg Phe Leu
            100                 105                 110

Glu Gln Gln Asn Lys Leu Leu Glu Thr Lys Trp Thr Leu Leu Gln Glu
        115                 120                 125

Gln Lys Ser Ala Lys Ser Ser Arg Leu Pro Asp Ile Phe Glu Ala Gln
    130                 135                 140

Ile Ala Gly Leu Arg Gly Gln Leu Glu Ala Leu Gln Val Asp Gly Gly
145                 150                 155                 160

Arg Leu Glu Ala Glu Leu Arg Ser Met Gln Asp Val Val Glu Asp Phe
                165                 170                 175

Lys Asn Lys Tyr Glu Asp Glu Ile Asn His Arg Thr Ala Ala Glu Asn
            180                 185                 190

Glu Phe Val Val Leu Lys Lys Asp Val Asp Ala Ala Tyr Met Ser Lys
        195                 200                 205

Val Glu Leu Glu Ala Lys Val Asp Ala Leu Asn Asp Glu Ile Asn Phe

```
                    210                 215                 220
Leu Arg Thr Leu Asn Glu Thr Glu Leu Thr Glu Leu Gln Ser Gln Ile
225                 230                 235                 240

Ser Asp Thr Ser Val Val Leu Ser Met Asp Asn Ser Arg Ser Leu Asp
                    245                 250                 255

Leu Asp Gly Ile Ile Ala Glu Val Lys Ala Gln Tyr Glu Glu Met Ala
                260                 265                 270

Lys Cys Ser Arg Ala Glu Ala Glu Ala Trp Tyr Gln Thr Lys Phe Glu
                275                 280                 285

Thr Leu Gln Ala Gln Ala Gly Lys His Gly Asp Asp Leu Arg Asn Thr
            290                 295                 300

Arg Asn Glu Ile Ser Glu Met Asn Arg Ala Ile Gln Arg Leu Gln Ala
305                 310                 315                 320

Glu Ile Asp Asn Ile Lys Asn Gln Arg Ala Lys Leu Glu Ala Ala Ile
                    325                 330                 335

Ala Glu Ala Glu Glu Arg Gly Glu Leu Ala Leu Lys Asp Ala Arg Ala
                340                 345                 350

Lys Gln Glu Glu Leu Glu Ala Ala Leu Gln Arg Gly Lys Gln Asp Met
            355                 360                 365

Ala Arg Gln Leu Arg Glu Tyr Gln Glu Leu Met Ser Val Lys Leu Ala
        370                 375                 380

Leu Asp Ile Glu Ile Ala Thr Tyr Arg Lys Leu Leu Glu Gly Glu Glu
385                 390                 395                 400

Ser Arg Leu Ala Gly Asp Gly Val Gly Ala Val Asn Ile Ser Val Met
                405                 410                 415

Asn Ser Thr Gly Gly Ser Ser Ser Gly Gly Gly Ile Gly Leu Thr Leu
                420                 425                 430

Gly Gly Thr Met Gly Ser Asn Ala Leu Ser Phe Ser Ser Ser Ala Gly
            435                 440                 445

Pro Gly Leu Leu Lys Ala Tyr Ser Ile Arg Thr Ala Ser Ala Ser Arg
        450                 455                 460

Arg Ser Ala Arg Asp
465

<210> SEQ ID NO 5
<211> LENGTH: 474
<212> TYPE: PRT
<213> ORGANISM: Homo sapiens

<400> SEQUENCE: 5

Met Arg Leu Ser Lys Thr Leu Val Asp Met Asp Met Ala Asp Tyr Ser
1               5                   10                  15

Ala Ala Leu Asp Pro Ala Tyr Thr Thr Leu Glu Phe Glu Asn Val Gln
                20                  25                  30

Val Leu Thr Met Gly Asn Asp Thr Ser Pro Ser Glu Gly Thr Asn Leu
            35                  40                  45

Asn Ala Pro Asn Ser Leu Gly Val Ser Ala Leu Cys Ala Ile Cys Gly
        50                  55                  60

Asp Arg Ala Thr Gly Lys His Tyr Gly Ala Ser Ser Cys Asp Gly Cys
65                  70                  75                  80

Lys Gly Phe Phe Arg Arg Ser Val Arg Lys Asn His Met Tyr Ser Cys
                85                  90                  95

Arg Phe Ser Arg Gln Cys Val Val Asp Lys Asp Lys Arg Asn Gln Cys
                100                 105                 110
```

```
Arg Tyr Cys Arg Leu Lys Lys Cys Phe Arg Ala Gly Met Lys Lys Glu
            115                 120                 125

Ala Val Gln Asn Glu Arg Asp Arg Ile Ser Thr Arg Arg Ser Ser Tyr
    130                 135                 140

Glu Asp Ser Ser Leu Pro Ser Ile Asn Ala Leu Leu Gln Ala Glu Val
145                 150                 155                 160

Leu Ser Arg Gln Ile Thr Ser Pro Val Ser Gly Ile Asn Gly Asp Ile
                165                 170                 175

Arg Ala Lys Lys Ile Ala Ser Ile Ala Asp Val Cys Glu Ser Met Lys
            180                 185                 190

Glu Gln Leu Leu Val Leu Val Glu Trp Ala Lys Tyr Ile Pro Ala Phe
    195                 200                 205

Cys Glu Leu Pro Leu Asp Asp Gln Val Ala Leu Leu Arg Ala His Ala
210                 215                 220

Gly Glu His Leu Leu Leu Gly Ala Thr Lys Arg Ser Met Val Phe Lys
225                 230                 235                 240

Asp Val Leu Leu Leu Gly Asn Asp Tyr Ile Val Pro Arg His Cys Pro
                245                 250                 255

Glu Leu Ala Glu Met Ser Arg Val Ser Ile Arg Ile Leu Asp Glu Leu
            260                 265                 270

Val Leu Pro Phe Gln Glu Leu Gln Ile Asp Asp Asn Glu Tyr Ala Tyr
    275                 280                 285

Leu Lys Ala Ile Ile Phe Phe Asp Pro Asp Ala Lys Gly Leu Ser Asp
290                 295                 300

Pro Gly Lys Ile Lys Arg Leu Arg Ser Gln Val Gln Val Ser Leu Glu
305                 310                 315                 320

Asp Tyr Ile Asn Asp Arg Gln Tyr Asp Ser Arg Gly Arg Phe Gly Glu
                325                 330                 335

Leu Leu Leu Leu Leu Pro Thr Leu Gln Ser Ile Thr Trp Gln Met Ile
            340                 345                 350

Glu Gln Ile Gln Phe Ile Lys Leu Phe Gly Met Ala Lys Ile Asp Asn
    355                 360                 365

Leu Leu Gln Glu Met Leu Leu Gly Gly Ser Pro Ser Asp Ala Pro His
370                 375                 380

Ala His His Pro Leu His Pro His Leu Met Gln Glu His Met Gly Thr
385                 390                 395                 400

Asn Val Ile Val Ala Asn Thr Met Pro Thr His Leu Ser Asn Gly Gln
                405                 410                 415

Met Cys Glu Trp Pro Arg Pro Arg Gly Gln Ala Ala Thr Pro Glu Thr
            420                 425                 430

Pro Gln Pro Ser Pro Pro Gly Gly Ser Gly Ser Glu Pro Tyr Lys Leu
    435                 440                 445

Leu Pro Gly Ala Val Ala Thr Ile Val Lys Pro Leu Ser Ala Ile Pro
450                 455                 460

Gln Pro Thr Ile Thr Lys Gln Glu Val Ile
465                 470

<210> SEQ ID NO 6
<211> LENGTH: 457
<212> TYPE: PRT
<213> ORGANISM: Homo sapiens

<400> SEQUENCE: 6

Met Leu Gly Ala Val Lys Met Glu Gly His Glu Pro Ser Asp Trp Ser
1               5                   10                  15
```

```
Ser Tyr Tyr Ala Glu Pro Glu Gly Tyr Ser Ser Val Ser Asn Met Asn
             20                  25                  30

Ala Gly Leu Gly Met Asn Gly Met Asn Thr Tyr Met Ser Met Ser Ala
         35                  40                  45

Ala Ala Met Gly Ser Gly Ser Gly Asn Met Ser Ala Gly Ser Met Asn
 50                  55                  60

Met Ser Ser Tyr Val Gly Ala Gly Met Ser Pro Ser Leu Ala Gly Met
 65                  70                  75                   80

Ser Pro Gly Ala Gly Ala Met Ala Gly Met Gly Ser Ala Gly Ala
                 85                  90                  95

Ala Gly Val Ala Gly Met Gly Pro His Leu Ser Pro Ser Leu Ser Pro
            100                 105                 110

Leu Gly Gly Gln Ala Ala Gly Ala Met Gly Gly Leu Ala Pro Tyr Ala
            115                 120                 125

Asn Met Asn Ser Met Ser Pro Met Tyr Gly Gln Ala Gly Leu Ser Arg
130                 135                 140

Ala Arg Asp Pro Lys Thr Tyr Arg Arg Ser Tyr Thr His Ala Lys Pro
145                 150                 155                 160

Pro Tyr Ser Tyr Ile Ser Leu Ile Thr Met Ala Ile Gln Gln Ser Pro
                165                 170                 175

Asn Lys Met Leu Thr Leu Ser Glu Ile Tyr Gln Trp Ile Met Asp Leu
            180                 185                 190

Phe Pro Phe Tyr Arg Gln Asn Gln Gln Arg Trp Gln Asn Ser Ile Arg
        195                 200                 205

His Ser Leu Ser Phe Asn Asp Cys Phe Leu Lys Val Pro Arg Ser Pro
    210                 215                 220

Asp Lys Pro Gly Lys Gly Ser Phe Trp Thr Leu His Pro Asp Ser Gly
225                 230                 235                 240

Asn Met Phe Glu Asn Gly Cys Tyr Leu Arg Arg Gln Lys Arg Phe Lys
                245                 250                 255

Cys Glu Lys Gln Leu Ala Leu Lys Glu Ala Ala Gly Ala Ala Gly Ser
            260                 265                 270

Gly Lys Lys Ala Ala Ala Gly Ala Gln Ala Ser Gln Ala Gln Leu Gly
            275                 280                 285

Glu Ala Ala Gly Pro Ala Ser Glu Thr Pro Ala Gly Thr Glu Ser Pro
290                 295                 300

His Ser Ser Ala Ser Pro Cys Gln Glu His Lys Arg Gly Gly Leu Gly
305                 310                 315                 320

Glu Leu Lys Gly Thr Pro Ala Ala Ala Leu Ser Pro Glu Pro Ala
                325                 330                 335

Pro Ser Pro Gly Gln Gln Gln Ala Ala Ala His Leu Leu Gly Pro
            340                 345                 350

Pro His His Pro Gly Leu Pro Pro Glu Ala His Leu Lys Pro Glu His
            355                 360                 365

His Tyr Ala Phe Asn His Pro Phe Ser Ile Asn Asn Leu Met Ser Ser
            370                 375                 380

Glu Gln Gln His His His Ser His His His His Gln Pro His Lys Met
385                 390                 395                 400

Asp Leu Lys Ala Tyr Glu Gln Val Met His Tyr Pro Gly Tyr Gly Ser
                405                 410                 415

Pro Met Pro Gly Ser Leu Ala Met Gly Pro Val Thr Asn Lys Thr Gly
            420                 425                 430
```

```
Leu Asp Ala Ser Pro Leu Ala Asp Thr Ser Tyr Tyr Gln Gly Val
        435                 440                 445

Tyr Ser Arg Pro Ile Met Asn Ser Ser
    450                 455

<210> SEQ ID NO 7
<211> LENGTH: 882
<212> TYPE: PRT
<213> ORGANISM: Homo sapiens

<400> SEQUENCE: 7

Met Gly Pro Trp Ser Arg Ser Leu Ser Ala Leu Leu Leu Leu Leu Gln
1               5                   10                  15

Val Ser Ser Trp Leu Cys Gln Glu Pro Glu Pro Cys His Pro Gly Phe
            20                  25                  30

Asp Ala Glu Ser Tyr Thr Phe Thr Val Pro Arg Arg His Leu Glu Arg
        35                  40                  45

Gly Arg Val Leu Gly Arg Val Asn Phe Glu Asp Cys Thr Gly Arg Gln
    50                  55                  60

Arg Thr Ala Tyr Phe Ser Leu Asp Thr Arg Phe Lys Val Gly Thr Asp
65                  70                  75                  80

Gly Val Ile Thr Val Lys Arg Pro Leu Arg Phe His Asn Pro Gln Ile
                85                  90                  95

His Phe Leu Val Tyr Ala Trp Asp Ser Thr Tyr Arg Lys Phe Ser Thr
            100                 105                 110

Lys Val Thr Leu Asn Thr Val Gly His His His Arg Pro Pro Pro His
        115                 120                 125

Gln Ala Ser Val Ser Gly Ile Gln Ala Glu Leu Leu Thr Phe Pro Asn
    130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
                165                 170                 175

Gln Ile Lys Ser Asn Lys Asp Lys Glu Gly Lys Val Phe Tyr Ser Ile
            180                 185                 190

Thr Gly Gln Gly Ala Asp Thr Pro Pro Val Gly Val Phe Ile Ile Glu
        195                 200                 205

Arg Glu Thr Gly Trp Leu Lys Val Thr Glu Pro Leu Asp Arg Glu Arg
    210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
                245                 250                 255

Asp Asn Lys Pro Glu Phe Thr Gln Glu Val Phe Lys Gly Ser Val Met
            260                 265                 270

Glu Gly Ala Leu Pro Gly Thr Ser Val Met Glu Val Thr Ala Thr Asp
        275                 280                 285

Ala Asp Asp Asp Val Asn Thr Tyr Asn Ala Ala Ile Ala Tyr Thr Ile
    290                 295                 300

Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
                325                 330                 335

Ser Phe Pro Thr Tyr Thr Leu Val Val Gln Ala Ala Asp Leu Gln Gly
            340                 345                 350
```

```
Glu Gly Leu Ser Thr Thr Ala Thr Ala Val Ile Thr Val Thr Asp Thr
            355                 360                 365

Asn Asp Asn Pro Pro Ile Phe Asn Pro Thr Thr Tyr Lys Gly Gln Val
        370                 375                 380

Pro Glu Asn Glu Ala Asn Val Val Ile Thr Thr Leu Lys Val Thr Asp
385                 390                 395                 400

Ala Asp Ala Pro Asn Thr Pro Ala Trp Glu Ala Val Tyr Thr Ile Leu
                405                 410                 415

Asn Asp Asp Gly Gly Gln Phe Val Val Thr Thr Asn Pro Val Asn Asn
            420                 425                 430

Asp Gly Ile Leu Lys Thr Ala Lys Gly Leu Asp Phe Glu Ala Lys Gln
        435                 440                 445

Gln Tyr Ile Leu His Val Ala Val Thr Asn Val Val Pro Phe Glu Val
    450                 455                 460

Ser Leu Thr Thr Ser Thr Ala Thr Val Thr Val Asp Val Leu Asp Val
465                 470                 475                 480

Asn Glu Ala Pro Ile Phe Val Pro Pro Glu Lys Arg Val Glu Val Ser
                485                 490                 495

Glu Asp Phe Gly Val Gly Gln Glu Ile Thr Ser Tyr Thr Ala Gln Glu
            500                 505                 510

Pro Asp Thr Phe Met Glu Gln Lys Ile Thr Tyr Arg Ile Trp Arg Asp
        515                 520                 525

Thr Ala Asn Trp Leu Glu Ile Asn Pro Asp Thr Gly Ala Ile Ser Thr
    530                 535                 540

Arg Ala Glu Leu Asp Arg Glu Asp Phe Glu His Val Lys Asn Ser Thr
545                 550                 555                 560

Tyr Thr Ala Leu Ile Ile Ala Thr Asp Asn Gly Ser Pro Val Ala Thr
                565                 570                 575

Gly Thr Gly Thr Leu Leu Leu Ile Leu Ser Asp Val Asn Asp Asn Ala
            580                 585                 590

Pro Ile Pro Glu Pro Arg Thr Ile Phe Phe Cys Glu Arg Asn Pro Lys
        595                 600                 605

Pro Gln Val Ile Asn Ile Asp Ala Asp Leu Pro Pro Asn Thr Ser
    610                 615                 620

Pro Phe Thr Ala Glu Leu Thr His Gly Ala Ser Ala Asn Trp Thr Ile
625                 630                 635                 640

Gln Tyr Asn Asp Pro Thr Gln Glu Ser Ile Ile Leu Lys Pro Lys Met
                645                 650                 655

Ala Leu Glu Val Gly Asp Tyr Lys Ile Asn Leu Lys Leu Met Asp Asn
            660                 665                 670

Gln Asn Lys Asp Gln Val Thr Thr Leu Glu Val Ser Val Cys Asp Cys
        675                 680                 685

Glu Gly Ala Ala Gly Val Cys Arg Lys Ala Gln Pro Val Glu Ala Gly
    690                 695                 700

Leu Gln Ile Pro Ala Ile Leu Gly Ile Leu Gly Gly Ile Leu Ala Leu
705                 710                 715                 720

Leu Ile Leu Ile Leu Leu Leu Leu Phe Leu Arg Arg Arg Ala Val
                725                 730                 735

Val Lys Glu Pro Leu Leu Pro Pro Glu Asp Asp Thr Arg Asp Asn Val
            740                 745                 750

Tyr Tyr Tyr Asp Glu Glu Gly Gly Glu Glu Asp Gln Asp Phe Asp
        755                 760                 765
```

```
Leu Ser Gln Leu His Arg Gly Leu Asp Ala Arg Pro Glu Val Thr Arg
    770                 775                 780
Asn Asp Val Ala Pro Thr Leu Met Ser Val Pro Arg Tyr Leu Pro Arg
785                 790                 795                 800
Pro Ala Asn Pro Asp Glu Ile Gly Asn Phe Ile Asp Glu Asn Leu Lys
                805                 810                 815
Ala Ala Asp Thr Asp Pro Thr Ala Pro Pro Tyr Asp Ser Leu Leu Val
            820                 825                 830
Phe Asp Tyr Glu Gly Ser Gly Ser Glu Ala Ala Ser Leu Ser Ser Leu
        835                 840                 845
Asn Ser Ser Glu Ser Asp Lys Asp Gln Asp Tyr Asp Tyr Leu Asn Glu
    850                 855                 860
Trp Gly Asn Arg Phe Lys Lys Leu Ala Asp Met Tyr Gly Gly Gly Glu
865                 870                 875                 880
Asp Asp
```

<210> SEQ ID NO 8
<211> LENGTH: 314
<212> TYPE: PRT
<213> ORGANISM: Homo sapiens

<400> SEQUENCE: 8

```
Met Ala Pro Pro Gln Val Leu Ala Phe Gly Leu Leu Leu Ala Ala Ala
1               5                   10                  15
Thr Ala Thr Phe Ala Ala Ala Gln Glu Glu Cys Val Cys Glu Asn Tyr
                20                  25                  30
Lys Leu Ala Val Asn Cys Phe Val Asn Asn Asn Arg Gln Cys Gln Cys
            35                  40                  45
Thr Ser Val Gly Ala Gln Asn Thr Val Ile Cys Ser Lys Leu Ala Ala
        50                  55                  60
Lys Cys Leu Val Met Lys Ala Glu Met Asn Gly Ser Lys Leu Gly Arg
65                  70                  75                  80
Arg Ala Lys Pro Glu Gly Ala Leu Gln Asn Asn Asp Gly Leu Tyr Asp
                85                  90                  95
Pro Asp Cys Asp Glu Ser Gly Leu Phe Lys Ala Lys Gln Cys Asn Gly
                100                 105                 110
Thr Ser Met Cys Trp Cys Val Asn Thr Ala Gly Val Arg Arg Thr Asp
            115                 120                 125
Lys Asp Thr Glu Ile Thr Cys Ser Glu Arg Val Arg Thr Tyr Trp Ile
        130                 135                 140
Ile Ile Glu Leu Lys His Lys Ala Arg Glu Lys Pro Tyr Asp Ser Lys
145                 150                 155                 160
Ser Leu Arg Thr Ala Leu Gln Lys Glu Ile Thr Thr Arg Tyr Gln Leu
                165                 170                 175
Asp Pro Lys Phe Ile Thr Ser Ile Leu Tyr Glu Asn Asn Val Ile Thr
            180                 185                 190
Ile Asp Leu Val Gln Asn Ser Ser Gln Lys Thr Gln Asn Asp Val Asp
        195                 200                 205
Ile Ala Asp Val Ala Tyr Tyr Phe Glu Lys Asp Val Lys Gly Glu Ser
    210                 215                 220
Leu Phe His Ser Lys Lys Met Asp Leu Thr Val Asn Gly Glu Gln Leu
225                 230                 235                 240
Asp Leu Asp Pro Gly Gln Thr Leu Ile Tyr Tyr Val Asp Glu Lys Ala
                245                 250                 255
```

```
Pro Glu Phe Ser Met Gln Gly Leu Lys Ala Gly Val Ile Ala Val Ile
            260                 265                 270

Val Val Val Val Ile Ala Val Ala Gly Ile Val Val Leu Val Ile
        275                 280                 285

Ser Arg Lys Lys Arg Met Ala Lys Tyr Glu Lys Ala Glu Ile Lys Glu
290                 295                 300

Met Gly Glu Met His Arg Glu Leu Asn Ala
305                 310

<210> SEQ ID NO 9
<211> LENGTH: 609
<212> TYPE: PRT
<213> ORGANISM: Homo sapiens

<400> SEQUENCE: 9

Met Lys Trp Val Glu Ser Ile Phe Leu Ile Phe Leu Leu Asn Phe Thr
1               5                   10                  15

Glu Ser Arg Thr Leu His Arg Asn Glu Tyr Gly Ile Ala Ser Ile Leu
            20                  25                  30

Asp Ser Tyr Gln Cys Thr Ala Glu Ile Ser Leu Ala Asp Leu Ala Thr
        35                  40                  45

Ile Phe Phe Ala Gln Phe Val Gln Glu Ala Thr Tyr Lys Glu Val Ser
    50                  55                  60

Lys Met Val Lys Asp Ala Leu Thr Ala Ile Glu Lys Pro Thr Gly Asp
65                  70                  75                  80

Glu Gln Ser Ser Gly Cys Leu Glu Asn Gln Leu Pro Ala Phe Leu Glu
                85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
        115                 120                 125

Lys Lys Pro Thr Pro Ala Ser Ile Pro Leu Phe Gln Val Pro Glu Pro
    130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175

Thr Ile Leu Leu Trp Ala Ala Arg Tyr Asp Lys Ile Ile Pro Ser Cys
            180                 185                 190

Cys Lys Ala Glu Asn Ala Val Glu Cys Phe Gln Thr Lys Ala Ala Thr
        195                 200                 205

Val Thr Lys Glu Leu Arg Glu Ser Ser Leu Leu Asn Gln His Ala Cys
    210                 215                 220

Ala Val Met Lys Asn Phe Gly Thr Arg Thr Phe Gln Ala Ile Thr Val
225                 230                 235                 240

Thr Lys Leu Ser Gln Lys Phe Thr Lys Val Asn Phe Thr Glu Ile Gln
                245                 250                 255

Lys Leu Val Leu Asp Val Ala His Val His Glu His Cys Cys Arg Gly
            260                 265                 270

Asp Val Leu Asp Cys Leu Gln Asp Gly Glu Lys Ile Met Ser Tyr Ile
        275                 280                 285

Cys Ser Gln Gln Asp Thr Leu Ser Asn Lys Ile Thr Glu Cys Cys Lys
    290                 295                 300

Leu Thr Thr Leu Glu Arg Gly Gln Cys Ile Ile His Ala Glu Asn Asp
305                 310                 315                 320
```

```
Glu Lys Pro Glu Gly Leu Ser Pro Asn Leu Asn Arg Phe Leu Gly Asp
            325                 330                 335

Arg Asp Phe Asn Gln Phe Ser Ser Gly Glu Lys Asn Ile Phe Leu Ala
        340                 345                 350

Ser Phe Val His Glu Tyr Ser Arg Arg His Pro Gln Leu Ala Val Ser
            355                 360                 365

Val Ile Leu Arg Val Ala Lys Gly Tyr Gln Glu Leu Leu Glu Lys Cys
        370                 375                 380

Phe Gln Thr Glu Asn Pro Leu Glu Cys Gln Asp Lys Gly Glu Glu Glu
385                 390                 395                 400

Leu Gln Lys Tyr Ile Gln Glu Ser Gln Ala Leu Ala Lys Arg Ser Cys
            405                 410                 415

Gly Leu Phe Gln Lys Leu Gly Glu Tyr Tyr Leu Gln Asn Ala Phe Leu
        420                 425                 430

Val Ala Tyr Thr Lys Lys Ala Pro Gln Leu Thr Ser Ser Glu Leu Met
            435                 440                 445

Ala Ile Thr Arg Lys Met Ala Ala Thr Ala Ala Thr Cys Cys Gln Leu
        450                 455                 460

Ser Glu Asp Lys Leu Leu Ala Cys Gly Glu Gly Ala Ala Asp Ile Ile
465                 470                 475                 480

Ile Gly His Leu Cys Ile Arg His Glu Met Thr Pro Val Asn Pro Gly
            485                 490                 495

Val Gly Gln Cys Cys Thr Ser Ser Tyr Ala Asn Arg Arg Pro Cys Phe
        500                 505                 510

Ser Ser Leu Val Val Asp Glu Thr Tyr Val Pro Pro Ala Phe Ser Asp
            515                 520                 525

Asp Lys Phe Ile Phe His Lys Asp Leu Cys Gln Ala Gln Gly Val Ala
        530                 535                 540

Leu Gln Thr Met Lys Gln Glu Phe Leu Ile Asn Leu Val Lys Gln Lys
545                 550                 555                 560

Pro Gln Ile Thr Glu Glu Gln Leu Glu Ala Val Ile Ala Asp Phe Ser
            565                 570                 575

Gly Leu Leu Glu Lys Cys Cys Gln Gly Gln Glu Gln Glu Val Cys Phe
        580                 585                 590

Ala Glu Glu Gly Gln Lys Leu Ile Ser Lys Thr Arg Ala Ala Leu Gly
            595                 600                 605

Val

<210> SEQ ID NO 10
<211> LENGTH: 3256
<212> TYPE: PRT
<213> ORGANISM: Homo sapiens

<400> SEQUENCE: 10

Met Trp Pro Thr Arg Arg Leu Val Thr Ile Lys Arg Ser Gly Val Asp
1               5                   10                  15

Gly Pro His Phe Pro Leu Ser Leu Ser Thr Cys Leu Phe Gly Arg Gly
            20                  25                  30

Ile Glu Cys Asp Ile Arg Ile Gln Leu Pro Val Val Ser Lys Gln His
        35                  40                  45

Cys Lys Ile Glu Ile His Glu Gln Glu Ala Ile Leu His Asn Phe Ser
    50                  55                  60

Ser Thr Asn Pro Thr Gln Val Asn Gly Ser Val Ile Asp Glu Pro Val
65                  70                  75                  80
```

```
Arg Leu Lys His Gly Asp Val Ile Thr Ile Asp Arg Ser Phe Arg
                85                  90                  95

Tyr Glu Asn Glu Ser Leu Gln Asn Gly Arg Lys Ser Thr Glu Phe Pro
            100                 105                 110

Arg Lys Ile Arg Glu Gln Glu Pro Ala Arg Arg Val Ser Arg Ser Ser
        115                 120                 125

Phe Ser Ser Asp Pro Asp Glu Lys Ala Gln Asp Ser Lys Ala Tyr Ser
    130                 135                 140

Lys Ile Thr Glu Gly Lys Val Ser Gly Asn Pro Gln Val His Ile Lys
145                 150                 155                 160

Asn Val Lys Glu Asp Ser Thr Ala Asp Asp Ser Lys Ser Val Ala
                165                 170                 175

Gln Gly Thr Thr Asn Val His Ser Ser Glu His Ala Gly Arg Asn Gly
                180                 185                 190

Arg Asn Ala Ala Asp Pro Ile Ser Gly Asp Phe Lys Glu Ile Ser Ser
            195                 200                 205

Val Lys Leu Val Ser Arg Tyr Gly Glu Leu Lys Ser Val Pro Thr Thr
        210                 215                 220

Gln Cys Leu Asp Asn Ser Lys Lys Asn Glu Ser Pro Phe Trp Lys Leu
225                 230                 235                 240

Tyr Glu Ser Val Lys Lys Glu Leu Asp Val Lys Ser Gln Lys Glu Asn
                245                 250                 255

Val Leu Gln Tyr Cys Arg Lys Ser Gly Leu Gln Thr Asp Tyr Ala Thr
            260                 265                 270

Glu Lys Glu Ser Ala Asp Gly Leu Gln Gly Glu Thr Gln Leu Leu Val
        275                 280                 285

Ser Arg Lys Ser Arg Pro Lys Ser Gly Gly Ser Gly His Ala Val Ala
    290                 295                 300

Glu Pro Ala Ser Pro Glu Gln Glu Leu Asp Gln Asn Lys Gly Lys Gly
305                 310                 315                 320

Arg Asp Val Glu Ser Val Gln Thr Pro Ser Lys Ala Val Gly Ala Ser
                325                 330                 335

Phe Pro Leu Tyr Glu Pro Ala Lys Met Lys Thr Pro Val Gln Tyr Ser
            340                 345                 350

Gln Gln Gln Asn Ser Pro Gln Lys His Lys Asn Lys Asp Leu Tyr Thr
        355                 360                 365

Thr Gly Arg Arg Glu Ser Val Asn Leu Gly Lys Ser Glu Gly Phe Lys
    370                 375                 380

Ala Gly Asp Lys Thr Leu Thr Pro Arg Lys Leu Ser Thr Arg Asn Arg
385                 390                 395                 400

Thr Pro Ala Lys Val Glu Asp Ala Ala Asp Ser Ala Thr Lys Pro Glu
                405                 410                 415

Asn Leu Ser Ser Lys Thr Arg Gly Ser Ile Pro Thr Asp Val Glu Val
            420                 425                 430

Leu Pro Thr Glu Thr Glu Ile His Asn Glu Pro Phe Leu Thr Leu Trp
        435                 440                 445

Leu Thr Gln Val Glu Arg Lys Ile Gln Lys Asp Ser Leu Ser Lys Pro
    450                 455                 460

Glu Lys Leu Gly Thr Thr Ala Gly Gln Met Cys Ser Gly Leu Pro Gly
465                 470                 475                 480

Leu Ser Ser Val Asp Ile Asn Asn Phe Gly Asp Ser Ile Asn Glu Ser
                485                 490                 495
```

```
Glu Gly Ile Pro Leu Lys Arg Arg Val Ser Phe Gly His Leu
            500                 505                 510
Arg Pro Glu Leu Phe Asp Glu Asn Leu Pro Pro Asn Thr Pro Leu Lys
        515                 520                 525
Arg Gly Glu Ala Pro Thr Lys Arg Lys Ser Leu Val Met His Thr Pro
        530                 535                 540
Pro Val Leu Lys Lys Ile Ile Lys Glu Gln Pro Gln Pro Ser Gly Lys
545                 550                 555                 560
Gln Glu Ser Gly Ser Glu Ile His Val Glu Val Lys Ala Gln Ser Leu
                565                 570                 575
Val Ile Ser Pro Pro Ala Pro Ser Pro Arg Lys Thr Pro Val Ala Ser
                580                 585                 590
Asp Gln Arg Arg Arg Ser Cys Lys Thr Ala Pro Ala Ser Ser Ser Lys
                595                 600                 605
Ser Gln Thr Glu Val Pro Lys Arg Gly Gly Arg Lys Ser Gly Asn Leu
        610                 615                 620
Pro Ser Lys Arg Val Ser Ile Ser Arg Ser Gln His Asp Ile Leu Gln
625                 630                 635                 640
Met Ile Cys Ser Lys Arg Arg Ser Gly Ala Ser Glu Ala Asn Leu Ile
                645                 650                 655
Val Ala Lys Ser Trp Ala Asp Val Val Lys Leu Gly Ala Lys Gln Thr
                660                 665                 670
Gln Thr Lys Val Ile Lys His Gly Pro Gln Arg Ser Met Asn Lys Arg
        675                 680                 685
Gln Arg Arg Pro Ala Thr Pro Lys Lys Pro Val Gly Glu Val His Ser
        690                 695                 700
Gln Phe Ser Thr Gly His Ala Asn Ser Pro Cys Thr Ile Ile Gly
705                 710                 715                 720
Lys Ala His Thr Glu Lys Val His Val Pro Ala Arg Pro Tyr Arg Val
                725                 730                 735
Leu Asn Asn Phe Ile Ser Asn Gln Lys Met Asp Phe Lys Glu Asp Leu
                740                 745                 750
Ser Gly Ile Ala Glu Met Phe Lys Thr Pro Val Lys Glu Gln Pro Gln
        755                 760                 765
Leu Thr Ser Thr Cys His Ile Ala Ile Ser Asn Ser Glu Asn Leu Leu
        770                 775                 780
Gly Lys Gln Phe Gln Gly Thr Asp Ser Gly Glu Glu Pro Leu Leu Pro
785                 790                 795                 800
Thr Ser Glu Ser Phe Gly Gly Asn Val Phe Phe Ser Ala Gln Asn Ala
                805                 810                 815
Ala Lys Gln Pro Ser Asp Lys Cys Ser Ala Ser Pro Pro Leu Arg Arg
        820                 825                 830
Gln Cys Ile Arg Glu Asn Gly Asn Val Ala Lys Thr Pro Arg Asn Thr
        835                 840                 845
Tyr Lys Met Thr Ser Leu Glu Thr Lys Thr Ser Asp Thr Glu Thr Glu
850                 855                 860
Pro Ser Lys Thr Val Ser Thr Ala Asn Arg Ser Gly Arg Ser Thr Glu
865                 870                 875                 880
Phe Arg Asn Ile Gln Lys Leu Pro Val Glu Ser Lys Ser Glu Glu Thr
                885                 890                 895
Asn Thr Glu Ile Val Glu Cys Ile Leu Lys Arg Gly Gln Lys Ala Thr
                900                 905                 910
Leu Leu Gln Gln Arg Arg Glu Gly Glu Met Lys Glu Ile Glu Arg Pro
```

-continued

```
                915                 920                 925
    Phe Glu Thr Tyr Lys Glu Asn Ile Glu Leu Lys Glu Asn Asp Glu Lys
        930                 935                 940
    Met Lys Ala Met Lys Arg Ser Arg Thr Trp Gly Gln Lys Cys Ala Pro
    945                 950                 955                 960
    Met Ser Asp Leu Thr Asp Leu Lys Ser Leu Pro Asp Thr Glu Leu Met
                    965                 970                 975
    Lys Asp Thr Ala Arg Gly Gln Asn Leu Leu Gln Thr Gln Asp His Ala
                    980                 985                 990
    Lys Ala Pro Lys Ser Glu Lys Gly Lys Ile Thr Lys Met Pro Cys Gln
                    995                 1000                1005
    Ser Leu Gln Pro Glu Pro Ile Asn Thr Pro Thr His Thr Lys Gln
        1010                1015                1020
    Gln Leu Lys Ala Ser Leu Gly Lys Val Gly Val Lys Glu Glu Leu
        1025                1030                1035
    Leu Ala Val Gly Lys Phe Thr Arg Thr Ser Gly Glu Thr Thr His
        1040                1045                1050
    Thr His Arg Glu Pro Ala Gly Asp Gly Lys Ser Ile Arg Thr Phe
        1055                1060                1065
    Lys Glu Ser Pro Lys Gln Ile Leu Asp Pro Ala Ala Arg Val Thr
        1070                1075                1080
    Gly Met Lys Lys Trp Pro Arg Thr Pro Lys Glu Ala Gln Ser
        1085                1090                1095
    Leu Glu Asp Leu Ala Gly Phe Lys Glu Leu Phe Gln Thr Pro Gly
        1100                1105                1110
    Pro Ser Glu Glu Ser Met Thr Asp Glu Lys Thr Thr Lys Ile Ala
        1115                1120                1125
    Cys Lys Ser Pro Pro Pro Glu Ser Val Asp Thr Pro Thr Ser Thr
        1130                1135                1140
    Lys Gln Trp Pro Lys Arg Ser Leu Arg Lys Ala Asp Val Glu Glu
        1145                1150                1155
    Glu Phe Leu Ala Leu Arg Lys Leu Thr Pro Ser Ala Gly Lys Ala
        1160                1165                1170
    Met Leu Thr Pro Lys Pro Ala Gly Gly Asp Glu Lys Asp Ile Lys
        1175                1180                1185
    Ala Phe Met Gly Thr Pro Val Gln Lys Leu Asp Leu Ala Gly Thr
        1190                1195                1200
    Leu Pro Gly Ser Lys Arg Gln Leu Gln Thr Pro Lys Glu Lys Ala
        1205                1210                1215
    Gln Ala Leu Glu Asp Leu Ala Gly Phe Lys Glu Leu Phe Gln Thr
        1220                1225                1230
    Pro Gly His Thr Glu Glu Leu Val Ala Ala Gly Lys Thr Thr Lys
        1235                1240                1245
    Ile Pro Cys Asp Ser Pro Gln Ser Asp Pro Val Asp Thr Pro Thr
        1250                1255                1260
    Ser Thr Lys Gln Arg Pro Lys Arg Ser Ile Arg Lys Ala Asp Val
        1265                1270                1275
    Glu Gly Glu Leu Leu Ala Cys Arg Asn Leu Met Pro Ser Ala Gly
        1280                1285                1290
    Lys Ala Met His Thr Pro Lys Pro Ser Val Gly Glu Glu Lys Asp
        1295                1300                1305
    Ile Ile Ile Phe Val Gly Thr Pro Val Gln Lys Leu Asp Leu Thr
        1310                1315                1320
```

```
Glu Asn Leu Thr Gly Ser Lys Arg Arg Pro Gln Thr Pro Lys Glu
    1325            1330                1335

Glu Ala Gln Ala Leu Glu Asp Leu Thr Gly Phe Lys Glu Leu Phe
    1340            1345                1350

Gln Thr Pro Gly His Thr Glu Glu Ala Val Ala Ala Gly Lys Thr
    1355            1360                1365

Thr Lys Met Pro Cys Glu Ser Ser Pro Glu Ser Ala Asp Thr
    1370            1375                1380

Pro Thr Ser Thr Arg Arg Gln Pro Lys Thr Pro Leu Glu Lys Arg
    1385            1390                1395

Asp Val Gln Lys Glu Leu Ser Ala Leu Lys Lys Leu Thr Gln Thr
    1400            1405                1410

Ser Gly Glu Thr Thr His Thr Asp Lys Val Pro Gly Gly Glu Asp
    1415            1420                1425

Lys Ser Ile Asn Ala Phe Arg Glu Thr Ala Lys Gln Lys Leu Asp
    1430            1435                1440

Pro Ala Ala Ser Val Thr Gly Ser Lys Arg His Pro Lys Thr Lys
    1445            1450                1455

Glu Lys Ala Gln Pro Leu Glu Asp Leu Ala Gly Leu Lys Glu Leu
    1460            1465                1470

Phe Gln Thr Pro Val Cys Thr Asp Lys Pro Thr Thr His Glu Lys
    1475            1480                1485

Thr Thr Lys Ile Ala Cys Arg Ser Gln Pro Asp Pro Val Asp Thr
    1490            1495                1500

Pro Thr Ser Ser Lys Pro Gln Ser Lys Arg Ser Leu Arg Lys Val
    1505            1510                1515

Asp Val Glu Glu Phe Phe Ala Leu Arg Lys Arg Thr Pro Ser
    1520            1525                1530

Ala Gly Lys Ala Met His Thr Pro Lys Pro Ala Val Ser Gly Glu
    1535            1540                1545

Lys Asn Ile Tyr Ala Phe Met Gly Thr Pro Val Gln Lys Leu Asp
    1550            1555                1560

Leu Thr Glu Asn Leu Thr Gly Ser Lys Arg Arg Leu Gln Thr Pro
    1565            1570                1575

Lys Glu Lys Ala Gln Ala Leu Glu Asp Leu Ala Gly Phe Lys Glu
    1580            1585                1590

Leu Phe Gln Thr Arg Gly His Thr Glu Glu Ser Met Thr Asn Asp
    1595            1600                1605

Lys Thr Ala Lys Val Ala Cys Lys Ser Ser Gln Pro Asp Pro Asp
    1610            1615                1620

Lys Asn Pro Ala Ser Ser Lys Arg Arg Leu Lys Thr Ser Leu Gly
    1625            1630                1635

Lys Val Gly Val Lys Glu Glu Leu Leu Ala Val Gly Lys Leu Thr
    1640            1645                1650

Gln Thr Ser Gly Glu Thr Thr His Thr His Thr Glu Pro Thr Gly
    1655            1660                1665

Asp Gly Lys Ser Met Lys Ala Phe Met Glu Ser Pro Lys Gln Ile
    1670            1675                1680

Leu Asp Ser Ala Ala Ser Leu Thr Gly Ser Lys Arg Gln Leu Arg
    1685            1690                1695

Thr Pro Lys Gly Lys Ser Glu Val Pro Glu Asp Leu Ala Gly Phe
    1700            1705                1710
```

-continued

```
Ile Glu Leu Phe Gln Thr Pro Ser His Thr Lys Glu  Ser Met Thr
1715                1720                1725

Asn Glu Lys Thr Thr Lys Val Ser Tyr Arg Ala Ser  Gln Pro Asp
1730                1735                1740

Leu Val Asp Thr Pro Thr Ser Ser Lys Pro Gln Pro  Lys Arg Ser
1745                1750                1755

Leu Arg Lys Ala Asp Thr Glu Glu Phe Leu Ala  Phe Arg Lys
1760                1765                1770

Gln Thr Pro Ser Ala Gly Lys Ala Met His Thr Pro  Lys Pro Ala
1775                1780                1785

Val Gly Glu Glu Lys Asp Ile Asn Thr Phe Leu Gly  Thr Pro Val
1790                1795                1800

Gln Lys Leu Asp Gln Pro Gly Asn Leu Pro Gly Ser  Asn Arg Arg
1805                1810                1815

Leu Gln Thr Arg Lys Glu Lys Ala Gln Ala Leu Glu  Glu Leu Thr
1820                1825                1830

Gly Phe Arg Glu Leu Phe Gln Thr Pro Cys Thr Asp  Asn Pro Thr
1835                1840                1845

Thr Asp Glu Lys Thr Thr Lys Lys Ile Leu Cys Lys  Ser Pro Gln
1850                1855                1860

Ser Asp Pro Ala Asp Thr Pro Thr Asn Thr Lys Gln  Arg Pro Lys
1865                1870                1875

Arg Ser Leu Lys Lys Ala Asp Val Glu Glu Glu Phe  Leu Ala Phe
1880                1885                1890

Arg Lys Leu Thr Pro Ser Ala Gly Lys Ala Met His  Thr Pro Lys
1895                1900                1905

Ala Ala Val Gly Glu Glu Lys Asp Ile Asn Thr Phe  Val Gly Thr
1910                1915                1920

Pro Val Glu Lys Leu Asp Leu Leu Gly Asn Leu Pro  Gly Ser Lys
1925                1930                1935

Arg Arg Pro Gln Thr Pro Lys Glu Lys Ala Lys Ala  Leu Glu Asp
1940                1945                1950

Leu Ala Gly Phe Lys Glu Leu Phe Gln Thr Pro Gly  His Thr Glu
1955                1960                1965

Glu Ser Met Thr Asp Asp Lys Ile Thr Glu Val Ser  Cys Lys Ser
1970                1975                1980

Pro Gln Pro Asp Pro Val Lys Thr Pro Thr Ser Ser  Lys Gln Arg
1985                1990                1995

Leu Lys Ile Ser Leu Gly Lys Val Gly Val Lys Glu  Glu Val Leu
2000                2005                2010

Pro Val Gly Lys Leu Thr Gln Thr Ser Gly Lys Thr  Thr Gln Thr
2015                2020                2025

His Arg Glu Thr Ala Gly Asp Gly Lys Ser Ile Lys  Ala Phe Lys
2030                2035                2040

Glu Ser Ala Lys Gln Met Leu Asp Pro Ala Asn Tyr  Gly Thr Gly
2045                2050                2055

Met Glu Arg Trp Pro Arg Thr Pro Lys Glu Glu Ala  Gln Ser Leu
2060                2065                2070

Glu Asp Leu Ala Gly Phe Lys Glu Leu Phe Gln Thr  Pro Asp His
2075                2080                2085

Thr Glu Glu Ser Thr Thr Asp Asp Lys Thr Thr Lys  Ile Ala Cys
2090                2095                2100

Lys Ser Pro Pro Pro Glu Ser Met Asp Thr Pro Thr  Ser Thr Arg
```

```
                2105                2110                2115
Arg Arg Pro Lys Thr Pro Leu Gly Lys Arg Asp Ile Val Glu Glu
        2120                2125                2130

Leu Ser Ala Leu Lys Gln Leu Thr Gln Thr Thr His Thr Asp Lys
        2135                2140                2145

Val Pro Gly Asp Glu Asp Lys Gly Ile Asn Val Phe Arg Glu Thr
        2150                2155                2160

Ala Lys Gln Lys Leu Asp Pro Ala Ala Ser Val Thr Gly Ser Lys
        2165                2170                2175

Arg Gln Pro Arg Thr Pro Lys Gly Lys Ala Gln Pro Leu Glu Asp
        2180                2185                2190

Leu Ala Gly Leu Lys Glu Leu Phe Gln Thr Pro Ile Cys Thr Asp
        2195                2200                2205

Lys Pro Thr Thr His Glu Lys Thr Thr Lys Ile Ala Cys Arg Ser
        2210                2215                2220

Pro Gln Pro Asp Pro Val Gly Thr Pro Thr Ile Phe Lys Pro Gln
        2225                2230                2235

Ser Lys Arg Ser Leu Arg Lys Ala Asp Val Glu Glu Glu Ser Leu
        2240                2245                2250

Ala Leu Arg Lys Arg Thr Pro Ser Val Gly Lys Ala Met Asp Thr
        2255                2260                2265

Pro Lys Pro Ala Gly Gly Asp Glu Lys Asp Met Lys Ala Phe Met
        2270                2275                2280

Gly Thr Pro Val Gln Lys Leu Asp Leu Pro Gly Asn Leu Pro Gly
        2285                2290                2295

Ser Lys Arg Trp Pro Gln Thr Pro Lys Glu Lys Ala Gln Ala Leu
        2300                2305                2310

Glu Asp Leu Ala Gly Phe Lys Glu Leu Phe Gln Thr Pro Gly Thr
        2315                2320                2325

Asp Lys Pro Thr Thr Asp Glu Lys Thr Thr Lys Ile Ala Cys Lys
        2330                2335                2340

Ser Pro Gln Pro Asp Pro Val Asp Thr Pro Ala Ser Thr Lys Gln
        2345                2350                2355

Arg Pro Lys Arg Asn Leu Arg Lys Ala Asp Val Glu Glu Glu Phe
        2360                2365                2370

Leu Ala Leu Arg Lys Arg Thr Pro Ser Ala Gly Lys Ala Met Asp
        2375                2380                2385

Thr Pro Lys Pro Ala Val Ser Asp Glu Lys Asn Ile Asn Thr Phe
        2390                2395                2400

Val Glu Thr Pro Val Gln Lys Leu Asp Leu Leu Gly Asn Leu Pro
        2405                2410                2415

Gly Ser Lys Arg Gln Pro Gln Thr Pro Lys Glu Lys Ala Glu Ala
        2420                2425                2430

Leu Glu Asp Leu Val Gly Phe Lys Glu Leu Phe Gln Thr Pro Gly
        2435                2440                2445

His Thr Glu Glu Ser Met Thr Asp Asp Lys Ile Thr Glu Val Ser
        2450                2455                2460

Cys Lys Ser Pro Gln Pro Glu Ser Phe Lys Thr Ser Arg Ser Ser
        2465                2470                2475

Lys Gln Arg Leu Lys Ile Pro Leu Val Lys Val Asp Met Lys Glu
        2480                2485                2490

Glu Pro Leu Ala Val Ser Lys Leu Thr Arg Thr Ser Gly Glu Thr
        2495                2500                2505
```

-continued

Thr Gln Thr His Thr Glu Pro Thr Gly Asp Ser Lys Ser Ile Lys
2510                2515                2520

Ala Phe Lys Glu Ser Pro Lys Gln Ile Leu Asp Pro Ala Ala Ser
2525                2530                2535

Val Thr Gly Ser Arg Arg Gln Leu Arg Thr Arg Lys Glu Lys Ala
2540                2545                2550

Arg Ala Leu Glu Asp Leu Val Asp Phe Lys Glu Leu Phe Ser Ala
2555                2560                2565

Pro Gly His Thr Glu Glu Ser Met Thr Ile Asp Lys Asn Thr Lys
2570                2575                2580

Ile Pro Cys Lys Ser Pro Pro Glu Leu Thr Asp Thr Ala Thr
2585                2590                2595

Ser Thr Lys Arg Cys Pro Lys Thr Arg Pro Arg Lys Glu Val Lys
2600                2605                2610

Glu Glu Leu Ser Ala Val Glu Arg Leu Thr Gln Thr Ser Gly Gln
2615                2620                2625

Ser Thr His Thr His Lys Glu Pro Ala Ser Gly Asp Glu Gly Ile
2630                2635                2640

Lys Val Leu Lys Gln Arg Ala Lys Lys Lys Pro Asn Pro Val Glu
2645                2650                2655

Glu Glu Pro Ser Arg Arg Arg Pro Arg Ala Pro Lys Glu Lys Ala
2660                2665                2670

Gln Pro Leu Glu Asp Leu Ala Gly Phe Thr Glu Leu Ser Glu Thr
2675                2680                2685

Ser Gly His Thr Gln Glu Ser Leu Thr Ala Gly Lys Ala Thr Lys
2690                2695                2700

Ile Pro Cys Glu Ser Pro Pro Leu Glu Val Val Asp Thr Thr Ala
2705                2710                2715

Ser Thr Lys Arg His Leu Arg Thr Arg Val Gln Lys Val Gln Val
2720                2725                2730

Lys Glu Glu Pro Ser Ala Val Lys Phe Thr Gln Thr Ser Gly Glu
2735                2740                2745

Thr Thr Asp Ala Asp Lys Glu Pro Ala Gly Glu Asp Lys Gly Ile
2750                2755                2760

Lys Ala Leu Lys Glu Ser Ala Lys Gln Thr Pro Ala Pro Ala Ala
2765                2770                2775

Ser Val Thr Gly Ser Arg Arg Arg Pro Arg Ala Pro Arg Glu Ser
2780                2785                2790

Ala Gln Ala Ile Glu Asp Leu Ala Gly Phe Lys Asp Pro Ala Ala
2795                2800                2805

Gly His Thr Glu Glu Ser Met Thr Asp Asp Lys Thr Thr Lys Ile
2810                2815                2820

Pro Cys Lys Ser Ser Pro Glu Leu Glu Asp Thr Ala Thr Ser Ser
2825                2830                2835

Lys Arg Arg Pro Arg Thr Arg Ala Gln Lys Val Glu Val Lys Glu
2840                2845                2850

Glu Leu Leu Ala Val Gly Lys Leu Thr Gln Thr Ser Gly Glu Thr
2855                2860                2865

Thr His Thr Asp Lys Glu Pro Val Gly Glu Gly Lys Gly Thr Lys
2870                2875                2880

Ala Phe Lys Gln Pro Ala Lys Arg Lys Leu Asp Ala Glu Asp Val
2885                2890                2895

Ile Gly Ser Arg Arg Gln Pro Arg Ala Pro Lys Glu Lys Ala Gln
2900                2905                2910

Pro Leu Glu Asp Leu Ala Ser Phe Gln Glu Leu Ser Gln Thr Pro
2915                2920                2925

Gly His Thr Glu Glu Leu Ala Asn Gly Ala Ala Asp Ser Phe Thr
2930                2935                2940

Ser Ala Pro Lys Gln Thr Pro Asp Ser Gly Lys Pro Leu Lys Ile
2945                2950                2955

Ser Arg Arg Val Leu Arg Ala Pro Lys Val Glu Pro Val Gly Asp
2960                2965                2970

Val Val Ser Thr Arg Asp Pro Val Lys Ser Gln Ser Lys Ser Asn
2975                2980                2985

Thr Ser Leu Pro Pro Leu Pro Phe Lys Arg Gly Gly Lys Asp
2990                2995                3000

Gly Ser Val Thr Gly Thr Lys Arg Leu Arg Cys Met Pro Ala Pro
3005                3010                3015

Glu Glu Ile Val Glu Glu Leu Pro Ala Ser Lys Lys Gln Arg Val
3020                3025                3030

Ala Pro Arg Ala Arg Gly Lys Ser Ser Glu Pro Val Val Ile Met
3035                3040                3045

Lys Arg Ser Leu Arg Thr Ser Ala Lys Arg Ile Glu Pro Ala Glu
3050                3055                3060

Glu Leu Asn Ser Asn Asp Met Lys Thr Asn Lys Glu Glu His Lys
3065                3070                3075

Leu Gln Asp Ser Val Pro Glu Asn Lys Gly Ile Ser Leu Arg Ser
3080                3085                3090

Arg Arg Gln Asn Lys Thr Glu Ala Glu Gln Ile Thr Glu Val
3095                3100                3105

Phe Val Leu Ala Glu Arg Ile Glu Ile Asn Arg Asn Glu Lys Lys
3110                3115                3120

Pro Met Lys Thr Ser Pro Glu Met Asp Ile Gln Asn Pro Asp Asp
3125                3130                3135

Gly Ala Arg Lys Pro Ile Pro Arg Asp Lys Val Thr Glu Asn Lys
3140                3145                3150

Arg Cys Leu Arg Ser Ala Arg Gln Asn Glu Ser Ser Gln Pro Lys
3155                3160                3165

Val Ala Glu Glu Ser Gly Gly Gln Lys Ser Ala Lys Val Leu Met
3170                3175                3180

Gln Asn Gln Lys Gly Lys Gly Glu Ala Gly Asn Ser Asp Ser Met
3185                3190                3195

Cys Leu Arg Ser Arg Lys Thr Lys Ser Gln Pro Ala Ala Ser Thr
3200                3205                3210

Leu Glu Ser Lys Ser Val Gln Arg Val Thr Arg Ser Val Lys Arg
3215                3220                3225

Cys Ala Glu Asn Pro Lys Lys Ala Glu Asp Asn Val Cys Val Lys
3230                3235                3240

Lys Ile Arg Thr Arg Ser His Arg Asp Ser Glu Asp Ile
3245                3250                3255

<210> SEQ ID NO 11
<211> LENGTH: 80
<212> TYPE: PRT
<213> ORGANISM: Homo sapiens

<400> SEQUENCE: 11

```
Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
            20                  25                  30

Thr Ser Ser Asn Ser Ser Gln Ser Thr Ser Asn Thr Gly Leu Ala Pro
        35                  40                  45

Asn Pro Thr Asn Ala Thr Thr Lys Ala Ala Gly Gly Ala Leu Gln Ser
50                  55                  60

Thr Ala Ser Leu Phe Val Val Ser Leu Ser Leu Leu His Leu Tyr Ser
65                  70                  75                  80
```

<210> SEQ ID NO 12
<211> LENGTH: 865
<212> TYPE: PRT
<213> ORGANISM: Homo sapiens

<400> SEQUENCE: 12

```
Met Ala Leu Val Leu Gly Ser Leu Leu Leu Gly Leu Cys Gly Asn
1               5                   10                  15

Ser Phe Ser Gly Gly Gln Pro Ser Ser Thr Asp Ala Pro Lys Ala Trp
            20                  25                  30

Asn Tyr Glu Leu Pro Ala Thr Asn Tyr Glu Thr Gln Asp Ser His Lys
        35                  40                  45

Ala Gly Pro Ile Gly Ile Leu Phe Glu Leu Val His Ile Phe Leu Tyr
    50                  55                  60

Val Val Gln Pro Arg Asp Phe Pro Glu Asp Thr Leu Arg Lys Phe Leu
65                  70                  75                  80

Gln Lys Ala Tyr Glu Ser Lys Ile Asp Tyr Asp Lys Pro Glu Thr Val
                85                  90                  95

Ile Leu Gly Leu Lys Ile Val Tyr Tyr Glu Ala Gly Ile Ile Leu Cys
            100                 105                 110

Cys Val Leu Gly Leu Leu Phe Ile Ile Leu Met Pro Leu Val Gly Tyr
        115                 120                 125

Phe Phe Cys Met Cys Arg Cys Cys Asn Lys Cys Gly Gly Glu Met His
130                 135                 140

Gln Arg Gln Lys Glu Asn Gly Pro Phe Leu Arg Lys Cys Phe Ala Ile
145                 150                 155                 160

Ser Leu Leu Val Ile Cys Ile Ile Ile Ser Ile Gly Ile Phe Tyr Gly
                165                 170                 175

Phe Val Ala Asn His Gln Val Arg Thr Arg Ile Lys Arg Ser Arg Lys
            180                 185                 190

Leu Ala Asp Ser Asn Phe Lys Asp Leu Arg Thr Leu Leu Asn Glu Thr
        195                 200                 205

Pro Glu Gln Ile Lys Tyr Ile Leu Ala Gln Tyr Asn Thr Thr Lys Asp
    210                 215                 220

Lys Ala Phe Thr Asp Leu Asn Ser Ile Asn Ser Val Leu Gly Gly Gly
225                 230                 235                 240

Ile Leu Asp Arg Leu Arg Pro Asn Ile Ile Pro Val Leu Asp Glu Ile
                245                 250                 255

Lys Ser Met Ala Thr Ala Ile Lys Glu Thr Lys Glu Ala Leu Glu Asn
            260                 265                 270

Met Asn Ser Thr Leu Lys Ser Leu His Gln Gln Ser Thr Gln Leu Ser
        275                 280                 285

Ser Ser Leu Thr Ser Val Lys Thr Ser Leu Arg Ser Ser Leu Asn Asp
```

```
            290                 295                 300
Pro Leu Cys Leu Val His Pro Ser Ser Glu Thr Cys Asn Ser Ile Arg
305                 310                 315                 320

Leu Ser Leu Ser Gln Leu Asn Ser Asn Pro Glu Leu Arg Gln Leu Pro
                325                 330                 335

Pro Val Asp Ala Glu Leu Asp Asn Val Asn Asn Val Leu Arg Thr Asp
            340                 345                 350

Leu Asp Gly Leu Val Gln Gln Gly Tyr Gln Ser Leu Asn Asp Ile Pro
            355                 360                 365

Asp Arg Val Gln Arg Gln Thr Thr Thr Val Val Ala Gly Ile Lys Arg
        370                 375                 380

Val Leu Asn Ser Ile Gly Ser Asp Ile Asp Asn Val Thr Gln Arg Leu
385                 390                 395                 400

Pro Ile Gln Asp Ile Leu Ser Ala Phe Ser Val Tyr Val Asn Asn Thr
                405                 410                 415

Glu Ser Tyr Ile His Arg Asn Leu Pro Thr Leu Glu Glu Tyr Asp Ser
            420                 425                 430

Tyr Trp Trp Leu Gly Gly Leu Val Ile Cys Ser Leu Leu Thr Leu Ile
            435                 440                 445

Val Ile Phe Tyr Tyr Leu Gly Leu Leu Cys Gly Val Cys Gly Tyr Asp
450                 455                 460

Arg His Ala Thr Pro Thr Thr Arg Gly Cys Val Ser Asn Thr Gly Gly
465                 470                 475                 480

Val Phe Leu Met Val Gly Val Gly Leu Ser Phe Leu Phe Cys Trp Ile
                485                 490                 495

Leu Met Ile Ile Val Val Leu Thr Phe Val Phe Gly Ala Asn Val Glu
                500                 505                 510

Lys Leu Ile Cys Glu Pro Tyr Thr Ser Lys Glu Leu Phe Arg Val Leu
            515                 520                 525

Asp Thr Pro Tyr Leu Leu Asn Glu Asp Trp Glu Tyr Tyr Leu Ser Gly
            530                 535                 540

Lys Leu Phe Asn Lys Ser Lys Met Lys Leu Thr Phe Glu Gln Val Tyr
545                 550                 555                 560

Ser Asp Cys Lys Lys Asn Arg Gly Thr Tyr Gly Thr Leu His Leu Gln
                565                 570                 575

Asn Ser Phe Asn Ile Ser Glu His Leu Asn Ile Asn Glu His Thr Gly
            580                 585                 590

Ser Ile Ser Ser Glu Leu Glu Ser Leu Lys Val Asn Leu Asn Ile Phe
            595                 600                 605

Leu Leu Gly Ala Ala Gly Arg Lys Asn Leu Gln Asp Phe Ala Ala Cys
        610                 615                 620

Gly Ile Asp Arg Met Asn Tyr Asp Ser Tyr Leu Ala Gln Thr Gly Lys
625                 630                 635                 640

Ser Pro Ala Gly Val Asn Leu Leu Ser Phe Ala Tyr Asp Leu Glu Ala
                645                 650                 655

Lys Ala Asn Ser Leu Pro Pro Gly Asn Leu Arg Asn Ser Leu Lys Arg
                660                 665                 670

Asp Ala Gln Thr Ile Lys Thr Ile His Gln Arg Val Leu Pro Ile
                675                 680                 685

Glu Gln Ser Leu Ser Thr Leu Tyr Gln Ser Val Lys Ile Leu Gln Arg
            690                 695                 700

Thr Gly Asn Gly Leu Leu Glu Arg Val Thr Arg Ile Leu Ala Ser Leu
705                 710                 715                 720
```

```
Asp Phe Ala Gln Asn Phe Ile Thr Asn Asn Thr Ser Val Ile Ile
                725                 730                 735

Glu Glu Thr Lys Lys Tyr Gly Arg Thr Ile Ile Gly Tyr Phe Glu His
            740                 745                 750

Tyr Leu Gln Trp Ile Glu Phe Ser Ile Ser Glu Lys Val Ala Ser Cys
                755                 760                 765

Lys Pro Val Ala Thr Ala Leu Asp Thr Ala Val Asp Val Phe Leu Cys
770                 775                 780

Ser Tyr Ile Ile Asp Pro Leu Asn Leu Phe Trp Phe Gly Ile Gly Lys
785                 790                 795                 800

Ala Thr Val Phe Leu Leu Pro Ala Leu Ile Phe Ala Val Lys Leu Ala
                805                 810                 815

Lys Tyr Tyr Arg Arg Met Asp Ser Glu Asp Val Tyr Asp Asp Val Glu
                820                 825                 830

Thr Ile Pro Met Lys Asn Met Glu Asn Gly Asn Asn Gly Tyr His Lys
                835                 840                 845

Asp His Val Tyr Gly Ile His Asn Pro Val Met Thr Ser Pro Ser Gln
            850                 855                 860

His
865

<210> SEQ ID NO 13
<211> LENGTH: 350
<212> TYPE: PRT
<213> ORGANISM: Homo sapiens

<400> SEQUENCE: 13

Met Leu Gly Ser Val Lys Met Glu Ala His Asp Leu Ala Glu Trp Ser
1               5                   10                  15

Tyr Tyr Pro Glu Ala Gly Glu Val Tyr Ser Pro Val Thr Pro Val Pro
                20                  25                  30

Thr Met Ala Pro Leu Asn Ser Tyr Met Thr Leu Asn Pro Leu Ser Ser
            35                  40                  45

Pro Tyr Pro Pro Gly Gly Leu Pro Ala Ser Pro Leu Pro Ser Gly Pro
50                  55                  60

Leu Ala Pro Pro Ala Pro Ala Ala Pro Leu Gly Pro Thr Phe Pro Gly
65                  70                  75                  80

Leu Gly Val Ser Gly Gly Ser Ser Ser Gly Tyr Gly Ala Pro Gly
                85                  90                  95

Pro Gly Leu Val His Gly Lys Glu Met Pro Lys Gly Tyr Arg Arg Pro
                100                 105                 110

Leu Ala His Ala Lys Pro Pro Tyr Ser Tyr Ile Ser Leu Ile Thr Met
            115                 120                 125

Ala Ile Gln Gln Ala Pro Gly Lys Met Leu Thr Leu Ser Glu Ile Tyr
130                 135                 140

Gln Trp Ile Met Asp Leu Phe Pro Tyr Tyr Arg Glu Asn Gln Gln Arg
145                 150                 155                 160

Trp Gln Asn Ser Ile Arg His Ser Leu Ser Phe Asn Asp Cys Phe Val
                165                 170                 175

Lys Val Ala Arg Ser Pro Asp Lys Pro Gly Lys Gly Ser Tyr Trp Ala
                180                 185                 190

Leu His Pro Ser Ser Gly Asn Met Phe Glu Asn Gly Cys Tyr Leu Arg
            195                 200                 205

Arg Gln Lys Arg Phe Lys Leu Glu Glu Lys Val Lys Lys Gly Gly Ser
```

```
            210                 215                 220
Gly Ala Ala Thr Thr Thr Arg Asn Gly Thr Gly Ser Ala Ala Ser Thr
225                 230                 235                 240

Thr Thr Pro Ala Ala Thr Val Thr Ser Pro Pro Gln Pro Pro Pro Pro
                245                 250                 255

Ala Pro Glu Pro Glu Ala Gln Gly Gly Glu Asp Val Gly Ala Leu Asp
                260                 265                 270

Cys Gly Ser Pro Ala Ser Ser Thr Pro Tyr Phe Thr Gly Leu Glu Leu
                275                 280                 285

Pro Gly Glu Leu Lys Leu Asp Ala Pro Tyr Asn Phe Asn His Pro Phe
                290                 295                 300

Ser Ile Asn Asn Leu Met Ser Glu Gln Thr Pro Ala Pro Pro Lys Leu
305                 310                 315                 320

Asp Val Gly Phe Gly Gly Tyr Gly Ala Glu Gly Gly Glu Pro Gly Val
                    325                 330                 335

Tyr Tyr Gln Gly Leu Tyr Ser Arg Ser Leu Leu Asn Ala Ser
                340                 345                 350

<210> SEQ ID NO 14
<211> LENGTH: 403
<212> TYPE: PRT
<213> ORGANISM: Homo sapiens

<400> SEQUENCE: 14

Met Lys Leu Glu Val Phe Val Pro Arg Ala Ala His Gly Asp Lys Gln
1               5                   10                  15

Gly Ser Asp Leu Glu Gly Ala Gly Gly Ser Asp Ala Pro Ser Pro Leu
                20                  25                  30

Ser Ala Ala Gly Asp Asp Ser Leu Gly Ser Asp Gly Asp Cys Ala Ala
                35                  40                  45

Asn Ser Pro Ala Ala Gly Gly Ala Arg Asp Thr Gln Gly Asp Gly
50                  55                  60

Glu Gln Ser Ala Gly Gly Pro Gly Ala Glu Ala Ile Pro Ala
65                  70                  75                  80

Ala Ala Ala Ala Val Val Ala Glu Gly Ala Glu Ala Gly Ala Ala
                85                  90                  95

Gly Pro Gly Ala Gly Ala Gly Ser Gly Glu Gly Ala Arg Ser Lys
                100                 105                 110

Pro Tyr Thr Arg Arg Pro Lys Pro Pro Tyr Ser Tyr Ile Ala Leu Ile
                115                 120                 125

Ala Met Ala Ile Arg Asp Ser Ala Gly Gly Arg Leu Thr Leu Ala Glu
130                 135                 140

Ile Asn Glu Tyr Leu Met Gly Lys Phe Pro Phe Phe Arg Gly Ser Tyr
145                 150                 155                 160

Thr Gly Trp Arg Asn Ser Val Arg His Asn Leu Ser Leu Asn Asp Cys
                165                 170                 175

Phe Val Lys Val Leu Arg Asp Pro Ser Arg Pro Trp Gly Lys Asp Asn
                180                 185                 190

Tyr Trp Met Leu Asn Pro Asn Ser Glu Tyr Thr Phe Ala Asp Gly Val
                195                 200                 205

Phe Arg Arg Arg Arg Lys Arg Leu Ser His Arg Ala Pro Val Pro Ala
                210                 215                 220

Pro Gly Leu Arg Pro Glu Glu Ala Pro Gly Leu Pro Ala Ala Pro Pro
225                 230                 235                 240
```

```
Pro Ala Pro Ala Ala Pro Ser Pro Arg Met Ser Pro Ala Arg
                245                 250                 255

Gln Glu Glu Arg Ala Ser Pro Ala Gly Lys Phe Ser Ser Phe Ala
        260                 265                 270

Ile Asp Ser Ile Leu Arg Lys Pro Phe Arg Ser Arg Arg Leu Arg Asp
            275                 280                 285

Thr Ala Pro Gly Thr Thr Leu Gln Trp Gly Ala Ala Pro Cys Pro Pro
290                 295                 300

Leu Pro Ala Phe Pro Ala Leu Leu Pro Ala Ala Pro Cys Arg Ala Leu
305                 310                 315                 320

Leu Pro Leu Cys Ala Tyr Gly Ala Gly Glu Pro Ala Arg Leu Gly Ala
                325                 330                 335

Arg Glu Ala Glu Val Pro Pro Thr Ala Pro Pro Leu Leu Leu Ala Pro
                340                 345                 350

Leu Pro Ala Ala Ala Pro Ala Lys Pro Leu Arg Gly Pro Ala Ala Gly
                355                 360                 365

Gly Ala His Leu Tyr Cys Pro Leu Arg Leu Pro Ala Ala Leu Gln Ala
        370                 375                 380

Ala Ser Val Arg Arg Pro Gly Pro His Leu Pro Tyr Pro Val Glu Thr
385                 390                 395                 400

Leu Leu Ala

<210> SEQ ID NO 15
<211> LENGTH: 737
<212> TYPE: PRT
<213> ORGANISM: Homo sapiens

<400> SEQUENCE: 15

Met Pro Asp His Asp Ser Thr Ala Leu Leu Ser Arg Gln Thr Lys Arg
1               5                   10                  15

Arg Arg Val Asp Ile Gly Val Lys Arg Thr Val Gly Thr Ala Ser Ala
            20                  25                  30

Phe Phe Ala Lys Ala Arg Ala Thr Phe Phe Ser Ala Met Asn Pro Gln
        35                  40                  45

Gly Ser Glu Gln Asp Val Glu Tyr Ser Val Val Gln His Ala Asp Gly
    50                  55                  60

Glu Lys Ser Asn Val Leu Arg Lys Leu Leu Lys Arg Ala Asn Ser Tyr
65                  70                  75                  80

Glu Asp Ala Met Met Pro Phe Pro Gly Ala Thr Ile Ile Ser Gln Leu
                85                  90                  95

Leu Lys Asn Asn Met Asn Lys Asn Gly Gly Thr Glu Pro Ser Phe Gln
            100                 105                 110

Ala Ser Gly Leu Ser Ser Thr Gly Ser Glu Val His Gln Glu Asp Ile
        115                 120                 125

Cys Ser Asn Ser Ser Arg Asp Ser Pro Pro Glu Cys Leu Ser Pro Phe
    130                 135                 140

Gly Arg Pro Thr Met Ser Gln Phe Asp Met Asp Arg Leu Cys Asp Glu
145                 150                 155                 160

His Leu Arg Ala Lys Arg Ala Arg Val Glu Asn Ile Ile Arg Gly Met
                165                 170                 175

Ser His Ser Pro Ser Val Ala Leu Arg Gly Asn Glu Asn Glu Arg Glu
            180                 185                 190

Met Ala Pro Gln Ser Val Ser Pro Arg Glu Ser Tyr Arg Glu Asn Lys
        195                 200                 205
```

```
Arg Lys Gln Lys Leu Pro Gln Gln Gln Gln Ser Phe Gln Gln Leu
    210             215                 220

Val Ser Ala Arg Lys Glu Gln Lys Arg Glu Glu Arg Arg Gln Leu Lys
225                 230                 235                 240

Gln Gln Leu Glu Asp Met Gln Lys Gln Leu Arg Gln Leu Gln Glu Lys
                245                 250                 255

Phe Tyr Gln Ile Tyr Asp Ser Thr Asp Ser Glu Asn Asp Glu Asp Gly
                260                 265                 270

Asn Leu Ser Glu Asp Ser Met Arg Ser Glu Ile Leu Asp Ala Arg Ala
            275                 280                 285

Gln Asp Ser Val Gly Arg Ser Asp Asn Glu Met Cys Glu Leu Asp Pro
    290                 295                 300

Gly Gln Phe Ile Asp Arg Ala Arg Ala Leu Ile Arg Glu Gln Glu Met
305                 310                 315                 320

Ala Glu Asn Lys Pro Lys Arg Glu Gly Asn Asn Lys Glu Arg Asp His
                325                 330                 335

Gly Pro Asn Ser Leu Gln Pro Glu Gly Lys His Leu Ala Glu Thr Leu
                340                 345                 350

Lys Gln Glu Leu Asn Thr Ala Met Ser Gln Val Val Asp Thr Val Val
            355                 360                 365

Lys Val Phe Ser Ala Lys Pro Ser Arg Gln Val Pro Gln Val Phe Pro
370                 375                 380

Pro Leu Gln Ile Pro Gln Ala Arg Phe Ala Val Asn Gly Glu Asn His
385                 390                 395                 400

Asn Phe His Thr Ala Asn Gln Arg Leu Gln Cys Phe Gly Asp Val Ile
                405                 410                 415

Ile Pro Asn Pro Leu Asp Thr Phe Gly Asn Val Gln Met Ala Ser Ser
                420                 425                 430

Thr Asp Gln Thr Glu Ala Leu Pro Leu Val Val Arg Lys Asn Ser Ser
            435                 440                 445

Asp Gln Ser Ala Ser Gly Pro Ala Ala Gly Gly His His Gln Pro Leu
    450                 455                 460

His Gln Ser Pro Leu Ser Ala Thr Thr Gly Phe Thr Thr Ser Thr Phe
465                 470                 475                 480

Arg His Pro Phe Pro Leu Pro Leu Met Ala Tyr Pro Phe Gln Ser Pro
                485                 490                 495

Leu Gly Ala Pro Ser Gly Ser Phe Ser Gly Lys Asp Arg Ala Ser Pro
                500                 505                 510

Glu Ser Leu Asp Leu Thr Arg Asp Thr Thr Ser Leu Arg Thr Lys Met
            515                 520                 525

Ser Ser His His Leu Ser His His Pro Cys Ser Pro Ala His Pro Pro
530                 535                 540

Ser Thr Ala Glu Gly Leu Ser Leu Ser Leu Ile Lys Ser Glu Cys Gly
545                 550                 555                 560

Asp Leu Gln Asp Met Ser Glu Ile Ser Pro Tyr Ser Gly Ser Ala Met
                565                 570                 575

Gln Glu Gly Leu Ser Pro Asn His Leu Lys Lys Ala Lys Leu Met Phe
                580                 585                 590

Phe Tyr Thr Arg Tyr Pro Ser Ser Asn Met Leu Lys Thr Tyr Phe Ser
                595                 600                 605

Asp Val Lys Phe Asn Arg Cys Ile Thr Ser Gln Leu Ile Lys Trp Phe
                610                 615                 620

Ser Asn Phe Arg Glu Phe Tyr Tyr Ile Gln Met Glu Lys Tyr Ala Arg
```

```
            625                 630                 635                 640
        Gln Ala Ile Asn Asp Gly Val Thr Ser Thr Glu Glu Leu Ser Ile Thr
                        645                 650                 655
        Arg Asp Cys Glu Leu Tyr Arg Ala Leu Asn Met His Tyr Asn Lys Ala
                        660                 665                 670
        Asn Asp Phe Glu Val Pro Glu Arg Phe Leu Glu Val Ala Gln Ile Thr
                        675                 680                 685
        Leu Arg Glu Phe Phe Asn Ala Ile Ile Ala Gly Lys Asp Val Asp Pro
                        690                 695                 700
        Ser Trp Lys Lys Ala Ile Tyr Lys Val Ile Cys Lys Leu Asp Ser Glu
        705                 710                 715                 720
        Val Pro Glu Ile Phe Lys Ser Pro Asn Cys Leu Gln Glu Leu Leu His
                        725                 730                 735
        Glu

<210> SEQ ID NO 16
<211> LENGTH: 609
<212> TYPE: PRT
<213> ORGANISM: Homo sapiens

<400> SEQUENCE: 16

Met Lys Trp Val Thr Phe Ile Ser Leu Leu Phe Leu Phe Ser Ser Ala
1               5                   10                  15
Tyr Ser Arg Gly Val Phe Arg Arg Asp Ala His Lys Ser Glu Val Ala
                20                  25                  30
His Arg Phe Lys Asp Leu Gly Glu Glu Asn Phe Lys Ala Leu Val Leu
            35                  40                  45
Ile Ala Phe Ala Gln Tyr Leu Gln Gln Cys Pro Phe Glu Asp His Val
        50                  55                  60
Lys Leu Val Asn Glu Val Thr Glu Phe Ala Lys Thr Cys Val Ala Asp
65                  70                  75                  80
Glu Ser Ala Glu Asn Cys Asp Lys Ser Leu His Thr Leu Phe Gly Asp
                85                  90                  95
Lys Leu Cys Thr Val Ala Thr Leu Arg Glu Thr Tyr Gly Glu Met Ala
            100                 105                 110
Asp Cys Cys Ala Lys Gln Glu Pro Glu Arg Asn Glu Cys Phe Leu Gln
        115                 120                 125
His Lys Asp Asp Asn Pro Asn Leu Pro Arg Leu Val Arg Pro Glu Val
    130                 135                 140
Asp Val Met Cys Thr Ala Phe His Asp Asn Glu Glu Thr Phe Leu Lys
145                 150                 155                 160
Lys Tyr Leu Tyr Glu Ile Ala Arg Arg His Pro Tyr Phe Tyr Ala Pro
                165                 170                 175
Glu Leu Leu Phe Phe Ala Lys Arg Tyr Lys Ala Ala Phe Thr Glu Cys
            180                 185                 190
Cys Gln Ala Ala Asp Lys Ala Ala Cys Leu Leu Pro Lys Leu Asp Glu
        195                 200                 205
Leu Arg Asp Glu Gly Lys Ala Ser Ser Ala Lys Gln Arg Leu Lys Cys
    210                 215                 220
Ala Ser Leu Gln Lys Phe Gly Glu Arg Ala Phe Lys Ala Trp Ala Val
225                 230                 235                 240
Ala Arg Leu Ser Gln Arg Phe Pro Lys Ala Glu Phe Ala Glu Val Ser
                245                 250                 255
Lys Leu Val Thr Asp Leu Thr Lys Val His Thr Glu Cys Cys His Gly
```

```
        260                 265                 270
Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
        290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
        370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
        450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
        530                 535                 540

Arg Gln Ile Lys Lys Gln Thr Ala Leu Val Glu Leu Val Lys His Lys
545                 550                 555                 560

Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu

<210> SEQ ID NO 17
<211> LENGTH: 1748
<212> TYPE: PRT
<213> ORGANISM: Homo sapiens

<400> SEQUENCE: 17

Met Ser Ala Arg Ala Ala Ala Lys Ser Thr Ala Met Glu Glu Thr
1               5                   10                  15

Ala Ile Trp Glu Gln His Thr Val Thr Leu His Arg Ala Pro Gly Phe
```

```
                20                  25                  30
Gly Phe Gly Ile Ala Ile Ser Gly Gly Arg Asp Asn Pro His Phe Gln
            35                  40                  45
Ser Gly Glu Thr Ser Ile Val Ile Ser Asp Val Leu Lys Gly Gly Pro
        50                  55                  60
Ala Glu Gly Gln Leu Gln Glu Asn Asp Arg Val Ala Met Val Asn Gly
65                  70                  75                  80
Val Ser Met Asp Asn Val Glu His Ala Phe Ala Val Gln Gln Leu Arg
                85                  90                  95
Lys Ser Gly Lys Asn Ala Lys Ile Thr Ile Arg Arg Lys Lys Lys Val
            100                 105                 110
Gln Ile Pro Val Ser Arg Pro Asp Pro Glu Pro Val Ser Asp Asn Glu
        115                 120                 125
Glu Asp Ser Tyr Asp Glu Ile His Asp Pro Arg Ser Gly Arg Ser
        130                 135                 140
Gly Val Val Asn Arg Arg Ser Glu Lys Ile Trp Pro Arg Asp Arg Ser
145                 150                 155                 160
Ala Ser Arg Glu Arg Ser Leu Ser Pro Arg Ser Asp Arg Arg Ser Val
                165                 170                 175
Ala Ser Ser Gln Pro Ala Lys Pro Thr Lys Val Thr Leu Val Lys Ser
            180                 185                 190
Arg Lys Asn Glu Glu Tyr Gly Leu Arg Leu Ala Ser His Ile Phe Val
        195                 200                 205
Lys Glu Ile Ser Gln Asp Ser Leu Ala Ala Arg Asp Gly Asn Ile Gln
        210                 215                 220
Glu Gly Asp Val Val Leu Lys Ile Asn Gly Thr Val Thr Glu Asn Met
225                 230                 235                 240
Ser Leu Thr Asp Ala Lys Thr Leu Ile Glu Arg Ser Lys Gly Lys Leu
                245                 250                 255
Lys Met Val Val Gln Arg Asp Glu Arg Ala Thr Leu Leu Asn Val Pro
            260                 265                 270
Asp Leu Ser Asp Ser Ile His Ser Ala Asn Ala Ser Glu Arg Asp Asp
        275                 280                 285
Ile Ser Glu Ile Gln Ser Leu Ala Ser Asp His Ser Gly Arg Ser His
        290                 295                 300
Asp Arg Pro Pro Arg Arg Ser Arg Ser Arg Ser Pro Asp Gln Arg Ser
305                 310                 315                 320
Glu Pro Ser Asp His Ser Arg His Ser Pro Gln Gln Pro Ser Asn Gly
                325                 330                 335
Ser Leu Arg Ser Arg Asp Glu Glu Arg Ile Ser Lys Pro Gly Ala Val
            340                 345                 350
Ser Thr Pro Val Lys His Ala Asp Asp His Thr Pro Lys Thr Val Glu
        355                 360                 365
Glu Val Thr Val Glu Arg Asn Glu Lys Gln Thr Pro Ser Leu Pro Glu
        370                 375                 380
Pro Lys Pro Val Tyr Ala Gln Val Gly Gln Pro Asp Val Asp Leu Pro
385                 390                 395                 400
Val Ser Pro Ser Asp Gly Val Leu Pro Asn Ser Thr His Glu Asp Gly
                405                 410                 415
Ile Leu Arg Pro Ser Met Lys Leu Val Lys Phe Arg Lys Gly Asp Ser
            420                 425                 430
Val Gly Leu Arg Leu Ala Gly Gly Asn Asp Val Gly Ile Phe Val Ala
        435                 440                 445
```

-continued

```
Gly Val Leu Glu Asp Ser Pro Ala Lys Glu Gly Leu Glu Glu Gly
    450             455                 460
Asp Gln Ile Leu Arg Val Asn Asn Val Asp Phe Thr Asn Ile Ile Arg
465                 470                 475                 480
Glu Glu Ala Val Leu Phe Leu Leu Asp Leu Pro Lys Gly Glu Val
                485                 490                 495
Thr Ile Leu Ala Gln Lys Lys Asp Val Tyr Arg Arg Ile Val Glu
                500                 505                 510
Ser Asp Val Gly Asp Ser Phe Tyr Ile Arg Thr His Phe Glu Tyr Glu
            515                 520                 525
Lys Glu Ser Pro Tyr Gly Leu Ser Phe Asn Lys Gly Glu Val Phe Arg
    530                 535                 540
Val Val Asp Thr Leu Tyr Asn Gly Lys Leu Gly Ser Trp Leu Ala Ile
545                 550                 555                 560
Arg Ile Gly Lys Asn His Lys Glu Val Glu Arg Gly Ile Ile Pro Asn
                565                 570                 575
Lys Asn Arg Ala Glu Gln Leu Ala Ser Val Gln Tyr Thr Leu Pro Lys
                580                 585                 590
Thr Ala Gly Gly Asp Arg Ala Asp Phe Trp Arg Phe Arg Gly Leu Arg
            595                 600                 605
Ser Ser Lys Arg Asn Leu Arg Lys Ser Arg Glu Asp Leu Ser Ala Gln
    610                 615                 620
Pro Val Gln Thr Lys Phe Pro Ala Tyr Glu Arg Val Val Leu Arg Glu
625                 630                 635                 640
Ala Gly Phe Leu Arg Pro Val Thr Ile Phe Gly Pro Ile Ala Asp Val
                645                 650                 655
Ala Arg Glu Lys Leu Ala Arg Glu Glu Pro Asp Ile Tyr Gln Ile Ala
                660                 665                 670
Lys Ser Glu Pro Arg Asp Ala Gly Thr Asp Gln Arg Ser Ser Gly Ile
            675                 680                 685
Ile Arg Leu His Thr Ile Lys Gln Ile Ile Asp Gln Asp Lys His Ala
    690                 695                 700
Leu Leu Asp Val Thr Pro Asn Ala Val Asp Arg Leu Asn Tyr Ala Gln
705                 710                 715                 720
Trp Tyr Pro Ile Val Val Phe Leu Asn Pro Asp Ser Lys Gln Gly Val
                725                 730                 735
Lys Thr Met Arg Met Arg Leu Cys Pro Glu Ser Arg Lys Ser Ala Arg
                740                 745                 750
Lys Leu Tyr Glu Arg Ser His Lys Leu Arg Lys Asn Asn His His Leu
            755                 760                 765
Phe Thr Thr Thr Ile Asn Leu Asn Ser Met Asn Asp Gly Trp Tyr Gly
    770                 775                 780
Ala Leu Lys Glu Ala Ile Gln Gln Gln Asn Gln Leu Val Trp Val
785                 790                 795                 800
Ser Glu Gly Lys Ala Asp Gly Ala Thr Ser Asp Asp Leu Asp Leu His
                805                 810                 815
Asp Asp Arg Leu Ser Tyr Leu Ser Ala Pro Gly Ser Glu Tyr Ser Met
                820                 825                 830
Tyr Ser Thr Asp Ser Arg His Thr Ser Asp Tyr Glu Asp Thr Asp Thr
            835                 840                 845
Glu Gly Gly Ala Tyr Thr Asp Gln Glu Leu Asp Glu Thr Leu Asn Asp
    850                 855                 860
```

```
Glu Val Gly Thr Pro Pro Glu Ser Ala Ile Thr Arg Ser Ser Glu Pro
865                 870                 875                 880

Val Arg Glu Asp Ser Ser Gly Met His His Glu Asn Gln Thr Tyr Pro
            885                 890                 895

Pro Tyr Ser Pro Gln Ala Gln Pro Gln Pro Ile His Arg Ile Asp Ser
        900                 905                 910

Pro Gly Phe Lys Pro Ala Ser Gln Gln Lys Ala Glu Ala Ser Ser Pro
            915                 920                 925

Val Pro Tyr Leu Ser Pro Glu Thr Asn Pro Ala Ser Ser Thr Ser Ala
    930                 935                 940

Val Asn His Asn Val Asn Leu Thr Asn Val Arg Leu Glu Glu Pro Thr
945                 950                 955                 960

Pro Ala Pro Ser Thr Ser Tyr Ser Pro Gln Ala Asp Ser Leu Arg Thr
            965                 970                 975

Pro Ser Thr Glu Ala Ala His Ile Met Leu Arg Asp Gln Glu Pro Ser
        980                 985                 990

Leu Ser Ser His Val Asp Pro Thr Lys Val Tyr Arg Lys Asp Pro Tyr
            995                1000                1005

Pro Glu Glu Met Met Arg Gln Asn His Val Leu Lys Gln Pro Ala
    1010                1015                1020

Val Ser His Pro Gly His Arg Pro Asp Lys Glu Pro Asn Leu Thr
    1025                1030                1035

Tyr Glu Pro Gln Leu Pro Tyr Val Glu Lys Gln Ala Ser Arg Asp
    1040                1045                1050

Leu Glu Gln Pro Thr Tyr Arg Tyr Glu Ser Ser Ser Tyr Thr Asp
    1055                1060                1065

Gln Phe Ser Arg Asn Tyr Glu His Arg Leu Arg Tyr Glu Asp Arg
    1070                1075                1080

Val Pro Met Tyr Glu Glu Gln Trp Ser Tyr Tyr Asp Asp Lys Gln
    1085                1090                1095

Pro Tyr Pro Ser Arg Pro Pro Phe Asp Asn Gln His Ser Gln Asp
    1100                1105                1110

Leu Asp Ser Arg Gln His Pro Glu Glu Ser Ser Glu Arg Gly Tyr
    1115                1120                1125

Phe Pro Arg Phe Glu Glu Pro Ala Pro Leu Ser Tyr Asp Ser Arg
    1130                1135                1140

Pro Arg Tyr Glu Gln Ala Pro Arg Ala Ser Ala Leu Arg His Glu
    1145                1150                1155

Glu Gln Pro Ala Pro Gly Tyr Asp Thr His Gly Arg Leu Arg Pro
    1160                1165                1170

Glu Ala Gln Pro His Pro Ser Ala Gly Pro Lys Pro Ala Glu Ser
    1175                1180                1185

Lys Gln Tyr Phe Glu Gln Tyr Ser Arg Ser Tyr Glu Gln Val Pro
    1190                1195                1200

Pro Gln Gly Phe Thr Ser Arg Ala Gly His Phe Glu Pro Leu His
    1205                1210                1215

Gly Ala Ala Ala Val Pro Pro Leu Ile Pro Ser Ser Gln His Lys
    1220                1225                1230

Pro Glu Ala Leu Pro Ser Asn Thr Lys Pro Leu Pro Pro Pro Pro
    1235                1240                1245

Thr Gln Thr Glu Glu Glu Glu Asp Pro Ala Met Lys Pro Gln Ser
    1250                1255                1260

Val Leu Thr Arg Val Lys Met Phe Glu Asn Lys Arg Ser Ala Ser
```

```
                1265                1270                1275

Leu Glu Thr Lys Lys Asp Val Asn Asp Thr Gly Ser Phe Lys Pro
        1280                1285                1290

Pro Glu Val Ala Ser Lys Pro Ser Gly Ala Pro Ile Ile Gly Pro
        1295                1300                1305

Lys Pro Thr Ser Gln Asn Gln Phe Ser Glu His Asp Lys Thr Leu
        1310                1315                1320

Tyr Arg Ile Pro Glu Pro Gln Lys Pro Gln Leu Lys Pro Pro Glu
        1325                1330                1335

Asp Ile Val Arg Ser Asn His Tyr Asp Pro Glu Asp Glu Glu
        1340                1345                1350

Tyr Tyr Arg Lys Gln Leu Ser Tyr Phe Asp Arg Arg Ser Phe Glu
        1355                1360                1365

Asn Lys Pro Pro Ala His Ile Ala Ala Ser His Leu Ser Glu Pro
        1370                1375                1380

Ala Lys Pro Ala His Ser Gln Asn Gln Ser Asn Phe Ser Ser Tyr
        1385                1390                1395

Ser Ser Lys Gly Lys Pro Pro Glu Ala Asp Gly Val Asp Arg Ser
        1400                1405                1410

Phe Gly Glu Lys Arg Tyr Glu Pro Ile Gln Ala Thr Pro Pro Pro
        1415                1420                1425

Pro Pro Leu Pro Ser Gln Tyr Ala Gln Pro Ser Gln Pro Val Thr
        1430                1435                1440

Ser Ala Ser Leu His Ile His Ser Lys Gly Ala His Gly Glu Gly
        1445                1450                1455

Asn Ser Val Ser Leu Asp Phe Gln Asn Ser Leu Val Ser Lys Pro
        1460                1465                1470

Asp Pro Pro Pro Ser Gln Asn Lys Pro Ala Thr Phe Arg Pro Pro
        1475                1480                1485

Asn Arg Glu Asp Thr Ala Gln Ala Ala Phe Tyr Pro Gln Lys Ser
        1490                1495                1500

Phe Pro Asp Lys Ala Pro Val Asn Gly Thr Glu Gln Thr Gln Lys
        1505                1510                1515

Thr Val Thr Pro Ala Tyr Asn Arg Phe Thr Pro Lys Pro Tyr Thr
        1520                1525                1530

Ser Ser Ala Arg Pro Phe Glu Arg Lys Phe Glu Ser Pro Lys Phe
        1535                1540                1545

Asn His Asn Leu Leu Pro Ser Glu Thr Ala His Lys Pro Asp Leu
        1550                1555                1560

Ser Ser Lys Thr Pro Thr Ser Pro Lys Thr Leu Val Lys Ser His
        1565                1570                1575

Ser Leu Ala Gln Pro Pro Glu Phe Asp Ser Gly Val Glu Thr Phe
        1580                1585                1590

Ser Ile His Ala Glu Lys Pro Lys Tyr Gln Ile Asn Asn Ile Ser
        1595                1600                1605

Thr Val Pro Lys Ala Ile Pro Val Ser Pro Ser Ala Val Glu Glu
        1610                1615                1620

Asp Glu Asp Glu Asp Gly His Thr Val Val Ala Thr Ala Arg Gly
        1625                1630                1635

Ile Phe Asn Ser Asn Gly Gly Val Leu Ser Ser Ile Glu Thr Gly
        1640                1645                1650

Val Ser Ile Ile Ile Pro Gln Gly Ala Ile Pro Glu Gly Val Glu
        1655                1660                1665
```

```
Gln Glu Ile Tyr Phe Lys Val Cys Arg Asp Asn Ser Ile Leu Pro
    1670            1675                1680

Pro Leu Asp Lys Glu Lys Gly Glu Thr Leu Leu Ser Pro Leu Val
    1685            1690                1695

Met Cys Gly Pro His Gly Leu Lys Phe Leu Lys Pro Val Glu Leu
1700            1705                1710

Arg Leu Pro His Cys Asp Pro Lys Thr Trp Gln Asn Lys Cys Leu
    1715            1720                1725

Pro Gly Asp Pro Asn Tyr Leu Val Gly Ala Asn Cys Val Ser Val
    1730            1735                1740

Leu Ile Asp His Phe
    1745

<210> SEQ ID NO 18
<211> LENGTH: 490
<212> TYPE: PRT
<213> ORGANISM: Homo sapiens

<400> SEQUENCE: 18

Met Asp Ser Leu Val Val Leu Val Leu Cys Leu Ser Cys Leu Leu Leu
1               5                   10                  15

Leu Ser Leu Trp Arg Gln Ser Ser Gly Arg Gly Lys Leu Pro Pro Gly
            20                  25                  30

Pro Thr Pro Leu Pro Val Ile Gly Asn Ile Leu Gln Ile Gly Ile Lys
        35                  40                  45

Asp Ile Ser Lys Ser Leu Thr Asn Leu Ser Lys Val Tyr Gly Pro Val
    50                  55                  60

Phe Thr Leu Tyr Phe Gly Leu Lys Pro Ile Val Val Leu His Gly Tyr
65                  70                  75                  80

Glu Ala Val Lys Glu Ala Leu Ile Asp Leu Gly Glu Glu Phe Ser Gly
                85                  90                  95

Arg Gly Ile Phe Pro Leu Ala Glu Arg Ala Asn Arg Gly Phe Gly Ile
            100                 105                 110

Val Phe Ser Asn Gly Lys Lys Trp Lys Glu Ile Arg Arg Phe Ser Leu
        115                 120                 125

Met Thr Leu Arg Asn Phe Gly Met Gly Lys Arg Ser Ile Glu Asp Arg
    130                 135                 140

Val Gln Glu Glu Ala Arg Cys Leu Val Glu Glu Leu Arg Lys Thr Lys
145                 150                 155                 160

Ala Ser Pro Cys Asp Pro Thr Phe Ile Leu Gly Cys Ala Pro Cys Asn
                165                 170                 175

Val Ile Cys Ser Ile Ile Phe His Lys Arg Phe Asp Tyr Lys Asp Gln
            180                 185                 190

Gln Phe Leu Asn Leu Met Glu Lys Leu Asn Glu Asn Ile Lys Ile Leu
        195                 200                 205

Ser Ser Pro Trp Ile Gln Ile Cys Asn Asn Phe Ser Pro Ile Ile Asp
    210                 215                 220

Tyr Phe Pro Gly Thr His Asn Lys Leu Leu Lys Asn Val Ala Phe Met
225                 230                 235                 240

Lys Ser Tyr Ile Leu Glu Lys Val Lys Glu His Gln Glu Ser Met Asp
                245                 250                 255

Met Asn Asn Pro Gln Asp Phe Ile Asp Cys Phe Leu Met Lys Met Glu
            260                 265                 270

Lys Glu Lys His Asn Gln Pro Ser Glu Phe Thr Ile Glu Ser Leu Glu
```

-continued

```
                275                 280                 285
Asn Thr Ala Val Asp Leu Phe Gly Ala Gly Thr Glu Thr Thr Ser Thr
            290                 295                 300

Thr Leu Arg Tyr Ala Leu Leu Leu Leu Lys His Pro Glu Val Thr
305                 310                 315                 320

Ala Lys Val Gln Glu Glu Ile Glu Arg Val Ile Gly Arg Asn Arg Ser
                325                 330                 335

Pro Cys Met Gln Asp Arg Ser His Met Pro Tyr Thr Asp Ala Val Val
            340                 345                 350

His Glu Val Gln Arg Tyr Ile Asp Leu Leu Pro Thr Ser Leu Pro His
        355                 360                 365

Ala Val Thr Cys Asp Ile Lys Phe Arg Asn Tyr Leu Ile Pro Lys Gly
    370                 375                 380

Thr Thr Ile Leu Ile Ser Leu Thr Ser Val Leu His Asp Asn Lys Glu
385                 390                 395                 400

Phe Pro Asn Pro Glu Met Phe Asp Pro His His Phe Leu Asp Glu Gly
                405                 410                 415

Gly Asn Phe Lys Lys Ser Lys Tyr Phe Met Pro Phe Ser Ala Gly Lys
            420                 425                 430

Arg Ile Cys Val Gly Glu Ala Leu Ala Gly Met Glu Leu Phe Leu Phe
        435                 440                 445

Leu Thr Ser Ile Leu Gln Asn Phe Asn Leu Lys Ser Leu Val Asp Pro
    450                 455                 460

Lys Asn Leu Asp Thr Thr Pro Val Val Asn Gly Phe Ala Ser Val Pro
465                 470                 475                 480

Pro Phe Tyr Gln Leu Cys Phe Ile Pro Val
                485                 490

<210> SEQ ID NO 19
<211> LENGTH: 503
<212> TYPE: PRT
<213> ORGANISM: Homo sapiens

<400> SEQUENCE: 19

Met Ala Leu Ile Pro Asp Leu Ala Met Glu Thr Trp Leu Leu Leu Ala
1               5                   10                  15

Val Ser Leu Val Leu Leu Tyr Leu Tyr Gly Thr His Ser His Gly Leu
            20                  25                  30

Phe Lys Lys Leu Gly Ile Pro Gly Pro Thr Pro Leu Pro Phe Leu Gly
        35                  40                  45

Asn Ile Leu Ser Tyr His Lys Gly Phe Cys Met Phe Asp Met Glu Cys
    50                  55                  60

His Lys Lys Tyr Gly Lys Val Trp Gly Phe Tyr Asp Gly Gln Gln Pro
65                  70                  75                  80

Val Leu Ala Ile Thr Asp Pro Asp Met Ile Lys Thr Val Leu Val Lys
                85                  90                  95

Glu Cys Tyr Ser Val Phe Thr Asn Arg Arg Pro Phe Gly Pro Val Gly
            100                 105                 110

Phe Met Lys Ser Ala Ile Ser Ile Ala Glu Asp Glu Glu Trp Lys Arg
        115                 120                 125

Leu Arg Ser Leu Leu Ser Pro Thr Phe Thr Ser Gly Lys Leu Lys Glu
    130                 135                 140

Met Val Pro Ile Ile Ala Gln Tyr Gly Asp Val Leu Val Arg Asn Leu
145                 150                 155                 160
```

Arg Arg Glu Ala Glu Thr Gly Lys Pro Val Thr Leu Lys Asp Val Phe
            165                 170                 175

Gly Ala Tyr Ser Met Asp Val Ile Thr Ser Thr Ser Phe Gly Val Asn
            180                 185                 190

Ile Asp Ser Leu Asn Asn Pro Gln Asp Pro Phe Val Glu Asn Thr Lys
            195                 200                 205

Lys Leu Leu Arg Phe Asp Phe Leu Asp Pro Phe Leu Ser Ile Thr
210                 215                 220

Val Phe Pro Phe Leu Ile Pro Ile Leu Glu Val Leu Asn Ile Cys Val
225                 230                 235                 240

Phe Pro Arg Glu Val Thr Asn Phe Leu Arg Lys Ser Val Lys Arg Met
            245                 250                 255

Lys Glu Ser Arg Leu Glu Asp Thr Gln Lys His Arg Val Asp Phe Leu
            260                 265                 270

Gln Leu Met Ile Asp Ser Gln Asn Ser Lys Glu Thr Glu Ser His Lys
            275                 280                 285

Ala Leu Ser Asp Leu Glu Leu Val Ala Gln Ser Ile Ile Phe Ile Phe
            290                 295                 300

Ala Gly Tyr Glu Thr Thr Ser Ser Val Leu Ser Phe Ile Met Tyr Glu
305                 310                 315                 320

Leu Ala Thr His Pro Asp Val Gln Gln Lys Leu Gln Glu Glu Ile Asp
            325                 330                 335

Ala Val Leu Pro Asn Lys Ala Pro Pro Thr Tyr Asp Thr Val Leu Gln
            340                 345                 350

Met Glu Tyr Leu Asp Met Val Val Asn Glu Thr Leu Arg Leu Phe Pro
            355                 360                 365

Ile Ala Met Arg Leu Glu Arg Val Cys Lys Lys Asp Val Glu Ile Asn
            370                 375                 380

Gly Met Phe Ile Pro Lys Gly Val Val Met Ile Pro Ser Tyr Ala
385                 390                 395                 400

Leu His Arg Asp Pro Lys Tyr Trp Thr Glu Pro Glu Lys Phe Leu Pro
            405                 410                 415

Glu Arg Phe Ser Lys Lys Asn Lys Asp Asn Ile Asp Pro Tyr Ile Tyr
            420                 425                 430

Thr Pro Phe Gly Ser Gly Pro Arg Asn Cys Ile Gly Met Arg Phe Ala
            435                 440                 445

Leu Met Asn Met Lys Leu Ala Leu Ile Arg Val Leu Gln Asn Phe Ser
            450                 455                 460

Phe Lys Pro Cys Lys Glu Thr Gln Ile Pro Leu Lys Leu Ser Leu Gly
465                 470                 475                 480

Gly Leu Leu Gln Pro Glu Lys Pro Val Val Leu Lys Val Glu Ser Arg
            485                 490                 495

Asp Gly Thr Val Ser Gly Ala
            500

<210> SEQ ID NO 20
<211> LENGTH: 491
<212> TYPE: PRT
<213> ORGANISM: Homo sapiens

<400> SEQUENCE: 20

Met Glu Leu Ser Val Leu Leu Phe Leu Ala Leu Leu Thr Gly Leu Leu
1               5                   10                  15

Leu Leu Leu Val Gln Arg His Pro Asn Thr His Asp Arg Leu Pro Pro
            20                  25                  30

-continued

Gly Pro Arg Pro Leu Pro Leu Leu Gly Asn Leu Leu Gln Met Asp Arg
             35                  40                  45

Arg Gly Leu Leu Lys Ser Phe Leu Arg Phe Arg Glu Lys Tyr Gly Asp
 50                  55                  60

Val Phe Thr Val His Leu Gly Pro Arg Pro Val Val Met Leu Cys Gly
 65                  70                  75                  80

Val Glu Ala Ile Arg Glu Ala Leu Val Asp Lys Ala Glu Ala Phe Ser
                 85                  90                  95

Gly Arg Gly Lys Ile Ala Met Val Asp Pro Phe Phe Arg Gly Tyr Gly
                100                 105                 110

Val Ile Phe Ala Asn Gly Asn Arg Trp Lys Val Leu Arg Arg Phe Ser
                115                 120                 125

Val Thr Thr Met Arg Asp Phe Gly Met Gly Lys Arg Ser Val Glu Glu
                130                 135                 140

Arg Ile Gln Glu Glu Ala Gln Cys Leu Ile Glu Glu Leu Arg Lys Ser
145                 150                 155                 160

Lys Gly Ala Leu Met Asp Pro Thr Phe Leu Phe Gln Ser Ile Thr Ala
                165                 170                 175

Asn Ile Ile Cys Ser Ile Val Phe Gly Lys Arg Phe His Tyr Gln Asp
                180                 185                 190

Gln Glu Phe Leu Lys Met Leu Asn Leu Phe Tyr Gln Thr Phe Ser Leu
                195                 200                 205

Ile Ser Ser Val Phe Gly Gln Leu Phe Glu Leu Phe Ser Gly Phe Leu
                210                 215                 220

Lys Tyr Phe Pro Gly Ala His Arg Gln Val Tyr Lys Asn Leu Gln Glu
225                 230                 235                 240

Ile Asn Ala Tyr Ile Gly His Ser Val Glu Lys His Arg Glu Thr Leu
                245                 250                 255

Asp Pro Ser Ala Pro Lys Asp Leu Ile Asp Thr Tyr Leu Leu His Met
                260                 265                 270

Glu Lys Glu Lys Ser Asn Ala His Ser Glu Phe Ser His Gln Asn Leu
                275                 280                 285

Asn Leu Asn Thr Leu Ser Leu Phe Phe Ala Gly Thr Glu Thr Thr Ser
                290                 295                 300

Thr Thr Leu Arg Tyr Gly Phe Leu Leu Met Leu Lys Tyr Pro His Val
305                 310                 315                 320

Ala Glu Arg Val Tyr Arg Glu Ile Glu Gln Val Ile Gly Pro His Arg
                325                 330                 335

Pro Pro Glu Leu His Asp Arg Ala Lys Met Pro Tyr Thr Glu Ala Val
                340                 345                 350

Ile Tyr Glu Ile Gln Arg Phe Ser Asp Leu Leu Pro Met Gly Val Pro
                355                 360                 365

His Ile Val Thr Gln His Thr Ser Phe Arg Gly Tyr Ile Ile Pro Lys
                370                 375                 380

Asp Thr Glu Val Phe Leu Ile Leu Ser Thr Ala Leu His Asp Pro His
385                 390                 395                 400

Tyr Phe Glu Lys Pro Asp Ala Phe Asn Pro Asp His Phe Leu Asp Ala
                405                 410                 415

Asn Gly Ala Leu Lys Lys Thr Glu Ala Phe Ile Pro Phe Ser Leu Gly
                420                 425                 430

Lys Arg Ile Cys Leu Gly Glu Gly Ile Ala Arg Ala Glu Leu Phe Leu
                435                 440                 445

```
Phe Phe Thr Thr Ile Leu Gln Asn Phe Ser Met Ala Ser Pro Val Ala
450                 455                 460

Pro Glu Asp Ile Asp Leu Thr Pro Gln Glu Cys Gly Val Gly Lys Ile
465                 470                 475                 480

Pro Pro Thr Tyr Gln Ile Arg Phe Leu Pro Arg
                485                 490

<210> SEQ ID NO 21
<211> LENGTH: 515
<212> TYPE: PRT
<213> ORGANISM: Homo sapiens

<400> SEQUENCE: 21

Met Ala Leu Ser Gln Ser Val Pro Phe Ser Ala Thr Glu Leu Leu Leu
1               5                   10                  15

Ala Ser Ala Ile Phe Cys Leu Val Phe Trp Val Leu Lys Gly Leu Arg
                20                  25                  30

Pro Arg Val Pro Lys Gly Leu Lys Ser Pro Pro Glu Pro Trp Gly Trp
            35                  40                  45

Pro Leu Leu Gly His Val Leu Thr Leu Gly Lys Asn Pro His Leu Ala
50                  55                  60

Leu Ser Arg Met Ser Gln Arg Tyr Gly Asp Val Leu Gln Ile Arg Ile
65                  70                  75                  80

Gly Ser Thr Pro Val Leu Val Leu Ser Arg Leu Asp Thr Ile Arg Gln
                85                  90                  95

Ala Leu Val Arg Gln Gly Asp Asp Phe Lys Gly Arg Pro Asp Leu Tyr
                100                 105                 110

Thr Ser Thr Leu Ile Thr Asp Gly Gln Ser Leu Thr Phe Ser Thr Asp
            115                 120                 125

Ser Gly Pro Val Trp Ala Ala Arg Arg Arg Leu Ala Gln Asn Ala Leu
130                 135                 140

Asn Thr Phe Ser Ile Ala Ser Asp Pro Ala Ser Ser Ser Ser Cys Tyr
145                 150                 155                 160

Leu Glu Glu His Val Ser Lys Glu Ala Lys Ala Leu Ile Ser Arg Leu
                165                 170                 175

Gln Glu Leu Met Ala Gly Pro Gly His Phe Asp Pro Tyr Asn Gln Val
                180                 185                 190

Val Val Ser Val Ala Asn Val Ile Gly Ala Met Cys Phe Gly Gln His
            195                 200                 205

Phe Pro Glu Ser Ser Asp Glu Met Leu Ser Leu Val Lys Asn Thr His
210                 215                 220

Glu Phe Val Glu Thr Ala Ser Ser Gly Asn Pro Leu Asp Phe Phe Pro
225                 230                 235                 240

Ile Leu Arg Tyr Leu Pro Asn Pro Ala Leu Gln Arg Phe Lys Ala Phe
                245                 250                 255

Asn Gln Arg Phe Leu Trp Phe Leu Gln Lys Thr Val Gln Glu His Tyr
                260                 265                 270

Gln Asp Phe Asp Lys Asn Ser Val Arg Asp Ile Thr Gly Ala Leu Phe
            275                 280                 285

Lys His Ser Lys Lys Gly Pro Arg Ala Ser Gly Asn Leu Ile Pro Gln
290                 295                 300

Glu Lys Ile Val Asn Leu Val Asn Asp Ile Phe Gly Ala Gly Phe Asp
305                 310                 315                 320

Thr Val Thr Thr Ala Ile Ser Trp Ser Leu Met Tyr Leu Val Thr Lys
                325                 330                 335
```

-continued

Pro Glu Ile Gln Arg Lys Ile Gln Lys Glu Leu Asp Thr Val Ile Gly
                340                 345                 350

Arg Glu Arg Arg Pro Arg Leu Ser Asp Arg Pro Gln Leu Pro Tyr Leu
            355                 360                 365

Glu Ala Phe Ile Leu Glu Thr Phe Arg His Ser Ser Phe Leu Pro Phe
        370                 375                 380

Thr Ile Pro His Ser Thr Thr Arg Asp Thr Thr Leu Asn Gly Phe Tyr
385                 390                 395                 400

Ile Pro Lys Lys Cys Cys Val Phe Val Asn Gln Trp Gln Val Asn His
                405                 410                 415

Asp Pro Glu Leu Trp Glu Asp Pro Ser Glu Phe Arg Pro Glu Arg Phe
            420                 425                 430

Leu Thr Ala Asp Gly Thr Ala Ile Asn Lys Pro Leu Ser Glu Lys Met
        435                 440                 445

Met Leu Phe Gly Met Gly Lys Arg Arg Cys Ile Gly Glu Val Leu Ala
450                 455                 460

Lys Trp Glu Ile Phe Leu Phe Leu Ala Ile Leu Gln Gln Leu Glu
465                 470                 475                 480

Phe Ser Val Pro Pro Gly Val Lys Val Asp Leu Thr Pro Ile Tyr Gly
            485                 490                 495

Leu Thr Met Lys His Ala Arg Cys Glu His Val Gln Ala Arg Arg Phe
        500                 505                 510

Ser Ile Asn
        515

<210> SEQ ID NO 22
<211> LENGTH: 497
<212> TYPE: PRT
<213> ORGANISM: Homo sapiens

<400> SEQUENCE: 22

Met Gly Leu Glu Ala Leu Val Pro Leu Ala Val Ile Val Ala Ile Phe
1               5                   10                  15

Leu Leu Leu Val Asp Leu Met His Arg Arg Gln Arg Trp Ala Ala Arg
                20                  25                  30

Tyr Pro Pro Gly Pro Leu Pro Leu Pro Gly Leu Gly Asn Leu Leu His
            35                  40                  45

Val Asp Phe Gln Asn Thr Pro Tyr Cys Phe Asp Gln Leu Arg Arg Arg
        50                  55                  60

Phe Gly Asp Val Phe Ser Leu Gln Leu Ala Trp Thr Pro Val Val Val
65                  70                  75                  80

Leu Asn Gly Leu Ala Ala Val Arg Glu Ala Leu Val Thr His Gly Glu
                85                  90                  95

Asp Thr Ala Asp Arg Pro Pro Val Pro Ile Thr Gln Ile Leu Gly Phe
            100                 105                 110

Gly Pro Arg Ser Gln Gly Val Phe Leu Ala Arg Tyr Gly Pro Ala Trp
        115                 120                 125

Arg Glu Gln Arg Arg Phe Ser Val Ser Thr Leu Arg Asn Leu Gly Leu
130                 135                 140

Gly Lys Lys Ser Leu Glu Gln Trp Val Thr Glu Glu Ala Ala Cys Leu
145                 150                 155                 160

Cys Ala Ala Phe Ala Asn His Ser Gly Arg Pro Phe Arg Pro Asn Gly
                165                 170                 175

Leu Leu Asp Lys Ala Val Ser Asn Val Ile Ala Ser Leu Thr Cys Gly 180                 185                 190
Arg Arg Phe Glu Tyr Asp Asp Pro Arg Phe Leu Arg Leu Leu Asp Leu
                195                 200                 205

Ala Gln Glu Gly Leu Lys Glu Ser Gly Phe Leu Arg Glu Val Leu
    210                 215                 220

Asn Ala Val Pro Val Leu Leu His Ile Pro Ala Leu Ala Gly Lys Val
225                 230                 235                 240

Leu Arg Phe Gln Lys Ala Phe Leu Thr Gln Leu Asp Glu Leu Leu Thr
                245                 250                 255

Glu His Arg Met Thr Trp Asp Pro Ala Gln Pro Pro Arg Asp Leu Thr
                260                 265                 270

Glu Ala Phe Leu Ala Glu Met Glu Lys Ala Lys Gly Asn Pro Glu Ser
            275                 280                 285

Ser Phe Asn Asp Glu Asn Leu Arg Ile Val Val Ala Asp Leu Phe Ser
            290                 295                 300

Ala Gly Met Val Thr Thr Ser Thr Thr Leu Ala Trp Gly Leu Leu Leu
305                 310                 315                 320

Met Ile Leu His Pro Asp Val Gln Arg Arg Val Gln Gln Glu Ile Asp
                325                 330                 335

Asp Val Ile Gly Gln Val Arg Arg Pro Glu Met Gly Asp Gln Ala His
                340                 345                 350

Met Pro Tyr Thr Thr Ala Val Ile His Glu Val Gln Arg Phe Gly Asp
            355                 360                 365

Ile Val Pro Leu Gly Val Thr His Met Thr Ser Arg Asp Ile Glu Val
370                 375                 380

Gln Gly Phe Arg Ile Pro Lys Gly Thr Thr Leu Ile Thr Asn Leu Ser
385                 390                 395                 400

Ser Val Leu Lys Asp Glu Ala Val Trp Glu Lys Pro Phe Arg Phe His
                405                 410                 415

Pro Glu His Phe Leu Asp Ala Gln Gly His Phe Val Lys Pro Glu Ala
                420                 425                 430

Phe Leu Pro Phe Ser Ala Gly Arg Arg Ala Cys Leu Gly Glu Pro Leu
            435                 440                 445

Ala Arg Met Glu Leu Phe Leu Phe Phe Thr Ser Leu Leu Gln His Phe
            450                 455                 460

Ser Phe Ser Val Pro Thr Gly Gln Pro Arg Pro Ser His His Gly Val
465                 470                 475                 480

Phe Ala Phe Leu Val Ser Pro Ser Pro Tyr Glu Leu Cys Ala Val Pro
                485                 490                 495

Arg

<210> SEQ ID NO 23
<211> LENGTH: 503
<212> TYPE: PRT
<213> ORGANISM: Homo sapiens

<400> SEQUENCE: 23

Met Asp Leu Ile Pro Asn Leu Ala Val Glu Thr Trp Leu Leu Leu Ala
1               5                   10                  15

Val Ser Leu Ile Leu Leu Tyr Leu Tyr Gly Thr Arg Thr His Gly Leu
                20                  25                  30

Phe Lys Lys Leu Gly Ile Pro Gly Pro Thr Pro Leu Pro Phe Leu Gly
            35                  40                  45

Asn Ala Leu Ser Phe Arg Lys Gly Tyr Trp Thr Phe Asp Met Glu Cys

```
                50                  55                  60
Tyr Lys Lys Tyr Arg Lys Val Trp Gly Ile Tyr Asp Cys Gln Gln Pro
 65                  70                  75                  80

Met Leu Ala Ile Thr Asp Pro Asp Met Ile Lys Thr Val Leu Val Lys
                 85                  90                  95

Glu Cys Tyr Ser Val Phe Thr Asn Arg Arg Pro Phe Gly Pro Val Gly
                100                 105                 110

Phe Met Lys Asn Ala Ile Ser Ile Ala Glu Asp Glu Glu Trp Lys Arg
                115                 120                 125

Ile Arg Ser Leu Leu Ser Pro Thr Phe Thr Ser Gly Lys Leu Lys Glu
                130                 135                 140

Met Val Pro Ile Ile Ala Gln Tyr Gly Asp Val Leu Val Arg Asn Leu
145                 150                 155                 160

Arg Arg Glu Ala Glu Thr Gly Lys Pro Val Thr Leu Lys His Val Phe
                165                 170                 175

Gly Ala Tyr Ser Met Asp Val Ile Thr Ser Thr Ser Phe Gly Val Ser
                180                 185                 190

Ile Asp Ser Leu Asn Asn Pro Gln Asp Pro Phe Val Glu Asn Thr Lys
                195                 200                 205

Lys Leu Leu Arg Phe Asn Pro Leu Asp Pro Phe Val Leu Ser Ile Lys
                210                 215                 220

Val Phe Pro Phe Leu Thr Pro Ile Leu Glu Ala Leu Asn Ile Thr Val
225                 230                 235                 240

Phe Pro Arg Lys Val Ile Ser Phe Leu Thr Lys Ser Val Lys Gln Ile
                245                 250                 255

Lys Glu Gly Arg Leu Lys Glu Thr Gln Lys His Arg Val Asp Phe Leu
                260                 265                 270

Gln Leu Met Ile Asp Ser Gln Asn Ser Lys Asp Ser Glu Thr His Lys
                275                 280                 285

Ala Leu Ser Asp Leu Glu Leu Met Ala Gln Ser Ile Ile Phe Ile Phe
                290                 295                 300

Ala Gly Tyr Glu Thr Thr Ser Ser Val Leu Ser Phe Ile Ile Tyr Glu
305                 310                 315                 320

Leu Ala Thr His Pro Asp Val Gln Gln Lys Val Gln Lys Glu Ile Asp
                325                 330                 335

Thr Val Leu Pro Asn Lys Ala Pro Pro Thr Tyr Asp Thr Val Leu Gln
                340                 345                 350

Leu Glu Tyr Leu Asp Met Val Val Asn Glu Thr Leu Arg Leu Phe Pro
                355                 360                 365

Val Ala Met Arg Leu Glu Arg Val Cys Lys Lys Asp Val Glu Ile Asn
                370                 375                 380

Gly Met Phe Ile Pro Lys Gly Val Val Met Ile Pro Ser Tyr Val
385                 390                 395                 400

Leu His His Asp Pro Lys Tyr Trp Arg Glu Pro Glu Lys Phe Leu Pro
                405                 410                 415

Glu Arg Phe Ser Lys Lys Asn Lys Asp Asn Ile Asp Pro Tyr Ile Tyr
                420                 425                 430

Thr Pro Phe Gly Ser Gly Pro Arg Asn Cys Ile Gly Met Arg Phe Ala
                435                 440                 445

Leu Val Asn Met Lys Leu Ala Leu Val Arg Val Leu Gln Asn Phe Ser
                450                 455                 460

Phe Lys Pro Cys Lys Glu Thr Gln Ile Pro Leu Lys Leu Arg Phe Gly
465                 470                 475                 480
```

```
Gly Leu Leu Leu Thr Glu Lys Pro Ile Val Leu Lys Ala Glu Ser Arg
                485                 490                 495

Asp Glu Thr Val Ser Gly Ala
            500
```

<210> SEQ ID NO 24
<211> LENGTH: 493
<212> TYPE: PRT
<213> ORGANISM: Homo sapiens

<400> SEQUENCE: 24

```
Met Ser Ala Leu Gly Val Thr Val Ala Leu Leu Val Trp Ala Ala Phe
1               5                   10                  15

Leu Leu Leu Val Ser Met Trp Arg Gln Val His Ser Ser Trp Asn Leu
                20                  25                  30

Pro Pro Gly Pro Phe Pro Leu Pro Ile Ile Gly Asn Leu Phe Gln Leu
            35                  40                  45

Glu Leu Lys Asn Ile Pro Lys Ser Phe Thr Arg Leu Ala Gln Arg Phe
    50                  55                  60

Gly Pro Val Phe Thr Leu Tyr Val Gly Ser Gln Arg Met Val Val Met
65                  70                  75                  80

His Gly Tyr Lys Ala Val Lys Glu Ala Leu Leu Asp Tyr Lys Asp Glu
                85                  90                  95

Phe Ser Gly Arg Gly Asp Leu Pro Ala Phe His Ala His Arg Asp Arg
            100                 105                 110

Gly Ile Ile Phe Asn Asn Gly Pro Thr Trp Lys Asp Ile Arg Arg Phe
        115                 120                 125

Ser Leu Thr Thr Leu Arg Asn Tyr Gly Met Gly Lys Gln Gly Asn Glu
    130                 135                 140

Ser Arg Ile Gln Arg Glu Ala His Phe Leu Leu Glu Ala Leu Arg Lys
145                 150                 155                 160

Thr Gln Gly Gln Pro Phe Asp Pro Thr Phe Leu Ile Gly Cys Ala Pro
                165                 170                 175

Cys Asn Val Ile Ala Asp Ile Leu Phe Arg Lys His Phe Asp Tyr Asn
            180                 185                 190

Asp Glu Lys Phe Leu Arg Leu Met Tyr Leu Phe Asn Glu Asn Phe His
        195                 200                 205

Leu Leu Ser Thr Pro Trp Leu Gln Leu Tyr Asn Asn Phe Pro Ser Phe
    210                 215                 220

Leu His Tyr Leu Pro Gly Ser His Arg Lys Val Ile Lys Asn Val Ala
225                 230                 235                 240

Glu Val Lys Glu Tyr Val Ser Glu Arg Val Lys Glu His His Gln Ser
                245                 250                 255

Leu Asp Pro Asn Cys Pro Arg Asp Leu Thr Asp Cys Leu Leu Val Glu
            260                 265                 270

Met Glu Lys Glu Lys His Ser Ala Glu Arg Leu Tyr Thr Met Asp Gly
        275                 280                 285

Ile Thr Val Thr Val Ala Asp Leu Phe Phe Ala Gly Thr Glu Thr Thr
    290                 295                 300

Ser Thr Thr Leu Arg Tyr Gly Leu Leu Ile Leu Met Lys Tyr Pro Glu
305                 310                 315                 320

Ile Glu Glu Lys Leu His Glu Glu Ile Asp Arg Val Ile Gly Pro Ser
                325                 330                 335

Arg Ile Pro Ala Ile Lys Asp Arg Gln Glu Met Pro Tyr Met Asp Ala
```

```
                340                 345                 350
Val Val His Glu Ile Gln Arg Phe Ile Thr Leu Val Pro Ser Asn Leu
        355                 360                 365

Pro His Glu Ala Thr Arg Asp Thr Ile Phe Arg Gly Tyr Leu Ile Pro
    370                 375                 380

Lys Gly Thr Val Val Pro Thr Leu Asp Ser Val Leu Tyr Asp Asn
385                 390                 395                 400

Gln Glu Phe Pro Asp Pro Glu Lys Phe Lys Pro Glu His Phe Leu Asn
                405                 410                 415

Glu Asn Gly Lys Phe Lys Tyr Ser Asp Tyr Phe Lys Pro Phe Ser Thr
                420                 425                 430

Gly Lys Arg Val Cys Ala Gly Glu Gly Leu Ala Arg Met Glu Leu Phe
            435                 440                 445

Leu Leu Leu Cys Ala Ile Leu Gln His Phe Asn Leu Lys Pro Leu Val
        450                 455                 460

Asp Pro Lys Asp Ile Asp Leu Ser Pro Ile His Ile Gly Phe Gly Cys
465                 470                 475                 480

Ile Pro Pro Arg Tyr Lys Leu Cys Val Ile Pro Arg Ser
                485                 490

<210> SEQ ID NO 25
<211> LENGTH: 512
<212> TYPE: PRT
<213> ORGANISM: Homo sapiens

<400> SEQUENCE: 25

Met Leu Phe Pro Ile Ser Met Ser Ala Thr Glu Phe Leu Leu Ala Ser
1               5                   10                  15

Val Ile Phe Cys Leu Val Phe Trp Val Ile Arg Ala Ser Arg Pro Gln
                20                  25                  30

Val Pro Lys Gly Leu Lys Asn Pro Pro Gly Pro Trp Gly Trp Pro Leu
            35                  40                  45

Ile Gly His Met Leu Thr Leu Gly Lys Asn Pro His Leu Ala Leu Ser
        50                  55                  60

Arg Met Ser Gln Gln Tyr Gly Asp Val Leu Gln Ile Arg Ile Gly Ser
65                  70                  75                  80

Thr Pro Val Val Leu Ser Gly Leu Asp Thr Ile Arg Gln Ala Leu
                85                  90                  95

Val Arg Gln Gly Asp Asp Phe Lys Gly Arg Pro Asp Leu Tyr Thr Phe
                100                 105                 110

Thr Leu Ile Ser Asn Gly Gln Ser Met Ser Phe Ser Pro Asp Ser Gly
        115                 120                 125

Pro Val Trp Ala Ala Arg Arg Arg Leu Ala Gln Asn Gly Leu Lys Ser
    130                 135                 140

Phe Ser Ile Ala Ser Asp Pro Ala Ser Ser Thr Ser Cys Tyr Leu Glu
145                 150                 155                 160

Glu His Val Ser Lys Glu Ala Glu Val Leu Ile Ser Thr Leu Gln Glu
                165                 170                 175

Leu Met Ala Gly Pro Gly His Phe Asn Pro Tyr Arg Tyr Val Val Val
            180                 185                 190

Ser Val Thr Asn Val Ile Cys Ala Ile Cys Phe Gly Arg Arg Tyr Asp
        195                 200                 205

His Asn His Gln Glu Leu Leu Ser Leu Val Asn Leu Asn Asn Asn Phe
    210                 215                 220
```

-continued

Gly Glu Val Val Gly Ser Gly Asn Pro Ala Asp Phe Ile Pro Ile Leu
225                 230                 235                 240

Arg Tyr Leu Pro Asn Pro Ser Leu Asn Ala Phe Lys Asp Leu Asn Glu
            245                 250                 255

Lys Phe Tyr Ser Phe Met Gln Lys Met Val Lys Glu His Tyr Lys Thr
                260                 265                 270

Phe Glu Lys Gly His Ile Arg Asp Ile Thr Asp Ser Leu Ile Glu His
            275                 280                 285

Cys Gln Glu Lys Gln Leu Asp Glu Asn Ala Asn Val Gln Leu Ser Asp
    290                 295                 300

Glu Lys Ile Ile Asn Ile Val Leu Asp Leu Phe Gly Ala Gly Phe Asp
305                 310                 315                 320

Thr Val Thr Thr Ala Ile Ser Trp Ser Leu Met Tyr Leu Val Met Asn
                325                 330                 335

Pro Arg Val Gln Arg Lys Ile Gln Glu Glu Leu Asp Thr Val Ile Gly
            340                 345                 350

Arg Ser Arg Arg Pro Arg Leu Ser Asp Arg Ser His Leu Pro Tyr Met
    355                 360                 365

Glu Ala Phe Ile Leu Glu Thr Phe Arg His Ser Ser Phe Val Pro Phe
370                 375                 380

Thr Ile Pro His Ser Thr Thr Arg Asp Thr Ser Leu Lys Gly Phe Tyr
385                 390                 395                 400

Ile Pro Lys Gly Arg Cys Val Phe Val Asn Gln Trp Gln Ile Asn His
            405                 410                 415

Asp Gln Lys Leu Trp Val Asn Pro Ser Glu Phe Leu Pro Glu Arg Phe
            420                 425                 430

Leu Thr Pro Asp Gly Ala Ile Asp Lys Val Leu Ser Glu Lys Val Ile
            435                 440                 445

Ile Phe Gly Met Gly Lys Arg Lys Cys Ile Gly Glu Thr Ile Ala Arg
            450                 455                 460

Trp Glu Val Phe Leu Phe Leu Ala Ile Leu Leu Gln Arg Val Glu Phe
465                 470                 475                 480

Ser Val Pro Leu Gly Val Lys Val Asp Met Thr Pro Ile Tyr Gly Leu
                485                 490                 495

Thr Met Lys His Ala Cys Cys Glu His Phe Gln Met Gln Leu Arg Ser
                500                 505                 510

<210> SEQ ID NO 26
<211> LENGTH: 622
<212> TYPE: PRT
<213> ORGANISM: Homo sapiens

<400> SEQUENCE: 26

Met Pro Pro Gln Leu Gln Asn Gly Leu Asn Leu Ser Ala Lys Val Val
1               5                   10                  15

Gln Gly Ser Leu Asp Ser Leu Pro Gln Ala Val Arg Glu Phe Leu Glu
            20                  25                  30

Asn Asn Ala Glu Leu Cys Gln Pro Asp His Ile His Ile Cys Asp Gly
        35                  40                  45

Ser Glu Glu Glu Asn Gly Arg Leu Leu Gly Gln Met Glu Glu Glu Gly
    50                  55                  60

Ile Leu Arg Arg Leu Lys Lys Tyr Asp Asn Cys Trp Leu Ala Leu Thr
65                  70                  75                  80

Asp Pro Arg Asp Val Ala Arg Ile Glu Ser Lys Thr Val Ile Val Thr
                85                  90                  95

```
Gln Glu Gln Arg Asp Thr Val Pro Ile Pro Lys Thr Gly Leu Ser Gln
            100                 105                 110

Leu Gly Arg Trp Met Ser Glu Asp Phe Glu Lys Ala Phe Asn Ala
        115                 120                 125

Arg Phe Pro Gly Cys Met Lys Gly Arg Thr Met Tyr Val Ile Pro Phe
    130                 135                 140

Ser Met Gly Pro Leu Gly Ser Pro Leu Ser Lys Ile Gly Ile Glu Leu
145                 150                 155                 160

Thr Asp Ser Pro Tyr Val Val Ala Ser Met Arg Ile Met Thr Arg Met
                165                 170                 175

Gly Thr Pro Val Leu Glu Ala Val Gly Asp Gly Glu Phe Val Lys Cys
            180                 185                 190

Leu His Ser Val Gly Cys Pro Leu Pro Leu Gln Lys Pro Leu Val Asn
        195                 200                 205

Asn Trp Pro Cys Asn Pro Glu Leu Thr Leu Ile Ala His Leu Pro Asp
    210                 215                 220

Arg Arg Glu Ile Ile Ser Phe Gly Ser Gly Tyr Gly Gly Asn Ser Leu
225                 230                 235                 240

Leu Gly Lys Lys Cys Phe Ala Leu Arg Met Ala Ser Arg Leu Ala Lys
                245                 250                 255

Glu Glu Gly Trp Leu Ala Glu His Met Leu Ile Leu Gly Ile Thr Asn
            260                 265                 270

Pro Glu Gly Glu Lys Lys Tyr Leu Ala Ala Phe Pro Ser Ala Cys
        275                 280                 285

Gly Lys Thr Asn Leu Ala Met Met Asn Pro Ser Leu Pro Gly Trp Lys
    290                 295                 300

Val Glu Cys Val Gly Asp Asp Ile Ala Trp Met Lys Phe Asp Ala Gln
305                 310                 315                 320

Gly His Leu Arg Ala Ile Asn Pro Glu Asn Gly Phe Phe Gly Val Ala
                325                 330                 335

Pro Gly Thr Ser Val Lys Thr Asn Pro Asn Ala Ile Lys Thr Ile Gln
            340                 345                 350

Lys Asn Thr Ile Phe Thr Asn Val Ala Glu Thr Ser Asp Gly Gly Val
        355                 360                 365

Tyr Trp Glu Gly Ile Asp Glu Pro Leu Ala Ser Gly Val Thr Ile Thr
    370                 375                 380

Ser Trp Lys Asn Lys Glu Trp Ser Ser Glu Asp Gly Glu Pro Cys Ala
385                 390                 395                 400

His Pro Asn Ser Arg Phe Cys Thr Pro Ala Ser Gln Cys Pro Ile Ile
                405                 410                 415

Asp Ala Ala Trp Glu Ser Pro Glu Gly Val Pro Ile Glu Gly Ile Ile
            420                 425                 430

Phe Gly Gly Arg Arg Pro Ala Gly Val Pro Leu Val Tyr Glu Ala Leu
        435                 440                 445

Ser Trp Gln His Gly Val Phe Val Gly Ala Ala Met Arg Ser Glu Ala
    450                 455                 460

Thr Ala Ala Ala Glu His Lys Gly Lys Ile Ile Met His Asp Pro Phe
465                 470                 475                 480

Ala Met Arg Pro Phe Phe Gly Tyr Asn Phe Gly Lys Tyr Leu Ala His
                485                 490                 495

Trp Leu Ser Met Ala Gln His Pro Ala Ala Lys Leu Pro Lys Ile Phe
            500                 505                 510
```

```
His Val Asn Trp Phe Arg Lys Asp Lys Glu Gly Lys Phe Leu Trp Pro
            515                 520                 525

Gly Phe Gly Glu Asn Ser Arg Val Leu Glu Trp Met Phe Asn Arg Ile
530                 535                 540

Asp Gly Lys Ala Ser Thr Lys Leu Thr Pro Ile Gly Tyr Ile Pro Lys
545                 550                 555                 560

Glu Asp Ala Leu Asn Leu Lys Gly Leu Gly His Ile Asn Met Met Glu
                565                 570                 575

Leu Phe Ser Ile Ser Lys Glu Phe Trp Glu Lys Val Glu Asp Ile
            580                 585                 590

Glu Lys Tyr Leu Glu Asp Gln Val Asn Ala Asp Leu Pro Cys Glu Ile
        595                 600                 605

Glu Arg Glu Ile Leu Ala Leu Lys Gln Arg Ile Ser Gln Met
    610                 615                 620

<210> SEQ ID NO 27
<211> LENGTH: 454
<212> TYPE: PRT
<213> ORGANISM: Homo sapiens

<400> SEQUENCE: 27

Met Asp Pro Tyr Met Ile Gln Met Ser Ser Lys Gly Asn Leu Pro Ser
1               5                   10                  15

Ile Leu Asp Val His Val Asn Val Gly Gly Arg Ser Ser Val Pro Gly
            20                  25                  30

Lys Met Lys Gly Arg Lys Ala Arg Trp Ser Val Arg Pro Ser Asp Met
        35                  40                  45

Ala Lys Lys Thr Phe Asn Pro Ile Arg Ala Ile Val Asp Asn Met Lys
50                  55                  60

Val Lys Pro Asn Pro Asn Lys Thr Met Ile Ser Leu Ser Ile Gly Asp
65                  70                  75                  80

Pro Thr Val Phe Gly Asn Leu Pro Thr Asp Pro Glu Val Thr Gln Ala
                85                  90                  95

Met Lys Asp Ala Leu Asp Ser Gly Lys Tyr Asn Gly Tyr Ala Pro Ser
            100                 105                 110

Ile Gly Phe Leu Ser Ser Arg Glu Glu Ile Ala Ser Tyr Tyr His Cys
        115                 120                 125

Pro Glu Ala Pro Leu Glu Ala Lys Asp Val Ile Leu Thr Ser Gly Cys
    130                 135                 140

Ser Gln Ala Ile Asp Leu Cys Leu Ala Val Leu Ala Asn Pro Gly Gln
145                 150                 155                 160

Asn Ile Leu Val Pro Arg Pro Gly Phe Ser Leu Tyr Lys Thr Leu Ala
                165                 170                 175

Glu Ser Met Gly Ile Glu Val Lys Leu Tyr Asn Leu Leu Pro Glu Lys
            180                 185                 190

Ser Trp Glu Ile Asp Leu Lys Gln Leu Glu Tyr Leu Ile Asp Glu Lys
        195                 200                 205

Thr Ala Cys Leu Ile Val Asn Asn Pro Ser Asn Pro Cys Gly Ser Val
    210                 215                 220

Phe Ser Lys Arg His Leu Gln Lys Ile Leu Ala Val Ala Ala Arg Gln
225                 230                 235                 240

Cys Val Pro Ile Leu Ala Asp Glu Ile Tyr Gly Asp Met Val Phe Ser
                245                 250                 255

Asp Cys Lys Tyr Glu Pro Leu Ala Thr Leu Ser Thr Asp Val Pro Ile
            260                 265                 270
```

```
Leu Ser Cys Gly Gly Leu Ala Lys Arg Trp Leu Val Pro Gly Trp Arg
        275                 280                 285

Leu Gly Trp Ile Leu Ile His Asp Arg Arg Asp Ile Phe Gly Asn Glu
    290                 295                 300

Ile Arg Asp Gly Leu Val Lys Leu Ser Gln Arg Ile Leu Gly Pro Cys
305                 310                 315                 320

Thr Ile Val Gln Gly Ala Leu Lys Ser Ile Leu Cys Arg Thr Pro Gly
                325                 330                 335

Glu Phe Tyr His Asn Thr Leu Ser Phe Leu Lys Ser Asn Ala Asp Leu
                340                 345                 350

Cys Tyr Gly Ala Leu Ala Ile Pro Gly Leu Arg Pro Val Arg Pro
                355                 360                 365

Ser Gly Ala Met Tyr Leu Met Val Gly Ile Glu Met Glu His Phe Pro
    370                 375                 380

Glu Phe Glu Asn Asp Val Glu Phe Thr Glu Arg Leu Val Ala Glu Gln
385                 390                 395                 400

Ser Val His Cys Leu Pro Ala Thr Cys Phe Glu Tyr Pro Asn Phe Ile
                405                 410                 415

Arg Val Val Ile Thr Val Pro Glu Val Met Met Leu Glu Ala Cys Ser
                420                 425                 430

Arg Ile Gln Glu Phe Cys Glu Gln His Tyr His Cys Ala Glu Gly Ser
            435                 440                 445

Gln Glu Glu Cys Asp Lys
            450

<210> SEQ ID NO 28
<211> LENGTH: 1207
<212> TYPE: PRT
<213> ORGANISM: Homo sapiens

<400> SEQUENCE: 28

Met Leu Leu Thr Leu Ile Ile Leu Leu Pro Val Val Ser Lys Phe Ser
1               5                   10                  15

Phe Val Ser Leu Ser Ala Pro Gln His Trp Ser Cys Pro Glu Gly Thr
            20                  25                  30

Leu Ala Gly Asn Gly Asn Ser Thr Cys Val Gly Pro Ala Pro Phe Leu
        35                  40                  45

Ile Phe Ser His Gly Asn Ser Ile Phe Arg Ile Asp Thr Glu Gly Thr
    50                  55                  60

Asn Tyr Glu Gln Leu Val Val Asp Ala Gly Val Ser Val Ile Met Asp
65                  70                  75                  80

Phe His Tyr Asn Glu Lys Arg Ile Tyr Trp Val Asp Leu Glu Arg Gln
                85                  90                  95

Leu Leu Gln Arg Val Phe Leu Asn Gly Ser Arg Gln Glu Arg Val Cys
            100                 105                 110

Asn Ile Glu Lys Asn Val Ser Gly Met Ala Ile Asn Trp Ile Asn Glu
        115                 120                 125

Glu Val Ile Trp Ser Asn Gln Gln Glu Gly Ile Ile Thr Val Thr Asp
    130                 135                 140

Met Lys Gly Asn Asn Ser His Ile Leu Leu Ser Ala Leu Lys Tyr Pro
145                 150                 155                 160

Ala Asn Val Ala Val Asp Pro Val Glu Arg Phe Ile Phe Trp Ser Ser
                165                 170                 175

Glu Val Ala Gly Ser Leu Tyr Arg Ala Asp Leu Asp Gly Val Gly Val
```

```
            180                 185                 190
Lys Ala Leu Leu Glu Thr Ser Glu Lys Ile Thr Ala Val Ser Leu Asp
            195                 200                 205

Val Leu Asp Lys Arg Leu Phe Trp Ile Gln Tyr Asn Arg Glu Gly Ser
210                 215                 220

Asn Ser Leu Ile Cys Ser Cys Asp Tyr Asp Gly Ser Val His Ile
225                 230                 235                 240

Ser Lys His Pro Thr Gln His Asn Leu Phe Ala Met Ser Leu Phe Gly
                245                 250                 255

Asp Arg Ile Phe Tyr Ser Thr Trp Lys Met Lys Thr Ile Trp Ile Ala
                260                 265                 270

Asn Lys His Thr Gly Lys Asp Met Val Arg Ile Asn Leu His Ser Ser
                275                 280                 285

Phe Val Pro Leu Gly Glu Leu Lys Val Val His Pro Leu Ala Gln Pro
            290                 295                 300

Lys Ala Glu Asp Asp Thr Trp Glu Pro Glu Gln Lys Leu Cys Lys Leu
305                 310                 315                 320

Arg Lys Gly Asn Cys Ser Ser Thr Val Cys Gly Gln Asp Leu Gln Ser
                325                 330                 335

His Leu Cys Met Cys Ala Glu Gly Tyr Ala Leu Ser Arg Asp Arg Lys
                340                 345                 350

Tyr Cys Glu Asp Val Asn Glu Cys Ala Phe Trp Asn His Gly Cys Thr
            355                 360                 365

Leu Gly Cys Lys Asn Thr Pro Gly Ser Tyr Tyr Cys Thr Cys Pro Val
            370                 375                 380

Gly Phe Val Leu Leu Pro Asp Gly Lys Arg Cys His Gln Leu Val Ser
385                 390                 395                 400

Cys Pro Arg Asn Val Ser Glu Cys Ser His Asp Cys Val Leu Thr Ser
                405                 410                 415

Glu Gly Pro Leu Cys Phe Cys Pro Glu Gly Ser Val Leu Glu Arg Asp
                420                 425                 430

Gly Lys Thr Cys Ser Gly Cys Ser Ser Pro Asp Asn Gly Gly Cys Ser
                435                 440                 445

Gln Leu Cys Val Pro Leu Ser Pro Val Ser Trp Glu Cys Asp Cys Phe
            450                 455                 460

Pro Gly Tyr Asp Leu Gln Leu Asp Glu Lys Ser Cys Ala Ala Ser Gly
465                 470                 475                 480

Pro Gln Pro Phe Leu Leu Phe Ala Asn Ser Gln Asp Ile Arg His Met
                485                 490                 495

His Phe Asp Gly Thr Asp Tyr Gly Thr Leu Leu Ser Gln Gln Met Gly
                500                 505                 510

Met Val Tyr Ala Leu Asp His Asp Pro Val Glu Asn Lys Ile Tyr Phe
            515                 520                 525

Ala His Thr Ala Leu Lys Trp Ile Glu Arg Ala Asn Met Asp Gly Ser
            530                 535                 540

Gln Arg Glu Arg Leu Ile Glu Glu Gly Val Asp Val Pro Glu Gly Leu
545                 550                 555                 560

Ala Val Asp Trp Ile Gly Arg Arg Phe Tyr Trp Thr Asp Arg Gly Lys
                565                 570                 575

Ser Leu Ile Gly Arg Ser Asp Leu Asn Gly Lys Arg Ser Lys Ile Ile
                580                 585                 590

Thr Lys Glu Asn Ile Ser Gln Pro Arg Gly Ile Ala Val His Pro Met
            595                 600                 605
```

```
Ala Lys Arg Leu Phe Trp Thr Asp Thr Gly Ile Asn Pro Arg Ile Glu
    610                 615                 620

Ser Ser Ser Leu Gln Gly Leu Gly Arg Leu Val Ile Ala Ser Ser Asp
625                 630                 635                 640

Leu Ile Trp Pro Ser Gly Ile Thr Ile Asp Phe Leu Thr Asp Lys Leu
                645                 650                 655

Tyr Trp Cys Asp Ala Lys Gln Ser Val Ile Glu Met Ala Asn Leu Asp
            660                 665                 670

Gly Ser Lys Arg Arg Leu Thr Gln Asn Asp Val Gly His Pro Phe
        675                 680                 685

Ala Val Ala Val Phe Glu Asp Tyr Val Trp Phe Ser Asp Trp Ala Met
690                 695                 700

Pro Ser Val Met Arg Val Asn Lys Arg Thr Gly Lys Asp Arg Val Arg
705                 710                 715                 720

Leu Gln Gly Ser Met Leu Lys Pro Ser Ser Leu Val Val His Pro
                725                 730                 735

Leu Ala Lys Pro Gly Ala Asp Pro Cys Leu Tyr Gln Asn Gly Gly Cys
                740                 745                 750

Glu His Ile Cys Lys Lys Arg Leu Gly Thr Ala Trp Cys Ser Cys Arg
            755                 760                 765

Glu Gly Phe Met Lys Ala Ser Asp Gly Lys Thr Cys Leu Ala Leu Asp
770                 775                 780

Gly His Gln Leu Leu Ala Gly Gly Glu Val Asp Leu Lys Asn Gln Val
785                 790                 795                 800

Thr Pro Leu Asp Ile Leu Ser Lys Thr Arg Val Ser Glu Asp Asn Ile
                805                 810                 815

Thr Glu Ser Gln His Met Leu Val Ala Glu Ile Met Val Ser Asp Gln
            820                 825                 830

Asp Asp Cys Ala Pro Val Gly Cys Ser Met Tyr Ala Arg Cys Ile Ser
            835                 840                 845

Glu Gly Glu Asp Ala Thr Cys Gln Cys Leu Lys Gly Phe Ala Gly Asp
850                 855                 860

Gly Lys Leu Cys Ser Asp Ile Asp Glu Cys Glu Met Gly Val Pro Val
865                 870                 875                 880

Cys Pro Pro Ala Ser Ser Lys Cys Ile Asn Thr Glu Gly Gly Tyr Val
                885                 890                 895

Cys Arg Cys Ser Glu Gly Tyr Gln Gly Asp Gly Ile His Cys Leu Asp
            900                 905                 910

Ile Asp Glu Cys Gln Leu Gly Glu His Ser Cys Gly Glu Asn Ala Ser
        915                 920                 925

Cys Thr Asn Thr Glu Gly Gly Tyr Thr Cys Met Cys Ala Gly Arg Leu
    930                 935                 940

Ser Glu Pro Gly Leu Ile Cys Pro Asp Ser Thr Pro Pro His Leu
945                 950                 955                 960

Arg Glu Asp Asp His His Tyr Ser Val Arg Asn Ser Asp Ser Glu Cys
                965                 970                 975

Pro Leu Ser His Asp Gly Tyr Cys Leu His Asp Gly Val Cys Met Tyr
                980                 985                 990

Ile Glu Ala Leu Asp Lys Tyr Ala  Cys Asn Cys Val Val  Gly Tyr Ile
            995                 1000                1005

Gly Glu  Arg Cys Gln Tyr Arg  Asp Leu Lys Trp Trp  Glu Leu Arg
    1010                1015                1020
```

His Ala Gly His Gly Gln Gln Gln Lys Val Ile Val Val Ala Val
    1025                1030                1035

Cys Val Val Val Leu Val Met Leu Leu Leu Leu Ser Leu Trp Gly
    1040                1045                1050

Ala His Tyr Tyr Arg Thr Gln Lys Leu Leu Ser Lys Asn Pro Lys
    1055                1060                1065

Asn Pro Tyr Glu Ser Ser Arg Asp Val Arg Ser Arg Arg Pro
    1070                1075                1080

Ala Asp Thr Glu Asp Gly Met Ser Ser Cys Pro Gln Pro Trp Phe
    1085                1090                1095

Val Val Ile Lys Glu His Gln Asp Leu Lys Asn Gly Gly Gln Pro
    1100                1105                1110

Val Ala Gly Glu Asp Gly Gln Ala Ala Asp Gly Ser Met Gln Pro
    1115                1120                1125

Thr Ser Trp Arg Gln Glu Pro Gln Leu Cys Gly Met Gly Thr Glu
    1130                1135                1140

Gln Gly Cys Trp Ile Pro Val Ser Ser Asp Lys Gly Ser Cys Pro
    1145                1150                1155

Gln Val Met Glu Arg Ser Phe His Met Pro Ser Tyr Gly Thr Gln
    1160                1165                1170

Thr Leu Glu Gly Gly Val Glu Lys Pro His Ser Leu Leu Ser Ala
    1175                1180                1185

Asn Pro Leu Trp Gln Gln Arg Ala Leu Asp Pro Pro His Gln Met
    1190                1195                1200

Glu Leu Thr Gln
    1205

<210> SEQ ID NO 29
<211> LENGTH: 263
<212> TYPE: PRT
<213> ORGANISM: Homo sapiens

<400> SEQUENCE: 29

Met Arg Leu Gly Leu Cys Val Val Ala Leu Val Leu Ser Trp Thr His
1               5                   10                  15

Leu Thr Ile Ser Ser Arg Gly Ile Lys Gly Lys Arg Gln Arg Ile
            20                  25                  30

Ser Ala Glu Gly Ser Gln Ala Cys Ala Lys Gly Cys Glu Leu Cys Ser
            35                  40                  45

Glu Val Asn Gly Cys Leu Lys Cys Ser Pro Lys Leu Phe Ile Leu Leu
50                  55                  60

Glu Arg Asn Asp Ile Arg Gln Val Gly Val Cys Leu Pro Ser Cys Pro
65                  70                  75                  80

Pro Gly Tyr Phe Asp Ala Arg Asn Pro Asp Met Asn Lys Cys Ile Lys
                85                  90                  95

Cys Lys Ile Glu His Cys Glu Ala Cys Phe Ser His Asn Phe Cys Thr
            100                 105                 110

Lys Cys Lys Glu Gly Leu Tyr Leu His Lys Gly Arg Cys Tyr Pro Ala
            115                 120                 125

Cys Pro Glu Gly Ser Ser Ala Ala Asn Gly Thr Met Glu Cys Ser Ser
            130                 135                 140

Pro Ala Gln Cys Glu Met Ser Glu Trp Ser Pro Trp Gly Pro Cys Ser
145                 150                 155                 160

Lys Lys Gln Gln Leu Cys Gly Phe Arg Arg Gly Ser Glu Glu Arg Thr
                165                 170                 175

```
Arg Arg Val Leu His Ala Pro Val Gly Asp His Ala Ala Cys Ser Asp
            180                 185                 190

Thr Lys Glu Thr Arg Arg Cys Thr Val Arg Arg Val Pro Cys Pro Glu
            195                 200                 205

Gly Gln Lys Arg Lys Gly Gln Gly Arg Glu Asn Ala Asn
            210                 215                 220

Arg Asn Leu Ala Arg Lys Glu Ser Lys Glu Ala Gly Ala Gly Ser Arg
225                 230                 235                 240

Arg Arg Lys Gly Gln Gln Gln Gln Gln Gly Thr Val Gly Pro
                245                 250                 255

Leu Thr Ser Ala Gly Pro Ala
            260

<210> SEQ ID NO 30
<211> LENGTH: 728
<212> TYPE: PRT
<213> ORGANISM: Homo sapiens

<400> SEQUENCE: 30

Met Trp Val Thr Lys Leu Leu Pro Ala Leu Leu Leu Gln His Val Leu
1               5                   10                  15

Leu His Leu Leu Leu Leu Pro Ile Ala Ile Pro Tyr Ala Glu Gly Gln
            20                  25                  30

Arg Lys Arg Arg Asn Thr Ile His Glu Phe Lys Lys Ser Ala Lys Thr
        35                  40                  45

Thr Leu Ile Lys Ile Asp Pro Ala Leu Lys Ile Lys Thr Lys Lys Val
    50                  55                  60

Asn Thr Ala Asp Gln Cys Ala Asn Arg Cys Thr Arg Asn Lys Gly Leu
65                  70                  75                  80

Pro Phe Thr Cys Lys Ala Phe Val Phe Asp Lys Ala Arg Lys Gln Cys
                85                  90                  95

Leu Trp Phe Pro Phe Asn Ser Met Ser Ser Gly Val Lys Lys Glu Phe
            100                 105                 110

Gly His Glu Phe Asp Leu Tyr Glu Asn Lys Asp Tyr Ile Arg Asn Cys
        115                 120                 125

Ile Ile Gly Lys Gly Arg Ser Tyr Lys Gly Thr Val Ser Ile Thr Lys
    130                 135                 140

Ser Gly Ile Lys Cys Gln Pro Trp Ser Ser Met Ile Pro His Glu His
145                 150                 155                 160

Ser Phe Leu Pro Ser Ser Tyr Arg Gly Lys Asp Leu Gln Glu Asn Tyr
                165                 170                 175

Cys Arg Asn Pro Arg Gly Glu Glu Gly Gly Pro Trp Cys Phe Thr Ser
            180                 185                 190

Asn Pro Glu Val Arg Tyr Glu Val Cys Asp Ile Pro Gln Cys Ser Glu
        195                 200                 205

Val Glu Cys Met Thr Cys Asn Gly Glu Ser Tyr Arg Gly Leu Met Asp
    210                 215                 220

His Thr Glu Ser Gly Lys Ile Cys Gln Arg Trp Asp His Gln Thr Pro
225                 230                 235                 240

His Arg His Lys Phe Leu Pro Glu Arg Tyr Pro Asp Lys Gly Phe Asp
                245                 250                 255

Asp Asn Tyr Cys Arg Asn Pro Asp Gly Gln Pro Arg Pro Trp Cys Tyr
            260                 265                 270

Thr Leu Asp Pro His Thr Arg Trp Glu Tyr Cys Ala Ile Lys Thr Cys
```

```
              275                 280                 285
Ala Asp Asn Thr Met Asn Asp Thr Asp Val Pro Leu Glu Thr Thr Glu
290                 295                 300
Cys Ile Gln Gly Gln Gly Glu Gly Tyr Arg Gly Thr Val Asn Thr Ile
305                 310                 315                 320
Trp Asn Gly Ile Pro Cys Gln Arg Trp Asp Ser Gln Tyr Pro His Glu
                    325                 330                 335
His Asp Met Thr Pro Glu Asn Phe Lys Cys Lys Asp Leu Arg Glu Asn
                340                 345                 350
Tyr Cys Arg Asn Pro Asp Gly Ser Glu Ser Pro Trp Cys Phe Thr Thr
            355                 360                 365
Asp Pro Asn Ile Arg Val Gly Tyr Cys Ser Gln Ile Pro Asn Cys Asp
370                 375                 380
Met Ser His Gly Gln Asp Cys Tyr Arg Gly Asn Gly Lys Asn Tyr Met
385                 390                 395                 400
Gly Asn Leu Ser Gln Thr Arg Ser Gly Leu Thr Cys Ser Met Trp Asp
                    405                 410                 415
Lys Asn Met Glu Asp Leu His Arg His Ile Phe Trp Glu Pro Asp Ala
                420                 425                 430
Ser Lys Leu Asn Glu Asn Tyr Cys Arg Asn Pro Asp Asp Ala His
            435                 440                 445
Gly Pro Trp Cys Tyr Thr Gly Asn Pro Leu Ile Pro Trp Asp Tyr Cys
450                 455                 460
Pro Ile Ser Arg Cys Glu Gly Asp Thr Thr Pro Thr Ile Val Asn Leu
465                 470                 475                 480
Asp His Pro Val Ile Ser Cys Ala Lys Thr Lys Gln Leu Arg Val Val
                    485                 490                 495
Asn Gly Ile Pro Thr Arg Thr Asn Ile Gly Trp Met Val Ser Leu Arg
                500                 505                 510
Tyr Arg Asn Lys His Ile Cys Gly Gly Ser Leu Ile Lys Glu Ser Trp
            515                 520                 525
Val Leu Thr Ala Arg Gln Cys Phe Pro Ser Arg Asp Leu Lys Asp Tyr
530                 535                 540
Glu Ala Trp Leu Gly Ile His Asp Val His Gly Arg Gly Asp Glu Lys
545                 550                 555                 560
Cys Lys Gln Val Leu Asn Val Ser Gln Leu Val Tyr Gly Pro Glu Gly
                    565                 570                 575
Ser Asp Leu Val Leu Met Lys Leu Ala Arg Pro Ala Val Leu Asp Asp
                580                 585                 590
Phe Val Ser Thr Ile Asp Leu Pro Asn Tyr Gly Cys Thr Ile Pro Glu
            595                 600                 605
Lys Thr Ser Cys Ser Val Tyr Gly Trp Gly Tyr Thr Gly Leu Ile Asn
610                 615                 620
Tyr Asp Gly Leu Leu Arg Val Ala His Leu Tyr Ile Met Gly Asn Glu
625                 630                 635                 640
Lys Cys Ser Gln His His Arg Gly Lys Val Thr Leu Asn Glu Ser Glu
                    645                 650                 655
Ile Cys Ala Gly Ala Glu Lys Ile Gly Ser Gly Pro Cys Glu Gly Asp
                660                 665                 670
Tyr Gly Gly Pro Leu Val Cys Glu Gln His Lys Met Arg Met Val Leu
            675                 680                 685
Gly Val Ile Val Pro Gly Arg Gly Cys Ala Ile Pro Asn Arg Pro Gly
690                 695                 700
```

```
Ile Phe Val Arg Val Ala Tyr Tyr Ala Lys Trp Ile His Lys Ile Ile
705                 710                 715                 720

Leu Thr Tyr Lys Val Pro Gln Ser
            725

<210> SEQ ID NO 31
<211> LENGTH: 252
<212> TYPE: PRT
<213> ORGANISM: Homo sapiens

<400> SEQUENCE: 31

Met Gly Val Leu Leu Thr Gln Arg Thr Leu Leu Ser Leu Val Leu Ala
1               5                   10                  15

Leu Leu Phe Pro Ser Met Ala Ser Met Ala Ala Ile Gly Ser Cys Ser
            20                  25                  30

Lys Glu Tyr Arg Val Leu Leu Gly Gln Leu Gln Lys Gln Thr Asp Leu
        35                  40                  45

Met Gln Asp Thr Ser Arg Leu Leu Asp Pro Tyr Ile Arg Ile Gln Gly
    50                  55                  60

Leu Asp Val Pro Lys Leu Arg Glu His Cys Arg Glu Arg Pro Gly Ala
65                  70                  75                  80

Phe Pro Ser Glu Glu Thr Leu Arg Gly Leu Gly Arg Arg Gly Phe Leu
                85                  90                  95

Gln Thr Leu Asn Ala Thr Leu Gly Cys Val Leu His Arg Leu Ala Asp
            100                 105                 110

Leu Glu Gln Arg Leu Pro Lys Ala Gln Asp Leu Glu Arg Ser Gly Leu
        115                 120                 125

Asn Ile Glu Asp Leu Glu Lys Leu Gln Met Ala Arg Pro Asn Ile Leu
    130                 135                 140

Gly Leu Arg Asn Asn Ile Tyr Cys Met Ala Gln Leu Leu Asp Asn Ser
145                 150                 155                 160

Asp Thr Ala Glu Pro Thr Lys Ala Gly Arg Gly Ala Ser Gln Pro Pro
                165                 170                 175

Thr Pro Thr Pro Ala Ser Asp Ala Phe Gln Arg Lys Leu Glu Gly Cys
            180                 185                 190

Arg Phe Leu His Gly Tyr His Arg Phe Met His Ser Val Gly Arg Val
        195                 200                 205

Phe Ser Lys Trp Gly Glu Ser Pro Asn Arg Ser Arg Arg His Ser Pro
    210                 215                 220

His Gln Ala Leu Arg Lys Gly Val Arg Arg Thr Arg Pro Ser Arg Lys
225                 230                 235                 240

Gly Lys Arg Leu Met Thr Arg Gly Gln Leu Pro Arg
                245                 250

<210> SEQ ID NO 32
<211> LENGTH: 431
<212> TYPE: PRT
<213> ORGANISM: Homo sapiens

<400> SEQUENCE: 32

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45
```

Gln Glu Arg Arg Glu Met Gln Arg Glu Ile Leu Ser Ile Leu Gly Leu
            50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
            115                 120                 125

Asp Ala Asp Met Val Met Ser Phe Val Asn Leu Val Glu His Asp Lys
130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
            195                 200                 205

Phe Leu Leu Asp Ser Arg Thr Leu Trp Ala Ser Glu Glu Gly Trp Leu
210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
            275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
            355                 360                 365

Ser Tyr Met Asn Ala Thr Asn His Ala Ile Val Gln Thr Leu Val His
370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
            420                 425                 430

<210> SEQ ID NO 33
<211> LENGTH: 216
<212> TYPE: PRT
<213> ORGANISM: Homo sapiens

```
<400> SEQUENCE: 33

Met Arg Ser Gly Cys Val Val His Val Trp Ile Leu Ala Gly Leu
1               5                   10                  15

Trp Leu Ala Val Ala Gly Arg Pro Leu Ala Phe Ser Asp Ala Gly Pro
                20                  25                  30

His Val His Tyr Gly Trp Gly Asp Pro Ile Arg Leu Arg His Leu Tyr
            35                  40                  45

Thr Ser Gly Pro His Gly Leu Ser Ser Cys Phe Leu Arg Ile Arg Ala
        50                  55                  60

Asp Gly Val Val Asp Cys Ala Arg Gly Gln Ser Ala His Ser Leu Leu
65                  70                  75                  80

Glu Ile Lys Ala Val Ala Leu Arg Thr Val Ala Ile Lys Gly Val His
                85                  90                  95

Ser Val Arg Tyr Leu Cys Met Gly Ala Asp Gly Lys Met Gln Gly Leu
            100                 105                 110

Leu Gln Tyr Ser Glu Glu Asp Cys Ala Phe Glu Glu Ile Arg Pro
        115                 120                 125

Asp Gly Tyr Asn Val Tyr Arg Ser Glu Lys His Arg Leu Pro Val Ser
130                 135                 140

Leu Ser Ser Ala Lys Gln Arg Gln Leu Tyr Lys Asn Arg Gly Phe Leu
145                 150                 155                 160

Pro Leu Ser His Phe Leu Pro Met Leu Pro Met Val Pro Glu Glu Pro
                165                 170                 175

Glu Asp Leu Arg Gly His Leu Glu Ser Asp Met Phe Ser Ser Pro Leu
            180                 185                 190

Glu Thr Asp Ser Met Asp Pro Phe Gly Leu Val Thr Gly Leu Glu Ala
        195                 200                 205

Val Arg Ser Pro Ser Phe Glu Lys
    210                 215

<210> SEQ ID NO 34
<211> LENGTH: 407
<212> TYPE: PRT
<213> ORGANISM: Homo sapiens

<400> SEQUENCE: 34

Met Val Leu Ala Ala Pro Leu Leu Leu Gly Phe Leu Leu Leu Ala Leu
1               5                   10                  15

Glu Leu Arg Pro Arg Gly Glu Ala Ala Glu Gly Pro Ala Ala Ala Ala
                20                  25                  30

Ala Ala Ala Ala Ala Ala Ala Ala Gly Val Gly Gly Glu Arg Ser
            35                  40                  45

Ser Arg Pro Ala Pro Ser Val Ala Pro Glu Pro Asp Gly Cys Pro Val
        50                  55                  60

Cys Val Trp Arg Gln His Ser Arg Glu Leu Arg Leu Glu Ser Ile Lys
65                  70                  75                  80

Ser Gln Ile Leu Ser Lys Leu Arg Leu Lys Glu Ala Pro Asn Ile Ser
                85                  90                  95

Arg Glu Val Val Lys Gln Leu Leu Pro Lys Ala Pro Pro Leu Gln Gln
            100                 105                 110

Ile Leu Asp Leu His Asp Phe Gln Gly Asp Ala Leu Gln Pro Glu Asp
        115                 120                 125

Phe Leu Glu Glu Asp Glu Tyr His Ala Thr Thr Glu Thr Val Ile Ser
        130                 135                 140
```

```
Met Ala Gln Glu Thr Asp Pro Ala Val Gln Thr Asp Gly Ser Pro Leu
145                 150                 155                 160

Cys Cys His Phe His Phe Ser Pro Lys Val Met Phe Thr Lys Val Leu
                165                 170                 175

Lys Ala Gln Leu Trp Val Tyr Leu Arg Pro Val Pro Arg Pro Ala Thr
            180                 185                 190

Val Tyr Leu Gln Ile Leu Arg Leu Lys Pro Leu Thr Gly Glu Gly Thr
        195                 200                 205

Ala Gly Gly Gly Gly Gly Arg Arg His Ile Arg Ile Arg Ser Leu
    210                 215                 220

Lys Ile Glu Leu His Ser Arg Ser Gly His Trp Gln Ser Ile Asp Phe
225                 230                 235                 240

Lys Gln Val Leu His Ser Trp Phe Arg Gln Pro Gln Ser Asn Trp Gly
                245                 250                 255

Ile Glu Ile Asn Ala Phe Asp Pro Ser Gly Thr Asp Leu Ala Val Thr
            260                 265                 270

Ser Leu Gly Pro Gly Ala Glu Gly Leu His Pro Phe Met Glu Leu Arg
        275                 280                 285

Val Leu Glu Asn Thr Lys Arg Ser Arg Arg Asn Leu Gly Leu Asp Cys
290                 295                 300

Asp Glu His Ser Ser Glu Ser Arg Cys Cys Arg Tyr Pro Leu Thr Val
305                 310                 315                 320

Asp Phe Glu Ala Phe Gly Trp Asp Trp Ile Ile Ala Pro Lys Arg Tyr
                325                 330                 335

Lys Ala Asn Tyr Cys Ser Gly Gln Cys Glu Tyr Met Phe Met Gln Lys
            340                 345                 350

Tyr Pro His Thr His Leu Val Gln Gln Ala Asn Pro Arg Gly Ser Ala
        355                 360                 365

Gly Pro Cys Cys Thr Pro Thr Lys Met Ser Pro Ile Asn Met Leu Tyr
    370                 375                 380

Phe Asn Asp Lys Gln Gln Ile Ile Tyr Gly Lys Ile Pro Gly Met Val
385                 390                 395                 400

Val Asp Arg Cys Gly Cys Ser
                405

<210> SEQ ID NO 35
<211> LENGTH: 1218
<212> TYPE: PRT
<213> ORGANISM: Homo sapiens

<400> SEQUENCE: 35

Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45

Leu Gln Asn Gly Asn Cys Cys Gly Gly Ala Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110
```

Arg Gly Asn Asp Arg Asn Arg Ile Val Leu Pro Phe Ser Phe Ala Trp
    115                 120                 125

Pro Arg Ser Tyr Thr Leu Leu Val Glu Ala Trp Asp Ser Ser Asn Asp
    130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Pro Glu Cys Asn Arg Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
            260                 265                 270

His Gly Ile Cys Asn Glu Pro Trp Gln Cys Leu Cys Glu Thr Asn Trp
        275                 280                 285

Gly Gly Gln Leu Cys Asp Lys Asp Leu Asn Tyr Cys Gly Thr His Gln
    290                 295                 300

Pro Cys Leu Asn Gly Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Leu Gly Phe Glu Cys Glu Cys Ser Pro Gly Trp Thr Gly
        355                 360                 365

Pro Thr Cys Ser Thr Asn Ile Asp Asp Cys Ser Pro Asn Asn Cys Ser
    370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Lys Ser Cys Lys Asn Leu Ile Ala
            420                 425                 430

Ser Tyr Tyr Cys Asp Cys Leu Pro Gly Trp Met Gly Gln Asn Cys Asp
        435                 440                 445

Ile Asn Ile Asn Asp Cys Leu Gly Gln Cys Gln Asn Asp Ala Ser Cys
    450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
        515                 520                 525

```
Cys Glu Pro Asn Pro Cys Gln Asn Gly Ala Gln Cys Tyr Asn Arg Ala
    530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Pro Cys Glu Val Ile Asp
                565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
        595                 600                 605

Ser Gly Gly Lys Phe Thr Cys Asp Cys Asn Lys Gly Phe Thr Gly Thr
    610                 615                 620

Tyr Cys His Glu Asn Ile Asn Asp Cys Glu Ser Asn Pro Cys Arg Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala Tyr Cys Glu Thr Asn Ile Asn Asp Cys Ser
            660                 665                 670

Gln Asn Pro Cys His Asn Gly Gly Thr Cys Arg Asp Leu Val Asn Asp
        675                 680                 685

Phe Tyr Cys Asp Cys Lys Asn Gly Trp Lys Gly Lys Thr Cys His Ser
    690                 695                 700

Arg Asp Ser Gln Cys Asp Glu Ala Thr Cys Asn Asn Gly Gly Thr Cys
705                 710                 715                 720

Tyr Asp Glu Gly Asp Ala Phe Lys Cys Met Cys Pro Gly Gly Trp Glu
                725                 730                 735

Gly Thr Thr Cys Asn Ile Ala Arg Asn Ser Ser Cys Leu Pro Asn Pro
            740                 745                 750

Cys His Asn Gly Gly Thr Cys Val Val Asn Gly Glu Ser Phe Thr Cys
        755                 760                 765

Val Cys Lys Glu Gly Trp Glu Gly Pro Ile Cys Ala Gln Asn Thr Asn
    770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
            820                 825                 830

Ala Thr Cys Val Asp Glu Ile Asn Gly Tyr Arg Cys Val Cys Pro Pro
        835                 840                 845

Gly His Ser Gly Ala Lys Cys Gln Glu Val Ser Gly Arg Pro Cys Ile
    850                 855                 860

Thr Met Gly Ser Val Ile Pro Asp Gly Ala Lys Trp Asp Asp Cys
865                 870                 875                 880

Asn Thr Cys Gln Cys Leu Asn Gly Arg Ile Ala Cys Ser Lys Val Trp
                885                 890                 895

Cys Gly Pro Arg Pro Cys Leu Leu His Lys Gly His Ser Glu Cys Pro
            900                 905                 910

Ser Gly Gln Ser Cys Ile Pro Ile Leu Asp Asp Gln Cys Phe Val His
        915                 920                 925

Pro Cys Thr Gly Val Gly Glu Cys Arg Ser Ser Leu Gln Pro Val
    930                 935                 940

Lys Thr Lys Cys Thr Ser Asp Ser Tyr Tyr Gln Asp Asn Cys Ala Asn
```

```
945                 950                 955                 960
Ile Thr Phe Thr Phe Asn Lys Glu Met Met Ser Pro Gly Leu Thr Thr
                965                 970                 975
Glu His Ile Cys Ser Glu Leu Arg Asn Leu Asn Ile Leu Lys Asn Val
                980                 985                 990
Ser Ala Glu Tyr Ser Ile Tyr Ile Ala Cys Glu Pro Ser Pro Ser Ala
                995                1000                1005
Asn Asn Glu Ile His Val Ala Ile Ser Ala Glu Asp Ile Arg Asp
       1010                1015                1020
Asp Gly Asn Pro Ile Lys Glu Ile Thr Asp Lys Ile Ile Asp Leu
       1025                1030                1035
Val Ser Lys Arg Asp Gly Asn Ser Ser Leu Ile Ala Ala Val Ala
       1040                1045                1050
Glu Val Arg Val Gln Arg Arg Pro Leu Lys Asn Arg Thr Asp Phe
       1055                1060                1065
Leu Val Pro Leu Leu Ser Ser Val Leu Thr Val Ala Trp Ile Cys
       1070                1075                1080
Cys Leu Val Thr Ala Phe Tyr Trp Cys Leu Arg Lys Arg Arg Lys
       1085                1090                1095
Pro Gly Ser His Thr His Ser Ala Ser Glu Asp Asn Thr Thr Asn
       1100                1105                1110
Asn Val Arg Glu Gln Leu Asn Gln Ile Lys Asn Pro Ile Glu Lys
       1115                1120                1125
His Gly Ala Asn Thr Val Pro Ile Lys Asp Tyr Glu Asn Lys Asn
       1130                1135                1140
Ser Lys Met Ser Lys Ile Arg Thr His Asn Ser Glu Val Glu Glu
       1145                1150                1155
Asp Asp Met Asp Lys His Gln Gln Lys Ala Arg Phe Ala Lys Gln
       1160                1165                1170
Pro Ala Tyr Thr Leu Val Asp Arg Glu Glu Lys Pro Pro Asn Gly
       1175                1180                1185
Thr Pro Thr Lys His Pro Asn Trp Thr Asn Lys Gln Asp Asn Arg
       1190                1195                1200
Asp Leu Glu Ser Ala Gln Ser Leu Asn Arg Met Glu Tyr Ile Val
       1205                1210                1215

<210> SEQ ID NO 36
<211> LENGTH: 1238
<212> TYPE: PRT
<213> ORGANISM: Homo sapiens

<400> SEQUENCE: 36

Met Arg Ala Gln Gly Arg Gly Arg Leu Pro Arg Leu Leu Leu Leu
1                   5                  10                  15
Leu Ala Leu Trp Val Gln Ala Ala Arg Pro Met Gly Tyr Phe Glu Leu
                20                  25                  30
Gln Leu Ser Ala Leu Arg Asn Val Asn Gly Glu Leu Leu Ser Gly Ala
                35                  40                  45
Cys Cys Asp Gly Asp Gly Arg Thr Thr Arg Ala Gly Gly Cys Gly His
                50                  55                  60
Asp Glu Cys Asp Thr Tyr Val Arg Val Cys Leu Lys Glu Tyr Gln Ala
65                  70                  75                  80
Lys Val Thr Pro Thr Gly Pro Cys Ser Tyr Gly His Gly Ala Thr Pro
                85                  90                  95
```

-continued

Val Leu Gly Gly Asn Ser Phe Tyr Leu Pro Pro Ala Gly Ala Ala Gly
              100                 105                 110

Asp Arg Ala Arg Ala Arg Ala Arg Ala Gly Gly Asp Gln Asp Pro Gly
            115                 120                 125

Leu Val Val Ile Pro Phe Gln Phe Ala Trp Pro Arg Ser Phe Thr Leu
        130                 135                 140

Ile Val Glu Ala Trp Asp Trp Asp Asn Asp Thr Thr Pro Asn Glu Glu
145                 150                 155                 160

Leu Leu Ile Glu Arg Val Ser His Ala Gly Met Ile Asn Pro Glu Asp
                165                 170                 175

Arg Trp Lys Ser Leu His Phe Ser Gly His Val Ala His Leu Glu Leu
            180                 185                 190

Gln Ile Arg Val Arg Cys Asp Glu Asn Tyr Tyr Ser Ala Thr Cys Asn
        195                 200                 205

Lys Phe Cys Arg Pro Arg Asn Asp Phe Phe Gly His Tyr Thr Cys Asp
210                 215                 220

Gln Tyr Gly Asn Lys Ala Cys Met Asp Gly Trp Met Gly Lys Glu Cys
225                 230                 235                 240

Lys Glu Ala Val Cys Lys Gln Gly Cys Asn Leu Leu His Gly Gly Cys
                245                 250                 255

Thr Val Pro Gly Glu Cys Arg Cys Ser Tyr Gly Trp Gln Gly Arg Phe
            260                 265                 270

Cys Asp Glu Cys Val Pro Tyr Pro Gly Cys Val His Gly Ser Cys Val
        275                 280                 285

Glu Pro Trp Gln Cys Asn Cys Glu Thr Asn Trp Gly Gly Leu Leu Cys
290                 295                 300

Asp Lys Asp Leu Asn Tyr Cys Gly Ser His His Pro Cys Thr Asn Gly
305                 310                 315                 320

Gly Thr Cys Ile Asn Ala Glu Pro Asp Gln Tyr Arg Cys Thr Cys Pro
                325                 330                 335

Asp Gly Tyr Ser Gly Arg Asn Cys Glu Lys Ala Glu His Ala Cys Thr
            340                 345                 350

Ser Asn Pro Cys Ala Asn Gly Gly Ser Cys His Glu Val Pro Ser Gly
        355                 360                 365

Phe Glu Cys His Cys Pro Ser Gly Trp Ser Gly Pro Thr Cys Ala Leu
    370                 375                 380

Asp Ile Asp Glu Cys Ala Ser Asn Pro Cys Ala Ala Gly Gly Thr Cys
385                 390                 395                 400

Val Asp Gln Val Asp Gly Phe Glu Cys Ile Cys Pro Glu Gln Trp Val
                405                 410                 415

Gly Ala Thr Cys Gln Leu Asp Ala Asn Glu Cys Glu Gly Lys Pro Cys
            420                 425                 430

Leu Asn Ala Phe Ser Cys Lys Asn Leu Ile Gly Gly Tyr Tyr Cys Asp
        435                 440                 445

Cys Ile Pro Gly Trp Lys Gly Ile Asn Cys His Ile Asn Val Asn Asp
    450                 455                 460

Cys Arg Gly Gln Cys Gln His Gly Gly Thr Cys Lys Asp Leu Val Asn
465                 470                 475                 480

Gly Tyr Gln Cys Val Cys Pro Arg Gly Phe Gly Gly Arg His Cys Glu
                485                 490                 495

Leu Glu Arg Asp Glu Cys Ala Ser Ser Pro Cys His Ser Gly Gly Leu
            500                 505                 510

Cys Glu Asp Leu Ala Asp Gly Phe His Cys His Cys Pro Gln Gly Phe

```
            515                 520                 525
Ser Gly Pro Leu Cys Glu Val Asp Val Asp Leu Cys Glu Pro Ser Pro
    530                 535                 540

Cys Arg Asn Gly Ala Arg Cys Tyr Asn Leu Glu Gly Asp Tyr Tyr Cys
545                 550                 555                 560

Ala Cys Pro Asp Asp Phe Gly Gly Lys Asn Cys Ser Val Pro Arg Glu
            565                 570                 575

Pro Cys Pro Gly Gly Ala Cys Arg Val Ile Asp Gly Cys Gly Ser Asp
        580                 585                 590

Ala Gly Pro Gly Met Pro Gly Thr Ala Ala Ser Gly Val Cys Gly Pro
        595                 600                 605

His Gly Arg Cys Val Ser Gln Pro Gly Gly Asn Phe Ser Cys Ile Cys
    610                 615                 620

Asp Ser Gly Phe Thr Gly Thr Tyr Cys His Glu Asn Ile Asp Asp Cys
625                 630                 635                 640

Leu Gly Gln Pro Cys Arg Asn Gly Gly Thr Cys Ile Asp Glu Val Asp
            645                 650                 655

Ala Phe Arg Cys Phe Cys Pro Ser Gly Trp Glu Gly Glu Leu Cys Asp
            660                 665                 670

Thr Asn Pro Asn Asp Cys Leu Pro Asp Pro Cys His Ser Arg Gly Arg
        675                 680                 685

Cys Tyr Asp Leu Val Asn Asp Phe Tyr Cys Ala Cys Asp Asp Gly Trp
    690                 695                 700

Lys Gly Lys Thr Cys His Ser Arg Glu Phe Gln Cys Asp Ala Tyr Thr
705                 710                 715                 720

Cys Ser Asn Gly Gly Thr Cys Tyr Asp Ser Gly Asp Thr Phe Arg Cys
            725                 730                 735

Ala Cys Pro Pro Gly Trp Lys Gly Ser Thr Cys Ala Val Ala Lys Asn
            740                 745                 750

Ser Ser Cys Leu Pro Asn Pro Cys Val Asn Gly Gly Thr Cys Val Gly
        755                 760                 765

Ser Gly Ala Ser Phe Ser Cys Ile Cys Arg Asp Gly Trp Glu Gly Arg
        770                 775                 780

Thr Cys Thr His Asn Thr Asn Asp Cys Asn Pro Leu Pro Cys Tyr Asn
785                 790                 795                 800

Gly Gly Ile Cys Val Asp Gly Val Asn Trp Phe Arg Cys Glu Cys Ala
            805                 810                 815

Pro Gly Phe Ala Gly Pro Asp Cys Arg Ile Asn Ile Asp Glu Cys Gln
            820                 825                 830

Ser Ser Pro Cys Ala Tyr Gly Ala Thr Cys Val Asp Glu Ile Asn Gly
        835                 840                 845

Tyr Arg Cys Ser Cys Pro Pro Gly Arg Ala Gly Pro Arg Cys Gln Glu
    850                 855                 860

Val Ile Gly Phe Gly Arg Ser Cys Trp Ser Arg Gly Thr Pro Phe Pro
865                 870                 875                 880

His Gly Ser Ser Trp Val Glu Asp Cys Asn Ser Cys Arg Cys Leu Asp
            885                 890                 895

Gly Arg Arg Asp Cys Ser Lys Val Trp Cys Gly Trp Lys Pro Cys Leu
        900                 905                 910

Leu Ala Gly Gln Pro Glu Ala Leu Ser Ala Gln Cys Pro Leu Gly Gln
        915                 920                 925

Arg Cys Leu Glu Lys Ala Pro Gly Gln Cys Leu Arg Pro Pro Cys Glu
    930                 935                 940
```

-continued

Ala Trp Gly Glu Cys Gly Ala Glu Glu Pro Pro Ser Thr Pro Cys Leu
945                 950                 955                 960

Pro Arg Ser Gly His Leu Asp Asn Asn Cys Ala Arg Leu Thr Leu His
            965                 970                 975

Phe Asn Arg Asp His Val Pro Gln Gly Thr Thr Val Gly Ala Ile Cys
        980                 985                 990

Ser Gly Ile Arg Ser Leu Pro Ala Thr Arg Ala Val Ala Arg Asp Arg
    995                 1000                1005

Leu Leu Val Leu Leu Cys Asp Arg Ala Ser Ser Gly Ala Ser Ala
    1010                1015                1020

Val Glu Val Ala Val Ser Phe Ser Pro Ala Arg Asp Leu Pro Asp
    1025                1030                1035

Ser Ser Leu Ile Gln Gly Ala Ala His Ala Ile Val Ala Ala Ile
    1040                1045                1050

Thr Gln Arg Gly Asn Ser Ser Leu Leu Leu Ala Val Thr Glu Val
    1055                1060                1065

Lys Val Glu Thr Val Val Thr Gly Gly Ser Ser Thr Gly Leu Leu
    1070                1075                1080

Val Pro Val Leu Cys Gly Ala Phe Ser Val Leu Trp Leu Ala Cys
    1085                1090                1095

Val Val Leu Cys Val Trp Trp Thr Arg Lys Arg Arg Lys Glu Arg
    1100                1105                1110

Glu Arg Ser Arg Leu Pro Arg Glu Glu Ser Ala Asn Asn Gln Trp
    1115                1120                1125

Ala Pro Leu Asn Pro Ile Arg Asn Pro Ile Glu Arg Pro Gly Gly
    1130                1135                1140

His Lys Asp Val Leu Tyr Gln Cys Lys Asn Phe Thr Pro Pro Pro
    1145                1150                1155

Arg Arg Ala Asp Glu Ala Leu Pro Gly Pro Ala Gly His Ala Ala
    1160                1165                1170

Val Arg Glu Asp Glu Glu Asp Glu Asp Leu Gly Arg Gly Glu Glu
    1175                1180                1185

Asp Ser Leu Glu Ala Glu Lys Phe Leu Ser His Lys Phe Thr Lys
    1190                1195                1200

Asp Pro Gly Arg Ser Pro Gly Arg Pro Ala His Trp Ala Ser Gly
    1205                1210                1215

Pro Lys Val Asp Asn Arg Ala Val Arg Ser Ile Asn Glu Ala Arg
    1220                1225                1230

Tyr Ala Gly Lys Glu
    1235

<210> SEQ ID NO 37
<211> LENGTH: 723
<212> TYPE: PRT
<213> ORGANISM: Homo sapiens

<400> SEQUENCE: 37

Met Gly Ser Arg Cys Ala Leu Ala Leu Ala Val Leu Ser Ala Leu Leu
1               5                   10                  15

Cys Gln Val Trp Ser Ser Gly Val Phe Glu Leu Lys Leu Gln Glu Phe
                20                  25                  30

Val Asn Lys Lys Gly Leu Leu Gly Asn Arg Asn Cys Cys Arg Gly Gly
            35                  40                  45

Ala Gly Pro Pro Pro Cys Ala Cys Arg Thr Phe Phe Arg Val Cys Leu

```
            50                  55                  60
Lys His Tyr Gln Ala Ser Val Ser Pro Glu Pro Cys Thr Tyr Gly
 65                  70                  75                  80

Ser Ala Val Thr Pro Val Leu Gly Val Asp Ser Phe Ser Leu Pro Asp
                     85                  90                  95

Gly Gly Gly Ala Asp Ser Ala Phe Ser Asn Pro Ile Arg Phe Pro Phe
                    100                 105                 110

Gly Phe Thr Trp Pro Gly Thr Phe Ser Leu Ile Ile Glu Ala Leu His
            115                 120                 125

Thr Asp Ser Pro Asp Asp Leu Ala Thr Glu Asn Pro Glu Arg Leu Ile
    130                 135                 140

Ser Arg Leu Ala Thr Gln Arg His Leu Thr Val Gly Glu Glu Trp Ser
145                 150                 155                 160

Gln Asp Leu His Ser Ser Gly Arg Thr Asp Leu Lys Tyr Ser Tyr Arg
                    165                 170                 175

Phe Val Cys Asp Glu His Tyr Tyr Gly Glu Gly Cys Ser Val Phe Cys
            180                 185                 190

Arg Pro Arg Asp Asp Ala Phe Gly His Phe Thr Cys Gly Glu Arg Gly
        195                 200                 205

Glu Lys Val Cys Asn Pro Gly Trp Lys Gly Pro Tyr Cys Thr Glu Pro
210                 215                 220

Ile Cys Leu Pro Gly Cys Asp Glu Gln His Gly Phe Cys Asp Lys Pro
225                 230                 235                 240

Gly Glu Cys Lys Cys Arg Val Gly Trp Gln Gly Arg Tyr Cys Asp Glu
                    245                 250                 255

Cys Ile Arg Tyr Pro Gly Cys Leu His Gly Thr Cys Gln Gln Pro Trp
            260                 265                 270

Gln Cys Asn Cys Gln Glu Gly Trp Gly Gly Leu Phe Cys Asn Gln Asp
        275                 280                 285

Leu Asn Tyr Cys Thr His His Lys Pro Cys Lys Asn Gly Ala Thr Cys
290                 295                 300

Thr Asn Thr Gly Gln Gly Ser Tyr Thr Cys Ser Cys Arg Pro Gly Tyr
305                 310                 315                 320

Thr Gly Ala Thr Cys Glu Leu Gly Ile Asp Glu Cys Asp Pro Ser Pro
                    325                 330                 335

Cys Lys Asn Gly Gly Ser Cys Thr Asp Leu Glu Asn Ser Tyr Ser Cys
            340                 345                 350

Thr Cys Pro Pro Gly Phe Tyr Gly Lys Ile Cys Glu Leu Ser Ala Met
        355                 360                 365

Thr Cys Ala Asp Gly Pro Cys Phe Asn Gly Gly Arg Cys Ser Asp Ser
    370                 375                 380

Pro Asp Gly Gly Tyr Ser Cys Arg Cys Pro Val Gly Tyr Ser Gly Phe
385                 390                 395                 400

Asn Cys Glu Lys Lys Ile Asp Tyr Cys Ser Ser Ser Pro Cys Ser Asn
                    405                 410                 415

Gly Ala Lys Cys Val Asp Leu Gly Asp Ala Tyr Leu Cys Arg Cys Gln
            420                 425                 430

Ala Gly Phe Ser Gly Arg His Cys Asp Asp Asn Val Asp Asp Cys Ala
        435                 440                 445

Ser Ser Pro Cys Ala Asn Gly Gly Thr Cys Arg Asp Gly Val Asn Asp
    450                 455                 460

Phe Ser Cys Thr Cys Pro Pro Gly Tyr Thr Gly Arg Asn Cys Ser Ala
465                 470                 475                 480
```

-continued

```
Pro Val Ser Arg Cys Glu His Ala Pro Cys His Asn Gly Ala Thr Cys
                485                 490                 495
His Glu Arg Gly His Arg Tyr Val Cys Glu Cys Ala Arg Gly Tyr Gly
            500                 505                 510
Gly Pro Asn Cys Gln Phe Leu Leu Pro Glu Leu Pro Pro Gly Pro Ala
        515                 520                 525
Val Val Asp Leu Thr Glu Lys Leu Glu Gly Gln Gly Gly Pro Phe Pro
    530                 535                 540
Trp Val Ala Val Cys Ala Gly Val Ile Leu Val Leu Met Leu Leu Leu
545                 550                 555                 560
Gly Cys Ala Ala Val Val Cys Val Arg Leu Arg Leu Gln Lys His
                565                 570                 575
Arg Pro Pro Ala Asp Pro Cys Arg Gly Glu Thr Glu Thr Met Asn Asn
                580                 585                 590
Leu Ala Asn Cys Gln Arg Glu Lys Asp Ile Ser Val Ser Ile Ile Gly
                595                 600                 605
Ala Thr Gln Ile Lys Asn Thr Asn Lys Lys Ala Asp Phe His Gly Asp
        610                 615                 620
His Ser Ala Asp Lys Asn Gly Phe Lys Ala Arg Tyr Pro Ala Val Asp
625                 630                 635                 640
Tyr Asn Leu Val Gln Asp Leu Lys Gly Asp Asp Thr Ala Val Arg Asp
                645                 650                 655
Ala His Ser Lys Arg Asp Thr Lys Cys Gln Pro Gln Gly Ser Ser Gly
                660                 665                 670
Glu Glu Lys Gly Thr Pro Thr Thr Leu Arg Gly Gly Glu Ala Ser Glu
        675                 680                 685
Arg Lys Arg Pro Asp Ser Gly Cys Ser Thr Ser Lys Asp Thr Lys Tyr
        690                 695                 700
Gln Ser Val Tyr Val Ile Ser Glu Glu Lys Asp Glu Cys Val Ile Ala
705                 710                 715                 720
Thr Glu Val
```

```
<210> SEQ ID NO 38
<211> LENGTH: 618
<212> TYPE: PRT
<213> ORGANISM: Homo sapiens

<400> SEQUENCE: 38
```

```
Met Val Ser Pro Arg Met Ser Gly Leu Leu Ser Gln Thr Val Ile Leu
1               5                   10                  15
Ala Leu Ile Phe Leu Pro Gln Thr Arg Pro Ala Gly Val Phe Glu Leu
            20                  25                  30
Gln Ile His Ser Phe Gly Pro Gly Pro Gly Pro Gly Ala Pro Arg Ser
        35                  40                  45
Pro Cys Ser Ala Arg Leu Pro Cys Arg Leu Phe Phe Arg Val Cys Leu
    50                  55                  60
Lys Pro Gly Leu Ser Glu Glu Ala Glu Ser Pro Cys Ala Leu Gly
65                  70                  75                  80
Ala Ala Leu Ser Ala Arg Gly Pro Val Tyr Thr Glu Gln Pro Gly Ala
                85                  90                  95
Pro Ala Pro Asp Leu Pro Leu Pro Asp Gly Leu Leu Gln Val Pro Phe
            100                 105                 110
Arg Asp Ala Trp Pro Gly Thr Phe Ser Phe Ile Ile Glu Thr Trp Arg
        115                 120                 125
```

```
Glu Glu Leu Gly Asp Gln Ile Gly Gly Pro Ala Trp Ser Leu Leu Ala
    130                 135                 140

Arg Val Ala Gly Arg Arg Leu Ala Ala Gly Gly Pro Trp Ala Arg
145                 150                 155                 160

Asp Ile Gln Arg Ala Gly Ala Trp Glu Leu Arg Phe Ser Tyr Arg Ala
                165                 170                 175

Arg Cys Glu Pro Pro Ala Val Gly Thr Ala Cys Thr Arg Leu Cys Arg
            180                 185                 190

Pro Arg Ser Ala Pro Ser Arg Cys Gly Pro Gly Leu Arg Pro Cys Ala
            195                 200                 205

Pro Leu Glu Asp Glu Cys Glu Ala Pro Leu Val Cys Arg Ala Gly Cys
    210                 215                 220

Ser Pro Glu His Gly Phe Cys Glu Gln Pro Gly Glu Cys Arg Cys Leu
225                 230                 235                 240

Glu Gly Trp Thr Gly Pro Leu Cys Thr Val Pro Val Ser Thr Ser Ser
                245                 250                 255

Cys Leu Ser Pro Arg Gly Pro Ser Ser Ala Thr Thr Gly Cys Leu Val
            260                 265                 270

Pro Gly Pro Gly Pro Cys Asp Gly Asn Pro Cys Ala Asn Gly Gly Ser
    275                 280                 285

Cys Ser Glu Thr Pro Arg Ser Phe Glu Cys Thr Cys Pro Arg Gly Phe
    290                 295                 300

Tyr Gly Leu Arg Cys Glu Val Ser Gly Val Thr Cys Ala Asp Gly Pro
305                 310                 315                 320

Cys Phe Asn Gly Gly Leu Cys Val Gly Gly Ala Asp Pro Asp Ser Ala
                325                 330                 335

Tyr Ile Cys His Cys Pro Pro Gly Phe Gln Gly Ser Asn Cys Glu Lys
            340                 345                 350

Arg Val Asp Arg Cys Ser Leu Gln Pro Cys Arg Asn Gly Gly Leu Cys
            355                 360                 365

Leu Asp Leu Gly His Ala Leu Arg Cys Arg Cys Arg Ala Gly Phe Ala
    370                 375                 380

Gly Pro Arg Cys Glu His Asp Leu Asp Asp Cys Ala Gly Arg Ala Cys
385                 390                 395                 400

Ala Asn Gly Gly Thr Cys Val Glu Gly Gly Gly Ala His Arg Cys Ser
                405                 410                 415

Cys Ala Leu Gly Phe Gly Gly Arg Asp Cys Arg Glu Arg Ala Asp Pro
            420                 425                 430

Cys Ala Ala Arg Pro Cys Ala His Gly Gly Arg Cys Tyr Ala His Phe
            435                 440                 445

Ser Gly Leu Val Cys Ala Cys Ala Pro Gly Tyr Met Gly Ala Arg Cys
    450                 455                 460

Glu Phe Pro Val His Pro Asp Gly Ala Ser Ala Leu Pro Ala Ala Pro
465                 470                 475                 480

Pro Gly Leu Arg Pro Gly Asp Pro Gln Arg Tyr Leu Pro Pro Ala
                485                 490                 495

Leu Gly Leu Leu Val Ala Ala Gly Val Ala Gly Ala Ala Leu Leu Leu
            500                 505                 510

Val His Val Arg Arg Arg Gly His Ser Gln Asp Ala Gly Ser Arg Leu
    515                 520                 525

Leu Ala Gly Thr Pro Glu Pro Ser Val His Ala Leu Pro Asp Ala Leu
530                 535                 540
```

Asn Asn Leu Arg Thr Gln Glu Gly Ser Gly Asp Gly Pro Ser Ser Ser
545                 550                 555                 560

Val Asp Trp Asn Arg Pro Glu Asp Val Asp Pro Gln Gly Ile Tyr Val
                565                 570                 575

Ile Ser Ala Pro Ser Ile Tyr Ala Arg Glu Val Ala Thr Pro Leu Phe
            580                 585                 590

Pro Pro Leu His Thr Gly Arg Ala Gly Gln Arg Gln His Leu Leu Phe
        595                 600                 605

Pro Tyr Pro Ser Ser Ile Leu Ser Val Lys
    610                 615

<210> SEQ ID NO 39
<211> LENGTH: 685
<212> TYPE: PRT
<213> ORGANISM: Homo sapiens

<400> SEQUENCE: 39

Met Ala Ala Ala Ser Arg Ser Ala Ser Gly Trp Ala Leu Leu Leu Leu
1               5                   10                  15

Val Ala Leu Trp Gln Gln Arg Ala Ala Gly Ser Gly Val Phe Gln Leu
            20                  25                  30

Gln Leu Gln Glu Phe Ile Asn Glu Arg Gly Val Leu Ala Ser Gly Arg
        35                  40                  45

Pro Cys Glu Pro Gly Cys Arg Thr Phe Phe Arg Val Cys Leu Lys His
    50                  55                  60

Phe Gln Ala Val Val Ser Pro Gly Pro Cys Thr Phe Gly Thr Val Ser
65                  70                  75                  80

Thr Pro Val Leu Gly Thr Asn Ser Phe Ala Val Arg Asp Asp Ser Ser
                85                  90                  95

Gly Gly Gly Arg Asn Pro Leu Gln Leu Pro Phe Asn Phe Thr Trp Pro
            100                 105                 110

Gly Thr Phe Ser Leu Ile Ile Glu Ala Trp His Ala Pro Gly Asp Asp
        115                 120                 125

Leu Arg Pro Glu Ala Leu Pro Pro Asp Ala Leu Ile Ser Lys Ile Ala
    130                 135                 140

Ile Gln Gly Ser Leu Ala Val Gly Gln Asn Trp Leu Leu Asp Glu Gln
145                 150                 155                 160

Thr Ser Thr Leu Thr Arg Leu Arg Tyr Ser Tyr Arg Val Ile Cys Ser
                165                 170                 175

Asp Asn Tyr Tyr Gly Asp Asn Cys Ser Arg Leu Cys Lys Lys Arg Asn
            180                 185                 190

Asp His Phe Gly His Tyr Val Cys Gln Pro Asp Gly Asn Leu Ser Cys
        195                 200                 205

Leu Pro Gly Trp Thr Gly Glu Tyr Cys Gln Gln Pro Ile Cys Leu Ser
    210                 215                 220

Gly Cys His Glu Gln Asn Gly Tyr Cys Ser Lys Pro Ala Glu Cys Leu
225                 230                 235                 240

Cys Arg Pro Gly Trp Gln Gly Arg Leu Cys Asn Glu Cys Ile Pro His
                245                 250                 255

Asn Gly Cys Arg His Gly Thr Cys Ser Thr Pro Trp Gln Cys Thr Cys
            260                 265                 270

Asp Glu Gly Trp Gly Gly Leu Phe Cys Asp Gln Asp Leu Asn Tyr Cys
        275                 280                 285

Thr His His Ser Pro Cys Lys Asn Gly Ala Thr Cys Ser Asn Ser Gly
    290                 295                 300

```
Gln Arg Ser Tyr Thr Cys Thr Cys Arg Pro Gly Tyr Thr Gly Val Asp
305                 310                 315                 320

Cys Glu Leu Glu Leu Ser Glu Cys Asp Ser Asn Pro Cys Arg Asn Gly
            325                 330                 335

Gly Ser Cys Lys Asp Gln Glu Asp Gly Tyr His Cys Leu Cys Pro Pro
        340                 345                 350

Gly Tyr Tyr Gly Leu His Cys Glu His Ser Thr Leu Ser Cys Ala Asp
            355                 360                 365

Ser Pro Cys Phe Asn Gly Ser Cys Arg Glu Arg Asn Gln Gly Ala
        370                 375                 380

Asn Tyr Ala Cys Glu Cys Pro Pro Asn Phe Thr Gly Ser Asn Cys Glu
385                 390                 395                 400

Lys Lys Val Asp Arg Cys Thr Ser Asn Pro Cys Ala Asn Gly Gly Gln
                405                 410                 415

Cys Leu Asn Arg Gly Pro Ser Arg Met Cys Arg Cys Arg Pro Gly Phe
            420                 425                 430

Thr Gly Thr Tyr Cys Glu Leu His Val Ser Asp Cys Ala Arg Asn Pro
            435                 440                 445

Cys Ala His Gly Gly Thr Cys His Asp Leu Glu Asn Gly Leu Met Cys
450                 455                 460

Thr Cys Pro Ala Gly Phe Ser Gly Arg Arg Cys Glu Val Arg Thr Ser
465                 470                 475                 480

Ile Asp Ala Cys Ala Ser Ser Pro Cys Phe Asn Arg Ala Thr Cys Tyr
                485                 490                 495

Thr Asp Leu Ser Thr Asp Thr Phe Val Cys Asn Cys Pro Tyr Gly Phe
            500                 505                 510

Val Gly Ser Arg Cys Glu Phe Pro Val Gly Leu Pro Pro Ser Phe Pro
            515                 520                 525

Trp Val Ala Val Ser Leu Gly Val Gly Leu Ala Val Leu Leu Val Leu
        530                 535                 540

Leu Gly Met Val Ala Val Ala Val Arg Gln Leu Arg Leu Arg Arg Pro
545                 550                 555                 560

Asp Asp Gly Ser Arg Glu Ala Met Asn Asn Leu Ser Asp Phe Gln Lys
                565                 570                 575

Asp Asn Leu Ile Pro Ala Ala Gln Leu Lys Asn Thr Asn Gln Lys Lys
            580                 585                 590

Glu Leu Glu Val Asp Cys Gly Leu Asp Lys Ser Asn Cys Gly Lys Gln
            595                 600                 605

Gln Asn His Thr Leu Asp Tyr Asn Leu Ala Pro Gly Pro Leu Gly Arg
        610                 615                 620

Gly Thr Met Pro Gly Lys Phe Pro His Ser Asp Lys Ser Leu Gly Glu
625                 630                 635                 640

Lys Ala Pro Leu Arg Leu His Ser Glu Lys Pro Glu Cys Arg Ile Ser
                645                 650                 655

Ala Ile Cys Ser Pro Arg Asp Ser Met Tyr Gln Ser Val Cys Leu Ile
            660                 665                 670

Ser Glu Glu Arg Asn Glu Cys Val Ile Ala Thr Glu Val
        675                 680                 685

<210> SEQ ID NO 40
<211> LENGTH: 390
<212> TYPE: PRT
<213> ORGANISM: Homo sapiens
```

<400> SEQUENCE: 40

```
Met Pro Pro Ser Gly Leu Arg Leu Leu Leu Leu Leu Pro Leu Leu
1               5                   10                  15

Trp Leu Leu Val Leu Thr Pro Gly Arg Pro Ala Ala Gly Leu Ser Thr
            20                  25                  30

Cys Lys Thr Ile Asp Met Glu Leu Val Lys Arg Lys Ile Glu Ala
            35                  40                  45

Ile Arg Gly Gln Ile Leu Ser Lys Leu Arg Leu Ala Ser Pro Pro Ser
    50                  55                  60

Gln Gly Glu Val Pro Pro Gly Pro Leu Pro Glu Ala Val Leu Ala Leu
65                  70                  75                  80

Tyr Asn Ser Thr Arg Asp Arg Val Ala Gly Glu Ser Ala Glu Pro Glu
                85                  90                  95

Pro Glu Pro Glu Ala Asp Tyr Tyr Ala Lys Glu Val Thr Arg Val Leu
            100                 105                 110

Met Val Glu Thr His Asn Glu Ile Tyr Asp Lys Phe Lys Gln Ser Thr
            115                 120                 125

His Ser Ile Tyr Met Phe Phe Asn Thr Ser Glu Leu Arg Glu Ala Val
130                 135                 140

Pro Glu Pro Val Leu Leu Ser Arg Ala Glu Leu Arg Leu Leu Arg Leu
145                 150                 155                 160

Lys Leu Lys Val Glu Gln His Val Glu Leu Tyr Gln Lys Tyr Ser Asn
                165                 170                 175

Asn Ser Trp Arg Tyr Leu Ser Asn Arg Leu Leu Ala Pro Ser Asp Ser
                180                 185                 190

Pro Glu Trp Leu Ser Phe Asp Val Thr Gly Val Val Arg Gln Trp Leu
            195                 200                 205

Ser Arg Gly Gly Glu Ile Glu Gly Phe Arg Leu Ser Ala His Cys Ser
210                 215                 220

Cys Asp Ser Arg Asp Asn Thr Leu Gln Val Asp Ile Asn Gly Phe Thr
225                 230                 235                 240

Thr Gly Arg Arg Gly Asp Leu Ala Thr Ile His Gly Met Asn Arg Pro
            245                 250                 255

Phe Leu Leu Leu Met Ala Thr Pro Leu Glu Arg Ala Gln His Leu Gln
            260                 265                 270

Ser Ser Arg His Arg Arg Ala Leu Asp Thr Asn Tyr Cys Phe Ser Ser
            275                 280                 285

Thr Glu Lys Asn Cys Cys Val Arg Gln Leu Tyr Ile Asp Phe Arg Lys
            290                 295                 300

Asp Leu Gly Trp Lys Trp Ile His Glu Pro Lys Gly Tyr His Ala Asn
305                 310                 315                 320

Phe Cys Leu Gly Pro Cys Pro Tyr Ile Trp Ser Leu Asp Thr Gln Tyr
                325                 330                 335

Ser Lys Val Leu Ala Leu Tyr Asn Gln His Asn Pro Gly Ala Ser Ala
            340                 345                 350

Ala Pro Cys Cys Val Pro Gln Ala Leu Glu Pro Leu Pro Ile Val Tyr
            355                 360                 365

Tyr Val Gly Arg Lys Pro Lys Val Glu Gln Leu Ser Asn Met Ile Val
            370                 375                 380

Arg Ser Cys Lys Cys Ser
385                 390
```

<210> SEQ ID NO 41

```
<211> LENGTH: 11
<212> TYPE: PRT
<213> ORGANISM: Artificial Sequence
<220> FEATURE:
<223> OTHER INFORMATION: synthetic peptide construct

<400> SEQUENCE: 41

Lys Glu Ala Pro Pro Ala Pro Pro Gln Ser Pro
1               5                   10

<210> SEQ ID NO 42
<211> LENGTH: 12
<212> TYPE: PRT
<213> ORGANISM: Artificial Sequence
<220> FEATURE:
<223> OTHER INFORMATION: synthetic peptide construct

<400> SEQUENCE: 42

Gly Lys Glu Ala Pro Pro Ala Pro Pro Gln Ser Pro
1               5                   10
```

DERIVATION OF HEPATIC STEM CELLS AND MATURE LIVER CELL TYPES AND USES THEREOF

CROSS-REFERENCES TO RELATED APPLICATIONS

This application is a divisional of U.S. patent application Ser. No. 15/735,321, filed Dec. 11, 2017, which is a U.S. National Stage of International Patent Application No.: PCT/SG2016/050270, filed on Jun. 10, 2016, which claims the benefit of priority to Singapore Application No. SG 10201504657Y, filed Jun. 12, 2015, and Singapore Application No. SG 10201504659X, filed Jun. 12, 2015, which are all incorporated by reference herein in their entireties.

REFERENCE TO A "SEQUENCE LISTING," A TABLE, OR A COMPUTER PROGRAM LISTING APPENDIX SUBMITTED ON A COMPACT DISK

The Sequence Listing written in file 1012194_ST25.txt, created on Jun. 9, 2016, 223,255 bytes, machine format IBM-PC, MS-Windows operating system, is hereby incorporated by reference in its entirety for all purposes.

BACKGROUND OF THE INVENTION

A Need for Self-Renewable Source of Mature Hepatocytes

The liver is the largest glandular organ in the body and performs multiple critical functions to keep the body pure of toxins and harmful substances. Liver function is mainly contributed by hepatocytes. Hepatocyte is the main cell type for glucose metabolism, lipid metabolism, urea metabolism and detoxification. It produces bile to digest fats; stores glucose, vitamins and iron; converts ammonia to urea and detoxifies the blood to rid it of harmful substances such as alcohol and drugs. In most liver diseases, hepatocytes are progressively loss to the extent where liver function fails and transplantation remains the gold standard of treatment. However, the medical complexity of the procedure coupled with a severe lack of healthy liver grafts creates an urgent need for more sustainable options. Worldwide, the mismatch between liver graft availability and patients waiting for a liver transplant has widened exponentially resulting in more patients dying while on the waiting list. This unmet clinical need has spurred much effort to develop cellular transplantation as an alternative to whole organ transplantation. Beside clinical needs, hepatocytes are constantly used in the industry for in vitro toxicology screens. Drug induced liver injury remains a major hurdle for many drugs in reaching clinical trials and in some cases drugs have been withdrawn from the shelf because of toxicity issues. This in part stems from the limitations of current in vitro hepatocyte toxicity models and mouse toxicity models to predict all forms of drug induced liver injury [1,2]. There is an urgent need for a renewable source of quality hepatocytes for both industrial and clinical applications. Hepatocytes isolated from fresh liver tissue lose their major drug metabolic enzyme Cytochrome p450 (CYP) activity after 24-48 hours of in vitro culture. Currently there is no method available for long term culture of primary hepatocyte, without the loss of their CYP drug metabolism functions. Besides the liver, a plausible renewable source of hepatocytes would be their derivation from pluripotent stem cells. However, these cells at best achieve functional activity of immature fetal hepatocytes which is much lower than mature adult hepatocytes [3]. In contrast, the liver stem cells described herein generate hepatocytes with adult hepatocyte features and the self-renewal capacity makes them a sustainable source of mature liver adult stem cells.

Structure and Cell Types in an Adult Liver

The liver lobule forms the functional basic unit of the liver [4]. Hepatocytes are compacted around a central vein and the portal triad (consisting of the bile ducts, hepatic vein and hepatic artery) are found at the edge of the lobule. While hepatocytes form the majority of the cells in the lobule, several other cells types are essential to form the ductal and vasculature networks, and immune surveillance of the organ. Other major cell types in the liver includes bile duct cells (cholangiocytes), liver sinusoidal endothelial cells, vasculature endothelial cells, immune cells including Pit cells, Kupffer cells and hepatic stellate cells. Within the liver lobules, hepatocytes are distributed to 3 different zones, determined by their proximity to the central vein or the portal triad located at the end of the lobule. Hepatocytes in the different zones are exposed to different niche environments and play specific functional roles in the liver. They can be distinguished by the expression of different markers, glucose and lipid metabolic functions.

Functional Hepatocytes and Cholangiocytes

Hepatocytes are the chief functional cells of the liver. As mentioned previously they perform an astonishing number of metabolic, endocrine and secretory functions. Roughly 80% of the mass of the liver is contributed by hepatocytes. In three dimensions, hepatocytes are arranged in plates that anastomose with one another. The cells are polygonal in shape with one or two prominent nucleoli and their sides can be in contact either with sinusoids (sinusoidal face) or neighboring hepatocytes (lateral faces). Hepatocyte function could be assessed by glucose storage, ion uptake, bile salt secretion, amino acid metabolic function, urea synthesis and drug metabolic function test.

The drug metabolizing function of hepatocytes is mediated by cytochrome P450s (CYPs). CYPs constitute the major enzyme family capable of catalyzing the oxidative biotransformation of most drugs. 90% of drugs are metabolized by six major CYPs (CYP3A4/5, CYP2C9, CYP2C19, CYP1A2, CYP2B6 and CYP2D6) [5]. CYP function can be enhanced by induction with specific drugs. CYP function and drug induction response is a major critical criterion used to assess the functional maturity of lab-made hepatocytes. While hepatocytes have been derived using various methods from embryonic and fetal tissues, the maturity and functionality of these hepatocytes as determined by the activities of the 6 major CYPs and their response to drug induction showed that they were functionally immature [6,13]. Therefore current methods known in the field of deriving hepatocytes do not solve the issue of obtaining large numbers of functionally mature hepatocytes for both industrial and clinical applications.

Besides hepatocytes, bile duct cells (cholangiocytes) are another type of liver parenchymal cell. Cholangiocytes are epithelial cells that line the intra- and extrahepatic ducts of the biliary tree [7]. The main physiologic function of cholangiocytes is modification of hepatocyte-derived bile. Typical cholangiocytes are polarized columnar cells. Their nucleoli are located near the basal membrane. Primary cilia extend from the cholangiocyte apical plasma membrane and into the ductal lumen. Microvilli formed by primary cilia on the apical plasma membrane significantly increase the cholangiocyte surface area. This enhances secretion and ion transport function of cholangiocytes [7]. Microvilli are a major structural characteristic used to assess the maturation of cholangiocytes. Currently, there are no reports of in vitro differentiated cholangiocytes with microvilli structures. Herein, we show that adult stem cells can generate mature cholangiocytes with microvilli.

Multiple Regenerative Cell Source in the Liver

In vivo, the liver is one of the most regenerative organs of the human body [8]. The human liver can lose up to ⅔ of its mass, maintains its critical functions and recover to the original mass within 8-15 days. Studies have shown during the recovery from a partial liver hepatectomy, hepatocytes from all regions of the liver proliferate [8,9], including bile duct cells. Recent lineage tracing experiments have identified proliferative hepatocytes in different regions of the liver, near the central vein [10] or the portal triad [11] during both normal liver homeostasis and liver injuries. Other than hepatocytes, potential proliferative cells have been identified in the bile duct regions that could replenish damage hepatocytes during injury [9,12].

Isolation of Adult Hepatic Stem Cells from the Adult Human Liver

The multi-cellular origin of liver stem cells suggests different methods can be used to isolate and derive stem cells from the liver. The ability to successfully isolate and expand liver stem cells and further differentiate them into functional hepatocytes for meaningful repopulation in an injured liver to deliver clinical benefit has become a top priority for liver stem cell biologists. To date, two groups have reported isolating stem cells from adult liver tissue that could be stably expanded in vitro for the long term. However, the hepatocytes derived from these stem cells are functionally immature and are unsuitable for use in clinical and industrial applications.

The first group (see WO2015/173425 A1) successfully isolated stem cells from liver tissue based on cells expressing 2 key markers, Leucine-rich repeat-containing G-protein coupled receptor 5 (LGR5) and Epithelial cell adhesion molecule (EPCAM). EPCAM expressing cells were embedded in matrigel to form a liver epithelial cell mass. The epithelial cell mass mainly consisted of cells expressing bile duct cell markers Keratin 19 (KRT19), Keratin 7 (KRT7) and EPCAM, suggesting that the origin of the cells was from bile ducts in the liver. While hepatocytes and cholangiocytes could be derived from this epithelial cell mass, no evidence was presented that the cells were mature. The hepatocytes were only shown to exhibit Cytochrome P450, Family 3, Subfamily A, Polypeptide 4 (CYP3A4) activity. This cytochrome activity is highly active in immature hepatocytes derived from embryonic or fetal tissues or stem cells [13]. There is no evidence that the cells exhibited mature Cytochrome P450, Family 2, Subfamily C, Polypeptide 9 (CYP2C9) functions, or that Cytochrome P450 (CYP) activity could be further induced with a drug. Similarly, derived cholangiocytes did not show mature phenotypes such as a polarized cell structure and the presence of cilia on the apical membrane. Thus, there is no evidence that the methods disclosed in WO2015/173425 were capable of generating mature hepatocytes and cholangiocytes.

A second group (see WO2014152321 A1) described isolating adult stem cells from various tissues or organs including stomach, small intestine, colon, intestinal metaplasia, fallopian tube (oviducts), kidney, pancreas, liver, and lung. Their isolated liver stem cell expressed mainly bile duct markers such as KRT7 and KRT19. The liver stem cells were shown to differentiate into Alpha-Fetoprotein (AFP) expressing hepatocytes. AFP is only found in embryonic and fetal immature hepatocytes. This suggested that these stem cells cannot generate fully mature hepatocytes. No metabolic functions were described, and no evidence was presented that the stem cells could differentiate into cholangiocytes. In addition, the in vivo transplantation data presented did not show that the liver stem cell could differentiate into functional hepatocytes in the mouse liver.

BRIEF SUMMARY OF THE INVENTION

The invention provides a method to isolate hepatic stem cells from adult human liver tissue, mouse liver, and fetal liver. The method used only a single media for the isolation and propagation of the liver stem cells. The media and feeder cells for isolating the stem cell could also be used for long term maintenance of these cells, cryopreservation of these cells and subsequent thawing of the cells for continuous culture. Using specific differentiation media, these stem cells could be used to generate both mature and functional hepatocytes and cholangiocytes.

In this application, we demonstrate that hepatic stem cells with a strong hepatocyte gene signature can be isolated. The isolated stem cells described herein expressed very low levels of KRT19 and no detectable KRT7, which distinguishes the stem cells described herein from stem cells known in the art. The stem cells described herein also expressed mature hepatocyte markers such as Hepatocyte Nuclear Factor 3, Beta (HNF3β) and Hepatocyte Nuclear Factor 4, Alpha (HNF4α). We were able to isolate stem cells both from EpCam+ and EpCam− liver cells. More importantly, we showed that the hepatic stem cells can generate hepatocytes that exhibited multiple CYP metabolic activities, including CYP2C9 activity, which is only found in adult hepatocytes. Furthermore, we showed that CYP activities were responsive to drug induction. The bipotent hepatic stem cells could also generate mature cholangiocytes in vitro. The bile duct cells were polarized and cilia can be found on the apical membrane of the cells, showing that the stem cell derived cholangiocytes were highly mature. We describe the first isolation of bipotent hepatic stem cells that are capable of differentiating into mature hepatocytes and mature cholangiocytes.

The methods described herein were used to isolate liver stem cells from mouse and human fetal stem cells (FIG. 6), and could potentially be used to isolate liver stem cells from other mammals from primate to rodent, such as pigs or monkeys. The liver stem cells could also be isolated and derived from both healthy and diseased liver (FIG. 8). The liver diseases includes liver metabolic disease, such as nonalcoholic fatty liver disease (NAFLD), nonalcoholic steatohepatitis (NASH); autoimmune disease, such as primary sclerosing cholangitis (PSC), primary biliary cirrhosis (PBC); infectious disease, such as hepatitis virus infected liver cirrhosis; drug induced acute and chronic liver failure, such as drug induced liver injury (DILI); alcoholic liver cirrhosis and liver cancer, such as hepatocarcinoma (HCC) and cholangiocarcinoma (FIG. 8, Tables 1 and 3).

Liver stem cells were isolated, maintained and cultured using a single serum free media from human liver tissue. The human liver tissue herein can refer to any parts of the liver dissected from diseased or normal and fetal or adult liver. Stem cells were derived, maintained and propagated on fibroblasts that included 3T3J2 cells, Swiss3T3, NIH3T3 and L1 (FIG. 14). The liver stem cells could be surprisingly maintained for more than 19 passages (280 days) in culture without detectable karyotype abnormalities (FIG. 10).

Liver stem cells could be differentiated into two of the major parenchymal cell types in the liver, hepatocytes and bile duct cells (cholangiocytes). These were achieved by specific media for each cell type.

Both liver stem cells and their in vitro differentiated hepatocytes were able to repopulate when transplanted into mouse liver. The transplanted liver stem cells and their differentiated hepatocyte rescued liver function in a drug-induced liver cirrhosis mouse model. This is the first report to show human liver stem cells and their differentiated hepatocytes function in liver regeneration to rescue a liver cirrhosis phenotype.

In one aspect, a liver stem cell is described herein, the liver stem cell comprising the following characteristics:
(i) expresses at least 1, 2, 3 or 4 of the protein markers selected from SOX9, HNF4a, HNF3β, and EPCAM;
(ii) expresses low levels of KRT19 protein,
(iii) does not express detectable protein levels of KRT7 or AFP; and
(iv) does not have a polarized cell phenotype.

In some embodiments, the liver stem cell further expresses 1, 2, 3, 4, or 5 protein markers selected from CD24, PROM1, FOXA3, FOXQ1 and ECAD. The characteristics of the stem cell are maintained in long-term culture, and comprise a normal karyotype after 19 passages in culture.

The liver stem cell can be derived from a mammal, such that the liver stem cell can be a mammalian liver stem cell, a human liver stem cell, a mouse liver stem cell, or a fetal liver stem cell. In some embodiments, the liver stem cell is isolated from a healthy subject. In some embodiments, the liver stem cell is isolated from a mammalian subject with liver disease, wherein the liver disease is selected from the group of metabolic disease, autoimmune disease, infectious disease, drug induced acute and chronic liver failure, and liver cancer. In some embodiments the subject is a human.

In a second aspect, a differentiated hepatocyte derived from a liver stem cell described herein is provided. In some embodiments, the differentiated hepatocyte comprises at least one of the following characteristics:
(i) expresses the markers HNF4a and ALB;
(ii) expresses at least 1, 2, 3, 4, 5, 6, 7 or 8 of the CYP enzymes selected from CYP3A4, CYP2C9, CYP2B6, CYP1A2, CYP1A1, CYP2D6, CYP3A7, and CYP2E1;
(iii) have at least 1, 2 or 3 of the following functions:
  a) functional glucose metabolism;
  b) functional lipid metabolism;
  c) functional albumin secretion;
(vi) indocyanine green (ICG) uptake; and
(vii) forms tight junctions when cultured with other differentiated hepatocytes under conditions sufficient to form an epithelium.

The differentiated hepatocyte can also express at least one of the terminal differentiation markers PEPCK1 or TAT. The differentiated hepatocyte has inducible CYP function for at least 2, 3, or 4 of the CYPs selected from CYP3A4, CYP2C9, CYP2B6, CYP1A2, CYP1A1, CYP2D6, CYP3A7, and CYP2E1. The differentiated hepatocyte can also store glycogen and uptake low density lipoprotein.

In some embodiments, the differentiated hepatocyte is differentiated from a liver stem cell isolated from a healthy human or from a human with liver disease selected from the group of metabolic disease, autoimmune disease, infectious disease, drug induced acute and chronic liver failure, and liver cancer.

In another aspect, a differentiated cholangiocyte derived from a liver stem cell described herein is provided. In some embodiments, the differentiated cholangiocyte comprises at least one of the following characteristics:

(i) expresses the markers KRT19 (Accession no: P08727.4) and KRT7 (Accession no: P08729.5) and ECAD;
(ii) has columnar epithelial cell polarity comprising an apical region and a basolateral region when cultured with other differentiated cholangiocytes under conditions sufficient to form an epithelium;
(iii) comprises microvilli on the apical region;
(iii) forms biliary duct-like 3 dimensional (3D) structure when cultured with other differentiated cholangiocytes under conditions sufficient to form 3D structures.

In some embodiments, the differentiated choloangiocyte is differentiated from a liver stem cell isolated from a healthy human or from a human with liver disease selected from the group of metabolic disease, autoimmune disease, infectious disease, drug induced acute and chronic liver failure, and liver cancer.

In another aspect, a cell culture system for culturing liver stem cells is provided. In some embodiments, the liver stem cell culture system described herein comprises a plurality of soluble agents in a stem cell culture media and a cellular support capable of providing structural and nutritional support. The cellular support helps maintain the liver stem cells in an adhesion layer. In some embodiments, the plurality of soluble agents comprises:
  at least one growth factor,
  an enhancer of the (canonical) WNT pathway,
  a stem cell differentiation inhibitor The cell culture system can enhance stem cell proliferation and/or prevent stem cell differentiation into mature liver cells. In some embodiments, the system is a BMP (Bone morphogenetic protein) inhibitor-free, and/or HGF (Hepatocyte growth factor)-free, and/or FGF (Fibroblast growth factor)-free system.

In some embodiments, the liver stem cells produced by the cell culture system are characterized by having at least one feature selected from the group consisting of:
  a. when cultured on the cellular support, the liver stem cells are small and round in shape and clustered together forming a disk like structure.
  b. the liver stem cells express low levels of KRT19.
  c. the liver stem cells are positive for the markers Epithelial Cadherin (E-CAD), Epithelial Cell Adhesion Molecule (EPCAM), Hepatocyte Nuclear Factor 4 Alpha (HNF4a), and SRY (Sex Determining Region Y)-Box 9 (SOX9);
  d. the liver stem cells are substantially negative for bile duct differentiation markers, such as KRT7. In some embodiments, less than 5%, less than 10% or less than 15% of the liver stem cells expresses KRT7;
  e. at least about 80%, about 85%, about 90%, or about 95% of the liver stem cells express a transcription factor for hepatocyte lineage differentiation, such as HNF4a;
  f. the liver stem cells comprise homogenous bipotential progenitor/stem cells; and
  g. the liver stem cells are capable of developing into mature adult hepatocytes that express having at least four major Cytochrome P450 (CYP) functions.

In some embodiments, the cellular support comprises feeder cells. In some embodiments, the growth factor is capable of increasing cell metabolism by assisting the cell in releasing cyclic AMP (adenosine monophosphate).

In some embodiments, the enhancer of the (canonical) WNT pathway activates the beta-catenin pathway. The enhancer of the canonical WNT pathway can be a Wnt agonist. In some embodiments, the Wnt agonist is selected from the group consisting of: a Wnt family member (Wnt-1/Int-1, Wnt-2/Irp (Int-1-related Protein), Wnt-2b/13, Wnt-3/Int-4, Wnt-3a, Wnt-4, Wnt-5a, Wnt-5b, Wnt-6, Wnt-7a, Wnt-7b, Wnt-8a/8d, Wnt-8b, Wnt-9a/14, Wnt-9b/14b/15, Wnt-10a, Wnt-10b/12, Wnt-11, and Wnt-16); an R-spondin family member (R-spondin 1, R-spondin 2, R-spondin 3, and R-spondin 4); Norrin (Norrie Disease Protein or NDP); a Glycogen synthase kinase 3 inhibitor selected from small-interfering RNAs, lithium, kenpaullone, 6-Bromoindirubin-30-acetoxime, SB 216763 (3-(2,4-Dichlorophenyl)-4-(1-methyl-1H-indol-3-yl)-1H-pyrrole-2,5-dione), SB 415286 (4-[4-(1,3-benzodioxol-5-yl)-5-(2-pyridinyl)-1H-imidazol-2-yl]benzamide; CHIR 99021 (6-[[2-[[4-(2,4-Dichlorophenyl)-5-(5-methyl-1H-imidazol-2-yl)-2-pyrimidinyl]amino]ethyl]amino]-3-pyridinecarbonitrile), CHIR 99021 trihydrochloride (6-[[2-[[4-(2,4-Dichlorophenyl)-5-(5-methyl-1H-imidazol-2-yl)-2-pyrimidinyl]amino]ethyl]amino]-3-pyridinecarbonitrile trihydrochloride), Kenpaullone, Indirubin-3'-oxime, MeBIO ((2'Z,3'E)-6-Bromo-1-methylindirubin-3'-oxime) TCS 2002 (2-Methyl-5-[3-[4-(methylsulfinyl)phenyl]-5-benzofuranyl]-1,3,4-oxadiazole), Lithium carbonate, NSC 693868 (1H-Pyrazolo[3,4-b]quinoxalin-3-amine), TCS 21311 (3-[5-[4-(2-Hydroxy-2-methyl-1-oxopropyl)-1-piperazinyl]-2-(trifluoromethyl)phenyl]-4-(1H-indol-3-yl)-1H-pyrrole-2,5-dione), AR-A 014418 (N-[(4-Methoxyphenyl)methyl]-N'-(5-nitro-2-thiazolyl)urea), 3F8 (5-Ethyl-7,8-dimethoxy-1H-pyrrolo[3,4-c]isoquinoline-1,3(2H)-dione), L803 (Peptide KEAP-PAPPQSP), A 1070722 (1-(7-Methoxyquinolin-4-yl)-3-[6-(trifluoromethyl)pyridin-2-yl]urea), 10Z-Hymenialdisine, TC-G 24 (N-(3-Chloro-4-methylphenyl)-5-(4-nitrophenyl)-1,3,4-oxadiazol-2-amine), TWS 119 3-[[6-(3-Aminophenyl)-7H-pyrrolo[2,3-d]pyrimidin-4-yl]oxyphenol ditrifluoroacetate]), and L803-mts (peptide GKEAPPAPPQSP); and a FRAT-family member (FRAT: frequently rearranged in advanced T-cell lymphomas) and FRAT-derived peptides. In some embodiments, the Wnt agonist is R-spondin 1.

In some embodiments, the stem cell differentiation inhibitor is a TGF-beta inhibitor. In some cases, the TGF-beta inhibitor is selected from the group consisting of A83-01 (3-(6-Methyl-2-pyridinyl)-N-phenyl-4-(4-quinolinyl)-1H-pyrazole-1-carbothioamide) and SB431542 (4-[4-(1,3-benzodioxol-5-yl)-5-(2-pyridinyl)-1H-imidazol-2-yl]benzamide).

In some embodiments, the growth factor is Epidermal Growth Factor (EGF) and/or thyroid hormone. Thyroid hormone can be selected from the group consisting of 3,3'-5-triiodo-1-thyronine (T3), (S)-thyroxine (T4) and hormones that stimulate cAMP.

In some embodiments, the system further comprises at least one component selected from the group consisting of an extracellular matrix, an agent for activating the Notch pathway, endotoxin, N-acetylcysteine and nicotinamide. In some cases, the agent for activating the Notch pathway is a notch ligand. In some embodiments, the endotoxin is Cholera endotoxin.

In some embodiments, the feeder cell is a fibroblast cell line, such as a mouse or human fibroblast cell line. The mouse fibroblast cell line can be a 3T3J2 feeder cell line.

In some embodiments, the extracellular matrix is matrigel, or a s a growth factor reduced matrigel.

In another aspect, a cell culture system is provided, the cell culture system comprising an extracellular matrix, an EGF, R-spondin1, SB431542, Jagged-1 (amino acid residues 188-204; CDDYYYGFGCNKFCRPR (SEQ ID NO:1), 3,3'-5-triiodo-1-thyronine (T3), Cholera endotoxin, Nicotinamide, N-acetylcysteine and a feeder cell.

In another aspect, a cell culture system is provided, the culture system comprising a growth factor reduced matrigel, an EGF, R-spondin1, SB431542, Jagged-1 (SEQ ID NO:1), 3,3'-5-triiodo-1-thyronine (T3), Cholera endotoxin, Nicotinamide, N-acetylcysteine and a feeder cell.

In another aspect, a cell culture system is provided, the cell culture system comprising a growth factor reduced matrigel, an EGF, R-spondin1, SB431542, Jagged-1 (SEQ ID NO:1), 3,3'-5-triiodo-1-thyronine (T3), Cholera endotoxin, Nicotinamide, N-acetylcysteine and a mouse fibroblast 3T3J2 feeder cell line.

In some embodiments, the concentration of Epidermal Growth Factor (EGF) in the system is from about 5 ng/ml to about 200 ng/ml, or about 10 ng/ml to about 150 ng/ml, or about 35 ng/ml to about 100 ng/ml, or about 40 ng/ml to about 60 ng/ml, or about 41 ng/ml, or about 42 ng/ml, or about 43 ng/ml, or about 44 ng/ml, or about 45 ng/ml, or about 46 ng/ml, or about 47 ng/ml, or about 48 ng/ml, or about 49 ng/ml, or about 50 ng/ml, or about 51 ng/ml, or about 52 ng/ml, or about 53 ng/ml, or about 54 ng/ml, or about 55 ng/ml, or about 56 ng/ml, or about 57 ng/ml, or about 58 ng/ml, or about 59 ng/ml.

In some embodiments, the concentration of R-spondin 1 in the system is from about 100 ng/ml to about 500 ng/ml, or about 110 ng/ml to about 400 ng/ml, or about 150 ng/ml to about 350 ng/ml, or about 200 ng/ml to about 300 ng/ml, or about 230 ng/ml to about 270 ng/ml, or about 235 ng/ml, or about 240 ng/ml, or about 245 ng/ml, or about 250 ng/ml, or about 255 ng/ml, or about 260 ng/ml, or about 265 ng/ml.

In some embodiments, the TGF-beta inhibitor is SB431542. In some embodiments, the concentration of SB431542 in the system is from about 0.1 ng/ml to about 10 ng/ml, or about 0.5 ng/ml to about 8 ng/ml, or about 2 ng/ml to about 7 ng/ml, or about 0.1 µM to about 10 µM, or about 1 µM to about 10 µM, or about 2 µM, or about 3 µM, or about 4 µM, or about 5 µM, or about 6 µM, or about 7 µM, or about 8 µM, or about 9 µM.

In some embodiments, the Notch ligand is Jagged-1 CDDYYYGFGCNKFCRPR (SEQ ID NO:1) (Jagged-1 (188-204)). In some embodiments, the concentration of Jagged-1 in the system is from about 0.1 µM to about 10 µM, or about 1 µM to about 10 µM, or about 2 µM, or about 3 µM, or about 4 µM, or about 5 µM, or about 6 µM, or about 7 µM, or about 8 µM, or about 9 µM.

In some embodiments, the thyroid hormone is 3,3'-5-triiodo-1-thyronine (T3). In some cases, the concentration of T3 in the system is from about 0.2 µM to about 20 µM, or about 0.1 µM to about 15 µM, or about 1 µM, or about 2 µM, or about 3 µM, or about 4 µM, or about 5 µM, or about 6 µM, or about 7 µM, or about 8 µM, or about 9 µM, or about 10 µM, or about 11 µM, or about 12 µM, or about 13 µM, or about 14 µM.

In some embodiments, the concentration of nicotinamide in the system is from about 1 mM to about 50 mM, or about 1 mM to about 25 mM, or about 5 mM to about 15 mM, or about 6 mM, or about 7 mM, or about 8 mM, or about 9 mM, or about 10 mM, or about 11 mM, or about 12 mM, or about 13 mM, or about 14 mM.

In some embodiments, the concentration of N-acetylcysteine in the system is from about 0.1 µM to about 10 µM or about 1 µM to about 10 µM, or about 2 µM, or about 3 µM, or about 4 µM, or about 5 µM, or about 6 µM, or about 7 µM, or about 8 µM, or about 9 µM.

In some embodiments, the concentration of Cholera endotoxin in the system is from about 0.01 µM to about 1 µM or about 0.05 µM to about 0.9 µM, or about 0.95 µM, or about 0.1 µM, or about 0.2 µM, or about 0.3 µM, or about 0.4 µM, or about 0.5 µM, or about 0.6 µM, or about 0.7 µM, or about 0.8 µM, or about 0.9 µM.

In another aspect, a cell culture medium for liver stem cells is provided, the cell culture medium comprising: basal media, about 0.1% to about 5% N2, about 0.1% to 5% B27, about 5 ng/ml to about 200 ng/ml EGF, about 25 to about 500 ng/ml R-Spondin 1, about 0.1 µM to about 10 µM SB431542 (4-[4-(1,3-benzodioxol-5-yl)-5-(2-pyridinyl)-1H-imidazol-2-yl]benzamide), about 0.1 µM to about 10 µM T3 (3,3',5-Triiodo-L-Thyronine), and about 1 mM to about 50 mM Nicotinamide. In some embodiments, the basal medium is advanced F12/DMEM reduced serum medium.

In some embodiments, the concentration of R-Spondin 1 in the culture medium is about 25 ng/ml to about 500 ng/ml, or about 100 ng/ml to about 500 ng/ml, or about 110 ng/ml to about 400 ng/ml, or about 150 ng/ml to about 350 ng/ml, or about 200 ng/ml to about 300 ng/ml, or about 230 ng/ml to about 270 ng/ml, or about 25 ng/ml, or about 50 ng/ml, or about 100 ng/ml, or about 125 ng/ml, or about 235 ng/ml, or about 240 ng/ml, or about 245 ng/ml, or about 250 ng/ml, or about 255 ng/ml, or about 260 ng/ml, or about 265 ng/ml, or about 500 ng/ml.

In some embodiments, the culture medium further comprises Jagged-1 (SEQ ID NO:1), wherein the concentration of Jagged-1 in the culture medium is about 0.1 µM to about 10 µM, or about 1 µM to about 10 µM, or about 0.1 µM, or about 0.5 µM, or about 1.0 µM, or about 2 µM, or about 3 µM, or about 4 µM, or about 5 µM, or about 6 µM, or about 7 µM, or about 8 µM, or about 9 µM.

In some embodiments, the culture medium further comprises Cholera enterotoxin (CTX), wherein the concentration of CTX in the culture medium is between about 0.01 µM and about 1 µM, or about 0.05 µM to about 0.9 µM, or about 0.05 µM, or about 0.1 µM, or about 0.2 µM, or about 0.3 µM, or about 0.4 µM, or about 0.5 µM, or about 0.6 µM, or about 0.7 µM, or about 0.8 µM, or about 0.9 µM.

In some embodiments, the culture medium further comprises N-Acetyl-Cysteine (NAC), wherein the concentration of NAC in the culture medium is about 0.1 µM to about 10 µM, or about 1 µM to about 10 µM, or about 2 µM, or about 3 µM, or about 4 µM, or about 5 µM, or about 6 µM, or about 7 µM, or about 8 µM, or about 9 µM.

In another aspect, a kit is provided, the kit comprising the components of the liver stem cell culture system or the liver stem cell media described herein. In some embodiments, the kit further comprises reagents for isolating hepatocytes from a liver, such as a collagenase digestion solution.

In another aspect, a method of obtaining and/or culturing a liver stem cell is described, the method comprising: culturing primary cells obtained from a liver in the cell culture system described herein; the medium described herein, or using the components of a kit described herein. In some embodiments, the liver stem cell is obtained from a human liver. In some embodiments, the liver stem cell is a non-differentiated (pluripotent) cell.

Also provided are isolated liver stem cells obtained from the methods described herein.

In another aspect, a method of generating differentiated cells is described, the method comprising: growing a liver stem in a cell culture system capable of differentiating the liver stem cell into a plurality of differentiated cells.

In another aspect, a cell culture system for differentiating a liver stem cell into a hepatocyte is provided, the cell culture system comprising:

a) a plurality of soluble components comprising:
   at least one Notch inhibitor;
   at least one TGF-beta inhibitor; and
b) conditions for inducing epithelial cell polarization of the a liver stem cell.

In some embodiments, the conditions for inducing epithelial cell polarization of the liver stem cell comprise culturing the liver stem cell at an air-liquid interface (ALI). When culturing the cell at the ALI, the basal side of the liver stem cell is configured to be in contact with the soluble components of the cell culture system and the apical surface of the liver stem cell is configured to be in contact with air.

In some embodiments, the plurality of soluble components further comprises at least one growth factor suitable for differentiating a liver stem cell into a hepatocyte. In some embodiments, the growth factor is selected from an IL6-like cytokine, oncostatin M, or LIF. In some cases, the concentration of the growth factor in the system is from about 5 ng/ml to about 200 ng/ml, or about 10 ng/ml to about 100 ng/ml, or about 15 ng/ml to about 70 ng/ml, or about 20 ng/ml to about 50 ng/ml, or about 16 ng/ml, or about 17 ng/ml, or about 18 ng/ml, or about 19 ng/ml, or about 20 ng/ml, or about 21 ng/ml, or about 22 ng/ml, or about 23 ng/ml, or about 24 ng/ml, or about 25 ng/ml.

In some embodiments, the TGF-beta inhibitor is 3-(6-Methyl-2-pyridinyl)-N-phenyl-4-(4-quinolinyl)-1H-pyrazole-1-carbothioamide (A83-01), LY 364947 (4-[3-(2-pyridinyl)-1H-pyrazol-4-yl]-quinoline, or HTS 466284), SD 208 (2-(5-Chloro-2-fluorophenyl)pteridin-4-yl]pyridin-4-yl-amine), D4476 (4-(4-(2,3-Dihydrobenzo[1,4]dioxin-6-yl)-5-pyridin-2-yl-1H-imidazol-2-yl)benzamide), GW 788388 (4-[4-[3-(2-Pyridinyl)-1H-pyrazol-4-yl]-2-pyridinyl]-N-(tetrahydro-2H-pyran-4-yl)-benzamide), SB 505124 (2-(5-Benzo[1,3]dioxol-5-yl-2-tert-butyl-3H-imidazol-4-yl)-6-methylpyridine), SB 525334 (6-[2-tert-Butyl-5-(6-methyl-pyridin-2-yl)-1H-imidazol-4-yl]-quinoxaline), RepSox (E-616452; or 2-[3-(6-Methyl-2-pyridinyl)-1H-pyrazol-4-yl]-1,5-naphthyridine), R 268712 (4-[2-Fluoro-5-[3-(6-methyl-2-pyridinyl)-1H-pyrazol-4-yl]phenyl]-1H-pyrazole-1-ethanol) or 4-[4-(1,3-benzodioxol-5-yl)-5-(2-pyridinyl)-1H-imidazol-2-yl]benzamide (SB 431542). In some embodiments, the concentration of TGF-beta inhibitor in the system is from about 0.1 µM to about 5 µM, or about 0.1 µM to about 2.5 µM, or about 0.1 µM to about or about 0.1 µM, or about 0.2 µM, or about 0.3 µM, or about 0.4 µM, or about 0.5 µM, or about 0.6 µM, or about 0.7 µM, or about 0.8 µM, or about 0.9 µM.

In some embodiments, the plurality of soluble component further comprises at least one steroid. In some cases, the steroid is selected from the group consisting of dexamethasone, betamethasone, cortisone, methylprednisolone, prednisolone, prednisone, triamcinolone, and hydrocortisone. In some embodiments, the concentration of steroid in the system is from about 1 µM to about 100 µM, or about 10 µM to about 75 µM, or about 20 µM to about 50 µM, or about 20 µM, or about 25 µM, or about 30 µM, or about 35 µM, or about 35 µM, or about 40 µM, or about 45 µM.

In some cases, the system comprises at least one Notch inhibitor. The Notch inhibitor can be selected from the group consisting of N2-[(2S)-2-(3,5-Difluorophenyl)-2-hydroxyethanoyl]-N1-[(7S)-5-methyl-6-oxo-6,7-dihydro-5H-dibenzo[b,d]azepin-7-yl]-L-alaninamide (Ly411575), gamma-secretase inhibitor XXI (or compound E (N-[(1S)-2-[[(3S)-2,3-Dihydro-1-methyl-2-oxo-5-phenyl-1H-1,4-benzodiazepin-3-yl]amino]-1-methyl-2-oxoethyl]-3,5-difluorobenzeneacetamide)), FLI-06 (1,4,5,6,7,8-Hexahydro-2,7,7-trimethyl-4-(4-nitrophenyl)-5-oxo-3-quinolinecarboxylic acid cyclohexyl ester), R04929097 (Propanediamide; or N1-[(7S)-6,7-dihydro-6-oxo-5H- dibenz[b,d]azepin-7-yl]-2,2-dimethyl-N3-(2,2,3,3,3-pentafluoropropyl)-malonamide), LY450139 ((2S)-2-hydroxy-3-methyl-N-((1S)-1-methyl-2-{[(1S)-3-methyl-2-oxo-2,3,4,5-tetrahydro-1H-3-benzazepin-1-yl]amino}-2-oxoethyl)butanamide), YO-01027 (7-(S)-[N'(3,5-difluorophenylacetyl)-L-alaninyl]amino-5-methyl-5,7-dihydro-6H-dibenz[b,d]azepin-6-one), BMS-708163 ((2R)-2-(N-(2-fluoro-4-(1,2,4-oxadiazol-3-yl)benzyl)-4-chlorophenylsulfonamido)-5,5,5-trifluoropentanamide), and BMS-906024 ((2R,3S)—N-[(3S)-1-Methyl-2-oxo-5-phenyl-2,3-dihydro-1H-1,4-benzodiazepin-3-yl]-2,3-bis(3,3,3-trifluoropropyl)succinamide). In some embodiments, the concentration of Notch inhibitor in the system is from about 0.05 µM to about 0.3 µM, or about 0.05 µM to about 0.2 µM, or about 0.05 µM to about 0.1 µM, or about 0.10 or about 0.15 µM.

In some embodiments, the system further comprises at least one Yes-associated protein (YAP) inhibitor. In some embodiments, the YAP inhibitor is selected from the group consisting of verteporfin (3-[(23S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoic acid), ML7 (1-(5-Iodonaphthalene-1-sulfonyl)-1H-hexahydro-1,4-diazepine hydrochloride); blebbistatin (1-Phenyl-1,2,3,4-tetrahydro-4-hydroxypyrrolo[2,3-b]-7-methylquinolin-4-one), and Y27632 (trans-4-[(1R)-1-Aminoethyl]-N-4-pyridinylcyclohexanecarboxamide dihydrochloride). In some cases, the concentration of YAP inhibitor in the system is from about 0.1 µM to about or about 0.1 µM to about 0.7 µM, or about 0.1 µM to about 0.5 µM, or about 0.2 or about 0.3 or about 0.4 µM, or about 0.5 µM, or about 0.6 µM, or about 0.7 µM, or about 0.8 µM.

In some cases, the system further comprises a basal medium. In some embodiments, the basal medium is a liver specific basal medium hepatocyte culture medium, such as Clonetics™ HCM™ Hepatocyte Culture Medium.

In some embodiments, the system further comprises a cellular support capable of providing structural and nutritional support. In some embodiments, the cellular support comprises feeder cells. In some embodiments, the feeder cells are from a fibroblast cell line, such as a mouse or human fibroblast cell line. In some embodiments, the mouse fibroblast cell line is a 3T3J2 feeder cell line.

In some embodiments, the conditions for culturing the liver stem cell at the air-liquid interface (ALI) is achieved by a permeable cell culture apparatus, such as a Transwell® Permeable Support.

In another aspect, a cell culture system for differentiating a liver stem cell into a hepatocyte is provided. In some embodiments, the cell culture system for differentiating a liver stem cell into a hepatocyte comprises or consists of:
  a plurality of soluble components comprising or consisting of:
  a liver specific basal medium, A83-01, dexamethasone, oncostatin M, compound E; IL6 and verteporfin;
  conditions for culturing the liver stem cell at the air-liquid interface (ALI),
  In some embodiments, the basal side of the liver stem cell is configured to be in contact with the soluble components of the cell culture system and the apical surface of the liver stem cell is configured to be in contact with air.

In some embodiments, the hepatocyte is a fully differentiated mature hepatocyte. In some embodiments, the fully differentiated mature hepatocyte is characterized by at least one of the characteristics selected from the group consisting of:
  a. functional CYP3A4 and CYP2C9 activity,
  b. upon stimulation, the hepatocyte can uptake LDL, and/or secrete albumin, and/or store glycogen,
  c. expresses six CYP450 family member genes, and
  d. does not express substantial amounts of AFP as compared to fetal liver cells.

In another aspect, a kit comprising the components of the cell culture system for differentiating a liver stem cell into a hepatocyte is provided.

In another aspect, a method of differentiating a liver stem cell into a hepatocyte is described, the method comprising:
  a. mixing the soluble components of the cell culture system or the kit for differentiating a liver stem cell into a hepatocyte with at least one liver stem cell;
  b. culturing the liver stem cell in the soluble components until confluency in cell population is obtained.

In some embodiments, after achieving confluency in cell population in step (b), the cells are cultured at the air-liquid interface (ALI), wherein the basal side of the liver stem cell is configured to be in contact with the soluble components of the cell culture system and the apical surface of the liver stem cell is configured to be in contact with air.

In another aspect, an isolated differentiated hepatocyte obtained from the methods described herein is provided.

In another aspect, a method of generating a plurality of differentiated liver cells is described, the method comprising: growing the liver stem cells described herein in a cell culture system capable of differentiating the cell into a plurality of differentiated liver cells.

In another aspect, a culture system for differentiating a liver stem cell into a biliary duct cell/cholangiocyte is provided. In some embodiments, the culture system is a substantially TGF-beta inhibitor and Notch inhibitor-free cell culture system. In some embodiments, the cell culture system comprises: an extracellular matrix for differentiating a liver stem cell into a 3D bile duct structure, and a liver stem cell described herein.

In some embodiments, the cell culture system further comprises at least one, at least two, at least three, or at least four growth factors suitable for differentiating a liver stem cell into a biliary duct cell. In some embodiments, the system comprises two, three or four growth factors suitable for differentiating a liver stem cell into a biliary duct cell. In some cases, the system comprises at least one growth factor selected from the group consisting of epidermal growth factor (EGF), fibroblast growth factor (FGF), TGF-beta, growth differentiation factor 11 (GDF11), a Notch pathway ligand, a Jag 1 protein having the amino acid sequence CDDYYYGFGCNKFCRPR; Jag 2; Delta-like protein 1 (DLL1); Delta-like protein 3 (DLL3), and Delta-like protein 4 (DLL4)). In some embodiments, the two growth factors are epidermal growth factor and fibroblast growth factor. In some embodiments, the fibroblast growth factor is selected from the group consisting of fibroblast growth factor 2 (FGF2) and fibroblast growth factor 10 (FGF10).

In some embodiments, the concentration of fibroblast growth factor in the system is from about 10 ng/ml to about 200 ng/ml, or about 30 ng/ml to about 150 ng/ml, or about 50 ng/ml to about 130 ng/ml, or about 60 ng/ml, or about 70 ng/ml, or about 80 ng/ml, or about 90 ng/ml, or about 100 ng/ml, or about 110 ng/ml, or about 120 ng/ml.

In some embodiments, the concentration of epidermal growth factor in the system is from about 5 ng/ml to about 100 ng/ml, or about 5 ng/ml to about 70 ng/ml, or about 5 ng/ml to about 50 ng/ml, or about 6 ng/ml, or about 7 ng/ml, or about 8 ng/ml, or about 9 ng/ml, or about 10 ng/ml, or about 11 ng/ml, or about 12 ng/ml, or about 13 ng/ml, or about 14 ng/ml, or about 15 ng/ml, or about 20 ng/ml, or about 25 ng/ml, or about 30 ng/ml, or about 35 ng/ml, or about 40 ng/ml, or about 45 ng/ml.

In some cases, the system is free of TGF-beta inhibitor and Notch inhibitor. In other words, the cell cultured system does not comprise a TGF-beta inhibitor or a Notch inhibitor.

In some embodiments, the biliary duct cell/cholangiocyte is a fully differentiated mature bile duct epithelial cell, which is characterized by at least one of the characteristics selected from the group consisting of:
   a. cells having biliary duct-like 3 dimensional (3D) structure;
   b. cells expressing KRT19 (Accession no: P08727.4) and KRT7 (Accession no: P08729.5) protein; and
   c. cells having epithelial polarity.

In some embodiments, the liver stem cell that is differentiated into a biliary duct cell/cholangiocyte is a mammalian liver stem cell, such as a human liver stem cell, a mouse liver stem cell, or a fetal liver stem cell. In some cases, the liver stem cell is a liver stem cell obtained from a subject with liver disease selected from the group of metabolic disease, autoimmune disease, infectious disease, drug induced acute and chronic liver failure, and liver cancer.

In some embodiments, the extracellular matrix is matrigel, such as a growth factor reduced matrigel.

In another aspect, a cell culture system for differentiating a liver stem cell into a biliary duct cell/cholangiocyte is provided, the cell culture system comprising an extracellular matrix, an epidermal growth factor and a fibroblast growth factor.

In another aspect, a kit comprising components of the cell culture system for differentiating a liver stem cell into a biliary duct cell/cholangiocyte described herein is provided.

In another aspect, a method of differentiating a liver stem cell into a biliary duct cell is described, the method comprising:
   a. contacting components of the cell culture system for differentiating a liver stem cell into a biliary duct cell, or the components of the kit described herein with at least one liver stem cell; and
   b. culturing the liver stem cell in the components of the cell culture system for at least one day to differentiate the liver stem cell into a biliary duct cell.

In some embodiments, the culturing in step (b) is performed for at least two days, at least three days, at least four days, at least five days, at least six days, at least seven days, at least two weeks, or at least four weeks before the liver stem cell differentiates into a biliary duct cell.

In some embodiments, the components of the system or kit are provided or added to step (b) once every two days, or once every three days, or once every four days, or once every five days, or once every six days.

In another aspect, an isolated biliary duct cell/cholangiocyte obtained from the methods of differentiating a liver stem cell into a biliary duct cell/cholangiocytes is provided.

In another aspect, a hepatocyte differentiation medium is provided, the hepatocyte differentiation medium comprising or consisting of culture medium, 0.5 µM to 1 µM A83-01, 0.1 µM to 100 µM dexamethasone (Dex), and a γ-secretase inhibitor XXI/compound E or a Notch pathway inhibitor. In some embodiments, the concentration of dexamethasone is 0.1 µM, 0.5 µM, 1 µM, 5 µM, 10 µM, 20 µM, 30 µM 50 µM, or 100 µM. In some embodiments, the culture medium is selected from Clonetics™ HCM™ Hepatocyte Culture Medium, advanced DMEM/F12 (1:1) medium with B27 and N2, or DMEM/F12 (1:1) medium with 10% FBS. In some cases, the hepatocyte differentiation medium further comprises about 10 to 300 ng/ml BMP7, about 5 to 200 ng/ml FGF19, and/or about 1 to 200 ng/ml oncostatin M (OSM).

In some embodiments, the hepatocyte differentiation medium further comprises 10, 15, 20, 25, 30, 35, 40, 45, 50, 60, 70, 80, 90, 100, 150, 200, 250, or 300 ng/ml BMP7. In some embodiments, the hepatocyte differentiation medium further comprises 5, 10, 15, 20, 25, 30, 35, 40, 45, 50, 60, 70, 80, 90, 100, 150, or 200 ng/ml FGF19. In some embodiments, the hepatocyte differentiation medium further comprises 1, 5, 10, 15, 20, 25, 30, 35, 40, 45, 50, 60, 70, 80, 90, 100, 150, or 200 ng/ml OSM.

In some embodiments, the concentration of the γ-secretase inhibitor XXI/compound E is between 0.1 nM and 100 nM, or about 0.1 µM.

In some embodiments, the Notch pathway inhibitor is DAPT (N—[N-(3,5-Difluorophenacetyl)-L-alanyl]-S-phenylglycine t-butyl ester) or Dibenzazepine (DBZ).

In another aspect, a cholangiocyte differentiation medium is provided, the cholangiocyte differentiation medium comprising or consisting of basal medium, 0.1% to 5% N2 (Gibco), 0.1% to 5% B27 (Gibco), 0.1 to 100 ng/ml EGF, and 5 to 200 ng/ml FGF10.

In the cell culture media embodiments described herein, the basal medium can be advanced F12/DMEM reduced serum medium. In some embodiments, the liver stem cell medium, hepatocyte differentiation medium, and/or cholangiocyte differentiation medium further comprise a buffer such as HEPES, an antibiotic such as Pen/Strep, and an amino acid such as L-Glutamine.

In another aspect, methods of treating a subject having liver disease are described. In some embodiments, the method comprises administering a liver stem cell described herein to the subject, such as by contacting the liver stem cell with the liver of the subject in vivo, or by transplanting a liver stem cell into the liver of the subject, wherein the administered or transplanted cell integrates into and repopulates the liver of the subject, thereby treating the liver disease. In some embodiments, the method comprises administering a differentiated liver stem cell described herein to the subject, such as by contacting the differentiated liver stem cell with the liver of the subject in vivo, or by transplanting a liver stem cell into the liver of the subject, wherein the administered or transplanted cell integrates into and repopulates the liver of the subject, thereby treating the liver disease. In some embodiments, the liver disease is selected from the group of metabolic disease, autoimmune disease, infectious disease, drug induced acute and chronic liver failure, cirrhosis, and liver cancer.

Also provided are liver stem cells, and differentiated liver stem cells, described herein for use in the treatment of liver disease. Also provided are liver stem cells, and differentiated liver stem cells, described herein for use as a medicament in the treatment of liver disease. Also provided are the use of the liver stem cells, and differentiated liver stem cells, described herein for the manufacture of a medicament for the treatment of liver disease.

BRIEF DESCRIPTION OF THE DRAWINGS

FIG. 1A). Protocol of liver stem cell isolation. FIG. 1B). Bright field images of each step of protocol.

FIG. 5A. Microarray hepatocyte gene expression heatmap of LSC, MRC5 human fibroblast and liver tissue. L1, L2 and L6 were individual healthy donors, CL1 and CL2 were liver cirrhosis patients. 2-6 cell lines from each patients were tested. LSC express low level of hepatocyte markers Albumin (ALB), Prospero Homeobox 1 (PROX1), HNF4α and Forkhead Box A2 (FOXA2), CYP2C9, 2E1 and 3A5. FIG. 5B. Quantitative polymerase chain reaction (qPCR) validation of hepatocyte gene expression in LSC and MRC5 fibroblast cell. This figure. shows bipotent liver stem cells have hepatocyte gene signature but are distinct from differentiated liver cells.

FIGS. 7A and 7B: LSC was derived from both Epcam+ and Epcam− liver cell population. A). Diagram of hepatic epithelial cell population classified by surface markers for cell sorting. Mouse liver epithelial cells were fluorescence-activated cell sorting (FACS) sorted by cell surface markers to separate cholangiocytes (EpCam+E-cad−) and hepatocytes (EpCam−E-cad+). B). Fluorescence-activated cell sorting (FACS) sorted cell populations were cultured with LSC media on feeder cells and were able to self-renew, as shown by the bright field images. Therefore LSC was derived from both Epcam+ cholangiocyte lineage and Epcam− hepatocyte lineage populations.

FIG. 13: Replacement of N2 and B27 with serum caused LSC differentiation. Bright view image of LSC culture in medium with 10% serum without B2 and N27, and control serum free medium with N2 and B27. We observed that the use of serum based media disclosed in WO2014152321 A1 did not maintain the liver cell morphology in an undifferentiated state.

FIG. 15: Feeder-free culture of LSC. Feeder-free culture of LSC in J2 conditional medium. Culture condition: Collagen I &IV and Laminin 521, 511 coated plate with feeder conditional medium. Result: LSC could be cultured for at least 5 passages in feeder-free 2D culture by J2 conditional medium.

FIG. 16A. LSC has self-renewal ability and bilineage differentiation potential. It is able to differentiate into both hepatocytes and bile duct cells. FIG. 16B. 3D bile duct cell (cholangiocytes) differentiation: 30000-50000 LSC cells was seeded in one well of an 8-chamber slide. The well was previously coated with 60 µl of matrigel. The matrigel form a dome shape in the well. LSC aggregated on the surface of matrigel to form a sphere structure. The sphere structures grew bigger and bigger in culture medium. When the medium was changed to bile duct differentiation medium, the sphere stopped growing and started bile duct differentiation. This figure shows the 3D bile duct differentiation model.

FIGS. 17A and 17B: LSC 2D hepatocytes differentiation. FIG. 17A. Diagram of LSC differentiate into hepatocyte in 2D culture model. FIG. 17B. LSC was cultured on feeder in culture dish until 100% confluence. The medium was changed into hepatocyte initiation medium for 3-5 days and then switched to hepatocyte differentiation medium for another 14 days. The differentiated cells expressed hepatocyte marker HNF4a, ALB, CYP2C9 and terminal differentiation marker Phosphoenolpyruvate Carboxykinase 1 (PEPCK). Tight junction marker Zona Occludens 1 (ZO1) was expressed between differentiated cells. This figure shows that LSC differentiated into hepatocyte in 2D culture with specific hepatocyte markers expression. The differentiated hepatocyte matured with terminal differentiation markers expression.

FIG. 20A: CYP activity of differentiated hepatocytes (dHep). A. LSC in vitro differentiated hepatocyte (dHep) Cytochrome P450 functions were tested by Promega P450-glo CYP450 Assay Kit. HepG2 cell line was used as positive control for comparison. Luciferin intensity were normalized by differentiated cell numbers. dHep had high CYP3A4, CYP2C9, CYP2B6 and CYP1A2 activities. It indicates the dHep were matured hepatocytes with matured hepatocyte function.

FIG. 20B: Drug induced CYP activity of differentiated hepatocytes. Drug induced CYP functions were tested by Promega P450-glo CYP450 Assay Kit. CYP3A4 and CYP2C9 were induced for 48 hrs with 10 µM rifampicin (RIF). Luciferin intensity were normalized by differentiated cell numbers. This figure shows that dHep were matured hepatocytes that respond to drug induction.

FIGS. 29A and 29B: LSC differentiated into bile duct cells in 3D culture. FIG. 29A). Bright view of bile duct-like structure. FIG. 29B). IF staining of bile duct markers on organoid sections. Cholangiocytes expressed KRT19 and KRT7, which are bile duct lineage markers. The columnar bile duct cells were well organized with the differentiated cholangiocyes being fully polarized with microvilli on the luminal apical part of the cells; nucleus near the basal membrane. Tight junction marker ZO-1 expressed in cell junction.

FIG. 30A). RNA-seq data analysis of LSC from NAFLD subjects, Hepatitis B virus (HBV) infected liver cirrhosis subjects and healthy liver donors. Two individual patient samples from each disease and a healthy control group. Principle component analysis (PCA) plot showed LSC from different disease groups are clustered within the disease group, indicating that LSC from subjects with the same disease have similar altered gene expression patterns. FIG. 30B). Gene enrichment analysis (GSEA) shows NAFLD stem cells enriched of fatty acid biosynthesis, amino acid metabolism imbalance and insulin pathway down regulation compared with healthy and HBV infected cirrhosis liver stem cells. This shows that NASH LSC keep NASH related phenotypes.

FIG. 32A). Human specific albumin IHC staining in mouse liver. Human albumin (hALB) was expressed in both tumor mass formed by transplanted HCC LSC. hALB was also expressed in mouse liver tissue adjacent to the tumor mass. Arrows indicate hALB staining. FIG. 32B). Human ALB (hALB) ELISA in mouse serum. HCC LSC transplanted mouse had hALB in its serum. This figure shows that the tumor were derived from transplanted HCC LSC which differentiated into albumin secreting cells in mouse liver.

FIG. 33A). Schematic of transplantation into TA liver cirrhosis mice model for liver regeneration. Thioacetamide (TA) was metabolized in adult mouse hepatocytes and produce toxic metabolite that damage the hepatocytes to induce liver cirrhosis. FIG. 33B). TA liver cirrhosis mice model showed that liver function was rescued in LSC transplanted mice. Transplanted mice blood serum ALB levels were significantly higher than control group which did not have LSC transplantation.

DEFINITIONS

Figure 1:
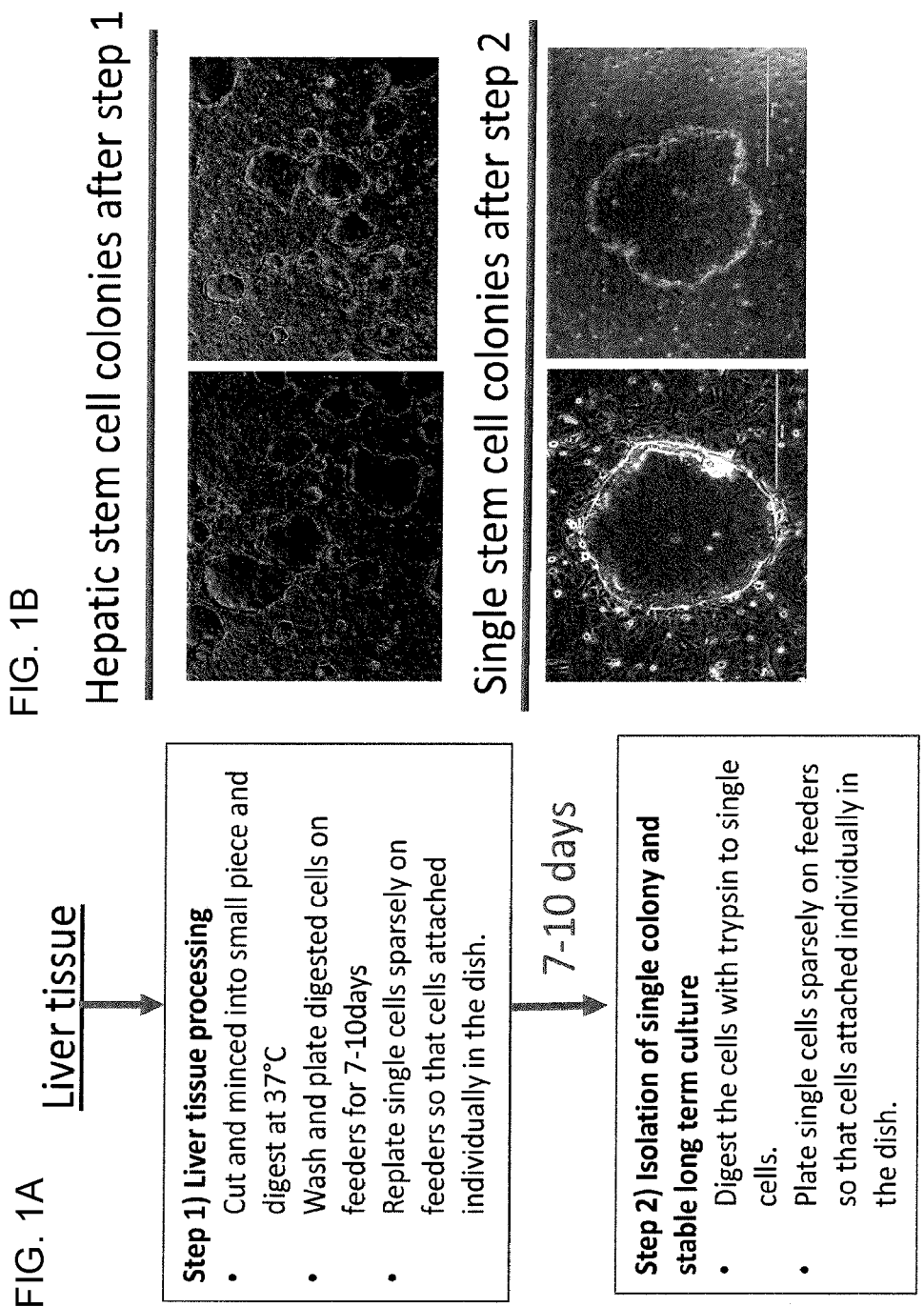
FIGS. 1A and 1B: Liver stem cell isolation method.

The term "about," when modifying any amount, refers to the variation in that amount typically encountered by one of skill in the art, i.e., in the field of liver stem cell derivation and differentiation. For example, the term "about" refers to the normal variation encountered in measurements for a given analytical technique, both within and between batches or samples. Thus, the term about can include variation of 1-10% of the measured amount or value, such as +/−1%, 2%, 3%, 4%, 5%, 6%, 7%, 8%, 9% or 10% variation. The amounts disclosed herein include equivalents to those amounts, including amounts modified or not modified by the term "about."

All numerical ranges disclosed herein include the lower and upper end points of the range, and all numerical values in between the end points, to the significant digit. For example, a range of 1 to 10 includes 1, 2, 3, 4, 5, 6, 7, 8, 9, and 10. A range of 0.1 to 5.0 includes 0.1, 0.2, 0.3, 0.4, 0.5, 0.6, 0.7, 0.8, 0.9, 1.0, 1.1, 1.2, . . . 4.8, 4.9, and 5.0.

The term "growth factor reduced" matrigel refers to a matrigel in which growth factors were partially removed. The term includes Corning® Matrigel® Growth Factor Reduced (GFR) Basement Membrane Matrix (Corning cat. #356230), which comprises a matrix comprising a solubilized basement membrane preparation extracted from the Engelbreth-Holm-Swarm (EHS) mouse sarcoma, a tumor rich in extracellular matrix proteins, including Laminin (a major component), Collagen IV, heparin sulfate proteoglycans, entactin/nidogen, and a number of growth factors.

The term "substantially" when referring to expression of a gene, protein or cellular marker refers to the complete or nearly complete extent or degree of expression. For example, a cell population that is "substantially" negative of a particular cellular marker is either completely negative for the particular cellular marker or at least 95%, or at least 96%, or at least 97%, or at least 98%, or at least 99%, or at least 99.9% of the cell population is negative for the particular cellular marker. A cell culture system that is "substantially" free of a particular agent would mean that the cell culture system is either completely free of the agent or is at least 95%, or at least 96%, or at least 97%, or at least 98%, or at least 99%, or at least 99.9% free of the particular agent.

The term "extracellular matrix" refers to natural or artificial cellular-free scaffolding for cell growth. In some embodiments, natural extracellular matrix is a complex mixture of structural and non-structural biomolecules, including but not limited to, collagens, elastins, laminins, glycosaminoglycans, proteoglycans, antimicrobials, chemoattractants, cytokines and growth factors. In one example, the extracellular matrix is a gelatinous protein mixture secreted by mouse sarcoma cells (such as Engelberth-Holm-Swarm (EHS)) cells.

The term "undetectable" refers to the absence of, or not more than 2-fold greater detectable marker expression when compared to background expression or expression by a negative control. For example, if the assay is an immunofluorescence (IF) staining assay, then expression is considered "undetectable" if the fluorescent signal is not greater than 2-fold the background signal when omitting the primary detection antibody, or has similar fluorescence staining to a control cell that does not express the marker (i.e., is negative for the marker). If the assay is a microarray assay, then expression of the marker is considered "undetectable" if the relative intensity is less than 2-fold higher than a negative control sample.

The term "low levels" refers to marker expression that is at least 2-fold, but not more that 5-fold greater than the background expression or expression by a negative control. For example, if the assay is an immunofluorescence (IF) staining assay, then expression is considered "low levels" if the fluorescent signal is at least 2-fold and not more than 5-fold greater than the background signal when omitting the primary detection antibody, or is at least 2-fold and not more than 5-fold greater than the fluorescence signal of a control cell that does not express the marker (i.e. is negative for the marker). In IF staining, low level of expression also means the fluorescent intensity is more than 2-fold lower than a positive control sample (e.g., a bile duct lineage differentiated cell). In microarray assays, low level of expression also means the RNA expression is at least 2-fold lower than a positive control sample (e.g., bile duct lineage differentiated cells).

DETAILED DESCRIPTION OF THE INVENTION

The present inventors have developed methods for producing liver stem cells (LSC) that can be used to produce mature, differentiated hepatocytes and cholangiocytes in culture. The inventors have developed cell culture systems that produce a homogenous population of liver stem cells that maintain the ability to proliferate in culture and remain in an undifferentiated state over multiple passages, which was confirmed by the expression of stem cell markers during extended culture. The methods and cells described herein provide the unexpected advantage of providing a source of liver stem cells that can be used to produce differentiated mature hepatocytes and cholangiocytes at high frequency.

Figure 11:
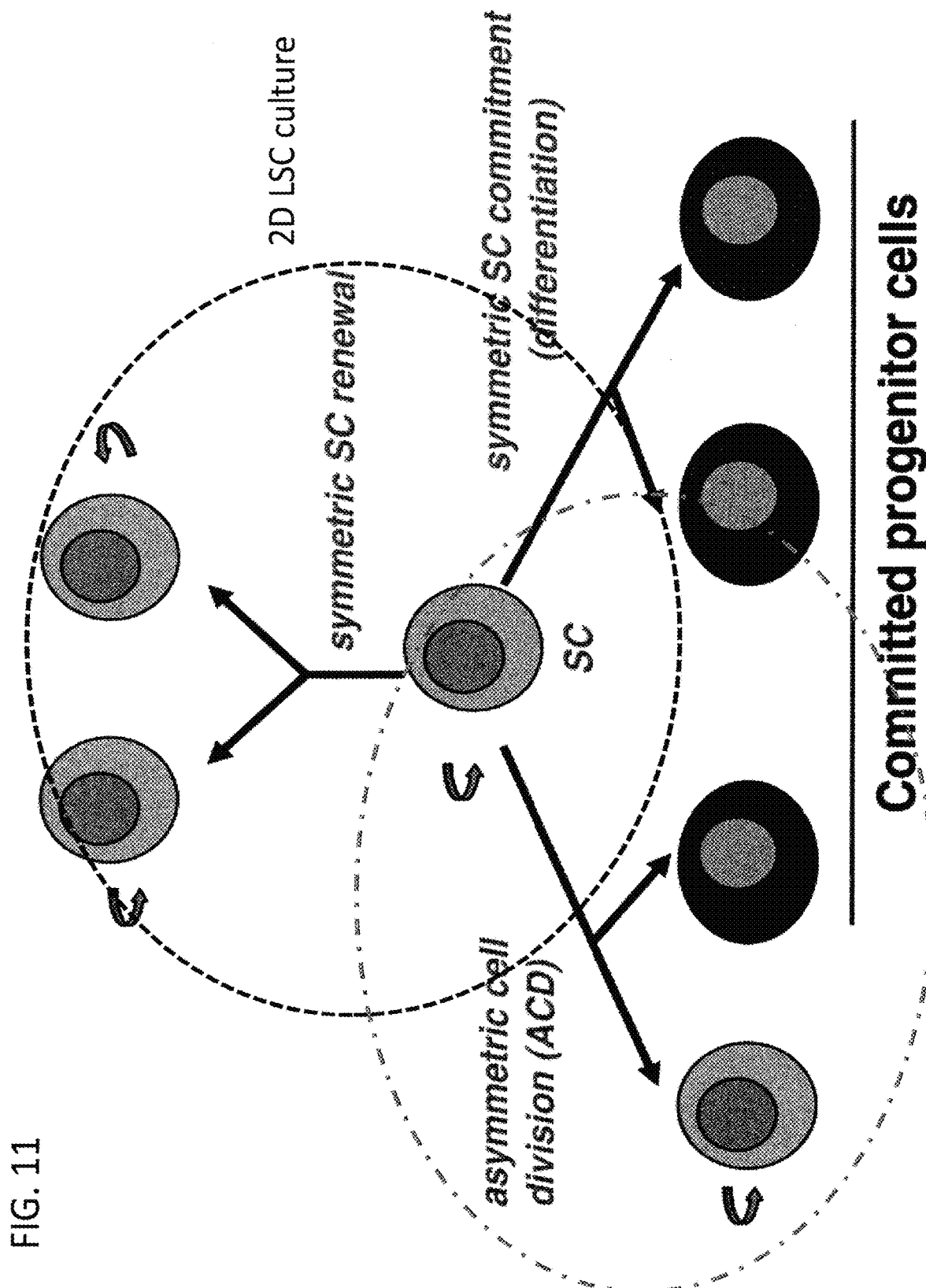
FIG. 11: Relationship between stem cell self-renewal and differentiation (or commitment). Stem cell self-renewal can occur in two ways: symmetric renewal and asymmetrical divisions. Stem cells go through symmetric renewal to expand the pool of stem cells, but they undergo asymmetric division to generate differentiated cells, and stem cells are present in a small proportion. Known liver organoids exhibit asymmetric division, and the organoid culture is a mixture of stem cells and differentiated bile duct cells. The 2D LSC culture goes through the symmetric renewal in that every stem cell was able to proliferate and maintained stem cell marker expression. This homogenous stem cells culture enables high efficiency differentiation to hepatocytes. Prior art cultures containing differentiated hepatocytes were always contaminated with a significant proportion of cholangiocytes. Furthermore, a pure stem cell population maintained in culture will increase the stem cell expansion efficiency.

Stem cell self-renewal and differentiation is tightly linked. Stem cells self-renew in two ways, symmetric renewal and asymmetrical divisions (FIG. 11). Symmetrical self-renewal enables stem cells to expand in numbers while during asymmetric division, differentiated cells are generated and stem cells are kept in a relatively small population. The hepatic stem cells described herein underwent symmetric self-renewal; every stem cell was able to proliferate and maintain stem cell marker expression. This homogenous stem cell culture provides the advantage of high efficiency in deriving hepatocytes and cholangiocytes. The homogeneity of stem cell culture also increases the stem cell expansion efficacy as fewer cells are lost through differentiation during maintenance or sub-culturing steps.

The ability to generate homogenous liver stem cell cultures enables efficient high-throughput generation of homogenous hepatocytes and cholangiocytes for downstream applications. When liver stem cell populations are non-homogenous, the differentiation process results in a mixture of immature and mature hepatocytes and cholangiocytes. This mixture of cells would result in deviations and erroneous observations in applications. For example in the assessment of drug induced toxicity, the drug may target only mature hepatocytes in the dish and remaining cells remain viable. This results in erroneous conclusions regarding drug toxicity. On the other hand, the compound may be affecting the immature cells and cholangiocytes instead of the mature hepatocytes. When the starting culture is non-homogenous, the proportion of cells varies in each set of differentiation, thus resulting in inconsistency between each set of experiments. This will be detrimental for assays such as in vitro toxicity which requires high standardization between each runs. Large amount of cells would be needed for in vivo transplantation. A heterogeneous stem cell culture will only generate small amount of target cells. It will be a challenging task to generate sufficient cells for transplantation without a homogenous starting population of stem cells.

The liver stem cells (LSC) described herein include the following desirable characteristics:
  (i) the stem cells are bipotential and maintained their undifferentiated and bipotential state during long term culture;
  (ii) the stem cells can be differentiated in vitro into mature bile duct cells (cholangiocytes) expressing the ductal markers KRT7 and KRT19, polarized columnar cell phenotype, typical tubular structure, and cilia on the luminal surface of the cells;
  (iii) the stem cells can be differentiated in vitro into mature functional hepatocytes by 2D, 3D and air-liquid interface (ALI) differentiation methods;

(iv) the differentiated hepatocytes (dHEP) were functional based on several different phenotypes, including glucose and lipid metabolism, and CYP function (four different CYP enzymes);
(v) the stem cells were generated from both healthy donor and liver disease patients, and the stem cells from diseased patients maintained the liver disease phenotype;
(vi) the stem cells differentiated into functional (albumin secreting) hepatocytes in vivo when transplanted into mouse liver using a in vivo model of liver cirrhosis (the chemical induced liver mouse model); and
(vii) stem cells differentiated in vitro into hepatocytes were able to repopulate injured mouse liver and execute hepatocyte functions.

Specific embodiments will now be described.

Liver Stem Cell Culture System

The liver stem cell culture system described herein comprises a plurality of soluble agents in a stem cell culture media and a cellular support capable of providing structural and nutritional support. The cellular support maintains the liver stem cells in a monolayer adhesion, thus preventing the formation of 3D structures such as spheroids or organoids. The cellular support provides both structural support and cytokines that plays a part in maintaining liver stem cells in the undifferentiated state. In some embodiments, the cellular support maintains the liver stem cells in a 2D structure (such as a monolayer). In some embodiments, the plurality of soluble agents comprises one or more growth factors, an enhancer of the (canonical) WNT pathway, and a stem cell differentiation inhibitor.

The liver stem cell culture system described herein comprises a liver stem cell culture media having one or more of the following ingredients: a stem cell differentiation inhibitor (e.g., a TGF-beta signaling inhibitor), a WNT agonist, thyroid hormone(s), a growth factor, and Nicotinamide. In some embodiments, the liver stem cell culture system comprises a liver stem cell culture media having or consisting of all of the following ingredients: a stem cell differentiation inhibitor (e.g., a TGF-beta signaling inhibitor), a WNT agonist, thyroid hormone(s), a growth factor, and Nicotinamide. In some embodiments, the liver stem cell culture system comprises a liver stem cell culture media having or consisting of all of the following ingredients: a stem cell differentiation inhibitor (e.g., a TGF-beta signaling inhibitor), a WNT agonist, cholera enterotoxin, a growth factor, and Nicotinamide.

In some embodiments, the stem cell differentiation inhibitor is a TGF-beta signaling inhibitor. For example, the TGF-beta inhibitor can block activation of TGF-beta pathway, which induces stem cell differentiation, whereas inactivation of the TGF-beta pathway maintains liver stem cells during long term culture. In some embodiments, the TGF-beta inhibitor is selected from the group consisting of A83-01 (3-(6-Methyl-2-pyridinyl)-N-phenyl-4-(4-quinolinyl)-1H-pyrazole-1-carbothioamide) and SB431542 (4-[4-(1,3-benzodioxol-5-yl)-5-(2-pyridinyl)-1H-imidazol-2-yl]benzamide). In some embodiments, the concentration of SB431542 in the cell culture system is between about 0.1 ng/ml and about 10 ng/ml, e.g., from about 0.1 ng/ml to about 10 ng/ml, or about 0.5 ng/ml to about 8 ng/ml, or about 2 ng/ml to about 7 ng/ml, or about 0.1 µM to about 10 µM, or about 1 µM to about 10 µM, or about 2 µM, or about 3 µM, or about 4 µM, or about 5 µM, or about 6 µM, or about 7 µM, or about 8 µM, or about 9 µM.

The enhancer of the canonical WNT pathway stimulates liver stem cell proliferation. In the absence of the enhancer of the canonical WNT pathway, the liver stem cells may undesirably differentiate into matured liver cells. In some embodiments, the enhancer of the canonical WNT pathway is a WNT agonist. In some embodiments, the WNT agonist is selected from the group consisting of a Wnt family member (Wnt-1/Int-1, Wnt-2/Irp (Int-1-related Protein), Wnt-2b/13, Wnt-3/Int-4, Wnt-3a, Wnt-4, Wnt-5a, Wnt-5b, Wnt-6, Wnt-7a, Wnt-7b, Wnt-8a/8d, Wnt-8b, Wnt-9a/14, Wnt-9b/14b/15, Wnt-10a, Wnt-10b/12, Wnt-11, and Wnt-16); an R-spondin family member (R-spondin 1, R-spondin 2, R-spondin 3, and R-spondin 4), Norrin (Norrie Disease Protein or NDP), and Norrin (Norrie Disease Protein or NDP), a Glycogen synthase kinase 3 inhibitor selected from small-interfering RNAs, lithium, kenpaullone, 6-Bromoindirubin-30-acetoxime, SB 216763 (3-(2,4-Dichlorophenyl)-4-(1-methyl-1H-indol-3-yl)-1H-pyrrole-2,5-dione), SB 415286 (4-[4-(1,3-benzodioxol-5-yl)-5-(2-pyridinyl)-1H-imidazol-2-yl]benzamide; CHIR 99021 (6-[[2-[[4-(2,4-Dichlorophenyl)-5-(5-methyl-1H-imidazol-2-yl)-2-pyrimidinyl]amino]ethyl]amino]-3-pyridinecarbonitrile), CHIR 99021 trihydrochloride (6-[[2-[[4-(2,4-Dichlorophenyl)-5-(5-methyl-1H-imidazol-2-yl)-2-pyrimidinyl]amino]ethyl]amino]-3-pyridinecarbonitrile trihydrochloride), Kenpaullone, Indirubin-3'-oxime, MeBIO ((2'Z,3'E)-6-Bromo-1-methylindirubin-3'-oxime) TCS 2002 (2-Methyl-5-[3-[4-(methylsulfinyl)phenyl]-5-benzofuranyl]-1,3,4-oxadiazole), Lithium carbonate, NSC 693868 (1H-Pyrazolo[3,4-b]quinoxalin-3-amine), TCS 21311 (3-[5-[4-(2-Hydroxy-2-methyl-1-oxopropyl)-1-piperazinyl]-2-(trifluoromethyl)phenyl]-4-(1H-indol-3-yl)-1H-pyrrole-2,5-dione), AR-A 014418 (N-[(4-Methoxyphenyl)methyl]-N'-(5-nitro-2-thiazolyl)urea), 3F8 (5-Ethyl-7,8-dimethoxy-1H-pyrrolo[3,4-c]isoquinoline-1,3(2H)-dione), L803 (Peptide KEAP-PAPPQSP), A 1070722 (1-(7-Methoxyquinolin-4-yl)-3-[6-(trifluoromethyl)pyridin-2-yl]urea), 10Z-Hymenialdisine, TC-G 24 (N-(3-Chloro-4-methylphenyl)-5-(4-nitrophenyl)-1,3,4-oxadiazol-2-amine), TWS 119 3-[[6-(3-Aminophenyl)-7H-pyrrolo[2,3-d]pyrimidin-4-yl]oxyphenol ditrifluoroacetate]), and L803-mts (peptide GKEAPPAPPQSP); a FRAT-family member (FRAT: frequently rearranged in advanced T-cell lymphomas) and FRAT-derived peptides. In some embodiments, the Wnt agonist is R-spondin. In certain embodiments, the concentration of R-spondin in the stem cell culture medium is between about 25 and about 500 ng/ml, e.g., about 25, 50, 100, 125, 250, or 500 ng/ml. In some embodiments, the concentration of R-spondin 1 in the stem cell culture system is between about 25 and about 500 ng/ml, or about 100 ng/ml to about 500 ng/ml, or about 110 ng/ml to about 400 ng/ml, or about 150 ng/ml to about 350 ng/ml, or about 200 ng/ml to about 300 ng/ml, or about 230 ng/ml to about 270 ng/ml, or about 25 ng/ml, or about 50 ng/ml, or about 100 ng/ml, or about 125 ng/ml, or about 235 ng/ml, or about 240 ng/ml, or about 245 ng/ml, or about 250 ng/ml, or about 255 ng/ml, or about 260 ng/ml, or about 265 ng/ml, or about 500 ng/ml.

In some embodiments, the growth factor is Epidermal Growth Factor (EGF) and/or thyroid hormone. In some embodiments, the growth factor is EGF. In some embodiments, the concentration of Epidermal Growth Factor (EGF) in the stem cell culture medium was between about 5 ng/ml and about 200 ng/ml, e.g., from about 5 ng/ml to about 200 ng/ml, or about 10 ng/ml to about 150 ng/ml, or about 35 ng/ml to about 100 ng/ml, or about 40 ng/ml to about 60 ng/ml, or about 41 ng/ml, or about 42 ng/ml, or about 43 ng/ml, or about 44 ng/ml, or about 45 ng/ml, or about 46 ng/ml, or about 47 ng/ml, or about 48 ng/ml, or about 49 ng/ml, or about 50 ng/ml, or about 51 ng/ml, or about 52 ng/ml, or about 53 ng/ml, or about 54 ng/ml, or about 55 ng/ml, or about 56 ng/ml, or about 57 ng/ml, or about 58 ng/ml, or about 59 ng/ml.

In some embodiments, the growth factor is thyroid hormone. In some embodiments, the thyroid hormone is selected from the group consisting of 3,3'-5-triiodo-1-thyronine (T3), (5)-thyroxine (T4), and hormones that stimulate cAMP, such as parathyroid hormone (PTH), the adenosine A2 receptor agonist 5'-(N-ethylcarboxamido)-adenosine (NECA), prostaglandin E2, or forskolin. In some embodiments, the thyroid hormone is T3. In some embodiments, the concentration of T3 in the cell culture system is between about 0.2 µM and about 20 µM, e.g., from about 0.2 µM to about 20 µM, or about 0.1 µM to about 15 µM, or about 1 µM, or about 2 µM, or about 3 µM, or about 4 µM, or about 5 µM, or about 6 µM, or about 7 µM, or about 8 µM, or about 9 µM, or about 10 µM, or about 11 µM, or about 12 µM, or about 13 µM, or about 14 µM.

In some embodiments, the concentration of Nicotinamide in the stem cell culture system is between about 1 mM and about 50 mM, e.g., from about 1 mM to about 50 mM, or about 1 mM to about 25 mM, or about 5 mM to about 15 mM, or about 6 mM, or about 7 mM, or about 8 mM, or about 9 mM, or about 10 mM, or about 11 mM, or about 12 mM, or about 13 mM, or about 14 mM.

Figure 12:
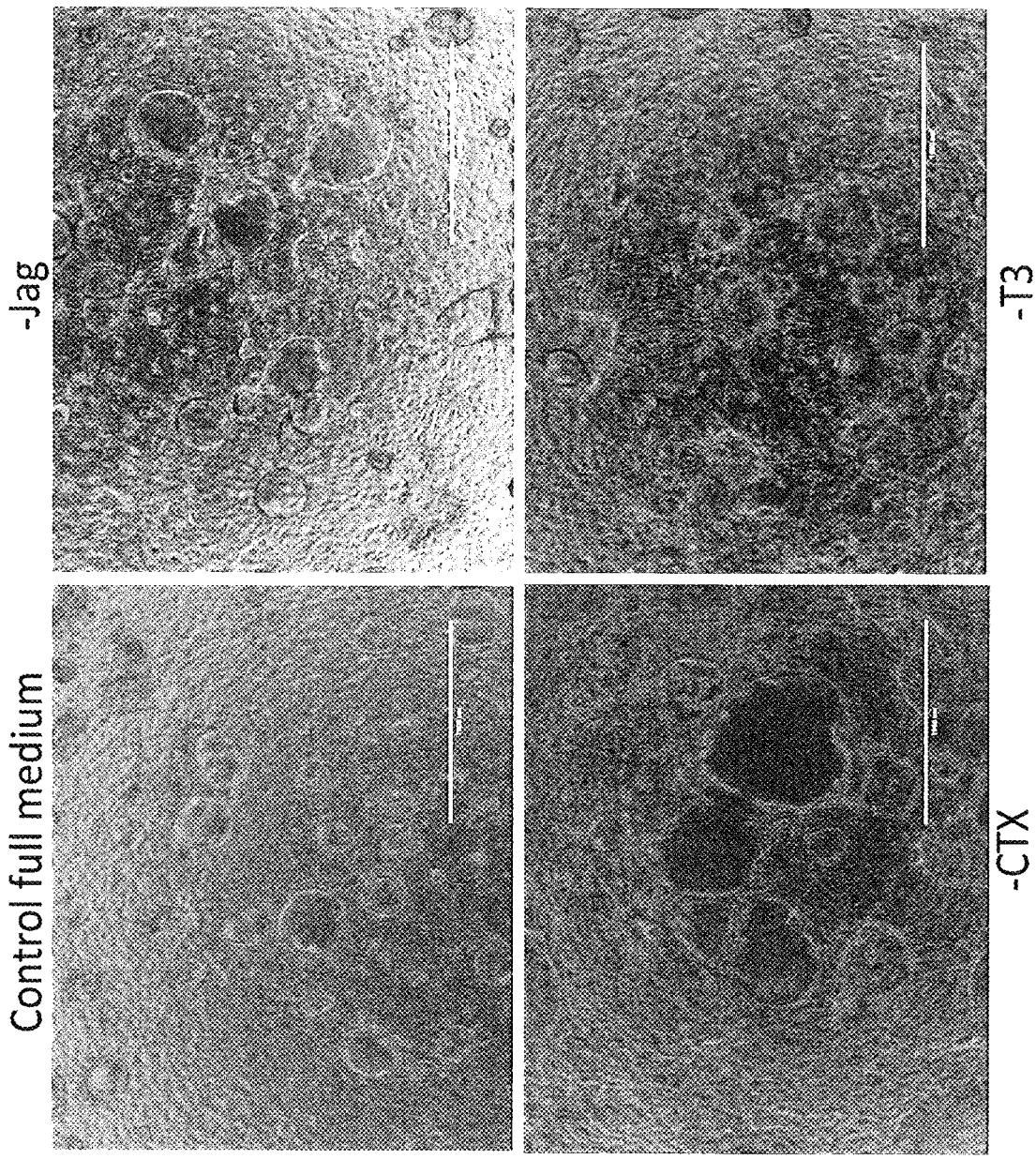
FIG. 12: Minimal medium for LSC culture. Bright field images of LSCs grown in different media conditions for six passages. Full medium—Jagged1: cells keep growing in undifferentiated status. Full medium—CTX (cholera enterotoxin): cells grow faster than full medium but cells are loose (not so compact) and can be passaged. CTX not critical but help to maintain the cells in good undifferentiated quality. Full medium—T3: cells colony morphology changed. Cells trend towards differentiation but still could be passaged.
Figure 14:
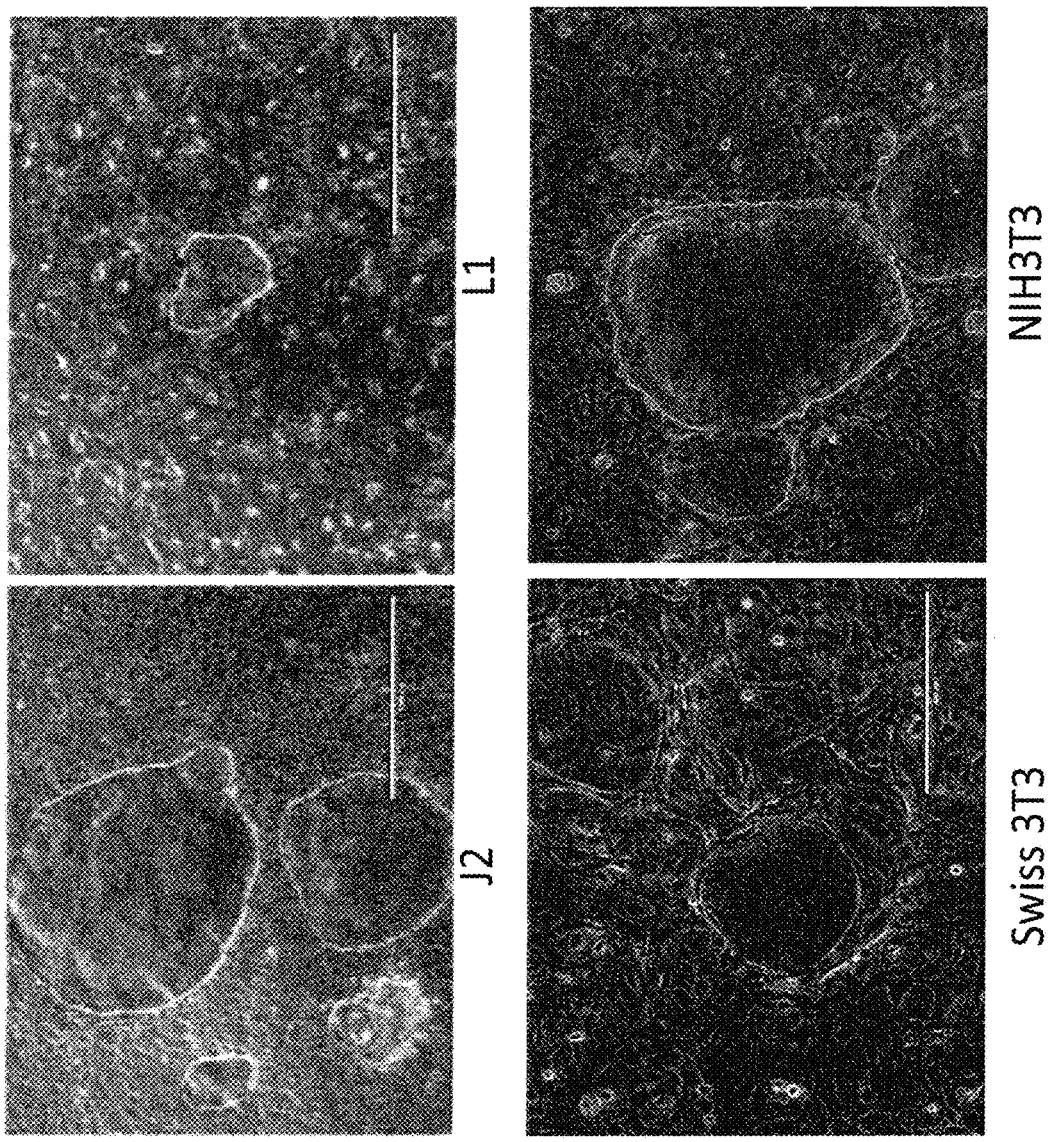
FIG. 14: LSC derived on fibroblast feeders. Brightfield images of LSC cells were cultured on J2, L1, Swiss 3T3, NIH3T3 separately. J2 feeder cultured LSC formed the largest colony. L1 formed the smallest colony. We continued culturing for more than one year for J2, but did not test beyond that time frame. Swiss3T3, NIH3T3, L1 also could support LSC growing for at least 5 passages. We did not test longer than this timeframe.

In some embodiments, the liver stem cell culture media can also optionally include Cholera enterotoxin (also called Cholera endotoxin) (CTX). Cholera toxin was added in the culture to minimize presence of differentiated cells. In some embodiments, the concentration of Cholera endotoxin in the media was between about 0.01 µM and about 1 µM, e.g., from about 0.01 µM to about 1 µM, or about 0.05 µM to about 0.9 µM, or about 0.95 µM, or about 0.05 µM, or about 0.1 µM, or about 0.2 µM, or about 0.3 µM, or about 0.4 µM, or about 0.5 µM, or about 0.6 µM, or about 0.7 µM, or about 0.8 µM, or about 0.9 µM. Higher concentrations (>0.1 µM) of cholera endotoxin inhibited cell proliferation rather than stimulating growth. As shown in FIG. 12, CTX is not required, but helps maintain the stem cells in an undifferentiated state. In some embodiments, CTX can replace thyroid hormone (such as T3) as an agent that can stimulate the cell to release cAMP and increase the cell's metabolic rate.

In some embodiments, the liver stem cell culture media is a serum-free media. Adding 2%, 5%, 8%, 10%, 15% and 20% fetal bovine serum (FBS) and withdrawing B27 and N2 from the culture medium simulated stem cell differentiation. The differentiated cells expressed higher Krt7 and Krt19 than undifferentiated stem cells, but lower or no HNF4α expression. Thus, including B27 and N2 in the medium helped to maintain the stem cells in the undifferentiated status, but FBS failed to do so and instead stimulated stem cell differentiation (FIG. 13).

Bone Morphogenetic Protein (BMP) antagonists have been reported to be essential for liver epithelial stem cell culture (see WO2014152321 A1). However, the culture medium does not require an antagonist or inhibitor of BMP. Thus, in some embodiments, the culture system does not comprise an antagonist or inhibitor of BMP. For example, the BMP antagonist Noggin was not added to the culture medium.

In some embodiments, the culture system does not comprise HGF (Hepatocyte Growth Factor), and/or FGF (Fibroblast Growth Factor).

In certain embodiments, N-Acetyl-Cysteine (NAC) was added in the culture medium to attenuate reactive-oxygen-species-mediated stress in cell culture. It helped to maintain the liver stem cell in undifferentiated status especially in long term culture. In some embodiments, the concentration of N-acetyl-cysteine in the cell culture media is between about 0.1 µM and about 10 µM, for example, from about 0.1 µM to about 10 µM, or about 1 µM to about 10 µM, or about 2 µM, or about 3 µM, or about 4 µM, or about 5 µM, or about 6 µM, or about 7 µM, or about 8 µM, or about 9 µM.

In certain embodiments, an agent for activating the Notch pathway was optionally added to the culture medium to stimulate cell proliferation. In some embodiments, the agent for activating the Notch pathway is a Notch ligand. In some embodiments, the Notch ligand is Jagged-1. In some embodiments, Jagged-1 has the amino acid sequence CDDYYYGFGCNKFCRPR (SEQ ID NO:1). In some embodiments, 0.1, 0.5, 1, 5, 10 µM Jagged-1 was added in the culture medium to stimulate the cell proliferation. In some embodiments, the concentration of Jagged-1 in the culture medium is between about 0.1 µM to about 10 µM, or about 1 µM to about 10 µM, or about 0.1 µM, or about 0.5 µM, or about 1.0 µM, or about 2 µM, or about 3 µM, or about 4 µM, or about 5 µM, or about 6 µM, or about 7 µM, or about 8 µM, or about 9 µM.

In some embodiments, the liver stem cell culture medium comprises or consists of about 0.1% to about 5% N2, about 0.1% to about 5% B27, between about 5 ng/ml and about 200 ng/ml EGF, between about 25 and about 500 ng/ml R-Spondin 1, between about 0.1 µM and about 10 µM SB431542 (4-[4-(1,3-benzodioxol-5-yl)-5-(2-pyridinyl)-1H-imidazol-2-yl]benzamide), between about 0.1 µM to about 10 µM T3 (3,3',5-Triiodo-L-Thyronine), and between about 1 mM and about 50 mM Nicotinamide. In some embodiments, the liver stem cell culture medium further comprises a basal medium such as advanced F12/DMEM reduced serum medium, a buffer such as HEPES (e.g., about 1 to about 50 mM HEPES), an antibiotic such as about 10 to about 200 U/ml Pen/Strep, and an amino acid, such as about 0.5 to about 5 mM L-Glutamine.

In one embodiment, the liver stem cell culture medium comprises or consists of Advanced F12/DMEM reduced serum medium (1:1)(Gibco. 12643), 10 mM HEPES (Gibco), 100 U/ml Pen/Strep (Gibco), 2 mM L-Glutamine (Gibco), 1% N2 (Gibco), 2% B27 (Gibco), 50 ng/ml EGF (Millipore), 250 ng/ml R-Spondin1 (R&D), 2 µM SB431542 (Tocris)), 2 µM T3 (3,3',5-Triiodo-L-Thyronine)(Sigma), and 10 mM Nicotinamide (Sigma).

In some embodiments, mouse fibroblasts were used as feeder cells in the liver stem cell culture. Mouse fibroblasts used as feeder cells for liver stem cell cultures included 3T3J2, Swiss3T3, NIH3T3 and L1 cells. However, it is understood that cells from other organisms, e.g., fibroblast cells from other mammals, can be used as feeder cells. For example, human fibroblast cells can be used as feeder cells.

In certain embodiments, 1%, 2%, 5%, or 10% Matrigel was used to coat the culture dish before thawing the cryopreserved fibroblast cells. Matrigel was diluted with advanced F12/DMEM basal medium. 10% Matrigel supplied nutrition to the fibroblast feeder cells and helped the fragile irradiated feeder cells to attach firmly to the culture plate, so that the feeder cells could be used for at least 2 weeks to support the stem cells. This coating step is optional, since early passage (<10 passage) J2 was able to support the stem cell without Matrigel coating.

In certain embodiments, fibroblast feeder density lower than $0.5 \times 10^6$ cells per 10 cm culture plate failed to maintain the stem cells in undifferentiated status. The fibroblast feeder provides both attachment support and secretes growth factors and cytokines that sustain the hepatic stem cell state.

Thus, low density of feeders may result in insufficient growth factors to support stem cell growth.

In certain embodiments, liver stem cells were maintained using feeder-cell free cultures. In some embodiments, the liver stem cells were cultured on an extracellular matrix comprising a mixture of Collagen I/Collagen IV, and Laminin 511/Laminin 521 without feeder cells in feeder-cell conditioned medium. As shown in FIG. 15, the feeder-free culture could be used to maintain the liver stem cells in an undifferentiated state for up to 5 passages. In some embodiments, the extracellular matrix does not induce stem cell differentiation. For example, the extracellular matrix can be a growth factor free (such as TGF-beta free) or growth factor reduced matrix, such that it does not stimulate stem cell differentiation.

Liver Stem Cells

Figure 2:
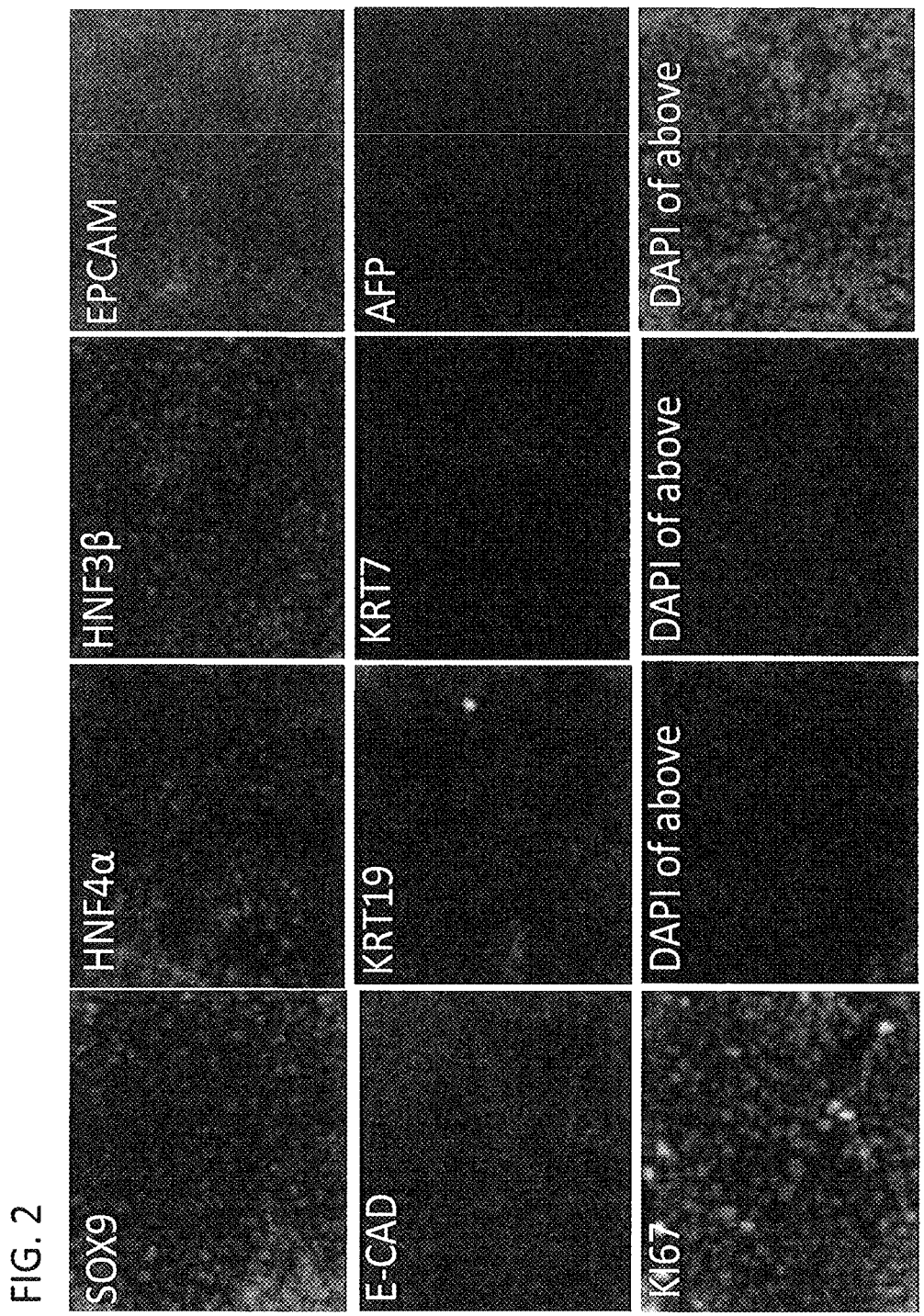
FIG. 2: Isolation and derivation of adult human liver bipotent stem cell. Isolation and derivation of liver stem cell (LSC) from human liver tissue. Immunofluorescence staining (IF) of LSC derived from human liver tissue. LSC expressed stem cell marker Sox9, epithelial marker EPCAM and hepatocyte markers HNF4a and HNF3β. Bile duct marker Krt19 was lowly expressed. KRT7 and AFP were not detected. KRT7 is a cholangiocyte differentiation marker and Afp is expressed by immature hepatocytes. E-Cadherin (E-CAD), another epithelial cell marker, was also expressed in LSC. KI67 was homogenously expressed in LSC, indicating that all of the stem cells were proliferating. The figure shows that LSC is a near homogenous proliferating epithelial stem cell population (hepatocytes and cholangiocytes are of the epithelial lineage), and their marker expression is consistent with bipotent (hepatocyte and cholangiocyte) differentiation potential. KRT7 and KRT19 are bile duct markers. In previous reports, the cells strongly expressed KRT19 and KRT7, suggesting they are primed towards the bile duct lineage. The LSC express low levels of KRT19 and did not express KRT7, indicating they were not primed towards the bile duct lineage.
Figure 4:
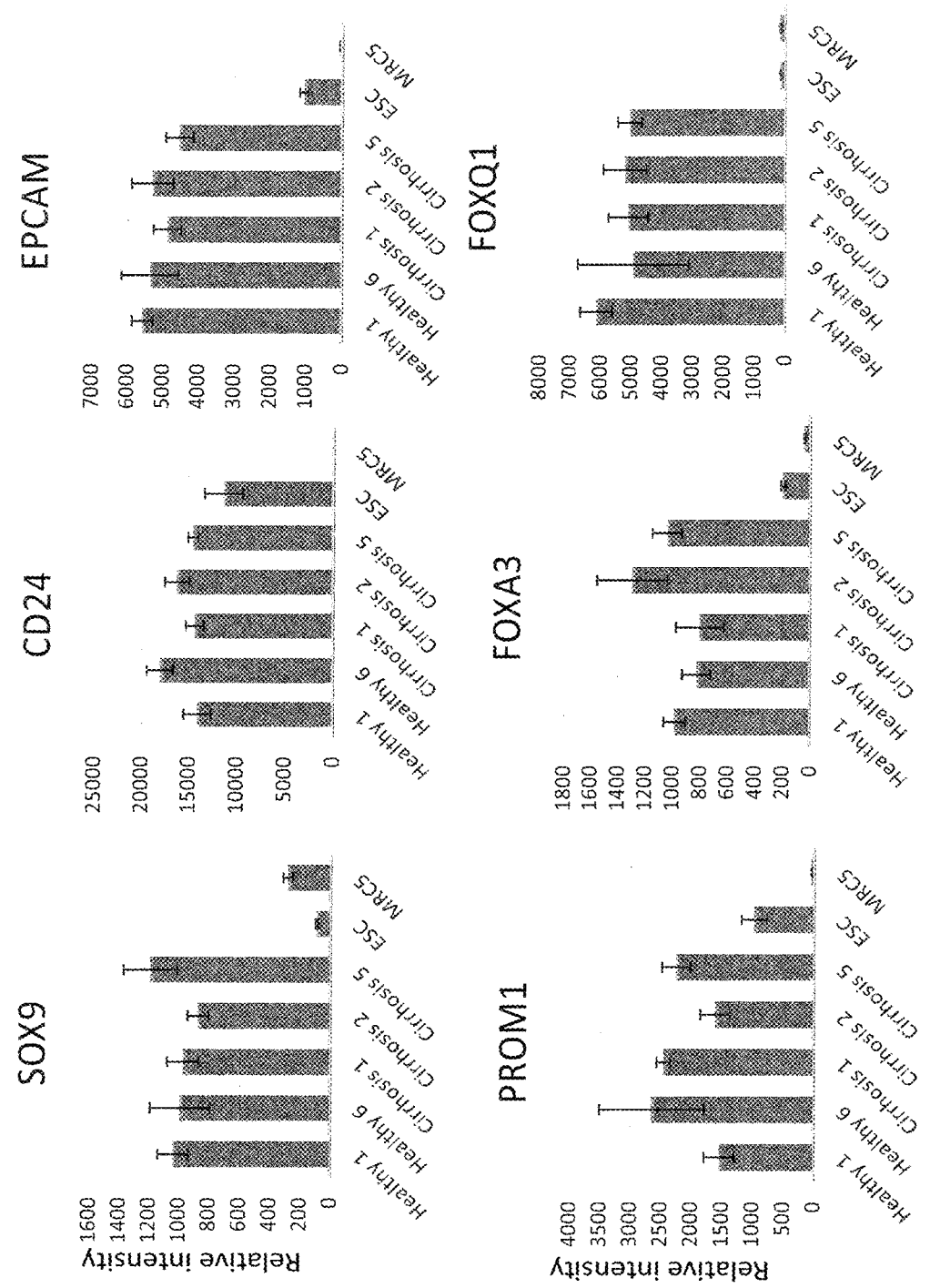
FIG. 4: Human liver stem cell express liver stem cell markers. Microarray analysis of LSC, ESC (embryonic stem cell) and MRC5 human fibroblast. LSC were isolated from individual healthy donors and liver cirrhosis patients. All of LSC from different patients and donors express human liver stem cell markers SOX9, CD24 Molecule (CD24), EPCAM, Prominin 1 (PROM1), Forkhead Box A3 (FOXA3) and Forkhead Box Q1 (FOXQ1). Y-axis indicated the gene expression relative intensity.
Figure 8:
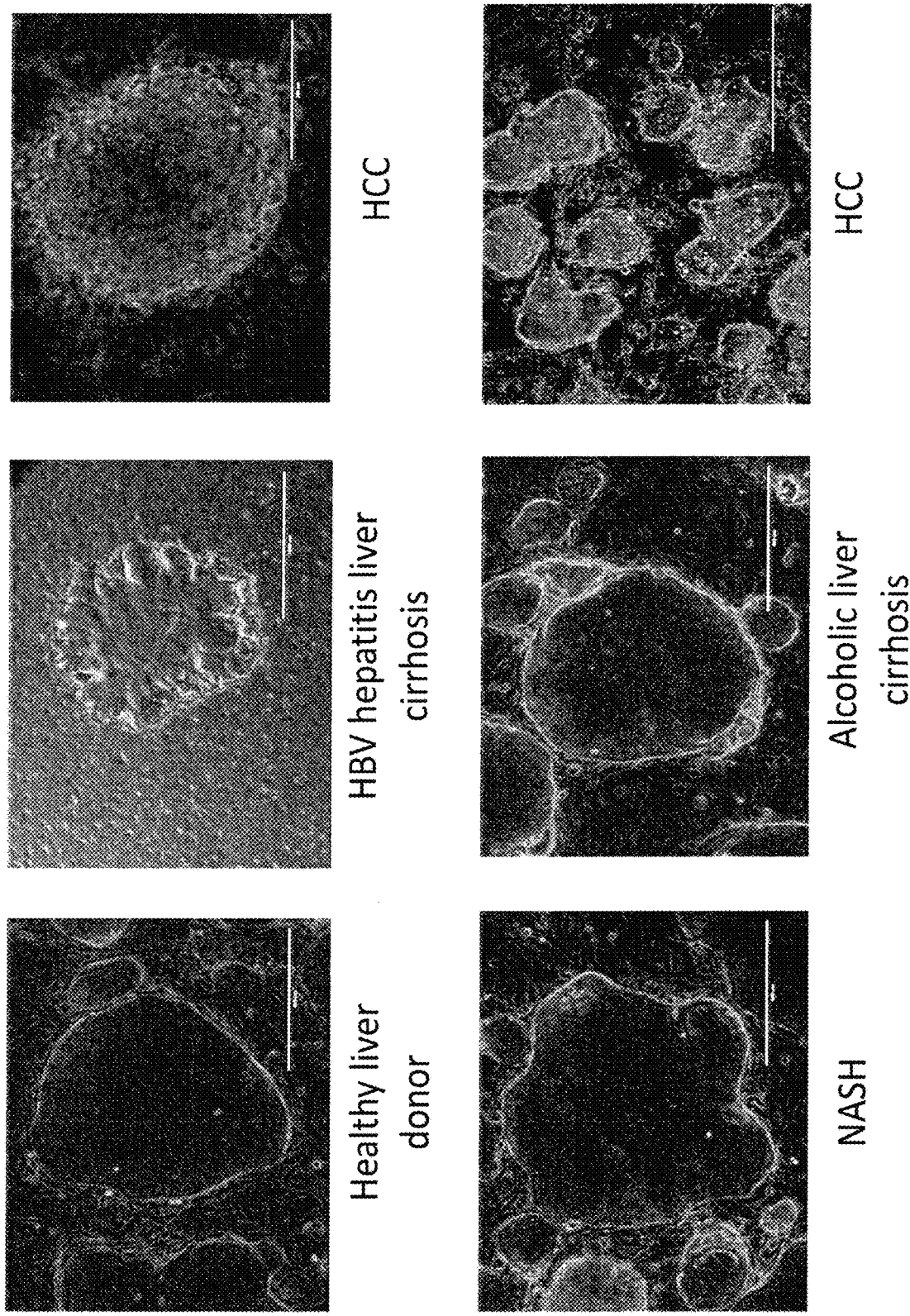
FIG. 8: LSC was derived from both healthy liver donor and liver disease patients. Brightfield images of LSC derived from liver diseased patients including HBV induced liver cirrhosis, alcoholic liver cirrhosis, hepatocarcinoma (HCC), Nonalcoholic Fatty Liver Disease (NAFLD) and Nonalcoholic Steatohepatitis (NASH). All of the LSC expressed liver stem cell markers: Epcam, SOX9, HNF4a, KRT19; HCC LSC expressed AFP and alb. Therefore LSC could be derived from both healthy and diseased livers.

Liver stem cells described herein could be generated from both hepatocyte and non-hepatocyte liver populations in the liver. The human hepatic stem cells express adult stem cell marker SOX9 and hepatocyte markers HNF4α and HNF3β (FIG. 2). The undifferentiated stem cells expressed low levels of Bile duct marker KRT19 (Accession no: P08727.4), but did not express detectable levels of bile duct marker KRT7 (Accession no: P08729.5) (protein expression level as determined by immunofluorescence staining). The hepatic stem cells also expressed other liver stem cell markers EPCAM, CD24, PROM1, FOXA3 and FOXQ1 (FIG. 2, FIG. 4). Morphologically, undifferentiated stem cells were small, round in shape and clustered tightly together. The hepatic stem cells were not polarized (FIG. 8). Almost all the cells in culture were proliferating as all the cells expressed Ki67 in the cell nucleus (FIG. 2). The hepatic stem cells described herein differ from naturally occurring stem cells. For example, naturally occurring stem cells have not been reported to express the FOXA3 and FOXQ1 markers.

In some embodiments, the liver stem cell described herein comprises the following characteristics:
  (i) expresses at least 1, 2, 3 or 4 of the protein markers selected from SOX9, HNF4a, HNF3β, and EPCAM;
  (ii) expresses low levels of KRT19 protein,
  (iii) does not express detectable protein levels of KRT7 or AFP; and
  (iv) does not have a polarized cell phenotype.

In some embodiments, the liver stem cell further expresses 1, 2, 3, 4, or 5 protein markers selected from CD24, PROM1, FOXA3, FOXQ1 and ECAD. The characteristics of the stem cell are maintained in long-term culture, and comprise a normal karyotype after 19 passages in culture.

The liver stem cell can be derived from a mammal, such that the liver stem cell can be a mammalian liver stem cell, a human liver stem cell, a mouse liver stem cell, or a fetal liver stem cell. In some embodiments, the liver stem cell is isolated from a healthy subject. In some embodiments, the liver stem cell is isolated from a subject with liver disease, wherein the liver disease is selected from the group of metabolic disease, autoimmune disease, infectious disease, drug induced acute and chronic liver failure, and liver cancer.

Figure 5A:
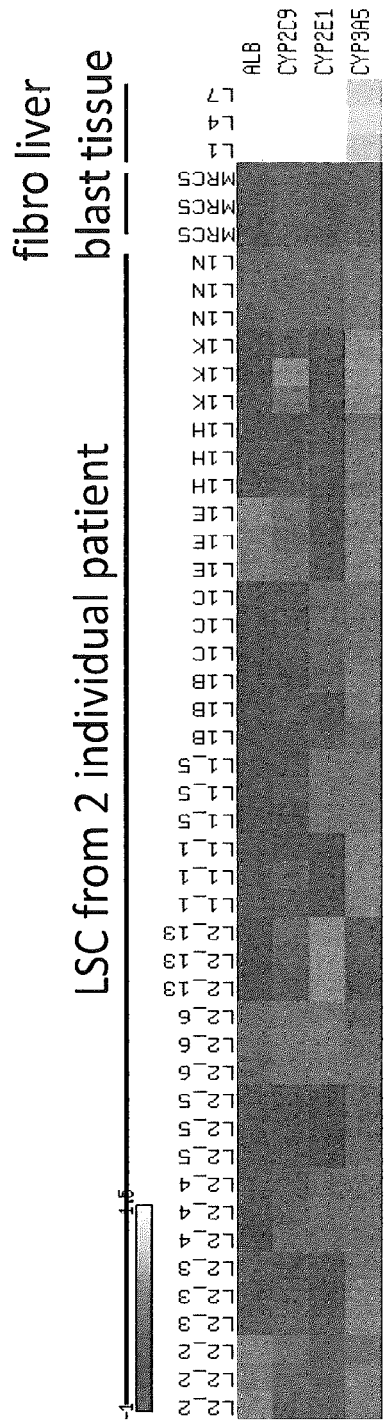
FIGS. 5A and 5B: Human liver stem cell express low level of hepatocyte markers.
Figure 5B:
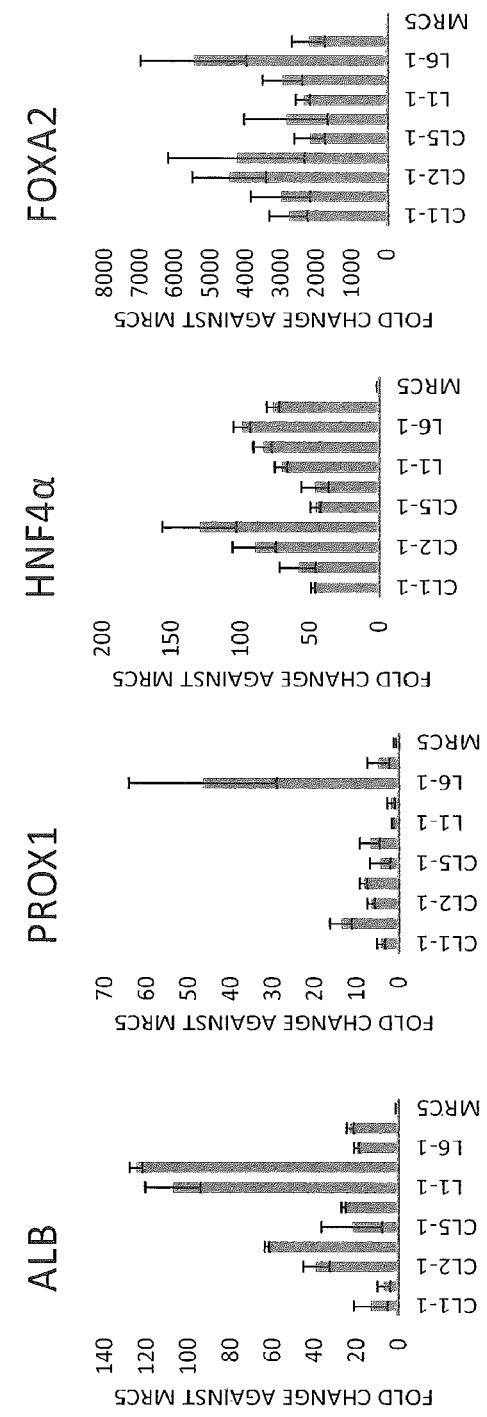
Figure 6:
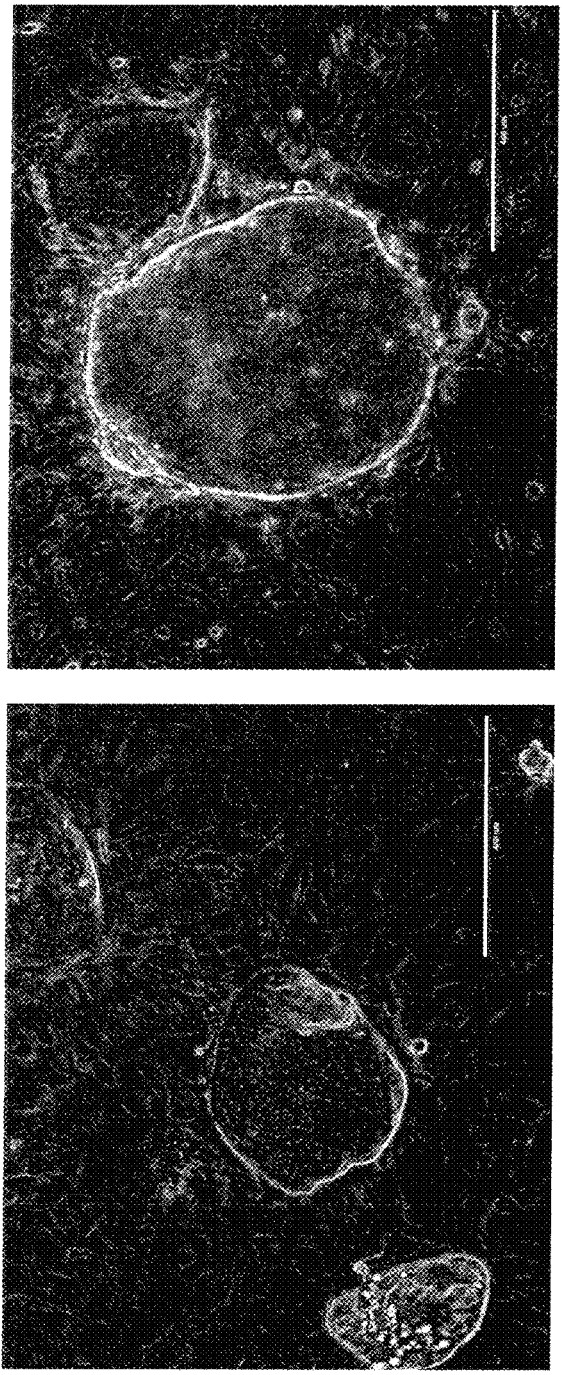
FIG. 6: The same culture system is able to derive liver stem cells from mouse and human fetal tissue. Mouse liver tissue and human fetal liver tissue was digested with the same adult human liver digestion method. The digested cells was plated on feeder with LSC medium. Mouse and human fetal liver stem cell formed colonies with small clustered cells. Bright field images of the LSCs are shown. These cells expressed liver stem cell marker Sox9, Hnf4a and EpCam. This figure shows human fetal, mouse and potentially other mammalian species' liver stem cells could be derived using the methods described herein.

As shown in FIG. 5A, human liver stem cells express low levels of hepatocyte markers Albumin (ALB), Prospero Homeobox 1 (PROX1), HNF4α and Forkhead Box A2 (FOXA2), CYP2C9, CYP 2E1 and CYP 3A5. As shown in FIG. 5B, qPCR validation of hepatocyte gene expression in LSC and MRC5 fibroblast cells shows that the bipotent liver stem cells have a hepatocyte gene signature but are distinct from differentiated liver cells.

Figure 3:
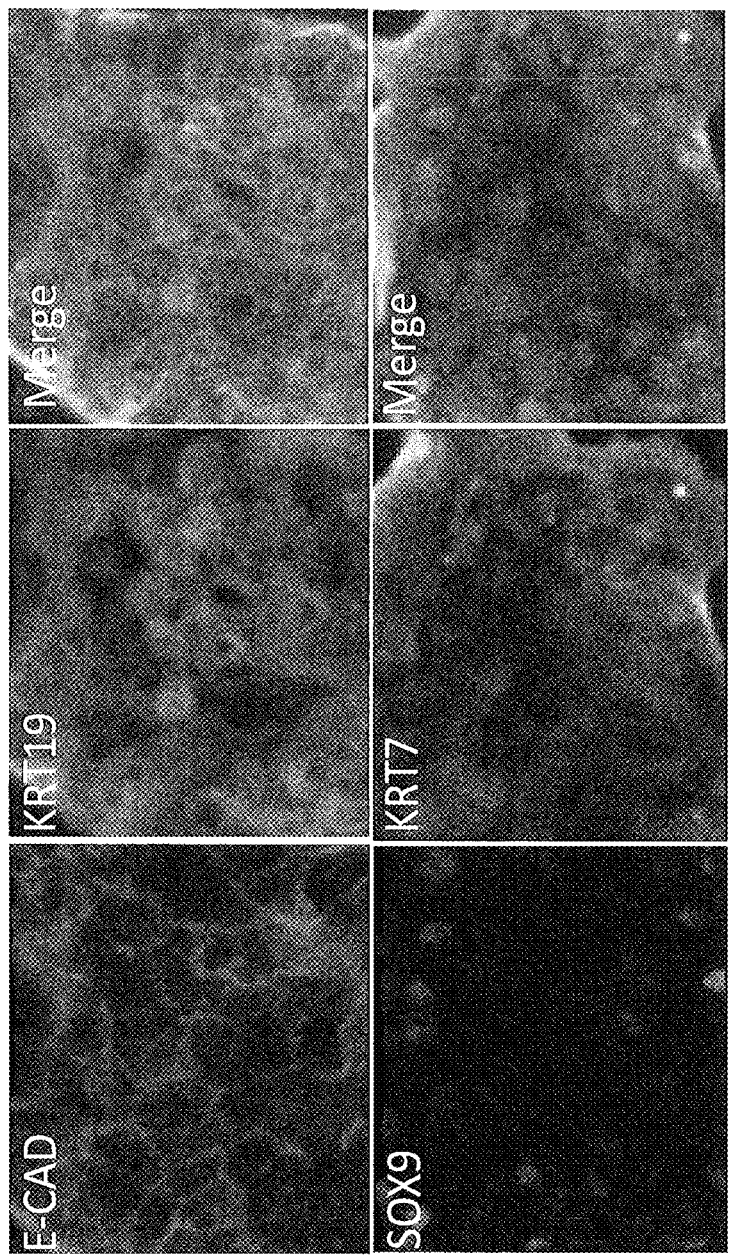
FIG. 3: Sporadic rare population of differentiated cells (bile duct lineage differentiation) express high level of KRT7 and KRT19, IF staining of LSC default differentiation with bile duct markers SRY (Sex Determining Region Y)-Box 9 (SOX9), KRT19 and KRT7. Undifferentiated LSC did not express KRT7 and low expression of KRT19, and rare sporadic differentiated LSC in the culture has strong expression of KRT7 and KRT19. The differentiated cells were irregular in shaped compared with undifferentiated LSC, which are round. They were flattened and were larger in size compared with undifferentiated LSC. The figure shows that differentiated cells were of bile duct lineage. KRT7 and KRT19 are not stem cell specific markers but are bile duct markers. In both prior art, their cells strongly expressed KRT19 and KRT7 suggesting they are primed towards the bile duct lineage.

During the maintenance of stem cells, colonies of differentiated cells were also observed. The differentiated liver cells showed strong levels of ECAD, KRT19, KRT7 expression and decreased expression of SOX9 (FIG. 3), consistent with the differentiated cells being ductal in nature. Sporadic differentiated cells were larger and flatter in shape (FIG. 3).

Figure 37:
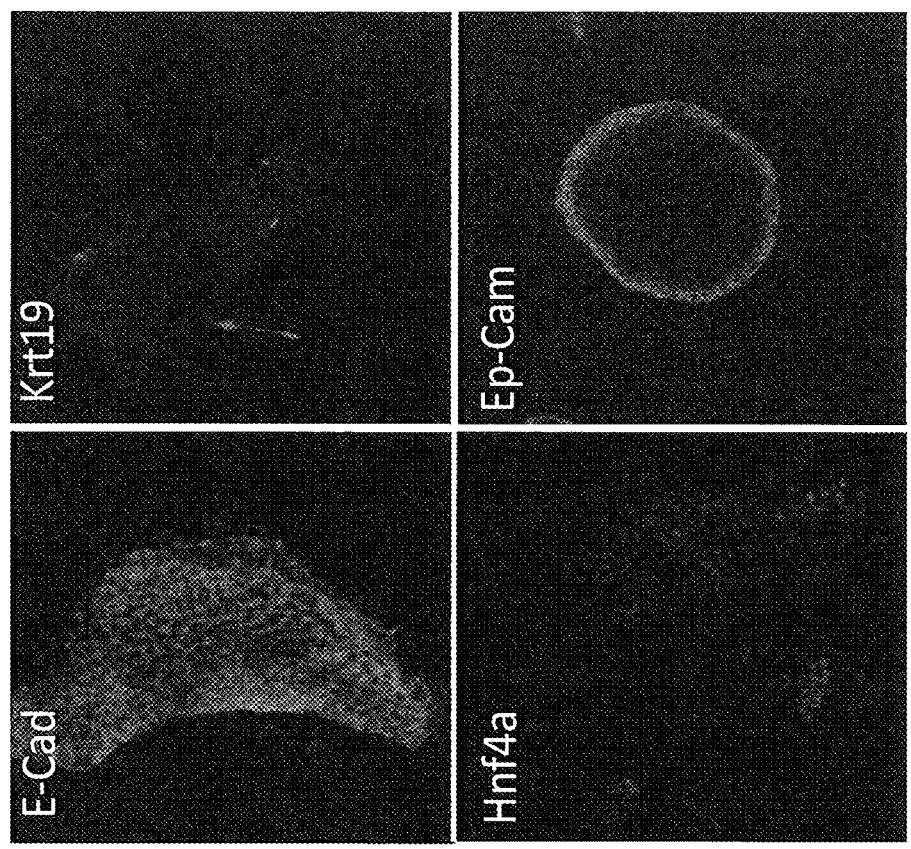
FIG. 37: Isolation and derivation of adult mouse liver stem cell (LSC). Immunofluorescence staining (IF) of LSC derived from mouse liver tissue. LSC expressed stem cell marker epithelial marker Epcam and hepatocyte marker Hnf4a. Bile duct marker Krt19 was lowly expressed and Krt7 was not detected. E-cad, an epithelial cell marker was also expressed in LSC. The figure shows that isolated and derived LSC is a homogenous epithelial stem cell population.

Mouse liver stem cells were also isolated using the methods described herein. As shown in FIG. 37, mouse liver stem cell expressed EPCAM and HNF4a, low levels of KRT19, but did not express detectable levels of KRT7.

The liver stem cells form disk like clones and push the non-soluble support (such as feeder cells) to the side. In one example, where the cellular support is provided under high density conditions (such as feeder cells at $>2\times10^6$ cells per 10 cm plate), the liver stem cells form dome shape clones, not spheres. In some embodiments, the liver stem cells form several wrinkle structures inside the clone in the early passage of cells when they were just derived from liver tissue. In some embodiments, the early passage is the first passage after isolation from liver tissue. "Early passage" refers to passage 0, or passage 0 to 1, or passage 0 to 2, or passage 0 to 3, or passage 0 to 4, where passage 0 is the first passage after isolation from liver tissue and before the isolated liver cells are cultured. The wrinkle structures typically disappear after continuing culture for several passages.

In contrast, the liver stem cells previously described in the art are:
  a. 100% positive of KRT19,
  b. around 50% KRT7 positive,
  c. E-CAD positive, EPCAM positive, SOX9 positive, and KRT7 positive,
  d. Less than about 70-100%, or less than about 100%, or less than about 90% or less than 80% positive for the transcription factor for hepatocyte lineage differentiation such as HNF4a,
  e. cultured as organoids with a mixture of partially differentiated bile duct cells and hepatocyte progenitor/stem cells; and
  f. when differentiated into hepatocytes, only have one functional CYP enzyme (CYP3A4).

Cell Culture System and Methods for Producing Differentiated Hepatocytes

Cell culture systems and methods for producing differentiated hepatocytes from liver stem cells are described herein. In some embodiments, the cell culture system comprises a plurality of soluble components comprising: at least one Notch inhibitor; at least one TGF-beta inhibitor; and conditions for inducing epithelial cell polarization of the liver stem cell. In some embodiments, the conditions for inducing epithelial cell polarization of the liver stem cell comprise culturing the liver stem cell at the air-liquid interface (ALI), Such that the basal side of the liver stem cell is in contact with the soluble components of the cell culture system and the apical surface of the liver stem cell is in contact with air.

In some embodiments, the plurality of soluble components further comprises at least one growth factor suitable for differentiating a liver stem cell into a hepatocyte. In some embodiments, the growth factor is selected from an IL6-like cytokine, including oncostatin M and LIF.

In some embodiments, the concentration of the growth factor in the system is from about 5 ng/ml to about 200 ng/ml, or about 10 ng/ml to about 100 ng/ml, or about 15 ng/ml to about 70 ng/ml, or about 20 ng/ml to about 50 ng/ml, or about 16 ng/ml, or about 17 ng/ml, or about 18 ng/ml, or about 19 ng/ml, or about 20 ng/ml, or about 21 ng/ml, or about 22 ng/ml, or about 23 ng/ml, or about 24 ng/ml, or about 25 ng/ml.

In some embodiments, the TGF-beta inhibitor is 3-(6-Methyl-2-pyridinyl)-N-phenyl-4-(4-quinolinyl)-1H-pyrazole-1-carbothioamide (A83-01), LY 364947 (4-[3-(2-pyridinyl)-1H-pyrazol-4-yl]-quinoline, or HTS 466284), SD 208 (2-(5-Chloro-2-fluorophenyl)pteridin-4-yl]pyridin-4-yl-amine), D4476 (4-(4-(2,3-Dihydrobenzo[1,4]dioxin-6-yl)-5-pyridin-2-yl-1H-imidazol-2-yl)benzamide), GW 788388 (4-[4-[3-(2-Pyridinyl)-1H-pyrazol-4-yl]-2-pyridinyl]-N-(tetrahydro-2H-pyran-4-yl)-benzamide), SB 505124 (2-(5-Benzo[1,3]dioxol-5-yl-2-tert-butyl-3H-imidazol-4-yl)-6-methylpyridine), SB 525334 (6-[2-tert-Butyl-5-(6-methyl-pyridin-2-yl)-1H-imidazol-4-yl]-quinoxaline), RepSox (E-616452; or 2-[3-(6-Methyl-2-pyridinyl)-1H-pyrazol-4-yl]-1,5-naphthyridine), R 268712 (4-[2-Fluoro-5-[3-(6-methyl-2-pyridinyl)-1H-pyrazol-4-yl]phenyl]-1H-pyrazole-1-ethanol) or 4-[4-(1,3-benzodioxol-5-yl)-5-(2-pyridinyl)-1H-imidazol-2-yl]benzamide (SB 431542). In some embodiments, the concentration of TGF-beta inhibitor in the system is about 0.1 µM to about 5 or about 0.1 µM to about 2.5 µM, or about 0.1 µM to about 1 or about 0.1 µM, or about 0.2 µM, or about 0.3 µM, or about 0.4 µM, or about 0.5 µM, or about 0.6 µM, or about 0.7 µM, or about 0.8 µM, or about 0.9 µM.

The plurality of soluble components can further comprise at least one steroid. In some embodiments, the steroid is selected from the group consisting of dexamethasone, betamethasone, cortisone, methylprednisolone, prednisolone, prednisone, triamcinolone, and hydrocortisone. In some embodiments, the concentration of the steroid in the system is about 1 µM to about 100 µM, or about 10 µM to about 75 µM, or about 20 µM to about 50 µM, or about 20 µM, or about 25 µM, or about 30 µM, or about 35 µM, or about 35 µM, or about 40 µM, or about 45 µM.

The system can also comprise at least one Notch inhibitor. In some embodiments, the at least one Notch inhibitor is selected from the group consisting of N2-[(2S)-2-(3,5-Difluorophenyl)-2-hydroxyethanoyl]-N1-[(7S)-5-methyl-6-oxo-6,7-dihydro-5H-dibenzo[b,d]azepin-7-yl]-L-alaninamide (Ly411575), gamma-secretase inhibitor XXI (or compound E (N-[(1S)-2-[[(3S)-2,3-Dihydro-1-methyl-2-oxo-5-phenyl-1H-1,4-benzodiazepin-3-yl]amino]-1-methyl-2-oxoethyl]-3,5-difluorobenzeneacetamide)), FLI-06 (1,4,5,6,7,8-Hexahydro-2,7,7-trimethyl-4-(4-nitrophenyl)-5-oxo-3-quinolinecarboxylic acid cyclohexyl ester), R04929097 (Propanediamide; or N1-[(7S)-6,7-dihydro-6-oxo-5H-dibenz[b,d]azepin-7-yl]-2,2-dimethyl-N3-(2,2,3,3,3-pentafluoropropyl)-malonamide), LY450139 ((2S)-2-hydroxy-3-methyl-N-((1 S)-1-methyl-2-{[(1 S)-3-methyl-2-oxo-2,3,4,5-tetrahydro-1H-3-benzazepin-1-yl]amino}-2-oxoethyl)butanamide), YO-01027 (7-(S)-[N'(3,5-difluorophenylacetyl)-L-alaninyl]amino-5-methyl-5,7-dihydro-6H-dibenz[b,d]azepin-6-one), BMS-708163 ((2R)-2-(N-(2-fluoro-4-(1,2,4-oxadiazol-3-yl)benzyl)-4-chlorophenylsulfonamido)-5,5,5-trifluoropentanamide), and BMS-906024 ((2R,3S)—N-[(3S)-1-Methyl-2-oxo-5-phenyl-2,3-dihydro-1H-1,4-benzodiazepin-3-yl]-2,3-bis(3,3,3-trifluoropropyl)succinamide). In some embodiments, the concentration of Notch inhibitor in the system is from about 0.05 µM to about 0.3 µM, or about 0.05 µM to about 0.2 µM, or about 0.05 µM to about 0.1 µM, or about 0.10 µM, or about 0.15 µM.

In some embodiments, the system further comprises at least one Yes-associated protein (YAP) inhibitor. The YAP inhibitor can be selected from the group consisting of verteporfin (3-[(23S,24R)-14-ethenyl-5-(3-methoxy-3-oxopropyl)-22,23-bis(methoxycarbonyl)-4,10,15,24-tetramethyl-25,26,27,28-tetraazahexacyclo[16.6.1.13,6.18,11.113,16.019,24]octacosa-1,3,5,7,9,11(27),12,14,16,18(25),19,21-dodecaen-9-yl]propanoic acid), ML7 (1-(5-Iodonaphthalene-1-sulfonyl)-1H-hexahydro-1,4-diazepine hydrochloride); blebbistatin (1-Phenyl-1,2,3,4-tetrahydro-4-hydroxypyrrolo[2,3-b]-7-methylquinolin-4-one), and Y27632 (trans-4-[(1R)-1-Aminoethyl]-N-4-pyridinylcyclohexanecarboxamide dihydrochloride). In some embodiments, the concentration of YAP inhibitor in the system is from about 0.1 µM to about or about 0.1 µM to about 0.7 µM, or about 0.1 µM to about 0.5 µM, or about 0.2 or about 0.3 or about 0.4 or about 0.5 or about 0.6 or about 0.7 or about 0.8 µM.

In some embodiments, the system further comprises a basal medium. The basal medium can be a liver specific basal medium hepatocyte culture medium, such as Clonetics™ HCM™ Hepatocyte Culture Medium.

In some embodiments, the system further comprises a cellular support capable of providing structural and nutritional support. In some embodiments, the cellular support comprises feeder cells. In some embodiments, the feeder cells are from a fibroblast cell line, such as a mouse or human fibroblast cell line. In some embodiments, the mouse fibroblast cell line is a 3T3J2 feeder cell line.

In some embodiments, the conditions for culturing the liver stem cell at the air-liquid interface (ALI) is achieved by a permeable cell culture apparatus, such as a Transwell® Permeable Support.

In some embodiments, the cell culture system for differentiating a liver stem cell into a hepatocyte comprises or consists of:
 a plurality of soluble components comprising or consisting of:
  a liver specific basal medium, A83-01, dexamethasone, oncostatin M, compound E; IL6 and verteporfin;
  conditions for culturing the liver stem cell at the air-liquid interface (ALI), In some embodiments, the basal side of the liver stem cell is configured to be in contact with the soluble components of the cell culture system and the apical surface of the liver stem cell is configured to be in contact with air.

In some embodiments, the hepatocyte is a fully differentiated mature hepatocyte. In some embodiments, the fully differentiated mature hepatocyte is characterized by at least one of the characteristics selected from the group consisting of:
 a. functional CYP3A4 and CYP2C9 activity,
 b. upon stimulation, the hepatocyte can uptake LDL, and/or secrete albumin, and/or store glycogen,
 c. expresses six CYP450 family member genes, and
 d. does not express substantial amounts of AFP as compared to fetal liver cells.

Also provided are kits comprising the components of the cell culture system for differentiating a liver stem cell into a hepatocyte.

In some embodiments, the method of differentiating a liver stem cell into a hepatocyte comprises:
 a. mixing the soluble components of the cell culture system or the kit for differentiating a liver stem cell into a hepatocyte with at least one liver stem cell;
 b. culturing the liver stem cell in the soluble components until confluency in cell population is obtained.

In some embodiments, after achieving confluency in cell population in step (b), the cells are cultured at the air-liquid interface (ALI), wherein the basal side of the liver stem cell is configured to be in contact with the soluble components of the cell culture system and the apical surface of the liver stem cell is configured to be in contact with air.

Also provided are methods of generating a plurality of differentiated liver cells, the method comprising: growing the liver stem cells described herein in a cell culture system capable of differentiating the cell into a plurality of differentiated liver cells.

Differentiated Hepatocytes

Figure 19:
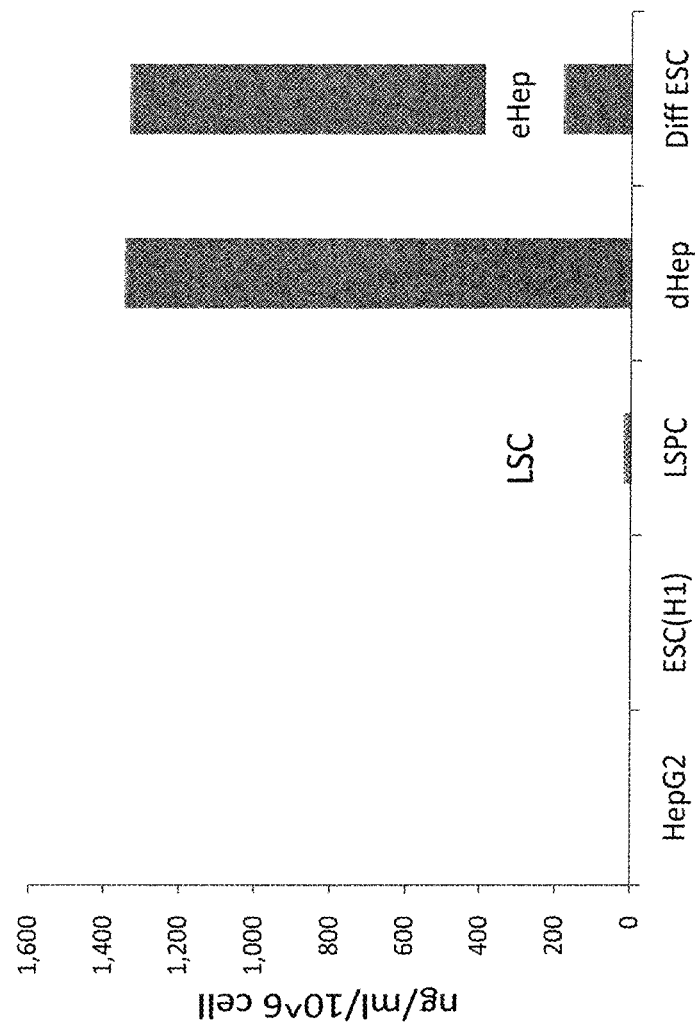
FIG. 19: Quantitative albumin secretion assay of LSC differentiated hepatocyte. Human alubumin (hAlb) ELISA assay to quantitative analysis albumin secretion in culture medium. HepG2 cell line and embryonic stem cell H1 line (ESC(H1)) were used as negative control, ESC differentiated hepatocyte (eHep) was used as positive control. This figure shows that LSC differentiated hepatocyte (dHep) were functional with albumin secretion.
Figure 22:
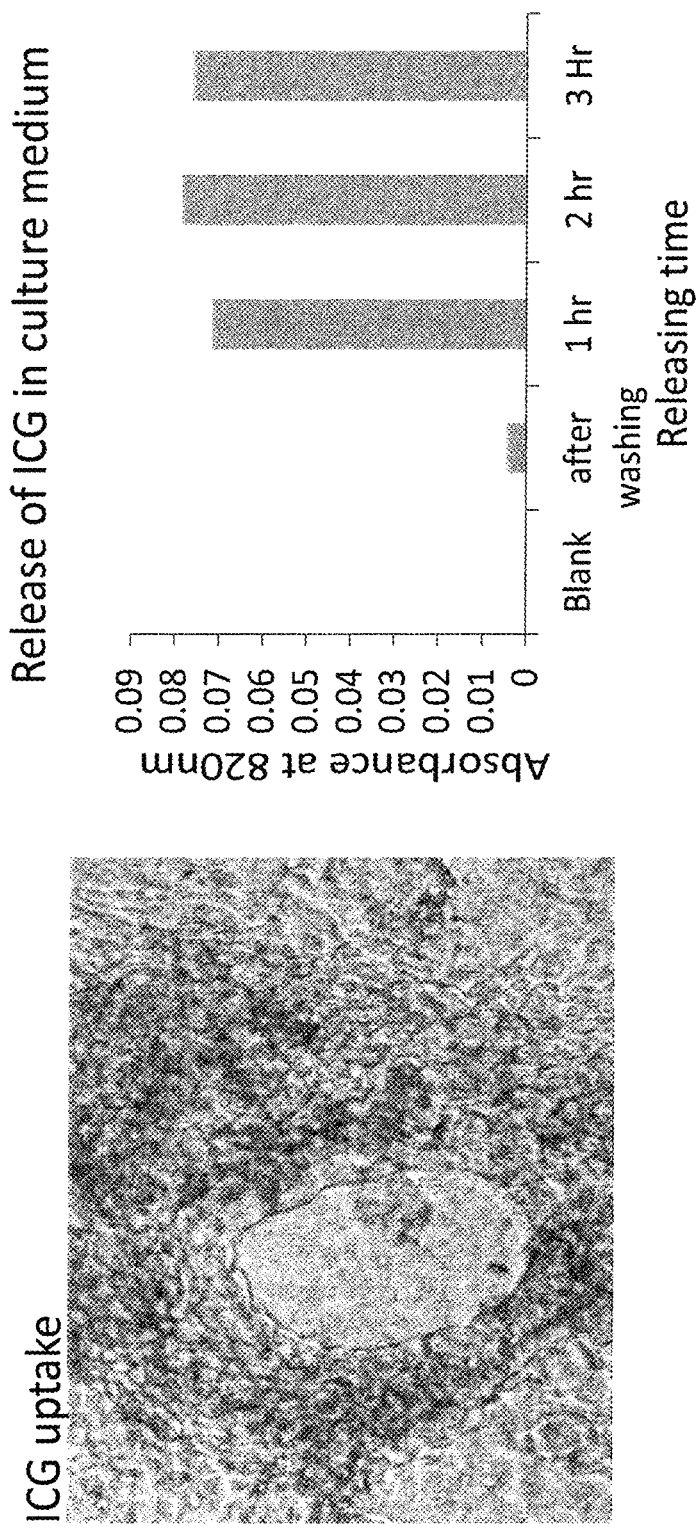
FIG. 22: ICG uptake and release assay of LSC 2D differentiated dHep. ICG (cardiogreen) uptake and release by dHep. 1 mg/ml ICG were incubated with dHep at 37° C. for 1 hour for uptake function test. Image was taken under bright view. Cells which uptook ICG were blue. After 1 hour of incubation, cells were washed and incubated with culture medium. Culture medium were harvest at 1, 2, 3 hour separately and tested by spectrometer at 820 nM. ICG were release into the culture medium by differentiated cell at 3 hours. This figure shows that dHep had ion transport function similar to primary hepatocytes.

The differentiated hepatocytes described herein are characterized by expression of hepatocyte markers HNF4a, ALB, CYP2C9, and can also express the terminal differentiation marker PEPCK1. The tight junction marker ZO1 was expressed between differentiated cells. The differentiated hepatocytes also expressed functional CYP enzymes, including CYP3A4, CYP2C9, CYP2B6, CYP1A2, CYP1A1, CYP2D6, CYP3A7, and CYP2E1. The differentiated hepatocytes exhibited other features of mature hepatocytes, including functional glucose metabolism (determined by PAS staining for glycogen synthesis and storage), functional lipid metabolism (determined by low-density lipoprotein (LDL) uptake assay) (FIG. 23), indocyanine green (ICG) uptake (FIG. 22), and albumin secretion (FIG. 19). ICG uptake is a medical diagnostic test used for diagnosis of hepatic functions, and is used demonstrates that hepatocytes have functional transporter functions to transport ions in and out of the hepatocytes.

The hepatocytes presented here exhibit metabolic functions of the major CYPs, CYP1A2, CYP3A4, CYP2B6 and CYP2C9 (FIGS. 20A and 20B), which accounts for majority of compound metabolism activities of the liver. The expression and activity of other CYPs presented here suggest we can detect metabolic activity for all compounds that can be process by the liver. More importantly, the hepatocytes are shown to be responsive to known CYP inducing drugs such as Rifampicin.

In some embodiments, the differentiated hepatocyte comprises at least one of the following characteristics:
(i) expresses the markers HNF4α and ALB;
(ii) expresses at least 1, 2, 3, 4, 5, 6, 7 or 8 of the CYP enzymes selected from CYP3A4, CYP2C9, CYP2B6, CYP1A2, CYP1A1, CYP2D6, CYP3A7, and CYP2E1;
(iii) have at least 1, 2 or 3 of the following functions:
　a) functional glucose metabolism;
　b) functional lipid metabolism;
　c) functional albumin secretion;
(vi) indocyanine green (ICG) uptake; and
(vii) forms tight junctions when cultured with other differentiated hepatocytes under conditions sufficient to form an epithelium.

The differentiated hepatocyte can also express at least one of the terminal differentiation markers PEPCK1 or TAT. The differentiated hepatocyte has inducible CYP function for at least 2, 3, or 4 of the CYPs selected from CYP3A4, CYP2C9, CYP2B6, CYP1A2, CYP1A1, CYP2D6, CYP3A7, and CYP2E1. The differentiated hepatocyte can also store glycogen and uptake low density lipoprotein.

In some embodiments, the differentiated hepatocyte is differentiated from a liver stem cell isolated from a healthy human or from a human with liver disease selected from the group of metabolic disease, autoimmune disease, infectious disease, drug induced acute and chronic liver failure, and liver cancer.

Cell Culture System and Methods for Producing Differentiated Cholangiocytes

In some embodiments, methods and culture systems for producing differentiated cholangiocytes are described herein. In some embodiments, a culture system for differentiating a liver stem cell into a biliary duct cell/cholangiocyte is provided. In some embodiments, the culture system is a substantially TGF-beta inhibitor and Notch inhibitor-free cell culture system. In some embodiments, the cell culture system comprises: an extracellular matrix for differentiating a liver stem cell into a 3D bile duct structure, and a liver stem cell described herein.

In some embodiments, the cell culture system further comprises at least one, at least two, at least three, or at least four growth factors suitable for differentiating a liver stem cell into a biliary duct cell. In some embodiments, the system comprises two, three or four growth factors suitable for differentiating a liver stem cell into a biliary duct cell. In some cases, the system comprises at least one growth factor selected from the group consisting of epidermal growth factor (EGF), fibroblast growth factor (FGF), TGF-beta, growth differentiation factor 11 (GDF11), a Notch pathway ligand, a Jag 1 protein having the amino acid sequence CDDYYYGFGCNKFCRPR; Jag 2; Delta-like protein 1 (DLL1); Delta-like protein 3 (DLL3), and Delta-like protein 4 (DLL4)). In some embodiments, the two growth factors are epidermal growth factor and fibroblast growth factor. In some embodiments, the fibroblast growth factor is selected from the group consisting of fibroblast growth factor 2 (FGF2) and fibroblast growth factor 10 (FGF10).

In some embodiments, the concentration of fibroblast growth factor in the system is from about 10 ng/ml to about 200 ng/ml, or about 30 ng/ml to about 150 ng/ml, or about 50 ng/ml to about 130 ng/ml, or about 60 ng/ml, or about 70 ng/ml, or about 80 ng/ml, or about 90 ng/ml, or about 100 ng/ml, or about 110 ng/ml, or about 120 ng/ml.

In some embodiments, the concentration of epidermal growth factor in the system is from about 5 ng/ml to about 100 ng/ml, or about 5 ng/ml to about 70 ng/ml, or about 5 ng/ml to about 50 ng/ml, or about 6 ng/ml, or about 7 ng/ml, or about 8 ng/ml, or about 9 ng/ml, or about 10 ng/ml, or about 11 ng/ml, or about 12 ng/ml, or about 13 ng/ml, or about 14 ng/ml, or about 15 ng/ml, or about 20 ng/ml, or about 25 ng/ml, or about 30 ng/ml, or about 35 ng/ml, or about 40 ng/ml, or about 45 ng/ml.

In some cases, the system is free of TGF-beta inhibitor and Notch inhibitor. In other words, the cell cultured system does not comprise a TGF-beta inhibitor or a Notch inhibitor.

In some embodiments, the biliary duct cell/cholangiocyte is a fully differentiated mature bile duct epithelial cell, which is characterized by at least one of the characteristics selected from the group consisting of:
　a. cells having biliary duct-like 3 dimensional (3D) structure;
　b. cells expressing KRT19 (Accession no: P08727.4) and KRT7 (Accession no: P08729.5) protein; and
　c. cells having epithelial polarity.

In some embodiments, the liver stem cell that is differentiated into a biliary duct cell/cholangiocyte is a mammalian liver stem cell, such as a human liver stem cell, a mouse liver stem cell, or a fetal liver stem cell. In some cases, the liver stem cell is a liver stem cell obtained from a subject with liver disease selected from the group of metabolic disease, autoimmune disease, infectious disease, drug induced acute and chronic liver failure, and liver cancer.

In some embodiments, the extracellular matrix is matrigel, such as a growth factor reduced matrigel.

In some embodiments, the cell culture system comprises an extracellular matrix, an epidermal growth factor and a fibroblast growth factor.

Also provided are kits comprising components of the cell culture system for differentiating a liver stem cell into a biliary duct cell/cholangiocyte described herein.

In some embodiments, methods for differentiating a liver stem cell into a biliary duct cell are described, the method comprising:
a. contacting components of the cell culture system for differentiating a liver stem cell into a biliary duct cell, or the components of the kit described herein with at least one liver stem cell; and
b. culturing the liver stem cell in the components of the cell culture system for at least one day to differentiate the liver stem cell into a biliary duct cell.

In some embodiments, the culturing in step (b) is performed for at least two days, at least three days, at least four days, at least five days, at least six days, at least seven days, at least two weeks, or at least four weeks before the liver stem cell differentiates into a biliary duct cell.

In some embodiments, the components of the system or kit are provided or added to step (b) once every two days, or once every three days, or once every four days, or once every five days, or once every six days.

Differentiated Cholangiocytes

The biliary duct cells/cholangiocytes described herein are fully differentiated mature bile duct epithelial cells. In some embodiments, the differentiated cholangiocytes are characterized by at least one of the characteristics below:
(i) expresses the markers KRT19 (Accession no: P08727.4) and KRT7 (Accession no: P08729.5) and ECAD;
(ii) has columnar epithelial cell polarity comprising an apical region and a basolateral region when cultured with other differentiated cholangiocytes under conditions sufficient to form an epithelium;
(iii) comprises microvilli on the apical region;
(iii) forms biliary duct-like 3 dimensional (3D) structure when cultured with other differentiated cholangiocytes under conditions sufficient to form 3D structures.

The differentiated cholangiocytes described herein have an asymmetrical organization that divides an individual cell unit into different regions such as an apical region and a basolateral region. The apical region is defined as the area lying above the tight junctions. The apical region may have microvilli structure on the luminal part of the 3D structure. The basolateral region is defined as the area below the tight junctions and contains the basolateral membrane which is in contact with basal lamina.

In some embodiments, the differentiated choloangiocyte is differentiated from a liver stem cell isolated from a healthy human or from a human with liver disease selected from the group of metabolic disease, autoimmune disease, infectious disease, drug induced acute and chronic liver failure, and liver cancer.

Kits

Also provided herein are kits comprising components of the cell culture systems or cell culture media described herein. In some embodiments, the kit comprises or consists of the components of the liver stem cell culture system or the liver stem cell media described herein. In some embodiments, the kit further comprises reagents for isolating hepatocytes from a liver, such as a collagenase digestion solution. In some embodiments, the kit comprises or consists of the components of the cell culture system for differentiating a liver stem cell into a hepatocyte. In some embodiments, the kit comprises or consists of components of the cell culture system for differentiating a liver stem cell into a biliary duct cell/cholangiocyte.

Methods of Treatment

In some embodiments, methods and pharmaceutical formulations for treating a subject having liver disease are provided. The subject can be a mammal suffering from liver disease. In some embodiments, the subject is a human suffering from liver disease or who otherwise could benefit from the methods described herein. In some embodiments, the method comprises administering a liver stem cell described herein to the subject, such as by contacting the liver stem cell with the liver of the subject in vivo, or by transplanting a liver stem cell into the liver of the subject, wherein the administered or transplanted cell integrates into and repopulates the liver of the subject, thereby treating the liver disease. In some embodiments, the method comprises administering a differentiated liver stem cell (dHEP) described herein to the subject, such as by contacting the differentiated liver stem cell with the liver of the subject in vivo, or by transplanting a liver stem cell into the liver of the subject, wherein the administered or transplanted cell integrates into and repopulates the liver of the subject, thereby treating the liver disease. In some embodiments, the liver disease is selected from the group of metabolic disease, autoimmune disease, infectious disease, drug induced acute and chronic liver failure, cirrhosis, and liver cancer.

The liver stem cells and/or dHEP cells can be administered to a subject in the form of a pharmaceutical composition. The pharmaceutical composition can comprise a sterile isotonic excipient suitable for human administration. For general methods in pharmaceutical formulations, please see Cell Therapy: Stem Cell Transplantation, Gene Therapy, and Cellular Immunotherapy, by G. Morstyn & W. Sheridan eds, Cambridge University Press, 1996; and Hematopoietic Stem Cell Therapy, E. D. Ball, J. Lister & P. Law, Churchill Livingstone, 2000. The pharmaceutical composition comprising liver stem cells and/or dHEP cells can be administered based on the route and device used for administration. In some embodiments, the pharmaceutical composition comprises additional components that aid the engraftment of the cells in the liver of the subject. The liver stem cells or dHEP cells can be administered in an amount effective to treat or reduce the symptoms of liver disease in the subject. For example, about $1\times10^6$, $2\times10^6$, $3\times10^6$, $4\times10^6$, $5\times10^6$ or more liver stem cells or dHEP cells can be administered in either a single dose or multiple doses.

EXAMPLES

Example 1

Isolation and Long Term Culture of Human Liver Stem Cells
Materials & Methods:
Collagenase digestion Solution: DEME/F12 (Gibco) with 10 mM Hepes, 5% FBS (Clonetech), 2 mg/ml collagenase (Sigma, C-5138). Warm collagenase solution to 37 degree C., filter sterilize after the collagenase has gone into solution through a 0.2 micron filter. Make this media fresh (collagenase will inactivate at high temperatures and over long periods of time).

Washing solution: DEME/F12 medium with 10 mM HEPES (Gibco), 100 U/ml Pen/Strep (Gibco), 100 µg/ml gentamicin (Gibco), filter sterilize solution through a 0.2 micron filter.

Coating medium: Growth factor reduced matrigel (Corning) 10%, diluted advanced F12/DMEM reduced serum medium (Gibco).

Liver stem cell culture medium: Advanced F12/DMEM reduced serum medium (1:1)(Gibco. 12643), 10 mM HEPES (Gibco), 100 U/ml Pen/Strep (Gibco), 2 mM L-Glutamine (Gibco), 1% N2 (Gibco), 2% B27 (Gibco), 50 ng/ml EGF (Millipore), 250 ng/ml R-Spondin1 (R&D), 2 µM SB431542 (Tocris)), 1 µM Jagged-1(188-204) (Anaspec), 2 µM T3 (3,3',5-Triiodo-L-Thyronine)(Sigma), 0.1 µM Cholera endotoxin (Sigma), 10 mM Nicotinamide (Sigma), 1.25 µM N-Acetyl-Cysteine (NAC)(Sigma).

Preparation of Feeder Cell:
1. The plates were coated with 10% matrigel. Matrigel was diluted with advanced F12/DMEM basal medium. After coating the plates, the plates were store in 37° C. incubator for 30 min.
2. Vials containing 7×10⁶ cells/vial were thawed into 3 six well plates with 2 mL medium each well. The cells were thawed quickly in the waterbath, and swabbed with 70% alcohol before bringing them into a laminar-flow hood. The cells were added into a 50 mL tube and warm medium was added drop by drop to dilute the cells.
3. Shake the plates in the incubator (left and right ×2 & back and front ×2) to evenly distribute the cells
4. The feeder could be used on the second day.

Liver stem cells were isolated from fresh human liver tissue (FIG. 1). The use of human liver samples for hepatocyte preparation for scientific purposes were approved by Institutional Review Boards (IRB s) and Human Research Ethics committee. Normal liver samples were obtained from donor livers for transplantation. Cirrhosis liver samples were obtained from recipient liver for transplantation. The tissues was cut and minced into small pieces and digested in collagenase solution. The digested cells were suspended in liver stem cell culture medium. The cells were pooled and plated on tissue culture plates with feeder cells and allowed to attach. After 7-10 days, cells were harvested and resuspended as single cells and plated onto the feeders. Hepatic stem cell colonies start to appear 3 days later. The cells were subcultured every 7 to 10 days for long term culture. Culture medium was changed every 2 days.

Single cell derived cell lines were generated by picking up single colonies on feeder for continual culture. Early passaged liver stem cell was digested in single cells and retrieved by flow cytometry. The sorted single cell was cultured in 96 well plate and further split into 48, 24 and 6 wells plates for expansion.

In certain embodiments, the digested early passage cells were filtered through a 40 µm strainer and plated at a low density on the culture dish. After 10 to 14 days, single cells grew to form colonies without merging wth other colonies. The single cell derived colonies were picked for continuing culture on 24 well plates. 1%, 10%, 20%, 30%, 40% and 50% of the cells repopulated in the next passaging.

Figure 9:
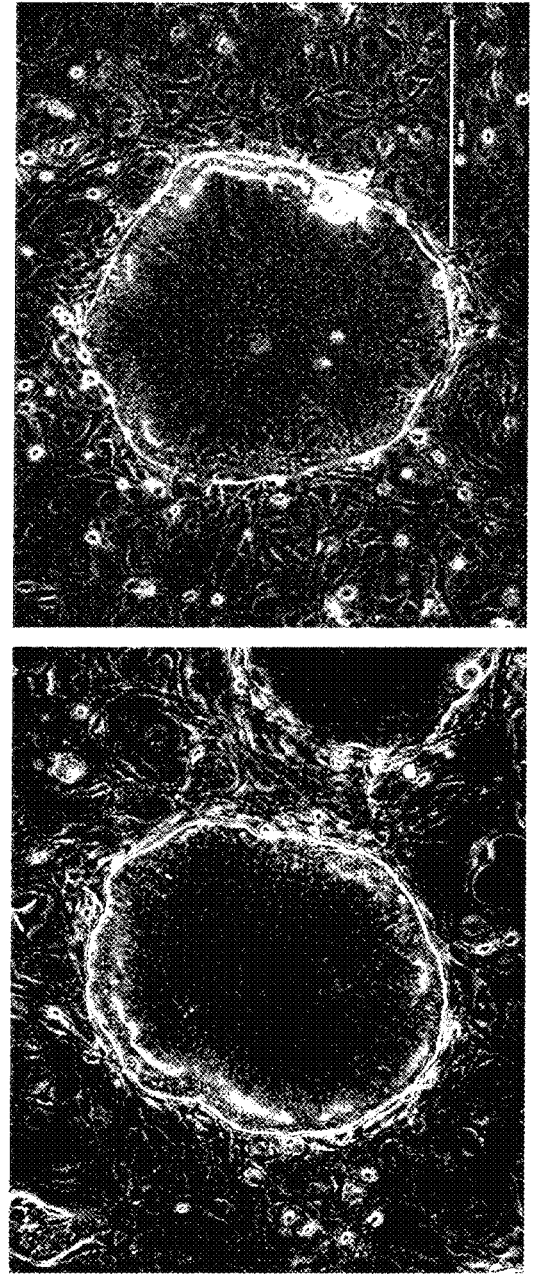
FIG. 9: Long term culture of human liver epithelial stem/progenitor (LSC) cells. Bright view image of LSC on feeder cells. Both early passage 1 and late passage 16 have similar morphology. LSC are small round shape cells clustered together to form colony on feeder. The cells are symmetrical and not polarized. The edge of the clone raised up. This figure is consistent with LSC being stem cells with long term self-renewal ability.
Figure 10:
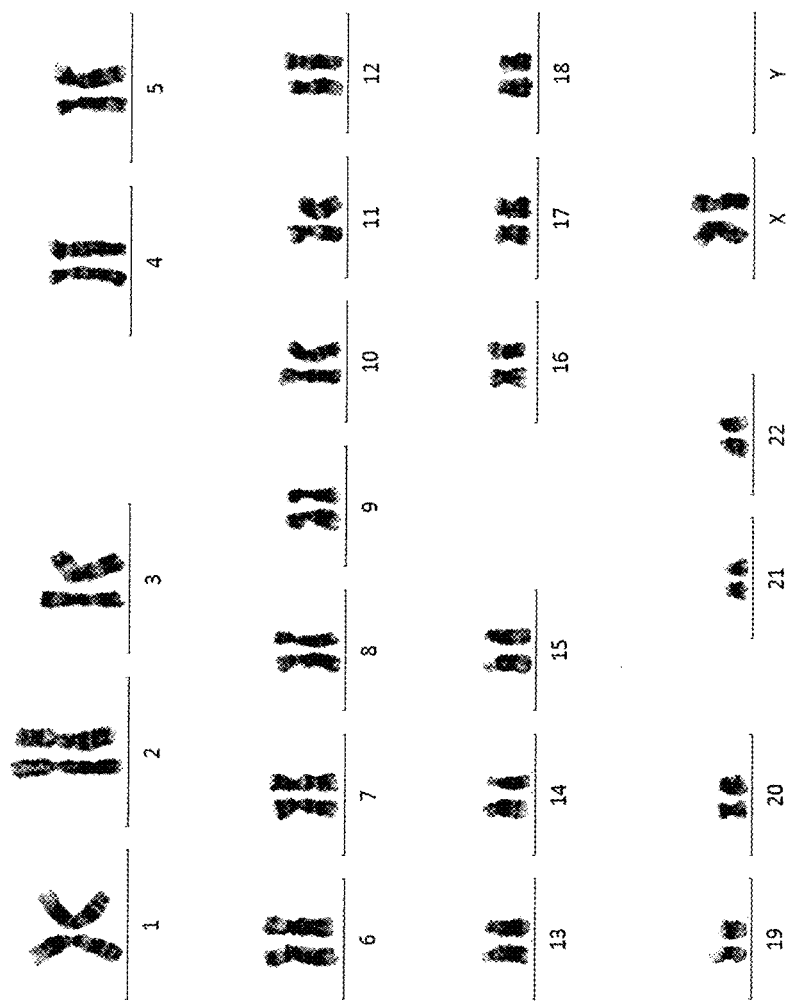
FIG. 10: Long term cultured human liver epithelial stem/progenitor (LSC) cells have normal karyotype. Long term cultured human liver stem cells at passage 19 (280 days in culture) show normal karyotype. Left panel showed karyotyping results for 20 cells. All of the cells have normal karyotype. This figure shows that LSC maintained a stable genome during long term culture.

Single cell derived hepatic stem cell line was passaged continuously every 7 to 14 days, early passage and late passage were checked for karyotyping. Cells at both passages have normal karyotype. This shows that the stem cell genomes were stable during long term culture (FIG. 9, FIG. 10).

Results:
The hepatic stem cells express adult stem cell marker SOX9 and hepatocyte markers HNF4α and HNF3β (FIG. 2). Bile duct marker KRT19 is lowly expressed and bile duct marker KRT7 is undetectable in the cells (protein level). The hepatic stem cell also expressed other liver stem cell marker EPCAM, CD24, PROM1, FOXA3 and FOXQ1 (FIG. 2, FIG. 4). During the maintenance of stem cells, colonies of differentiated cells were observed (~1-2% of total number of colonies). The differentiated liver cells showed strong levels of ECAD, KRT19, KRT7 expression and decreased express SOX9 (FIG. 3), consistent with the differentiated cells being ductal in nature. Morphologically, undifferentiated cells were small, round in shape and clustered tightly together. The hepatic stem cells were not polarized (FIG. 8). Sporadic differentiated cells were larger and flatter in shape (FIG. 3). Almost all the cells in culture were proliferating as all the cells expressed KI67 in the cell nucleus (FIG. 2). Morphologically, all of them were small round shape. The undifferentiated cells expressed low levels of KRT19, but did not express detectable levels of KRT7.

Example 2

Isolation and Long Term Culture of Mouse Liver Stem Cells

Figure 7A:
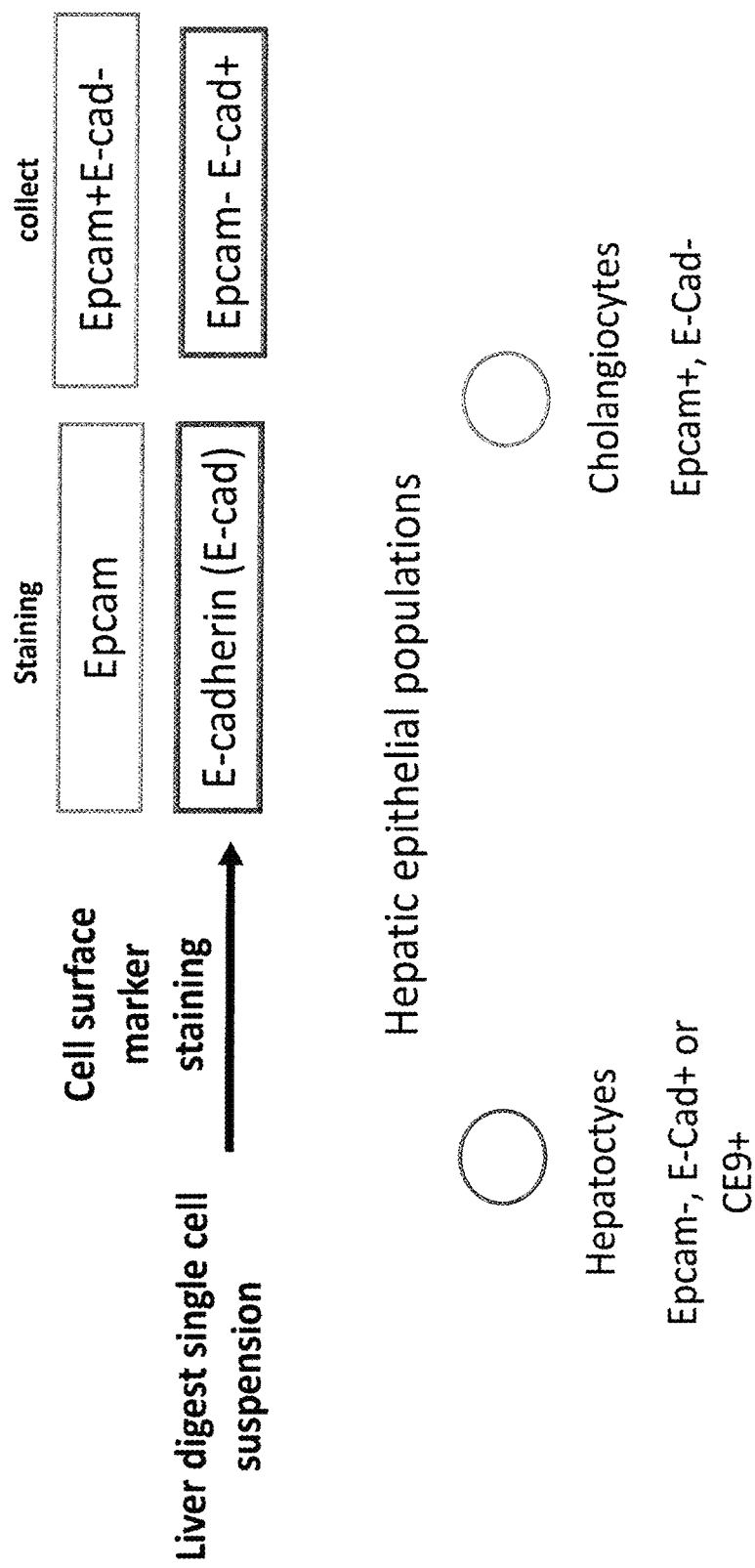

Liver stem cells described herein could be generated from both hepatocyte and non-hepatocyte liver populations in the liver. Mouse liver was digested into single cell suspension and labeled with bile duct marker EPCAM and the epithelial marker E-CAD. Cells of bile duct origin were EPCAM-positive and E-CAD-negative. Cells of hepatocyte origin were EPCAM-negative and E-cad-positive. Both bile duct and hepatocytes were isolated using FACS sorting and separately cultured using the methods described in the Examples. Liver stem cells were generated from both two cell populations (FIG. 7).

Liver stem cell culture medium was composed of Advanced F12/DMEM reduced serum medium (1:1) (Gibco. 12643), 10 mM HEPES (Gibco), 100 U/ml Pen/Strep (Gibco), 2 mM L-Glutamine (Gibco), 1% N2 (Gibco), 2% B27 (Gibco), 50 ng/ml EGF (Millipore), 250 ng/ml R-Spondin1 (R&D), 2 µM SB431542 (Tocris)), 2 µM T3 (3,3',5-Triiodo-L-Thyronine)(Sigma), 10 mM Nicotinamide (Sigma).

Jagged-1 (0.1, 0.5, 1, 5, 10 µM) was optionally added to the culture medium to stimulate the cell proliferation (FIG. 12).

Cholera endotoxin (0.05, 0.1 µM) was optionally added in the culture to minimize presence of differentiated cells. Higher concentrations (>0.1 µM) of cholera endotoxin inhibited cell proliferation rather than stimulating growth. However, the use of cholera endotoxin was not required to keep the stem cells in an undifferentiated state optional in the culture medium (FIG. 12).

N-Acetyl-Cysteine (1.25 µM) was added in the culture medium to attenuate reactive-oxygen-species-mediated stress in cell culture. It helped to maintain the liver stem cell in undifferentiated status especially in long term culture.

Mouse fibroblasts were used as feeders in liver stem cell culture. The fibroblast cells were cultured in DMEM medium with high glucose, 10% bovine calf serum, 100 U/ml Pen/Strep and 2 mM L-Glutamine. Cells were grown to 70-80% confluence and irradiated with 6000 Rads. Mouse fibroblast used for liver stem cells including 3T3J2, Swiss3T3, NIH3T3 and L1.

Various concentrations of Matrigel (1%, 2%, 5%, 10%) was used to coat the culture dish before thawing the cryopreserved fibroblast cells. Matrigel was diluted with advanced F12/DMEM basal medium. After coating the plate, they were put in 37° C. incubator for 30 min. 10% Matrigel supplied nutrition to the fibroblast feeder and helped the irradiated fragile feeder to attach firmly to the culture plate, so that the feeder could be used for at least 2 weeks to support the stem cells. This coating step is optional, since early passage (<10 passage) J2 was able to support the stem cell without Matrigel coating.

Example 3

Differentiation of Liver Stem Cells to Hepatocytes

Figure 16A:
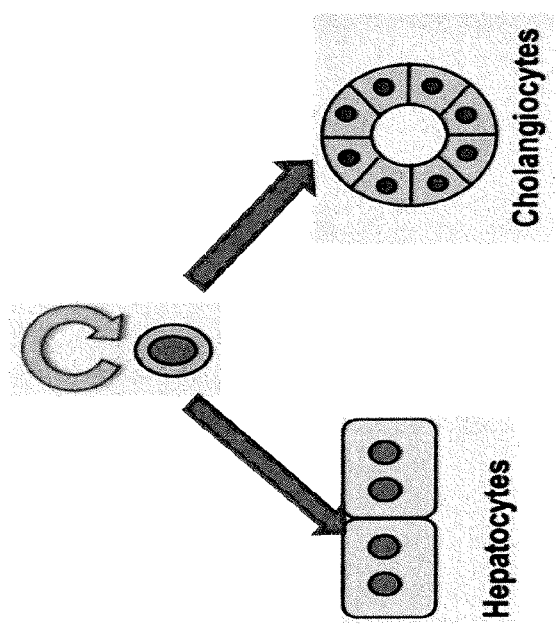
FIGS. 16A and 16B: Differentiation of LSC.
Figure 16B:
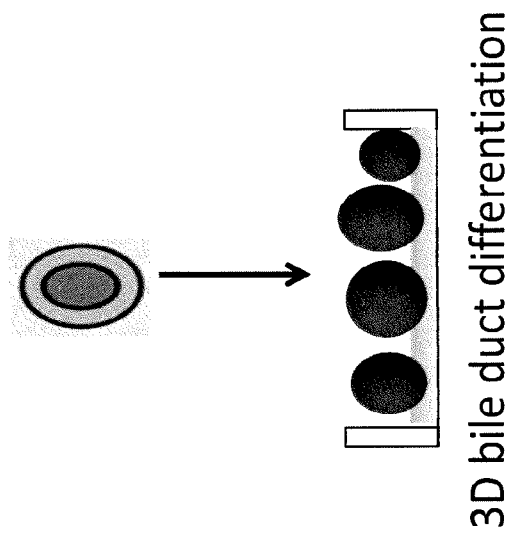
Figure 26:
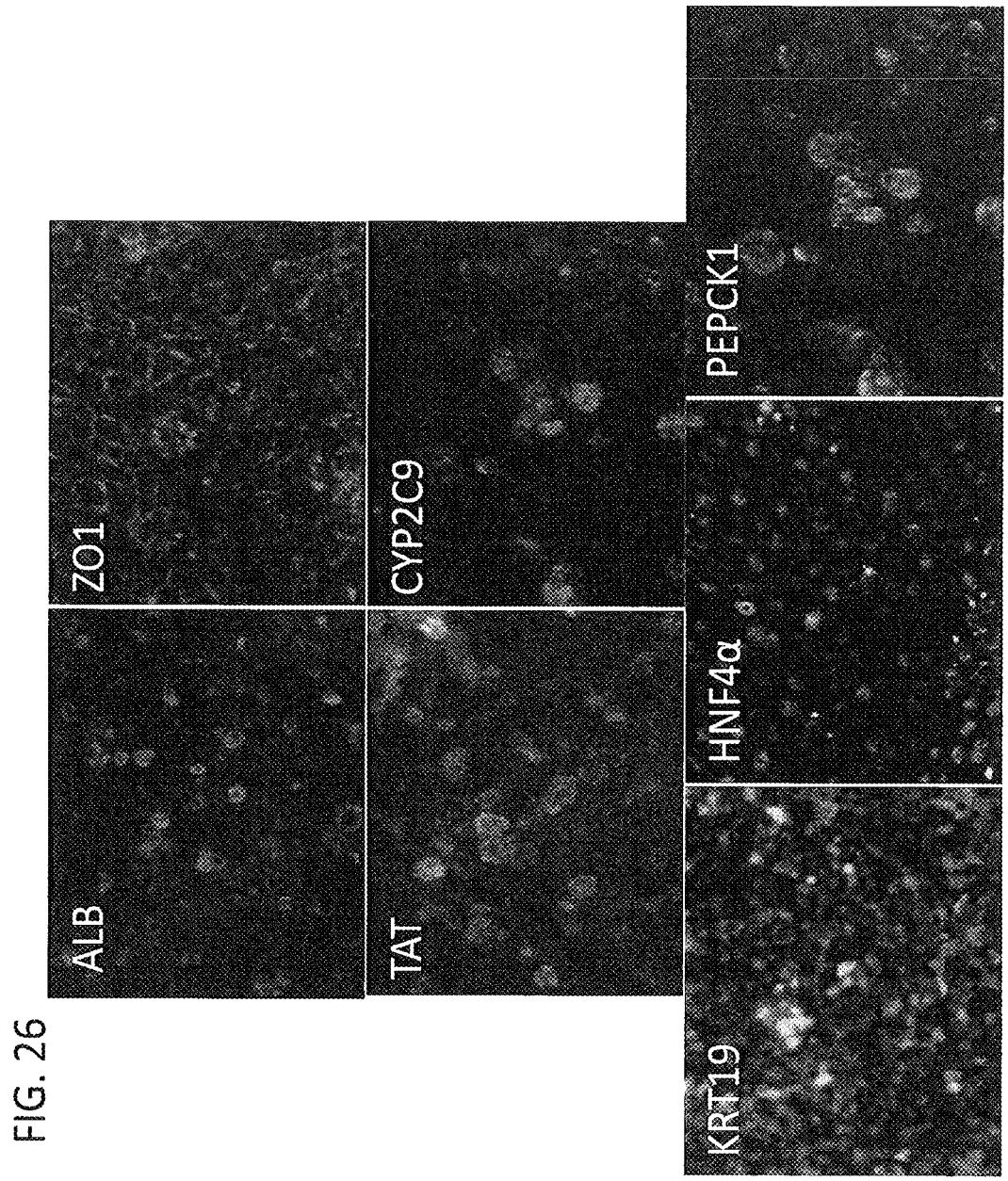
FIG. 26: LSC differentiated into hepatocytes in air liquid interface (ALI) culture. IF staining of hepatocyte markers on LSC differentiated hepatocyte by ALI. LSC differentiated cells had terminal differentiated hepatocyte markers ALB, PEPCK and TAT expression. They also expressed drug metabolism enzyme CYP p450 family proteins CYP2C9. Key hepatocyte transcription factor Hnf4a was expressed in cell nucleus. dHep also have tight junctions, as indicated by ZO1. This figure shows LSC differentiated into mature hepatocyte in ALI culture.

Liver Stem cells were able to differentiate into both hepatocyte and bile duct cell at near 100% efficiency. Hepatocyte differentiation were conducted in both 2D (FIG. 17), 3D (FIG. 24) and air liquid interface (ALI) format (FIG. 26). Bile duct differentiation was in 3D format (FIGS. 16A and 16B).

Hepatocyte differentiation medium consisted of Clonetics™ HCM™ Hepatocyte Culture Medium (Lonza) supplemented with 0.5 µM A83-01 (Tocris), 30 µM dexamethasone (Dex) (Sigma), 20 ng/ml oncostatin M (OSM) (Prospecbio), 0.1 µM γ-secretase inhibitor XXI, also called compound E (Santa cruz), 25 ng/ml Bmp7 and 25 ng/ml Fgf19.

In certain embodiments, Clonetics™ HCM™ Hepatocyte Culture Medium (Lonza) could be replaced with advanced DMEM/F12 (1:1) medium with B27, N2 or DMEM/F12 (1:1) medium with 10% FBS.

In certain embodiments, γ-secretase inhibitor XXI could be replaced with the Notch pathway inhibitor DAPT, DBZ.

In certain embodiments, BMP7, FGF19, and oncostatin M (OSM) were optional. Either one of them could be removed, and the cells were still able to differentiate into hepatocyte with lower efficiency.

2D Hepatocyte Differentiation

Hepatic stem cells were cultured on feeder for 7 to 10 days. After stem cells reach 50% to 70% confluence, cell culture medium was added with BMP4 20, 50, 100 ng/ml and Fgf2 10, 20, 50, 100 ng/ml for 3-5 days and change to hepatocytes differentiation medium to initiate hepatocyte differentiation. The medium was changed every 2-3 days for 14 days. Prolonged culture in hepatocyte differentiation medium could increase the hepatocyte maturation. The differentiated cells could be continued cultured for more than 30 days in Clonetics™ HMM™ Hepatocyte Maintenance Medium (HMM).

In certain embodiments, liver stem cells were seeded on feeders at high density $1\times10^5$ cells/cm$^2$ in stem cell culture medium. When the liver stem cells reach confluency, the culture media is replaced with the differentiation media. Mature hepatocyte will form after 14 to 21 days (FIGS. 17A and 17B).

3D Hepatocyte Differentiation

Liver stem cells were cultured on feeders for 6 to 10 days. The cells are subsequently retrieved and seeded as single cells in ultra-low attachment cell culture dish at a density of $1\times10^5$ cells/cm$^2$ in human liver stem cell culture medium.

In certain embodiments, cells was seeded on low attachment 96 well plate at $2-5\times10^4$/well.

Figure 24:
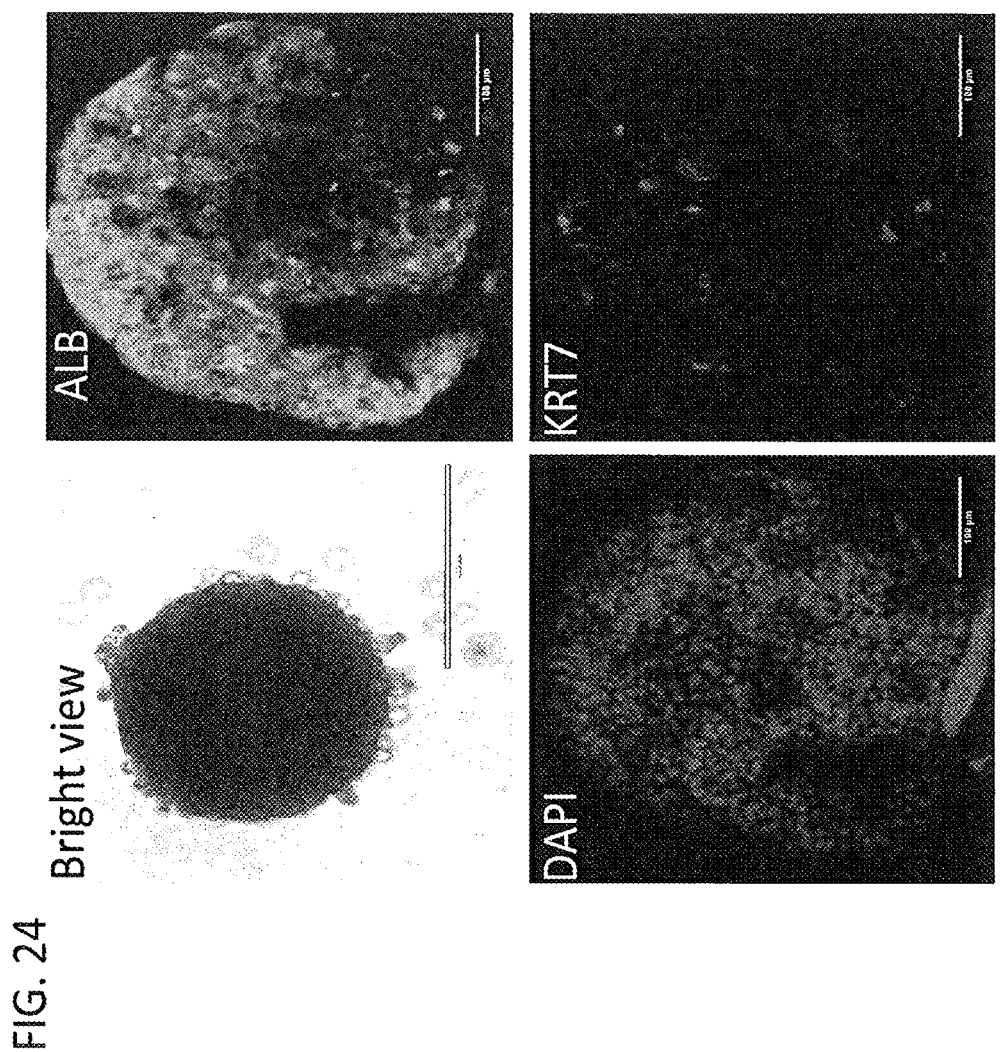
FIG. 24: 3D hepatocyte differentiation in suspension culture. LSC were dissociated from culture dish and cultured in 96 plate in hepatocyte initiation medium for 7 days and switched to hepatocyte differentiation medium for another 14 days. Cells aggregated and formed a spheroid. The hepatocyte 3D spheroids were fixed and stained with hepatocyte marker ALB (red) and bile duct marker KRT7 (green). Almost 100% of cells differentiated into hepatocytes (ALB+KRT7−). This figure shows almost 100% differentiation of LSC into hepatocytes.

On the second day, the stem cells were cultured in liver stem cell medium with BMP4 20, 50, 100 ng/m and Fgf2 10, 20, 50, 100 ng/ml for another 3-5 days to form sphere structures. Hepatocyte differentiation medium were used to culture the sphere structures in low attachment plate to initiate hepatocyte differentiation. Medium was changed every 2-3 days. The mature hepatocytes were derived in 8th to 14th days of differentiation. Prolonged culture in hepatocyte differentiation medium increased the 3D hepatocyte maturation. The 3D hepatocytes were cultured in differentiation medium as long as 30 days with medium changing every 2-3 days. The 3D hepatocyte could be maintained in Clonetics™ HMM™ Hepatocyte Maintenance Medium (HMM) for 2-3 months (FIG. 24).

Hepatocytes Air-Liquid Interface (ALI) Differentiation

Figure 27:
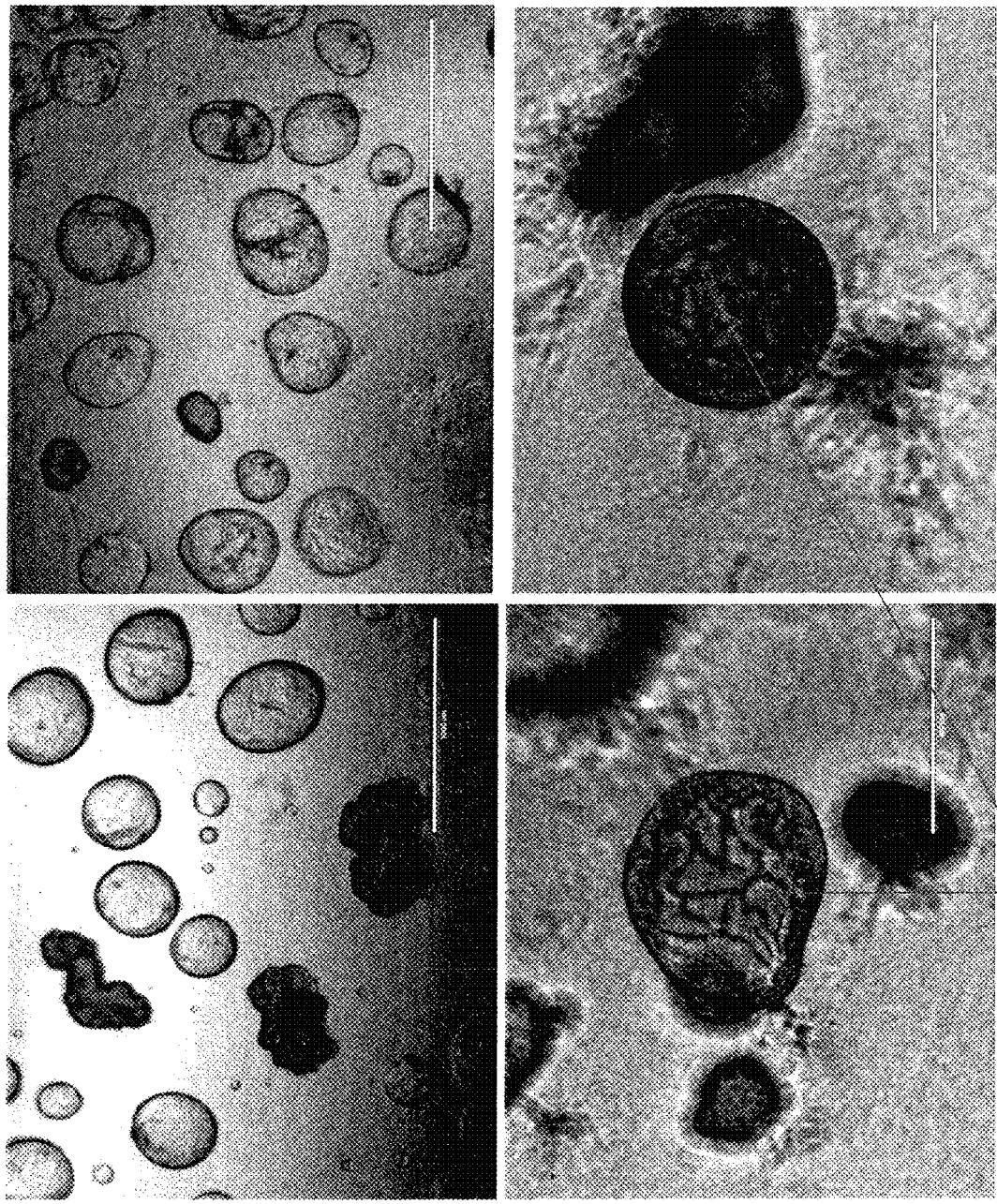
FIG. 27: 3D differentiated cholangiocytes cultured on matrigel formed organoids with bile duct structure. Bright view image of organoids with bile-duct-like structures. Majority of the organoids are spheriodal in structure with columnar shaped epithelial cells. Liquid can be observed in the spheres suggesting that the cholangiocytes are secreting mucus.

Liver stem cells were plated on 3T3J2 feeders in transwells (Corning, 0.4 µm pore size, polyester membrane) at a density of $3\times10^4$ cell/cm$^2$. The cells in transwells were cultured in liver stem cell medium for 7 to 10 days. The medium inside the inserts were removed and the medium outside the insert were changed to hepatocyte differentiation. The cells on air-liquid interface were cultured for another 14 days with medium changes every 2-3 days. In day 10 to 14, the mature hepatocyte were derived. Prolonged culture in hepatocyte differentiation medium could increase the hepatocyte maturation. The differentiated cells could be continued cultured for more than 30 days (FIG. 27).

Figure 18:
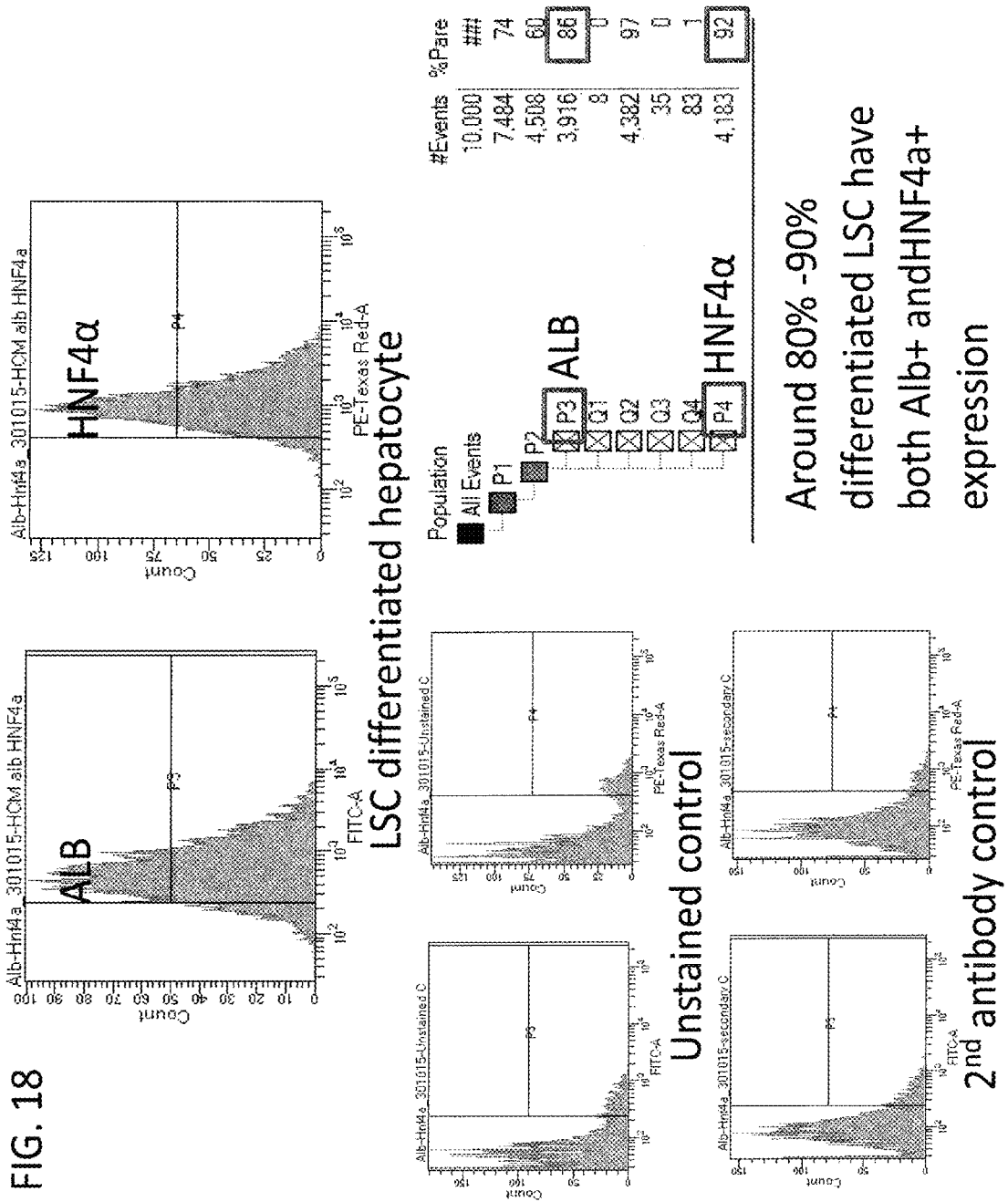
FIG. 18: High efficiency hepatocyte differentiation from LSC. High efficiency 2D hepatocyte differentiation. Differentiated cells were dissociate into single cells, fixed and stained with hepatocyte marker HNF4α (FITC) and ALB (Texas red). Stained cells were analyzed by fluorescence-activated cell sorting (FACS). Histogram showed 86% of cells were ALB+, and 92% of cells were HNF4α+. This figure shows that LSC hepatocyte differentiation were highly efficient and produced a high purity hepatocyte population.
Figure 21:
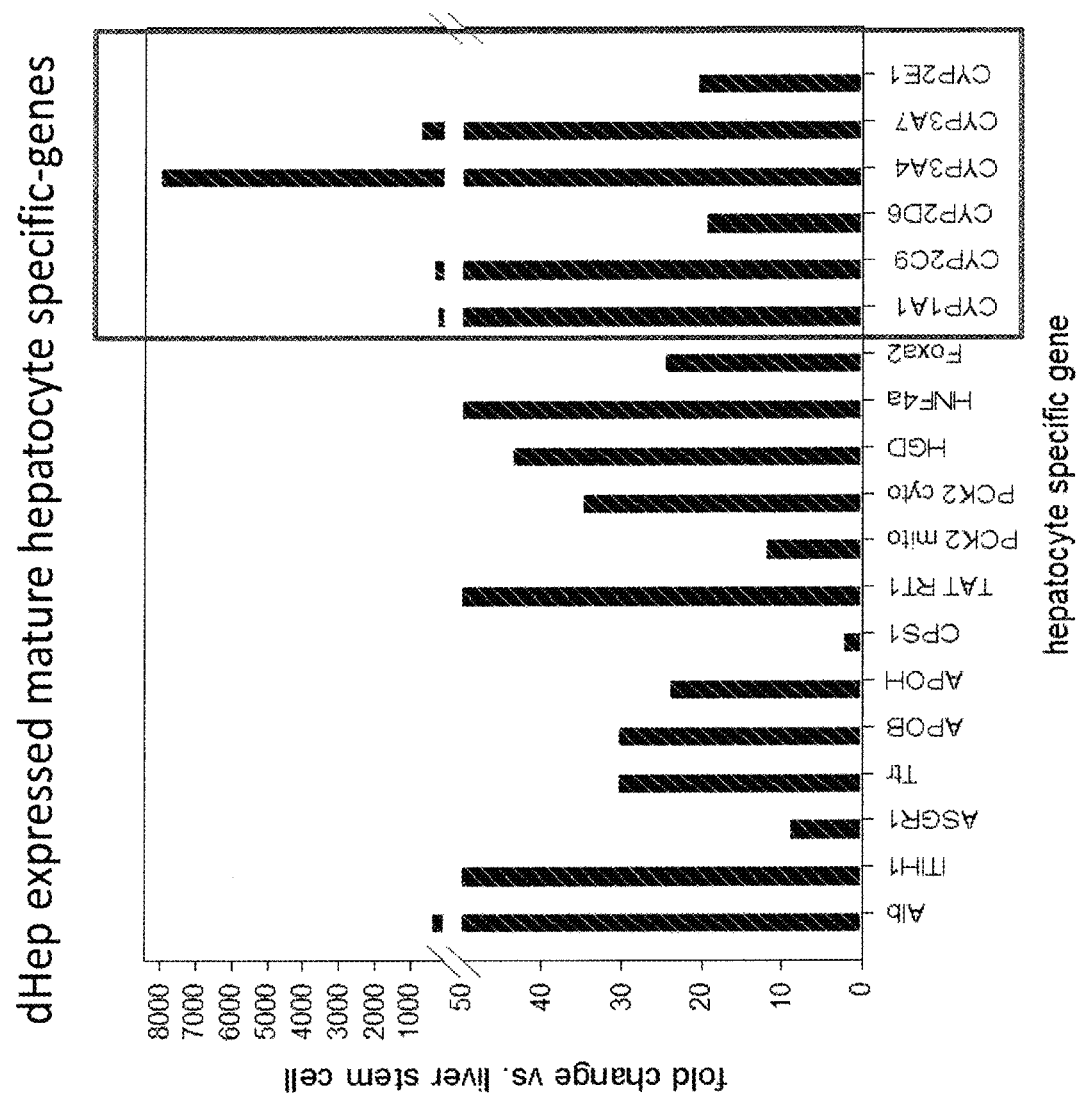
FIG. 21: Major CYP p450 family members have detectable RNA expression. qPCR analysis of LSC in vitro differentiated hepatocyte (dHep). Mature hepatocyte specific genes expression of differentiated LSC were compared with undifferentiated LSC. Fold change is as indicated by the y-axis. This figure shows that dHep expressed major CYPs. That indicated dHep were mature hepatocytes.
Figure 23:
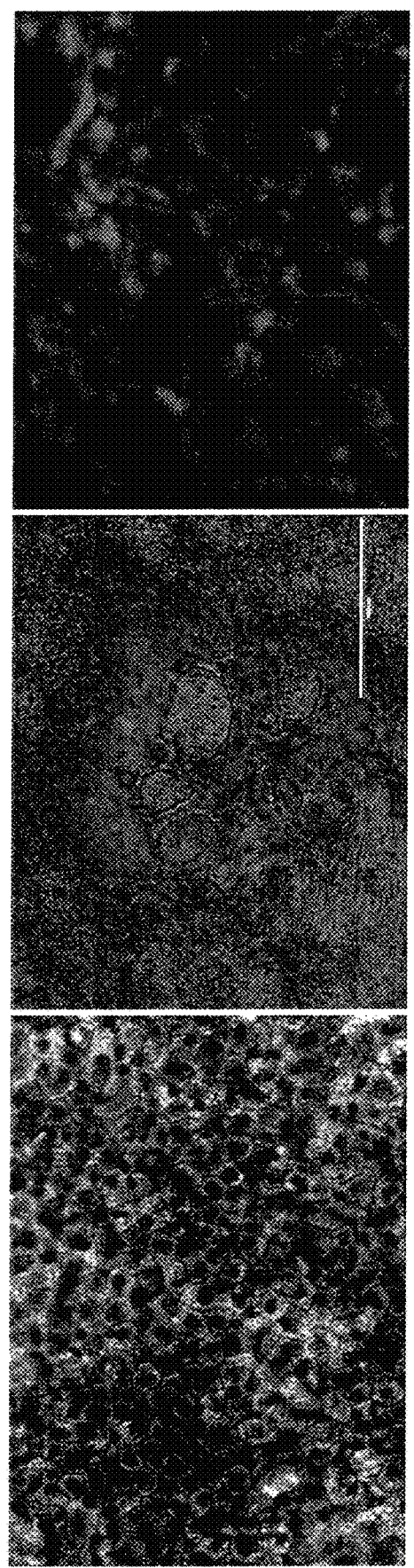
FIG. 23: Lipid uptake assay and glycogen storage capability of LSPC 2D differentiated hepatocyte. Periodic acid Schiff (PAS) staining and low-density lipoprotein (LDL) uptake assay. PAS staining was carried on 2D differentiated hepatocyte. Ubiquitous staining of glycogen stored in dHep cytosol (left panel). LDL uptake assay was shown in middle and left panels. dHep was incubated with fluorescently-labeled LDL at 37° C. for 1 hour. Cells that uptake LDL were stained red. This figure shows that dHep had lipid uptake function similar to primary hepatocytes.
Figure 25:
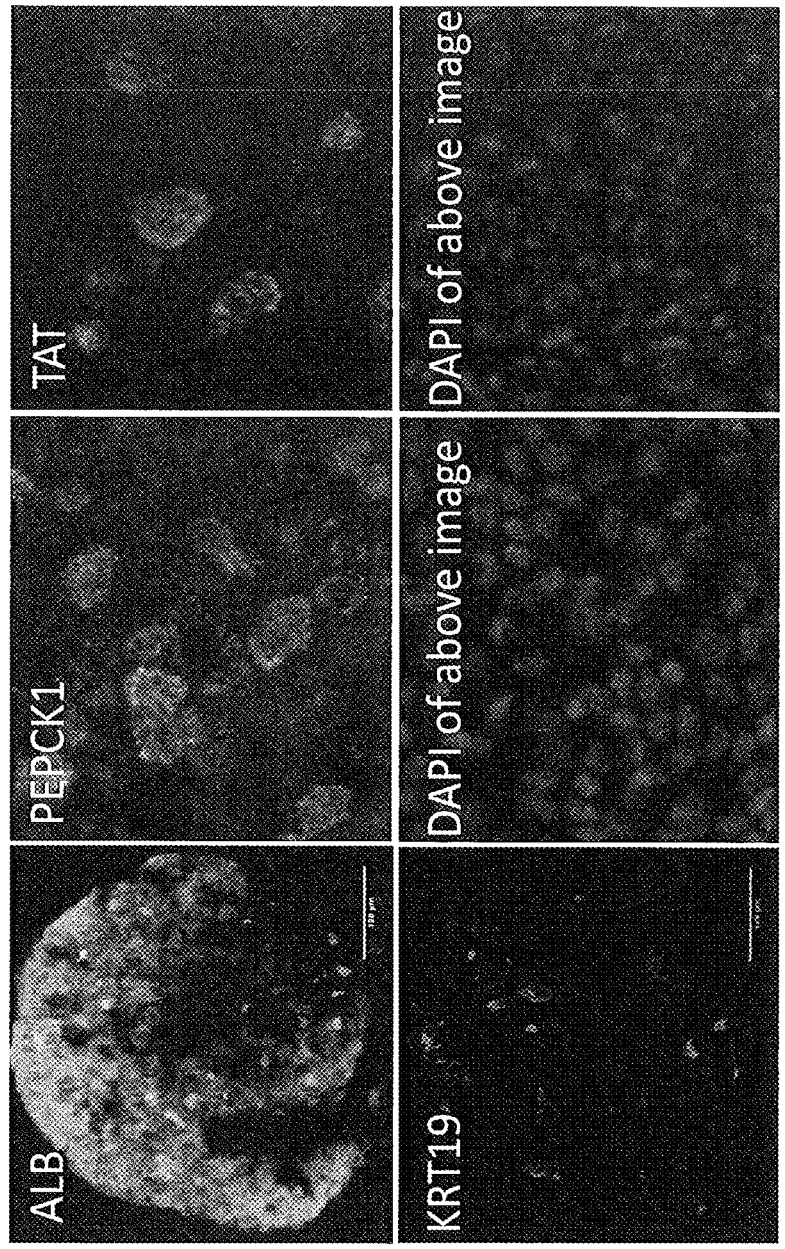
FIG. 25: LSC differentiated hepatocyte (dHep) expressed ALB. The dHep cells were around 100% ALB+. Terminal differentiation marker PEPCK1 and Tyrosine Aminotransferase (TAT) were also expressed.

All described hepatocyte differentiation methods produced functional human hepatocytes without fetal and immature hepatocyte markers expression such as AFP (except for hepatocytes derived from LSCs from hepatocarcinoma patients, which do express AFP). Differentiated hepatocytes had Cytochrome p450 drug metabolism function (FIG. 20), glycogen storage and LDL uptake function (FIG. 23). Currently the efficiency of 2D and 3D differentiation was around 80% to 90% (FIG. 18). The highest differentiation efficiency of 3D could reach 100% in certain individual 3D hepatocyte spheres (FIG. 24, FIG. 25). The 3D differentiated hepatocytes expressed the hepatocyte terminal differentiation markers PEPCK and TAT. Six major CYPs p450 family members had increased RNA expression (FIG. 21). CYP1A2, 2C9, 2B6, and 3A4/5 function was determined by metabolic assays. The hepatocytes also show drug induced response for CYP3A4 and CYP2C9 activity (FIG. 20B).

Although Hepatic stem cell differentiated hepatocyte displayed many features of primary adult hepatocyte, they are different in several aspects (Table 2). Liver stem cell differentiated hepatocyte (dHep) was smaller than adult primary hepatocyte (aHep) in cell size. aHep size is 2-10 times larger than dHep. Majority of the dHep are diploid with single nucleus, but a significant numbers of aHep are polyploid, and can also be binucleated. aHep CYPs function could only be maintained in vitro for 24-48 hours in cell culture, but dHep CYPs function could be maintained for more than 30 days (FIG. 24).

Example 4

Differentiation of Liver Stem Cells to Cholangiocytes

Biliary duct differentiation medium consisted of advanced F12/DMEM reduced serum medium (1:1)(Gibco. 12643), 10 mM HEPES (Gibco), 100 U/ml Pen/Strep (Gibco), 2 mM L-Glutamine (Gibco), 1% N2 (Gibco), 2% B27 (Gibco), 10 ng/ml EGF (Millipore), 100 ng/ml Fgf10 (R&D).

Tgfβ inhibitor and Notch inhibitor were not present in the medium. The bile duct differentiation medium is Tgfβ inhibitor and Notch inhibitor free.

In certain embodiments, Tgfβ and Notch ligand jagged-1 were added in the differentiation medium to help bile duct forming. Either of them was optional.

Growth factor reduced matrigel was thawed one day before at 4° C. 50 ul of matrigel was put in one well of the 8 chamber slide. The chamber slides with matrigel were incubated at 37° C. Half an hour later, the materiel solidified and formed dome shape and jelly like structure on each well. Liver stem cells were digested by 0.05% trypsin for 30 to 60 seconds. The liver stem cells were seeded in the growth factor reduced matrigel suspension at a density of $3-5\times10^4$ cells/400 µl/well. After 3 to 5 days, when the sphere structures formed, the liver stem cell medium was changed to biliary duct differentiation medium. The differentiation medium was changed every 2 days. Cholangiocytes are form 14 days later.

Figure 28:
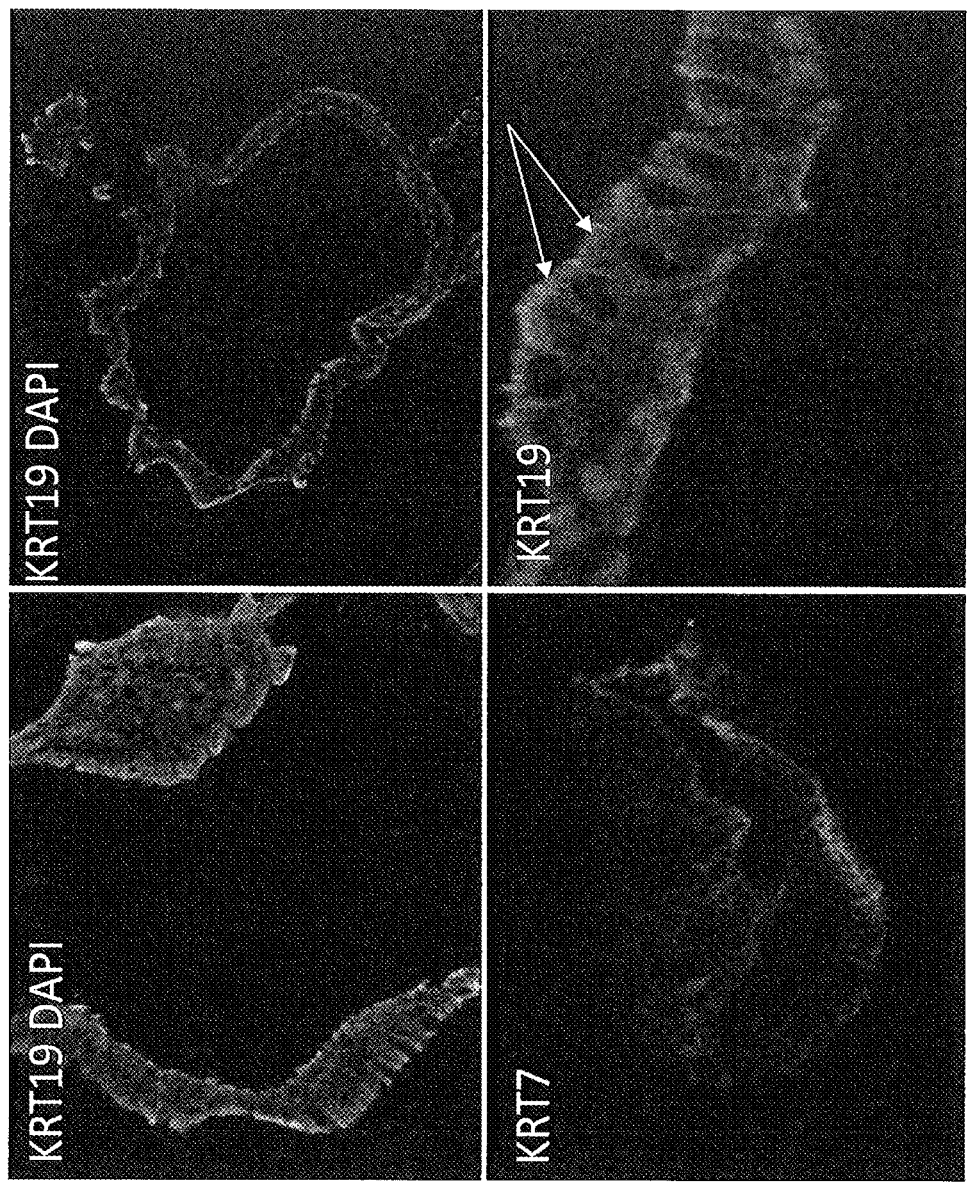
FIG. 28: Differentiated cholangiocytes are 100% positive for bile duct epithelial cell markers KRT19 and KRT7. Cryosections of 3D bile duct structures were stained with bile duct marker KRT19 and KRT7. The cells are columnar shape and well organized. They strongly express bile duct marker KRT7 and KRT19. They were well polarized. Their nucleus located in the bottom part near basal membrane (matrigel side). In the luminal part microvilli are formed. This figure showed terminally differentiated bile duct cells. This is the first report of terminally differentiated bile duct cells in vitro.

The biliary duct differentiation method gave rise to biliary duct-like 3D structure (FIGS. 27, 28, 29A and 29B). This structure mimics a closed duct in which the cells are arranged in a sphere or tubular structure with an enclosed lumen or space surrounded by the cholangiocytes which have tight junctions between them. In some of the biliary duct-like structures mucus can be observed to be secreted into the lumen. All the cells stained positive for biliary markers KRT19 and KRT7 suggesting close to 100% differentiation efficiency (FIG. 29B). The cells were fully polarized with microvilli on the luminal apical part of the structures (FIG. 28). Nucleus in the cells were located near the basal membrane (FIG. 28). Tight junction marker ZO-1 was expressed between the cells (FIG. 29). The biliary duct organoids display organization that mimicked in vivo biliary duct structure.

The process of bile duct 3D differentiation can comprise of the following steps: placing extracellular matrix in a suitable container (such as 50-60 µl of matrigel on one well of 8 well chamber slides); solidifying the extracellular matrix (such as matrigel) to form a dome shape jelly-like structure in the suitable container (such as cell culture chamber); placing the liver stem cells (optionally with suitable digestion enzymes such as trypsin) on the extracellular matrix (such as seeding the liver stem cells on top of the matrigel); incubating the extracellular matrix and the liver stem cells and allowing the aggregated cells to form a sphere structure on top of the extracellular matrix (such as matrigel). Without wishing to be bound by theory, it is believed that the extracellular matrix (such as matrigel) supports cells aggregation and form 3D structure, which helps to initiate bile duct differentiation. Furthermore, it is believed that TGF-beta and other cytokine in the extracellular matrix (such as matrigel) facilitate the sphere structures to further differentiate into bile duct-like structure. Extracellular matrix (such as matrigel) supports the sphere structure formation and assists in the polarization of the sphere structure to further differentiate into bile duct-like structure. Although Hepatic stem cell differentiated cholangiocytes displayed many features of primary adult cholangiocytes, they are different in several aspects (Table 5). The LSC-derived cholangiocytes lack cuboidal cholangiocytes which have proliferative potential. No proliferation of LSC cholangiocytes was observed. While ECAD expression varies in the adult primary cholangiocyte, all the cholangiocyte in our culture expressed ECAD.

Example 5

Liver Stem Cells Obtained from Patients with Liver Diseases

Figure 30A:
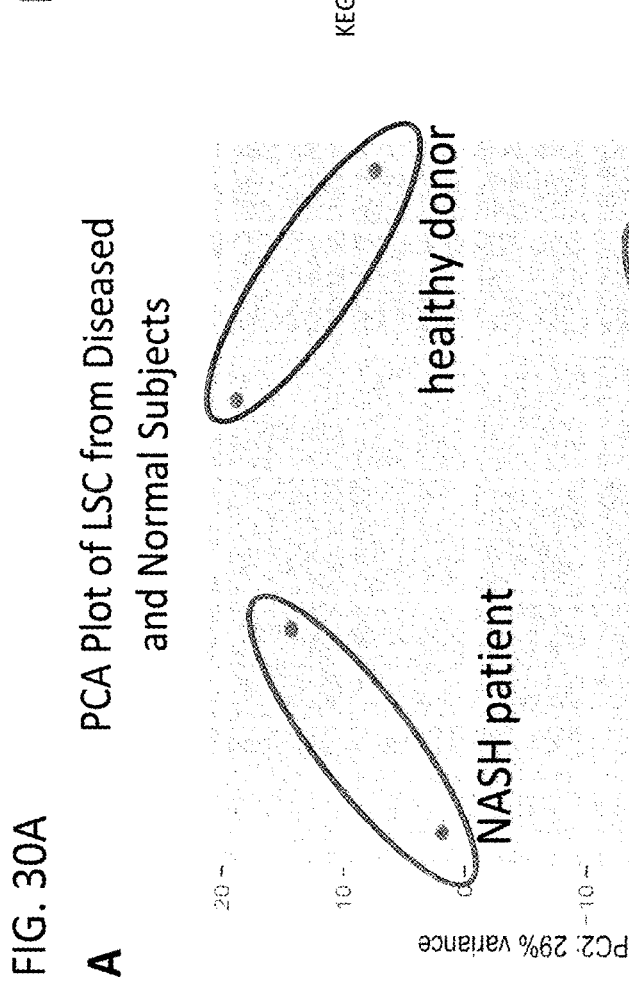
FIGS. 30A and 30B: Liver stem cell derived from liver disease subjects have altered gene expression reflective of their disease phenotype.
Figure 30B:
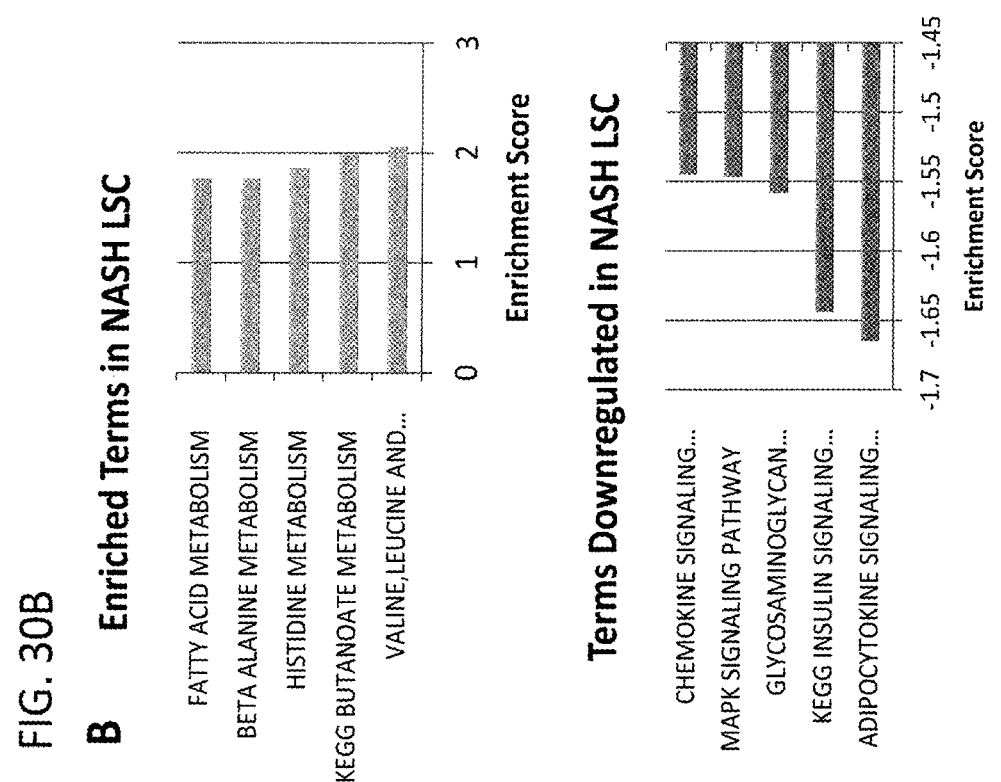
Figure 31:
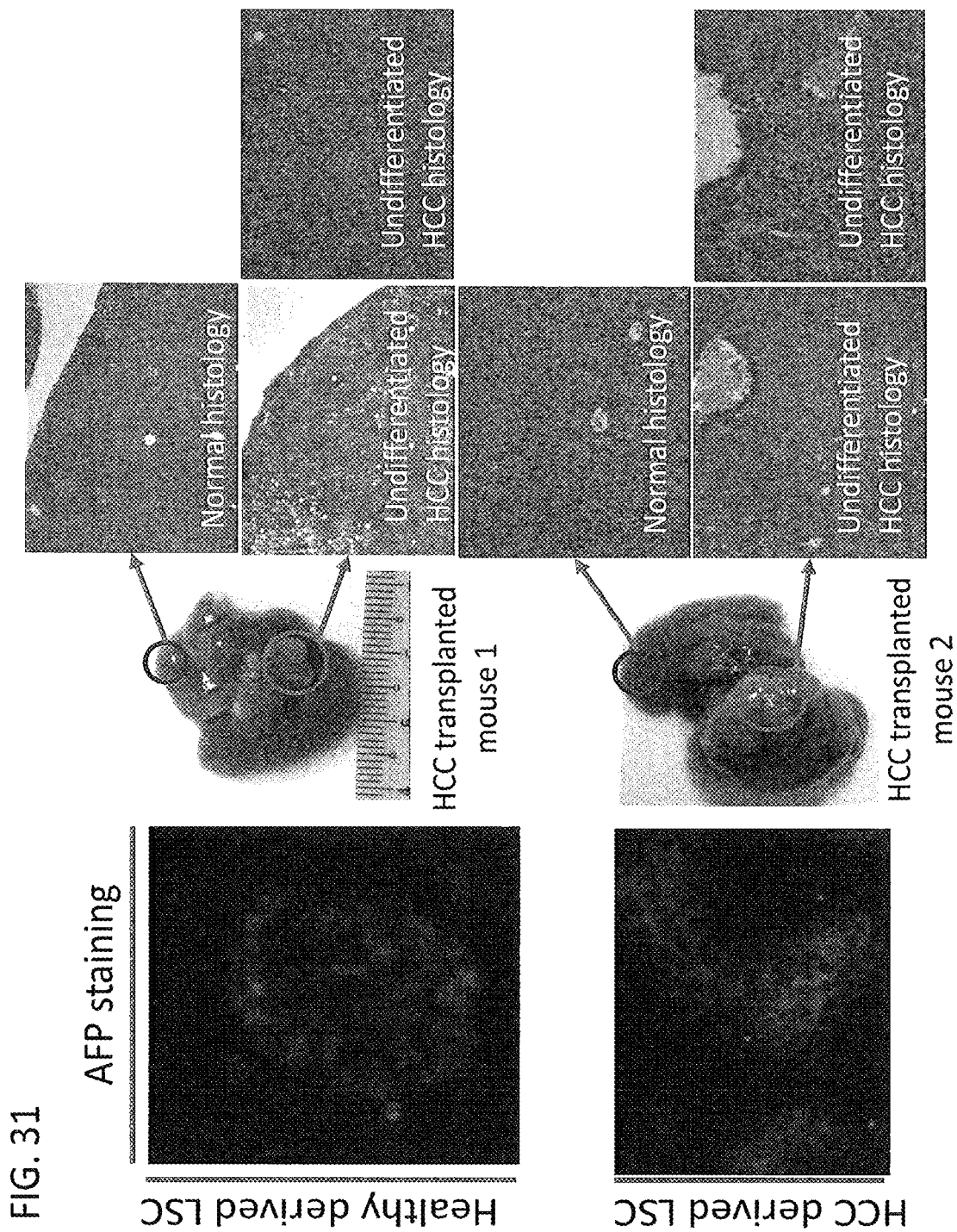
FIG. 31: Single cell derived HCC stem cells form tumor in mouse liver. LSC from a hepatocellular carcinoma (HCC) patient were derived from a single cell culture. These HCC LSCs expressed AFP, in contrast with LSC derived from healthy donors. HCC LSC were transplanted into NSG (NOD.Cg-Prkdcscid Il2rgtm1Wjl/SzJ) mouse strains, which are immunodeficient. Transplanted HCC LSCs developed into tumors in mouse liver of both mouse 1 & mouse 2 (photographs with tumors circled with large circle). H&E staining showed undifferentiated HCC from tumor regions compared with normal histology from normal tissue. This figure showed single cell derived HCC LSC are able to form tumors.
Figures 32A, 32B:
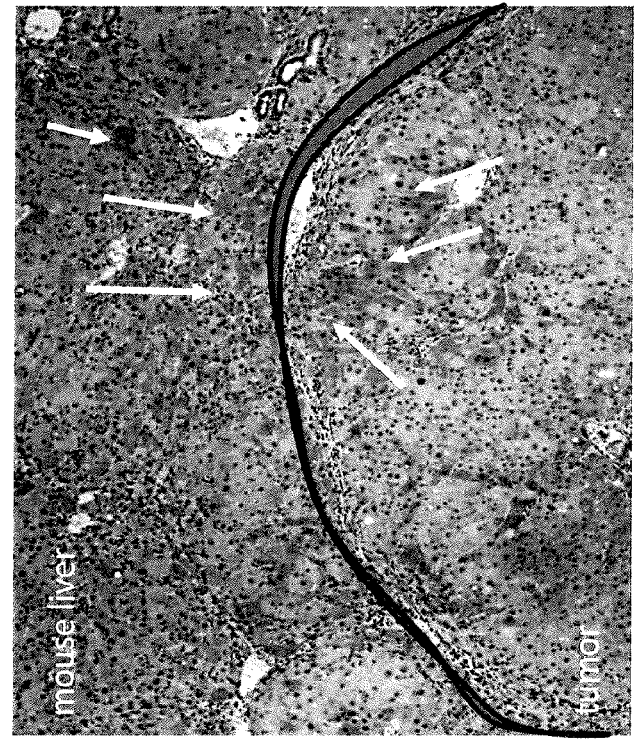
FIGS. 32A and 32B: Human albumin-expressing HCC cells were present in tumor mass and infiltrated adjacent mouse liver tissue.

Liver stem cells were derived not only from healthy liver donors, but also from patient with liver diseases (Table 1). We derived fatty liver stem cells from Non Alcoholic Fatty Liver Disease (NAFLD) patient HBV-infected cirrhotic liver patient and from a patient with hepatocellular carcinoma (HCC), from both tumor and adjacent healthy liver. We performed RNASeq gene expression analysis on the derived liver stem cells from these patients and from healthy donors. Our data showed that fatty liver stem cells were enriched in gene pathways consistent with the disease phenotype observed in disease liver in NAFLD patient (Table 3). Stem cells from NAFLD patient were enriched in cholesterol biosynthesis and leucine degradation genes compared to healthy and HBV infected cirrhotic liver stem cells. NAFLD patient also had high blood cholesterol and an amino acid imbalance phenotype (FIGS. 30A and 30B). Liver stem cells isolated from HCC tumor and tumor adjacent normal liver tissues were morphologically different even though they were derived using identical method and medium (FIG. 31). Single cell derived HCC liver stem cells were injected to NSG mice by intrasplenic injection. The transplanted mice developed HCC in the mouse liver (FIG. 31). Human HCC stem cells formed HCC tumor in mice and also express human specific albumin (FIG. 32A, 32B).

Example 6

Liver Regeneration

Figures 33A, 33B:
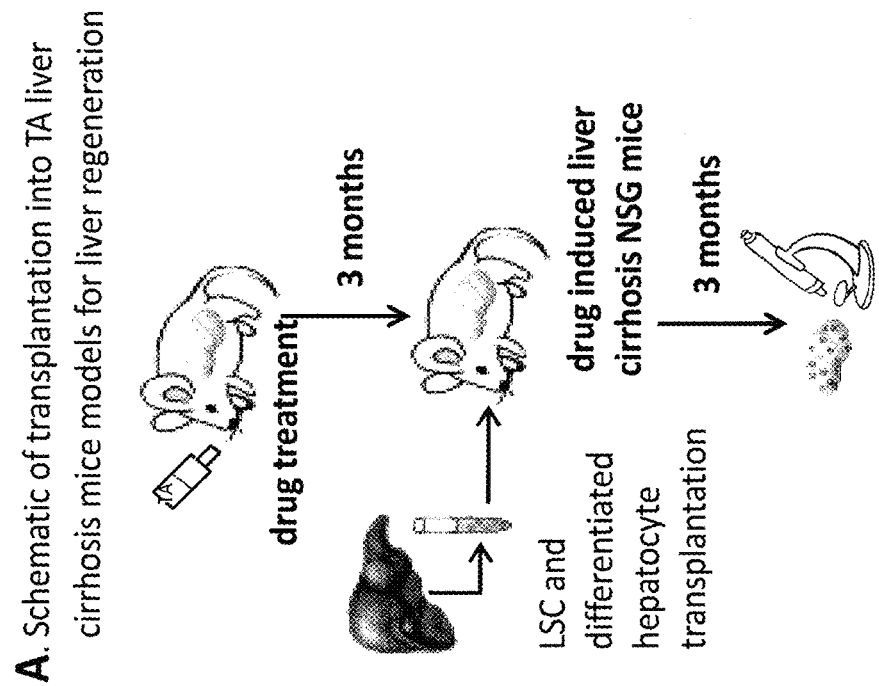
FIGS. 33A and 33B: Rescued liver function on LSC transplanted TA induced liver cirrhosis mice model.
Figure 34:
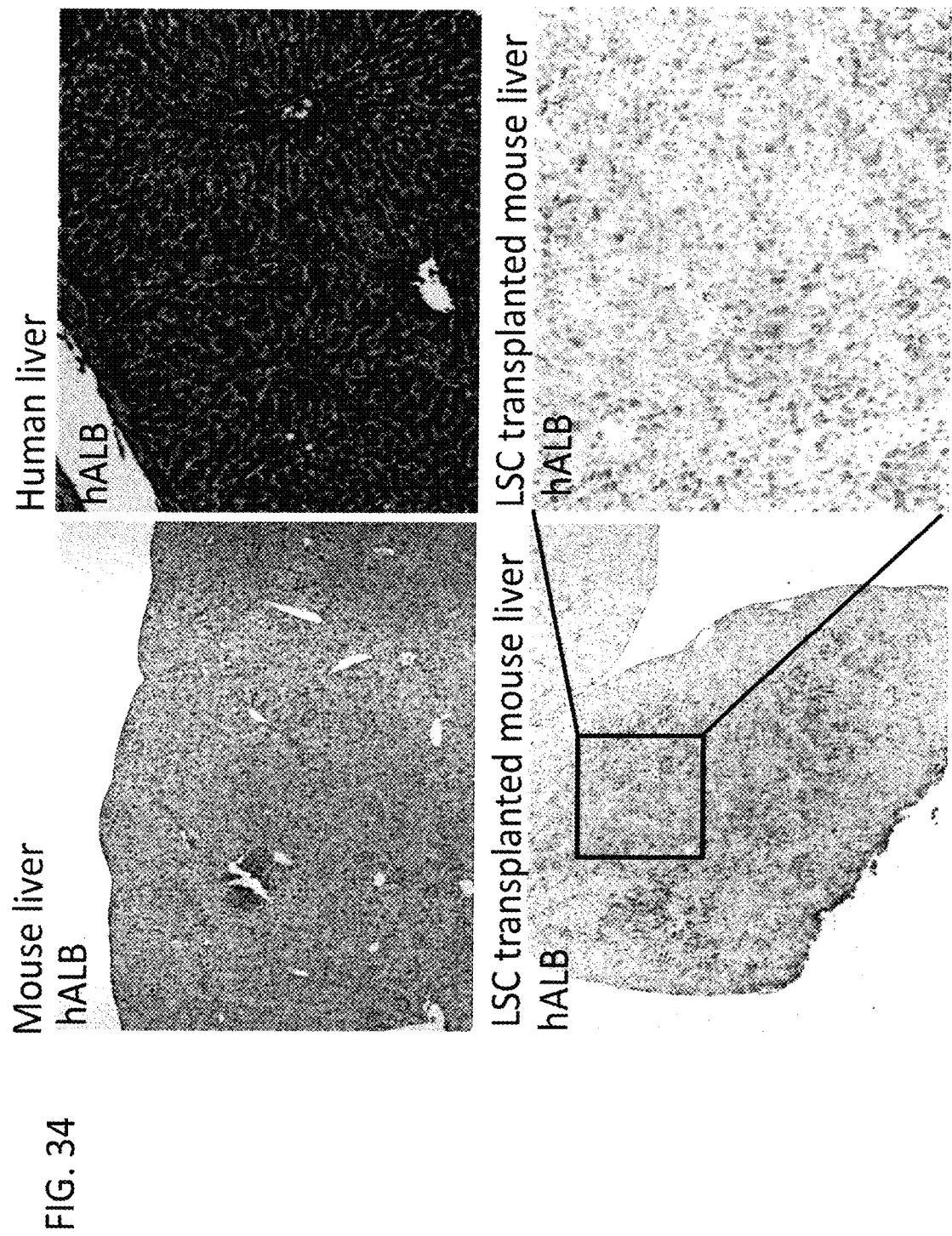
FIG. 34: LSC differentiated into human Alb positive hepatocyte when transplanted into mouse liver. Human ALB immunohistochemistry (IHC) staining on mouse liver, human liver and mouse liver with transplanted LSC. LSC transplanted into mouse liver tissue were detected by staining with hALB-specific antibody in IHC. This figure showed LSC differentiate into functional ALB-expressing hepatocyte in mouse liver.
Figure 35:
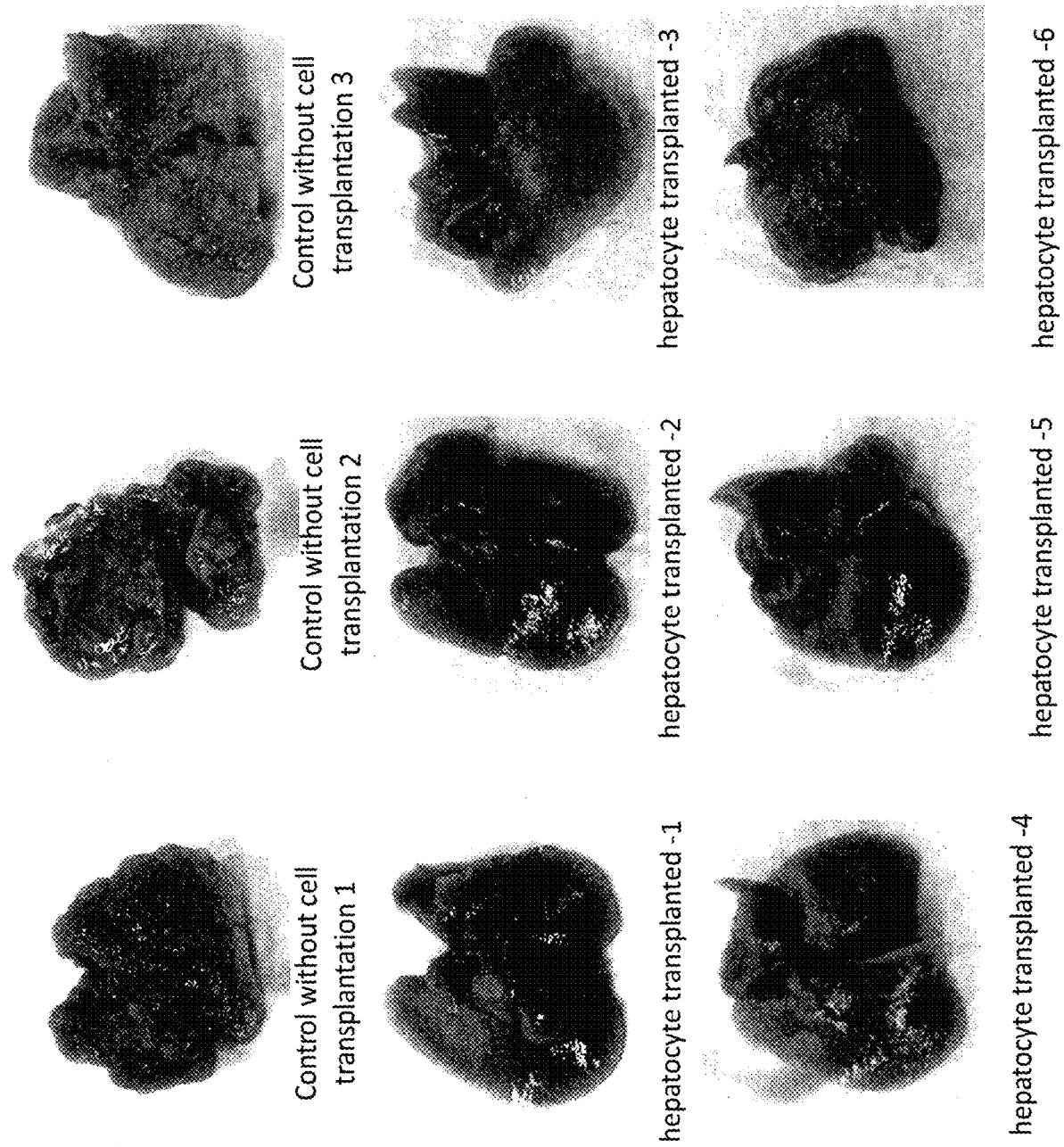
FIG. 35: Gross view of LSC differentiated hepatocyte transplanted mice liver. Gross view of LSC differentiated hepatocyte (dHep) transplanted mice liver. dHep were transplanted into TA induced liver cirrhosis mice. Control group had 3 mice without dHep transplantation. Transplanted group had 6 mice. This figure shows that dHep transplanted livers were rescued from liver cirrhosis as judged by liver morphology. The control cirrhotic liver with no cell transplanted have multiple cirrhotic nodules on the surface of the liver. In contrast, the liver with transplanted hepatocytes have a smooth surface similar to normal healthy liver.
Figure 36:
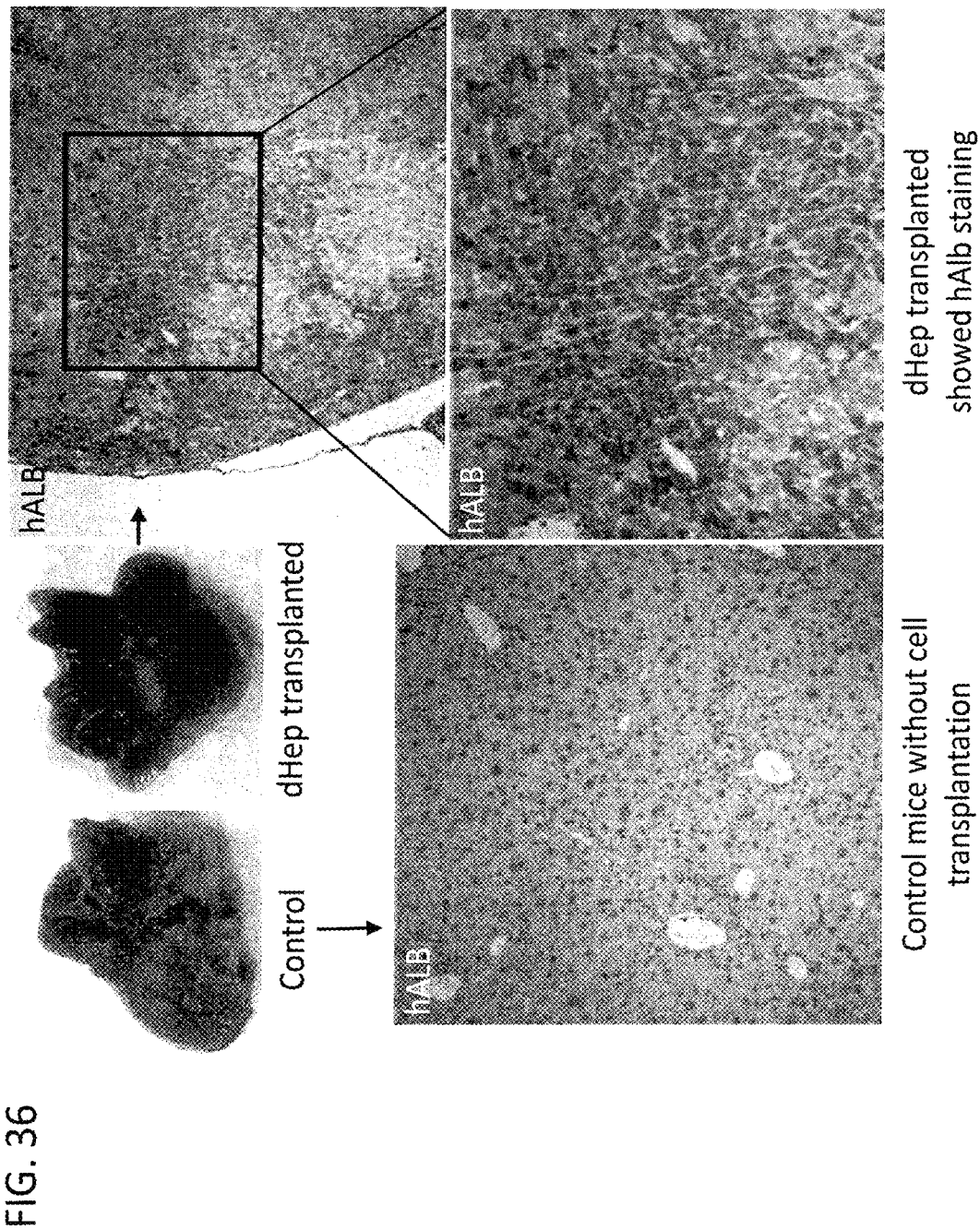
FIG. 36: dHep repopulated mouse liver in TA liver cirrhosis model. Livers from control and dHep transplanted livers in TA liver cirrhosis model were stained for hALB using a hALB-specific antibody. hALB staining was detected only in dHep transplanted mouse livers demonstrating repopulation of mouse liver by dHep.

This example demonstrates that both liver stem cells and differentiated liver stem cells (dHep) rescued the liver cirrhosis phenotype when transplanted into a mice treated with thioacetamide to induce liver cirrhosis mice (FIG. 33A). The mice developed liver cirrhosis by continuing thioacetamide treatment for 2-3 months. Liver stem cells and liver stem cell differentiated dHep cells were transplanted into the mice by intrasplenic injection. After transplantation, the mice continued to receive drug treatment for another 3 months (FIG. 33A). Mouse liver functions were tested in the third month. Transplanted mice group had higher serum albumin than non-transplanted control group (FIG. 33B). Their liver functions were therefore partially rescued. The livers of mice receiving transplanted dHEP cells have less fibrosis and inflammation than control group (FIG. 35). dHep was repopulated in transplanted mouse liver (FIG. 36). Both liver stem cells and dHEP cells integrated into mouse liver tissue and expressed human specific albumin (FIG. 34, 36. Table 4).

The liver stem cell (LSC) and their differentiated hepatocyte (dHep) and bile duct cells have the potential to treat liver cirrhosis caused by different liver diseases. In vitro derived autologous LSC, dHep and bile duct cells can be delivered to the same patient to rescue liver failure and reduce liver cirrhosis. LSC can be derived from the same patient and in vitro cultured for expansion. dHep and bile duct cells are in vitro differentiated from LSC. These stem cells and differentiated cells are autologous and will not induce transplant rejection in patients.

REFERENCES

1. Gebhardt R, Baldysiak-Figiel A, Krugel V, Ueberham E, Gaunitz F. Hepatocellular expression of glutamine synthetase: An indicator of morphogen actions as master regulators of zonation in adult liver. Prog Histochem Cytochem. 2007; 41(4):201-66. Epub 2007 Feb. 8.
2. Lee W. M. Drug-induced hepatotoxicity. N. Engl. J. Med. (2003) 349 474-485.
3. Si-Tayeb K., Noto F. K., Nagaoka M., Li J., Battle M. A., Duris C., North P. E., Dalton S., Duncan S. A. Highly efficient generation of human hepatocyte-like cells from induced pluripotent stem cells. Hepatology. 2010; 51:297-305.
4. Si-Tayeb K1, Lemaigre F P, Duncan S A. Organogenesis and development of the liver. Dev Cell. 2010 Feb. 16; 18(2):175-89. doi: 10.1016/j.devcel.2010.01.011.
5. Zanger U M1, Schwab M. Cytochrome P450 enzymes in drug metabolism: regulation of gene expression, enzyme activities, and impact of genetic variation. Pharmacol Ther. 2013 April; 138(1):103-41. doi: 10.1016/j.pharmthera.2012.12.007. Epub 2013 Jan. 16.
6. Schwartz R E1, Fleming H E2, Khetani S R3, Bhatia S N4. Pluripotent stem cell-derived hepatocyte-like cells.

7. Tabibian J H, Masyuk A I, Masyuk T V, O'Hara S P, LaRusso N F. Physiology of Cholangiocytes. Comprehensive Physiology. 2013; 3(1):10.1002/cphy.c120019. doi:10.1002/cphy.c120019.
8. Michalopoulos G K, DeFrances M C. Liver regeneration. Science 1997; 276:60-66. [PubMed: 9082986]
9. Okabe M, Tsukahara Y, Tanaka M, et al. (2009) Potential hepatic stem cells reside in EpCAM+ cells of normal and injured mouse liver. Development 136, 1951-1960.
10. B Wang, Self-renewing diploid Axin2+ cells fuel homeostatic renewal of the liver. Nature. 2015 Aug. 13; 524 (7564): 180-185.
11. J Font Burgada et al. Hybrid Periportal Hepatocytes Regenerate the Injured Liver without Giving Rise to Cancer, ce11.2015.07.026
12. Schmelzer E, Zhang L, Bruce A, et al. (2007) Human hepatic stem cells from fetal and postnatal donors. J Exp Med 204, 1973-1987.
13. Melissa Baxter et al Phenotypic and functional analyses show stem cell-derived hepatocyte-like cells better mimic fetal rather than adult hepatocytes. J Hepatol. 2015 March; 62(3): 581-589. doi: 10.1016/j.jhep.2014.10.016

List of Abbreviations

CYP: Cytochrome p450; LGR5: Leucine-rich repeat-containing G-protein coupled receptor 5; EPCAM: Epithelial cell adhesion molecule; KRT19: Cyto-keratin 19; KRT7: Cyto-keratin 7; CYP3A4: Cytochrome P450, Family 3, Subfamily A, Polypeptide 4; CYP2C9: Cytochrome P450, Family 2, Subfamily C, Polypeptide 9; AFP: Alpha-Fetoprotein; HNF3B: Hepatocyte Nuclear Factor 3, Beta; HNF4A: Hepatocyte Nuclear Factor 4, Alpha; NAFLD: nonalcoholic fatty liver disease; NASH: nonalcoholic steatohepatitis; PSC: Primary sclerosing cholangitis; PBC: Primary biliary cirrhosis; DILI: drug induced liver injury; HCC: hepatocarcinoma; LSC: liver stem cell; IF: Immunofluorescence; E-CAD: E-Cadherin; KI67: Antigen KI-67; SOX9: SRY (Sex Determining Region Y)-Box 9; ESC: embryonic stem cell; CD24: Signal transducer CD24; PROM1: Prominin 1; FOXA3: Forkhead Box A3; FOXQ1: Forkhead Box Q1; ALB: Albumin; PROX1: Prospero Homeobox 1; FOXA2: Forkhead Box A2; qPCR: Quantitative polymerase chain reaction; FACS: Fluorescence-activated cell sorting; 2D: 2 dimensional; 3D: 3 dimensional; CTX: cholera enterotoxin; PEPCK: Phosphoenolpyruvate Carboxykinase 1; ZO1: Zona Occludens 1; eHep: ESC differentiated hepatocyte; dhep: LSC in vitro differentiated hepatocyte; PAS: Periodic acid Schiff; LDL: Low-density lipoprotein; TAT: Tyrosine Aminotransferase; ALI: air liquid interface; HBV: Hepatitis B virus; PCA: Principle component analysis; GSEA: Gene enrichment analysis; TA: Thioacetamide; IHC: immunohistochemistry; NSG: NOD.Cg-Prkdcscid Il2rgtm1Wjl/SzJ; EHS: Engelberth-Holm-Swarm.

A83-01:3-(6-Methyl-2-pyridinyl)-N-phenyl-4-(4-quinolinyl)-1H-pyrazole-1-carbothioamide); SB431542: 4-[4-(1,3-benzodioxol-5-yl)-5-(2-pyridinyl)-1H-imidazol-2-yl]benzamide; SB 216763 (3-(2,4-Dichlorophenyl)-4-(1-methyl-1H-indol-3-yl)-1H-pyrrole-2,5-dione), SB 415286: 4-[4-(1, 3-benzodioxol-5-yl)-5-(2-pyridinyl)-1H-imidazol-2-yl] benzamide; CHIR 99021: 6-[[2-[[4-(2,4-Dichlorophenyl)-5-(5-methyl-1H-imidazol-2-yl)-2-pyrimidinyl]amino]ethyl] amino]-3-pyridinecarbonitrile; CHIR 99021 trihydrochloride: 6-[[2-[[4-(2,4-Dichlorophenyl)-5-(5-methyl-1H-imidazol-2-yl)-2-pyrimidinyl]amino]ethyl] amino]-3-pyridinecarbonitrile trihydrochloride; MeBIO: (2'Z,3'E)-6-Bromo-1-methylindirubin-3'-oxime; TCS 2002: 2-Methyl-5-[3-[4-(methylsulfinyl)phenyl]-5-benzofuranyl]-1,3,4-oxadiazole; NSC 693868: 1H-Pyrazolo[3,4-b]quinoxalin-3-amine; TCS 21311: 3-[5-[4-(2-Hydroxy-2-methyl-1-oxopropyl)-1-piperazinyl]-2-(trifluoromethyl) phenyl]-4-(1H-indol-3-yl)-1H-pyrrole-2,5-dione; AR-A 014418: N-[(4-Methoxyphenyl)methyl]-N'-(5-nitro-2-thiazolyl)urea; 3F8: 5-Ethyl-7,8-dimethoxy-1H-pyrrolo[3,4-c] isoquinoline-1,3(2H)-dione; L803: Peptide KEAP-PAPPQSP, A 1070722: 1-(7-Methoxyquinolin-4-yl)-3-[6-(trifluoromethyl)pyridin-2-yl]urea; TC-G 24: N-(3-Chloro-4-methylphenyl)-5-(4-nitrophenyl)-1,3,4-oxadiazol-2-amine; TWS 119: 3-[[6-(3-Aminophenyl)-7H-pyrrolo[2,3-d]pyrimidin-4-yl]oxyphenol ditrifluoroacetate; L803-mts: peptide GKEAPPAPPQSP; FRAT: frequently rearranged in advanced T-cell lymphomas; T3: 3,3'-5-triiodo-1-thyronine; T4: (S)-thyroxine; PTH: parathyroid hormone; NECA: 5'-(N-ethylcarboxamido)-adenosine; cAMP: cyclic adenosine monophosphate; NAC: N-Acetyl-Cysteine; BMP: Bone Morphogenetic Protein; HGF: Hepatocyte Growth Factor; FGF: Fibroblast Growth Factor; IRBs: Institutional Review Boards; ALI: air-liquid interface; LY 364947: (4-[3-(2-pyridinyl)-1H-pyrazol-4-yl]-quinoline; SD 208: (2-(5-Chloro-2-fluorophenyl)pteridin-4-yl]pyridin-4-yl-amine); D4476: (4-(4-(2,3-Dihydrobenzo[1,4]dioxin-6-yl)-5-pyridin-2-yl-1H-imidazol-2-yl)benzamide); GW 788388: (4-[4-[3-(2-Pyridinyl)-1H-pyrazol-4-yl]-2-pyridinyl]-N-(tetrahydro-2H-pyran-4-yl)-benzamide); SB 505124: (2-(5-Benzo[1,3]dioxol-5-yl-2-tert-butyl-3H-imidazol-4-yl)-6-methylpyridine), SB 525334: (6-[2-tert-Butyl-5-(6-methyl-pyridin-2-yl)-1H-imidazol-4-yl]-quinoxaline); RepSox: (E-616452; or 2-[3-(6-Methyl-2-pyridinyl)-1H-pyrazol-4-yl]-1,5-naphthyridine); R 268712 (4-[2-Fluoro-5-[3-(6-methyl-2-pyridinyl)-1H-pyrazol-4-yl]phenyl]-1H-pyrazole-1-ethanol)

DEPOSIT STATEMENT

Cultures of the liver stem cells (cell line L1-5 hLSC) and differentiated hepatocytes (cell line RFPL1-5 dHep) described herein were deposited on 8 Mar. 2017 under terms of the Budapest Treaty of 1977 with the European Collection of Authenticated Cell Cultures (Public Health England, Porton Down, Salisbury, SP4 0JG, UK), and given the patent deposit designation numbers 17030801 and 17030802, respectively. The microorganism deposit was made under the provisions of the "Budapest Treaty on the International Recognition of the Deposit of Microorganisms for the Purposes of Patent Procedure." All restrictions on the availability to the public of these deposited microorganisms will be irrevocably removed upon issuance of a patent based on this application. For the purposes of this disclosure, any isolate having the identifying characteristics of the deposited cells, including subcultures and variants thereof having the identifying characteristics and activity as described herein, are included.

It is understood that the examples and embodiments described herein are for illustrative purposes only and that various modifications or changes in light thereof will be suggested to persons skilled in the art and are to be included within the spirit and purview of this application and scope of the appended claims. All publications, sequence accession numbers, patents, and patent applications cited herein are hereby incorporated by reference in their entirety for all purposes.

TABLE 1

Derived liver diseased cell lines

| Donor and subject (patient) recruitment | | Personalized Stem Cell (Total number of subjects) | Single cell derived LSC lines of each subject | Successful Isolation Rate |
|---|---|---|---|---|
| Healthy Donor | | 7 | 3/subject | 83.3% |
| Patient with liver cirrhosis | HIV infection | 7 | 3/subject | 90% |
| | Alcohol induced cirrhosis | 1 | 3/subject | |
| | Fatty Liver | 3 | 3/subject | |
| With liver cancer (HCC) | Subject has Hepatitis B Virus infection | 3 | 3/subject | 20% |

TABLE 2

Comparison between LSC differentiated hepatocyte and primary hepatocyte.

| | dHep | Primary hepatocyte |
|---|---|---|
| Cell Size | Smaller | Larger, about 2-10x larger than dHep |
| Nucleus | Single nucleus, diploid | Binucleate and polyploid cells common |
| CYP functional activity | High CYPs activity, but not more than 70%, 80%, 90% of freshly isolated primary hepatocyte | Full CYPs family functional activity when freshly isolated |
| Maintenance in culture | Could be maintained for more than 30 days in culture, retaining CYPs functions | Cannot be maintained in culture. Full CYP functional activity cannot be retained for more than about 24-48 hours post-isolation from liver tissue |

TABLE 3

LSC was derived from both healthy liver donor and liver disease subjects.
LSC was derived from both healthy liver donor and liver disease subjects.
LSCs could be derived from the following liver diseases:

| Metabolic disease | Nonalcoholic fatty liver disease (NAFLD) Nonalcoholic steatohepatitis (NASH) |
|---|---|
| Autoimmune disease | primary sclerosing cholangitis (PSC) primary biliary cirrhosis (PBC) |
| Infectious disease | Hepatitis A, B, C virus infected liver cirrhosis |

TABLE 3-continued

LSC was derived from both healthy liver donor and liver disease subjects.
LSC was derived from both healthy liver donor and liver disease subjects.
LSCs could be derived from the following liver diseases:

| Drug induced acute and chronic liver failure | Drug induced liver injury (DILI) Alcoholic liver cirrhosis |
|---|---|
| Liver cancer | Hepatocellular carcinoma (HCC) cholangiocarcinoma |

TABLE 4

Partially rescued mouse liver function by LSC in vitro differentiated hepatocyte (dHEP).
Liver Function test

| sample | *PT (sec) | ALB (g/L) |
|---|---|---|
| Control 1 | 12.7 | 12.2 |
| Control 2 | 11.6 | 16.55 |
| Control 3 | 11.4 | 16.77 |
| Transplanted-1 | 11 | 28.61 |
| Transplanted-2 | 10.8 | 45.41 |
| Transplanted-3 | 10.9 | 21.94 |
| Transplanted-4 | 11.1 | 32.08 |
| Transplanted-5 | 10.7 | 33.11 |
| Transplanted-6 | 10.9 | 30.63 |

*PT time: Prothrombin time (PT) is a blood test that measures how long it takes blood to clot.

Table 4. Mouse liver function test table. Alb level was significantly higher in the transplanted group than the control group. It indicated in vitro LSC differentiated hepatocyte (dHep) partially rescued liver function in the TA induced liver cirrhosis mouse model. This figure shows that dHep partially rescued mouse liver function in liver cirrhosis mouse model.

TABLE 5

Comparison between LSC differentiated cholangiocyte and primary cholangiocyte.

| | LSC differentiated cholangiocyte | Primary cholangiocyte |
|---|---|---|
| Function | Able to secrete mucus | Able to secrete mucus |
| Ciliary structure | Have ciliary structure | Have ciliary structure |
| Cell shape | Only columnar in shape | Cuboidal in shape in the small interlobular bile ducts, but become columnar and mucus secreting in larger bile ducts. |
| Proliferative potential | No proliferative potential | Cuboidal cholangiocytes have proliferative potential |
| Cell surface markers | Expressed E-cadherin | Varied expression of E-cadherin |

What is claimed is:

1. A cell culture system for culturing liver stem cells, wherein the system comprises:
   a) a plurality of soluble agents in a stem cell culture medium comprising:
      thyroid hormone,
      an enhancer of the canonical WNT pathway,
      a TGF-beta inhibitor; and
   b) a cellular support capable of providing structural and nutritional support;
   (i) wherein the thyroid hormone is selected from the group consisting of 3,3'-5-triiodo-1-thyronine (T3), (S)-thyroxine (T4) and hormones that stimulate cAMP; and
   wherein the concentration of T3 in the system is from about 0.2 μM to about 20 μM, and
   (ii) wherein the cellular support comprises feeder cells.

2. The cell culture system of claim 1, wherein:
   the system enhances stem cell proliferation and/or prevents stem cell differentiation into mature liver cells;
   the cellular support maintains the liver stem cells in an adhesion layer;
   and
   the enhancer of the canonical WNT pathway activates the beta-catenin pathway.

3. The cell culture system of claim 1, wherein the system is a BMP (Bone morphogenetic protein) inhibitor-free, and/or HGF (Hepatocyte growth factor)-free and/or FGF (Fibroblast growth factor)-free system.

4. The cell culture system of claim 1, wherein the liver stem cells are characterized by having at least one feature selected from the group consisting of:
   a. when cultured on the cellular support, the liver stem cells are small and round in shape and clustered together forming a disk like structure;
   b. the liver stem cells express low levels of KRT19;
   c. the liver stem cells are positive for the markers selected from the group comprising Epithelial Cadherin (E-CAD), Epithelial Cell Adhesion Molecule (EP-CAM), Hepatocyte Nuclear Factor 4 Alpha (HNF4α), and SRY (Sex Determining Region Y)-Box 9 (SOX9);
   d. wherein less than 15% of the liver stem cells expresses Krt7;
   e. at least 80% of the liver stem cells express a transcription factor for hepatocyte lineage differentiation;
   f. the liver stem cells comprise bipotential progenitor/stem cells; and
   g. the liver stem cells are capable of developing into mature adult hepatocytes having at least four major Cytochrome P450 (CYP) functions.

5. The cell culture system of claim 4, wherein less than 5% of the liver stem cells expresses Krt7, and the transcription factor for hepatocyte lineage differentiation is HNF4a.

6. The cell culture system of claim 1, wherein the enhancer of the canonical WNT pathway is a Wnt agonist; wherein the Wnt agonist is selected from the group consisting of:
   a Wnt family member selected from the group consisting of Wnt-1/Int-1, Wnt-2/Irp (Int-1-related Protein), Wnt-2b/13, Wnt-3/Int-4, Wnt-3a, Wnt-4, Wnt-5a, Wnt-5b, Wnt-6, Wnt-7a, Wnt-7b, Wnt-8a/8d, Wnt-8b, Wnt-9a/14, Wnt-9b/14b/15, Wnt-10a, Wnt-10b/12, Wnt-11, and Wnt-16;
   an R-spondin family member selected from R-spondin 1, R-spondin 2, R-spondin 3, or R-spondin 4;
   Norrin (Norrie Disease Protein or NDP);
   a Glycogen synthase kinase 3 inhibitor selected from small-interfering RNAs, lithium, kenpaullone, 6-Bromoindirubin-30-acetoxime, SB 216763 (3-(2,4-Dichlorophenyl)-4-(1-methyl-1H-indol-3-yl)-1H-pyrrole-2,5-dione), SB 415286 (4-[4-(1,3-benzodioxol-5-yl)-5-(2-pyridinyl)-1H-imidazol-2-yl]benzamide; CHIR 99021 (6-[[2-[[4-(2,4-Dichlorophenyl)-5-(5-methyl-1H-imidazol-2-yl)-2-pyrimidinyl]amino]ethyl]amino]-3-pyridinecarbonitrile), CHIR 99021 trihydrochloride (6-[[2-[[4-(2,4-Dichlorophenyl)-5-(5-methyl-1H-imidazol-2-yl)-2-pyrimidinyl]amino]ethyl]amino]-3-pyridinecarbonitrile trihydrochloride), Kenpaullone, Indirubin-3'-oxime, MeBIO ((2'Z, 3'E)-6-Bromo-1-methylindirubin-3'-oxime), TCS 2002 (2-Methyl-5-[3-[4-(methylsulfinyl)phenyl]-5-benzofuranyl]-1,3,4-oxadiazole), Lithium carbonate, NSC 693868 (1H-Pyrazolo[3,4-b]quinoxalin-3-amine), TCS 21311 (34544-(2-Hydroxy-2-methyl-1-oxopropyl)-1-piperazinyl]-2-(trifluoromethyl)phenyl]-4-(1H-indol-3-yl)-1H-pyrrole-2,5-dione), AR-A 014418 (N-[(4-Methoxyphenyl)methyl]-N'-(5-nitro-2-thiazolyl)urea), 3F8 (5-Ethyl-7,8-dimethoxy-1H-pyrrolo[3,4-c]isoquinoline-1,3(2H)-dione), L803 (Peptide KEAPPAPPQSP (SEQ ID NO:41)), A 1070722 (1-(7-Methoxyquinolin-4-yl)-3-[6-(trifluoromethyl)pyridin-2-yl]urea), 10Z-Hymenialdisine, TC-G 24 (N-(3-Chloro-4-methylphenyl)-5-(4-nitrophenyl)-1,3,4-oxadiazol-2-amine), TWS 119 3-[[6-(3-Aminophenyl)-7H-pyrrolo[2,3-d]pyrimidin-4-yl]oxyphenol ditrifluoroacetate]), and L803-mts (peptide GKEAPPAPPQSP (SEQ ID NO:42)); and a Frequently Rearranged in Advanced T-cell lymphomas (FRAT)-family member and FRAT-derived peptides.

7. The cell culture system claim 1, wherein the TGF-beta inhibitor is selected from the group consisting of A83-01 (3-(6-Methyl-2-pyridinyl)-N-phenyl-4-(4-quinolinyl)-1H-pyrazole-1-carbothioamide) and SB431542 (4-[4-(1,3-benzodioxol-5-yl)-5-(2-pyridinyl)-1H-imidazol-2-yl]benzamide).

8. The cell culture system of claim 1, further comprising Epidermal Growth Factor (EGF), wherein the concentration of EGF in the system is from about 5 ng/ml to about 200 ng/ml.

9. The cell culture system of claim 1, wherein the system further comprises at least one component selected from the group consisting of an extracellular matrix, an agent for activating the Notch pathway, endotoxin, N-acetylcysteine and nicotinamide;
    wherein the extracellular matrix is matrigel or a growth factor reduced matrigel;
    wherein the agent for activating the Notch pathway is a notch ligand; or
    wherein the endotoxin is Cholera endotoxin.

10. The cell culture system of claim 1, wherein the feeder cells are from a fibroblast cell line; optionally
    wherein the fibroblast cell line is a mouse or human fibroblast cell line; or
    wherein the mouse fibroblast cell line is a 3T3J2 feeder cell line.

11. A cell culture system comprising an extracellular matrix, an EGF, R-spondin1, SB431542, Jagged-1 encoded by SEQ ID NO: 1, 3,3'-5-triiodo-1-thyronine (T3), Cholera endotoxin, Nicotinamide, N-acetylcysteine and a feeder cell,
    wherein the concentration of T3 in the system is from about 0.2 µM to about 20 µM.

12. The cell culture system of claim 11, wherein the extracellular matrix is a growth factor reduced matrigel, and the feeder cell is a mouse fibroblast 3T3J2 feeder cell line.

13. The cell culture system of claim 6, wherein the concentration of R-spondin 1 in the system is from about 100 ng/ml to about 500 ng/ml.

14. The cell culture system of claim 9, wherein the notch ligand is Jagged-1 encoded by SEQ ID NO: 1; optionally
    wherein the concentration of Jagged-1 in the system is from about 0.1 µM to about 10 µM.

15. The cell culture system of claim 9, wherein the concentration of nicotinamide in the system is from about 1 mM to about 50 mM;
    the concentration of N-acetylcysteine in the system is from about 0.1 µM to about 10 µM or about 1 µM to about 10 µM, or about 2 µM, or about 3 µM, or about 4 µM; or
    the concentration of Cholera endotoxin in the system is from about 0.01 µM to about 1 µM or about 0.05 µM to about 0.9 µM, or about 0.95 µM, or about 0.1 µM, or about 0.2 µM, or about 0.3 µM, or about 0.4 µM, or about 0.5 µM, or about 0.6 µM, or about 0.7 µM, or about 0.8 µM, or about 0.9 µM.

16. The cell culture system claim 7, wherein the concentration of SB431542 is from about 0.1 ng/ml to about 10 ng/ml, or about 0.1 µM to about 10 µM.

* * * * *